(12) United States Patent
Li et al.

(10) Patent No.: US 9,676,750 B2
(45) Date of Patent: Jun. 13, 2017

(54) BICYCLIC AROMATIC CARBOXAMIDE COMPOUNDS USEFUL AS PIM KINASE INHIBITORS

(71) Applicants: Incyte Corporation, Wilmington, DE (US); Incyte Holdings Corporation, Wilmington, DE (US)

(72) Inventors: Yun-Long Li, Chadds Ford, PA (US); David M. Burns, Glen Mills, PA (US); Hao Feng, Glen Mills, PA (US); Chu-Biao Xue, Hockessin, DE (US); Anlai Wang, Wilmington, DE (US); Jun Pan, Media, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

(21) Appl. No.: 15/001,826

(22) Filed: Jan. 20, 2016

(65) Prior Publication Data

US 2016/0137626 A1    May 19, 2016

Related U.S. Application Data

(63) Continuation of application No. 14/155,134, filed on Jan. 14, 2014, now Pat. No. 9,278,950.

(60) Provisional application No. 61/791,275, filed on Mar. 15, 2013, provisional application No. 61/752,249, filed on Jan. 14, 2013.

(51) Int. Cl.

| C07D 471/02 | (2006.01) |
|---|---|
| C07D 401/12 | (2006.01) |
| C07D 401/14 | (2006.01) |
| C07D 405/14 | (2006.01) |
| C07D 413/14 | (2006.01) |
| C07D 471/04 | (2006.01) |
| C07D 498/04 | (2006.01) |
| C07D 491/048 | (2006.01) |
| C07D 498/22 | (2006.01) |

(52) U.S. Cl.
CPC ......... *C07D 401/12* (2013.01); *C07D 401/14* (2013.01); *C07D 405/14* (2013.01); *C07D 413/14* (2013.01); *C07D 471/04* (2013.01); *C07D 491/048* (2013.01); *C07D 498/04* (2013.01); *C07D 498/22* (2013.01)

(58) Field of Classification Search
CPC .................................................. C07D 401/12
USPC ....................................................... 546/123
See application file for complete search history.

(56) References Cited

U.S. PATENT DOCUMENTS

| 8,168,794 B2 | 5/2012 | Burger et al. |
|---|---|---|
| 8,329,732 B2 | 12/2012 | Burger et al. |
| 9,200,004 B2 | 12/2015 | Xue |
| 9,278,950 B2 | 3/2016 | Li et al. |
| 9,340,546 B2 | 5/2016 | Ahmad |
| 2011/0059961 A1 | 3/2011 | Wang et al. |
| 2012/0114663 A1 | 5/2012 | Gelfand et al. |
| 2012/0225062 A1 | 9/2012 | Burger et al. |
| 2013/0057956 A1 | 3/2013 | Iwasa |
| 2014/0086941 A1 | 3/2014 | Reddy et al. |
| 2014/0088117 A1 | 3/2014 | Burch et al. |
| 2014/0163000 A1 | 6/2014 | Ahmad |
| 2014/0200216 A1 | 7/2014 | Li et al. |
| 2015/0057265 A1 | 2/2015 | Li et al. |
| 2015/0329534 A1 | 11/2015 | Xue et al. |
| 2016/0009714 A1 | 1/2016 | Sun et al. |
| 2016/0009726 A1 | 1/2016 | Vechorkin et al. |
| 2016/0347735 A1 | 12/2016 | Vechorkin et al. |

FOREIGN PATENT DOCUMENTS

| CN | 101568527 | 10/2009 |
|---|---|---|
| CN | 103664878 | 3/2014 |
| EP | 2637650 | 9/2013 |
| EP | 2743269 | 6/2014 |
| WO | WO 02/00196 | 1/2002 |
| WO | WO 02/055489 | 7/2002 |
| WO | WO 02/093173 | 11/2002 |
| WO | WO 03/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |

(Continued)

OTHER PUBLICATIONS

Venkatesh et al., J. Pharm. Sci. 89, 145-54 (2000).*

(Continued)

*Primary Examiner* — Nizal Chandrakumar
(74) *Attorney, Agent, or Firm* — Fish & Richardson P.C.

(57) ABSTRACT

The present disclosure describes bicyclic aromatic carboxamide derivatives, as well as their compositions and methods of use. The compounds inhibit the activity of the Pim kinases, and are useful in the treatment of diseases related to the activity of Pim kinases including, e.g., cancer and other diseases.

53 Claims, No Drawings

(56) References Cited

FOREIGN PATENT DOCUMENTS

| | | |
|---|---|---|
| WO | WO 2008/002676 | 1/2008 |
| WO | WO 2008/022164 | 2/2008 |
| WO | WO 2008/045252 | 4/2008 |
| WO | WO 2008/054749 | 5/2008 |
| WO | WO 2008/058126 | 5/2008 |
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/135650 | 11/2010 |
| WO | WO 2010/148351 | 12/2010 |
| WO | WO 2011/008487 | 1/2011 |
| WO | WO 2011/025859 | 3/2011 |
| WO | WO 2011/028685 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130342 | 10/2011 |
| WO | WO 2011/163195 | 12/2011 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/020370 | 2/2013 |
| WO | WO 2013/020371 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/089379 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014/106706 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |

(56) References Cited

FOREIGN PATENT DOCUMENTS

| WO | WO 2014/150276 | 9/2014 |
|---|---|---|
| WO | WO 2014/151008 | 9/2014 |
| WO | WO 2014/151634 | 9/2014 |
| WO | WO 2015/021153 | 2/2015 |
| WO | WO 2015/027124 | 2/2015 |
| WO | WO 2015/131031 | 9/2015 |
| WO | WO 2015/157257 | 10/2015 |
| WO | WO 2015/168246 | 11/2015 |
| WO | WO 2015/184305 | 12/2015 |
| WO | WO 2015/191677 | 12/2015 |

OTHER PUBLICATIONS

Ogawa et al. Expert Opin. Drug Discov. (2012) 7(12):1177-1192.*
Arunesh Expert Opin. Ther. Patents (2014) 24(1):5-17.*
Freshney, Culture of Animal Cells, A Manual of Basic Technique, Alan R. Liss, Inc., 1983, New York, p. 4.*
Kelly et al. British Journal of Haematology, 2011, 156, 129-152.*
Amson et al., "The human protooncogene product p33pim is expressed during fetal hematopoiesis and in diverse leukemias," Proc. Nat. Acad. Sci., USA, 1989, 86:8857-61.
Arunesh et al., "Small molecule inhibitors of PIM1 kinase. Jul. 2009 to Feb. 2013 patent update," Expert Opin Ther Pat, Jan. 2014, 24(1): 5-17.
Bamborough, "Assessment of Chemical Coverage of Kinome Space and Its Implications for Kinase Drug Discovery," J. Med. Chem., 2008, 51: 7898-7914.
Berge et al., "Pharmaceutical Salts," J. Pharm. Sci., 1977, 66(1):1-19.
Blanco-Aparicio, Biochemical Pharmacology, vol. 85, pp. 629-643, 2013.
Blom et al., "Optimizing Preparative LC-MS Configurations and Methods for Parallel Synthesis Purification," J. Comb. Chem., 2003, 5:670-83.
Blom et al., "Preparative LC-MS Purification: Improved Compound Specific Method Optimization," J. Comb. Chem., 2004, 6:874-883.
Blom, "Two-Pump at Column Dilution Configuration for Preparative Liquid Chromatography—Mass Spectrometry," J. Comb. Chem., 2002, 4:295-301.
Burger et al. "Structure Guided Optimization, in Vitro Activity, and in Vivo Activity of Pan-PIM Kinase Inhibitors," ACS Med Chem Lett., 2013, 4:1193-1197.
Chaichian "Targeted Therapies in Systemic Lupus Erythematosus: A State-of-the-Art-Review" J Clin Cell Immunol 2013, S6, 1-8.
Chan et al., "New N- and O-arylations with phenylboronic acids and cupric acetate," Tetrahedron Letters, May 1998, 39(19): 2933-2936.
Chen et al., "Pim kinase inhibitor, SGI-1776, induces apoptosis in chronic lymphocytic leukemia cells," Blood, 2009, 114:4150-57.
Damia "Contemporary pre-clinical development of anticancer agents—What are the optimal preclinical models?" European Journal of Cancer, 2009, 45, 2768-2781.
Davis et al., "Small Molecule Dual Antagonist of Pim 1 and 3 Kinases Ameliorate Experimental Autoimmune Encephalomyelitis," 26th Congress of the European Committee for Treatment and Research in Multiple Sclerosis, Oct. 13-16, 2010, Gothenburg, Sweden, Poster P436.
Dorwald F. A. Side Reactions in Organic Synthesis, 2005, Wiley: VCH, Weinheim p. IX of Preface p. 1-15.
Freshney, Culture of Animal Cells, A Manual of Basic Technique, Alan R Liss, Inc., 1983, New York, p. 4.
Fujii et al., "Aberrant expression of serine-threonine kinase Pim-3 in hepatocellular carcinoma development and its role in the proliferation of human hepatoma cell lines," Int. J. Canc., 2005, 114:209-18.
Georg Pilz, "Modern multiple sclerosis treatment—what is approved, what is on the horizon" Drug Discovery Today Dec. 2008, vol. 13, Nos. 23/24 1013-1025.
Gomez-Abad et al., "PIM2 inhibition as a rational therapeutic approach in B-cell lymphoma," Blood, 2011, 118:5517-27.

Gu and Li, "A concise synthesis of (2S,4R)- and (2S,4S)-4-methylglutamic acid," Tetrahedron Lett., 2003, 44:3203-3205.
Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-90.
Hsu et al., "Pim-1 knockdown potentiates paclitaxel-induced apoptosis in human hormone-refractory prostate cancers through inhibition of NHEJ DNA repair," Cancer Lett., 2012, 319:214-222.
Huang et al., "Structure-based design and optimization of 2-aminothiazole-4-carboxamide as a new class of CHK1 inhibitors," Bioorganic Med Chem Lett., Mar. 2013, 23(9):2590-2594.
International Preliminary Report on Patentability in International Application No. PCT/US2014/011486, mailed Jul. 21, 2015, 7 pages.
International Preliminary Report on Patentability in International Application No. PCT/US2014/011487, mailed Jul. 23, 2015, 6 pages.
International Search Report and Written Opinion in International Application No. PCT/US2014/011486, mailed Mar. 17, 2014, 12 pages.
International Search Report and Written Opinion in International Application No. PCT/US2014/011487, mailed Apr. 4, 2014, 11 pages.
International Search Report and Written Opinion in International Application No. PCT/US2014/052214, mailed Oct. 28, 2014, 13 pages.
International Search Report and Written Opinion in International Application No. PCT/US2015/040146, dated Oct. 5, 2015, 12 pages.
International Preliminary Report on Patentability in International Application No. PCT/US2014/052214, dated Feb. 23, 2016, 7 pages.
Isaac et al., "The oncogenic PIM kinase family regulates drug resistance through multiple mechanisms," Drug Resis. Updates, 2011, 14:203-11.
Ishchenko et al., "Structure-based design of low-nanomolar PIM kinase inhibitors," Bioorg Med Chem Lett., 2015, 25:474-480.
Jiang et al., "3,5-Disubstituted quinolines as novel c-Jun N-terminal kinase inhibitors," Bioorganic & Medicinal Chemistry Letters, 2007, 17: 6378-6382.
Johnson et al., "Relationship between drug activity in NCI preclinical in vitro and in vivo models and early clinical trials" British Journal of Cancer, 2001, 84, 1424-1437.
Kelly et al., "Targeting PIM kinase activity significantly augments the efficacy of cytarabine," British Journal of Haematology, 2011, 156, 129-152.
Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.
Lam et al., "New aryl/heteroaryl C N bond cross-coupling reactions via arylboronic acid/cupric acetate arylation," Tetrahedron Letters, May 1998, 39(19): 2941-2944.
Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.
Liu et al., "Overexpression of Pim-1 is associated with poor prognosis in patients with esophageal squamous cell carcinoma," J. Surg. Oncol., 2010,102:683-88.
Liu et al., "Synthesis and Sar of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16: 2590-2594.
Merkel et al., "PIM1 kinase as a target for cancer therapy," Exp. Opin. Investig. Drugs, 2012, 21:425-38.
Michelotti et al., "Two classes of p38a MAP kinase inhibitors having a common diphenylether core but exhbiting divergent binding modes," 2005, 15: 5274-5279.
Mikkers et al., "High-throughput retroviral tagging to identify components of specific signaling pathways in cancer," Nature Genet., 2002, 32:153-159.

(56) References Cited

OTHER PUBLICATIONS

Mikkers et al., "Mice deficient for all PIM kinases display reduced body size and impaired responses to hematopoietic growth factors," Mol. Cell. Biol., 2004, 24:6104-15.

Miyazaki et al., "Design and effective synthesis of novel templates, 3,7-diphenyl-4-amino-thieno and furo[3,2-c]pyridines as protein kinase inhibitors and in vitro evaluation targeting angiogenetic kinases," Bioorganic & Medicinal Chemistry Letters, 2007, 17: 250-254.

Mizuki et al., "Suppression of myeloid transcription factors and induction of STAT response genes by AML-specific Flt3 mutations," Blood, 2003, 101:3164-73.

Morwick, "Pim kinase inhibitors: a survey of the patent literature," Exp. Opin. Ther. Patents, 2010, 20(2):193-212.

Mulvihill et al., "Novel 2-phenylquinolin-7-yl-derived imidazo [1,5-a]pyrazines as potent insulin-like growth factor-I receptor (IFG-IR) inhibitors," Bioorganic & Medicinal Chemistry, 2008, 16: 1359-1375.

Ocana, A. "Preclinical development of molecular targeted agents for cancer" Nat. Rev. Clin. Oncol. 2011, 8, 200-209.

Ogawa et al., "Insights from Pim1 structure for anti-cancer drug design," Expert Opin Drug Discov, Dec. 2012, 7(12): 1177-92.

Peltola et al., "Pim-1 kinase expression predicts radiation response in squamocellular carcinoma of head and neck and is under the control of epidermal growth factor receptor," Neoplasia, 2009, 11:629-36.

Peturssion, "Protecting Groups in Carbohydrate Chemistry," J. Chem. Educ., 1997, 74(11):1297-1303.

Ravin, "Preformulation," Remington's Pharmaceutical Sciences, 17th Ed., (Mack Publishing Company, Easton, 1985), p. 1409-1423.

Robinson et al., "A Dual PIM 1/3 Kinase Inhibitor Demonstrates Efficacy in Murine Models of Lupus and Multiple Sclerosis," J. Immunol., 2012, 188:119.9.

Schatz, et al., "Targeting cap-dependent translation blocks converging survival signals by AKT and PIM kinases in lymphoma," J. Exp. Med., 2011, 208:1799-1807.

Shen et al , "Inhibition of Pim-1 kinase ameliorates dextran sodium sulfate-induced colitis in mice," Dig. Dis. Sci., 2012, 57:1822-31.

Search Report, Jul. 2, 2014, 6 pages.

Search Report, Jul. 8, 2014, 4 pages.

Search Report, Jul. 3, 2014, 4 pages.

Sharma "Cell line-based platforms to evaluate the therapeutic efficacy of candidate anticancer agents" Nature Reviews Cancer Apr. 2010, vol. 10, 241-253.

Shinto et al., "Moloney murine leukemia virus infection accelerates lymphomagenesis in Eμ-bcl-2 transfenic mice," Oncogene, 1995, 11:1729-36.

Simone, Oncology: Introduction, Cecil Textbook of Medicine, 20th Edition, 1996 vol. 1, pp. 1004-1010.

Swords et al., "The Pim kinases: new targets for drug development," Curr. Drug Targets, 2011, 12(14):2059-66.

United States Office Action in U.S. Appl. No. 14/155,134, mailed Jul. 27, 2015, 12 pages.

Venkatesh et al., "Role of the Development Scientist in Compound Lead Selection and Optimization," J. Pharm. Sci., 2000, 89:145-54.

Wang et al , "Inhibition of Pim1 kinase prevents peanut allergy by enhancing Runx3 expression and suppressing T(H)2 and T(H)17 T-cell differentiation," J. All. Clin. Immunol., 2012, 130:932-44.

Yang et al., "Proviral integration site 2 is required for interleukin-6 expression induced by interleukin-1, tumour necrosis factor-α and lipopolysaccharide," Immunol., 2010, 131:174-182.

Zippo, et al., "PIM1-dependent phosphorylation of histone H3 at serine 10 is required for MYC-dependent transcriptional activation and oncogenic transformation," Nature Cell Biol., 2007, 9:932-44.

Asano et al., "The serine/threonine kinase Pim-2 is a novel anti-apoptotic mediator in myeloma cells," Leukemia, 2011, 25: 1182-1188.

Baron et al., "PIM1 gene cooperates with human BCL6 gene to promote the development of lymphomas," PNAS, Apr. 2012, 109(15): 5735-5739.

Brault et al., "PIM kinases are progression markers and emerging therapeutic targets in diffuse large B-cell lymphoma," British Journal of Cancer, 2012, 107: 491-500.

Caira, "Crystalline Polymorphism of Organic Compounds," Topics in Current Chemistry, Jan. 1998, 198: 163-208.

Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.

Chen et al., "Mechanisms of cytotoxicity to Pim kinase inhibitor, SGI-1776, in acute myeloid leukemia," Blood, Jul. 2011, 118(3): 693-702.

Chilean Office Action, Patent Application No. 1985-2015, dated Jul. 7, 2016, 22 pages (English Translation).

Chinese Office Action in Chinese Application No. 201480012783.3. dated Sep. 6, 2016, 16 pages (English Translation).

Claudio et al., "A molecular compendium of genes expressed in multiple myeloma," Blood, 2002, 100:2175-86.

Colombian Office Action in Colombian Application No. 15-168. 544, dated Aug. 10, 2016, 10 pages.

Coperet, "A simple and efficient method for the preparation of pyridine N-Oxides," The Journal of Organic Chemistry, Jan. 1998, 63: 1740-1741.

Gozgit et al., "Effects of the JAK2 Inhibitor, AZ960, on Pim/BAD/BCL-xL, Survival Signaling in the Human JAK2 V617F Cell Line SET-2," Journal of Biological Chemistry, Nov. 2008, 283(47): 32334-32343.

Hammerman et al., "Lymphocyte Transformation by Pim-2 Is Dependent on Nuclear Factor-kB Activation," Cancer Research, Nov. 2004, 64: 8341-8348.

International Search Report and Written Opinion in International Application No. PCT/US2016/034520, dated Jul. 12, 2016, 11 pages.

International Search Report and Written Opinion in International Application No. PCT/US2016/050925, dated Oct. 21, 2016, 13 pages.

Katano et al., "Synthesis and biological activity of (cyclopentenopyridinium)thiomethylcephalosporins," The Journal of Antibiotics, Jan. 1990, 43(9): 1150-1159.

Lu et al., "Pim2 is required for maintaining multiple myeloma cell growth through modulating TSC2 phosphorylation," Blood, Aug. 2013, 122(9): 1610-1620.

Schwemmers et al., "JAK2V617F-negative ET Patients do not display constitutively active JAK/STAT signaling," Exp. Hematol., Nov. 2007, 35(11): 1695-1703.

www.leukaemia org' [online]. "Myeloproliferative neoplasms (MPN)," 2016, [retrieved on Dec. 5, 2016]. Retrieved from the Internet: URL<http://www.leukaemia.org.au/blood-cancers/myeloproliferative-neoplasms-mpn>, 3 pages.

* cited by examiner

BICYCLIC AROMATIC CARBOXAMIDE COMPOUNDS USEFUL AS PIM KINASE INHIBITORS

CROSS-REFERENCE TO RELATED APPLICATIONS

The present application is a continuation of U.S. application Ser. No. 14/155,134, filed Jan. 14, 2014, which claims the benefit of U.S. Provisional Application No. 61/752,249, filed Jan. 14, 2013, and U.S. Provisional Application No. 61/791,275, filed Mar. 15, 2013, the entire disclosures of which are incorporated herein by reference in their entirety.

TECHNICAL FIELD

The present application is concerned with pharmaceutically useful compounds. The disclosure provides new compounds as well as their compositions and methods of use. The compounds inhibit the activity of Pim kinases and are therefore useful in the treatment of diseases related to the activity of Pim kinases including, e.g., cancers and other diseases.

BACKGROUND

Protein kinases regulate diverse biological processes including cell growth, survival, differentiation, organ formation, morphogenesis, neovascularization, tissue repair, and regeneration, among others. Protein kinases also play specialized roles in a host of human diseases including cancer. The three members of the Pim kinase family, one example of a protein kinase family, were initially identified as preferential integration sites of Moloney leukemia virus in mouse models of cancer. Although possessing modest but measurable oncogenic activity alone, they potentiate pro-proliferative and pro-survival oncogenes, e.g., causing a dramatic acceleration of lymphomagenesis in Myc-transgenic or Bcl2-transgenic mice. Mikkers et al., *Nature Genet.*, 2002, 32, 153-159; Shinto et al., *Oncogene*, 1995, 11, 1729-35.

The three non-receptor serine/threonine kinases Pim1, Pim2 and Pim3 regulate cell proliferation and survival by impacting gene transcription and protein translation. Zippo, et al., *Nature Cell Biol.*, 2007, 9, 932-44; Schatz, et al., *J. Exp. Med.*, 2011, 208, 1799-1807. As opposed to numerous other protein kinases which require activation by phosphorylation, the Pim kinases are constitutively activated and family members have overlapping substrate targets and biological functions, with differences between family members dictated, in part, by their varied tissue distribution. Expression of the Pim kinases is induced by cytokines and growth factors. Among the cytokines activating Pim kinase expression are cytokines which signal through the JAK/STAT pathway. Pim kinases act in parallel to the PI3K/AKT pathway, and they share several phosphorylation targets (e.g., pBAD, p4EBP1). Inhibitors of Pim kinases may therefore potentiate regimens including inhibitors of either the JAK pathway or the PI3K/AKT pathway.

Overexpression of Pim kinases is detected in a wide variety of hematologic and solid cancers. Overexpression of various family members have been noted in multiple myeloma, AML, pancreatic and hepatocellular cancers. Claudio et al., *Blood*, 2002, 100, 2175-86; Amson et al., *Proc. Nat. Acad. Sci., USA*, 1989, 86, 8857-61; Mizuki et al., *Blood*, 2003, 101, 3164-73; Li et al., *Canc. Res.*, 2006, 66, 6741-7; Fujii et al., *Int. J. Canc.*, 2005, 114, 209-18. Pim1 overexpression is associated with poor prognosis in mantle cell lymphoma, esophageal and head and neck cancers. Hsi et al., *Leuk. Lymph.*, 2008, 49, 2081-90; Liu et al., *J. Surg. Oncol.*, 2010, 102, 683-88; Peltola et al., *Neoplasia*, 2009, 11, 629-36. Pim2 overexpression is associated with an aggressive clinical course in a subset of DLBCL patients. Gomez-Abad et al., *Blood*, 2011, 118, 5517-27. Overexpression is often seen where Myc is overexpressed and Pim kinases can convey resistance to traditional chemotherapeutic agents and radiation. Chen et al., *Blood*, 2009, 114, 4150-57; Isaac et al., *Drug Resis. Updates*, 2011, 14, 203-11; Hsu et al., *Cancer Lett.*, 2012, 319, 214; Peltola et al., *Neoplasia*, 2009, 11, 629-36.

As such, these data indicate that inhibition of Pim kinases will be useful to provide therapeutic benefit in cancer patients.

Data from mice deficient for one or multiple Pim kinase family members suggests that pan-Pim inhibitor would have a favorable toxicity profile. Triple knockout mice are viable, but are slightly smaller than their wild type littermates. Mikkers et al., *Mol. Cell. Biol.*, 2004, 24. 6104-15. Since Pim kinases are also involved in a variety of immunologic and inflammatory responses and these indications require drug agents with fewer side effects, Pim kinase inhibitors are expected to be useful in treating patients with colitis (Shen et al., *Dig. Dis. Sci.*, 2012, 57, 1822-31), peanut allergy (Wang et al., *J. All. Clin. Immunol.*, 2012, 130, 932-44), multiple sclerosis and lupus (Davis et al., "Small Molecule Dual Antagonist of Pim 1 and 3 Kinases Ameliorate Experimental Autoimmune Encephalomyelitis", 26th Congress of the European Committee for Treatment and Research in Multiple Sclerosis, 13-16 Oct. 2010, Gothenburg, Sweden, Poster P436; Robinson et al., *J. Immunol.*, 2012, 188, 119.9) and rheumatoid arthritis (Yang et al., *Immunol.* 2010, 131, 174-182) and other immunological and inflammatory disorders.

The Pim kinases have therefore been identified as useful targets for drug development efforts. Swords et al., *Curr. Drug Targets*, 2011, 12(14), 2059-66; Merkel et al., *Exp. Opin. Investig. Drugs*, 2012, 21, 425-38; Morwick et al., *Exp. Opin. Ther. Patents*, 2010, 20(2), 193-212.

Accordingly, there is a need for new compounds that inhibit Pim kinases. The present application describes new inhibitors of Pim kinases that are useful for treating diseases associated with the expression or activity of one or more Pim kinases, e.g., cancer and other diseases.

SUMMARY

The present disclosure provides, inter alia, a compound of formula (I):

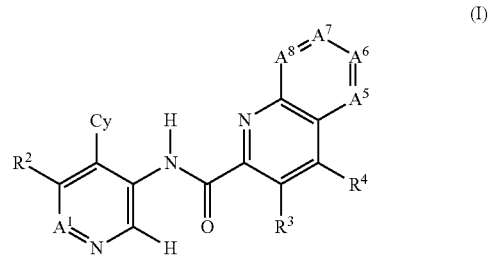

or a pharmaceutically acceptable salt thereof; wherein the variables are as defined below.

The present disclosure also provides a composition comprising a compound of formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of formula (I), or a pharmaceutically acceptable salt thereof.

The details of one or more embodiments are set forth in the description below. Other features, objects and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or min.us approximately 10% of the indicated value).

I. Compounds

The present disclosure provides, inter alia, a compound of formula (I):

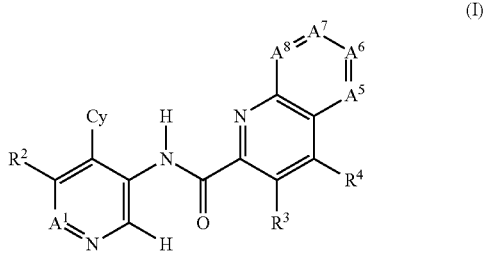

(I)

or a pharmaceutically acceptable salt thereof, wherein:

Cy is unsubstituted or substituted $C_{3-7}$ cycloalkyl or unsubstituted or substituted 4-10 membered heterocycloalkyl, wherein the ring atoms of the heterocycloalkyl consist of carbon atoms and 1, 2 or 3 heteroatoms selected from O, N or S, wherein the substituted $C_{3-7}$ cycloalkyl or substituted 4-10 membered heterocycloalkyl forming Cy is substituted with 1, 2, 3, 4 or 5 substituents each independently selected from halogen, $R^{Cy1}$, $C_{1-6}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$, wherein each $R^{Cy1}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-7}$ cycloalkyl and 4-7 membered heterocycloalkyl, each of which is independently unsubstituted or substituted with 1, 2 or 3 substituents independently selected from halogen, $R^{Cy2}$, $C_{1-6}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$, and wherein each $R^{Cy2}$ is independently $C_{1-6}$ alkyl, $C_{2-6}$ alkenyl, $C_{2-6}$ alkynyl, $C_{6-10}$ aryl, 5-10 membered heteroaryl, $C_{3-7}$ cycloalkyl and 4-7 membered heterocycloalkyl, each of which is independently unsubstituted or substituted with 1, 2 or 3 substituents independently selected from halogen, CN, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$ and $S(O)_2NR^{c1}R^{d1}$;

$A^1$ is N or $CR^1$;

$R^1$ is H, halogen, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$; and $R^2$ is H, halogen, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$;

or $A^1$ and $R^2$ in combination, together with the carbon atom to which $R^2$ is attached, form a 5, 6 or 7-membered unsaturated or partially saturated carbocyclic or heterocyclic ring containing 3 to 7 ring carbon atoms and 0, 1 or 2 ring heteroatoms, each independently selected from N, O and S, wherein the ring formed by the combination of $A^1$ and $R^2$ is unsubstituted or substituted by 1, 2 or 3 substituents independently selected from halogen, $C_{1-6}$ alkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^cC(O)R^{b2}$, $NR^{c2}C(O)NR^{c2}R^{d2}$, $NR^{c2}C(O)OR^{a2}$ and oxo;

$R^3$ is H, halogen or $NH_2$;

$R^4$ is H or halogen;

$A^5$ is N or $CR^5$;

$A^6$ is N or $CR^6$;

$A^7$ is N or $CR^7$;

$A^8$ is N or $CR^8$;

provided that 0, 1 or 2 of $A^5$, $A^6$, $A^7$ and $A^8$ are N;

$R^5$ is H or halogen;

$R^6$ is H or halogen;

$R^7$ is H, halogen, $C_{1-6}$ alkyl, $C_{2-6}$ alkenyl, $C_{2-6}$ alkynyl, $C_{1-6}$ haloalkyl, $Cy^7$, -$L^7$-$Cy^7$, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, or $S(O)_2NR^{c3}R^{d3}$, wherein said $C_{1-6}$ alkyl, $C_{2-6}$ alkenyl or $C_{2-6}$ alkynyl forming $R^7$ are each independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

$Cy^7$ is unsubstituted or substituted $C_{6-10}$ aryl, unsubstituted or substituted 5-10 membered heteroaryl, unsubstituted or substituted $C_{3-6}$ cycloalkyl or unsubstituted or substituted 4-7 membered heterocycloalkyl, wherein the substituted $C_{6-10}$ aryl, 5-10 membered heteroaryl, $C_{3-6}$ cycloalkyl or 4-7 membered heterocycloalkyl forming Cy$^7$ is substituted with 1, 2, 3, 4 or 5 substituents each independently selected from halogen, R$^{Cy7}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$;

wherein each R$^{Cy7}$ is C$_{1-6}$ alkyl, each of which is independently unsubstituted or substituted by 1, 2 or 3 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$;

L$^7$ is unsubstituted C$_{1-6}$ alkylene or C$_{1-6}$ alkylene substituted with 1, 2 or 3 substituents independently selected from F, Cl, CN, OH, O(C$_{1-6}$ alkyl), NH$_2$, NH(C$_{1-6}$ alkyl) and N(C$_{1-6}$ alkyl)$_2$;

R$^8$ is H, halogen, CN or C$_{1-6}$ alkyl;

R$^{a1}$, R$^{b1}$, R$^{c1}$ and R$^{d1}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a1}$, R$^{b1}$, R$^{c1}$ and R$^{d1}$ are each optionally substituted with 1, 2, 3, 4 or 5 substituents independently selected from C$_{1-6}$ alkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, and S(O)$_2$NR$^{c4}$R$^{d4}$;

or R$^{c1}$ and R$^{d1}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, and S(O)$_2$NR$^{c4}$R$^{d4}$;

R$^{a2}$, R$^{b2}$, R$^{c2}$ and R$^{d2}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a2}$, R$^{b2}$, R$^{c2}$ and R$^{d2}$ are each optionally substituted with 1, 2, 3, 4 or 5 substituents independently selected from C$_{1-6}$ alkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$ and S(O)$_2$NR$^{c5}$R$^{d5}$;

or R$^{c2}$ and R$^{d2}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$ and S(O)$_2$NR$^{c5}$R$^{d5}$;

R$^{a3}$, R$^{b3}$, R$^{c3}$ and R$^{d3}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a3}$, R$^{b3}$, R$^{c3}$ and R$^{d3}$ are each optionally substituted with 1, 2, 3, 4 or 5 substituents independently selected from C$_{1-6}$ alkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, and S(O)$_2$NR$^{c6}$R$^{d6}$;

or R$^{c3}$ and R$^{d3}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, and S(O)$_2$NR$^{c6}$R$^{d6}$;

R$^{a4}$, R$^{b4}$, R$^{c4}$ and R$^{d4}$ are each independently selected from H, C$_{1-6}$ alkyl, C$_{1-6}$ haloalkyl, C$_{2-6}$ alkenyl, C$_{2-6}$ alkynyl, aryl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{1-6}$ haloalkyl, C$_{2-6}$ alkenyl, C$_{2-6}$ alkynyl C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a4}$, R$^{b4}$, R$^{c4}$ and R$^{d4}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

or R$^{c4}$ and R$^{d4}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

R$^{a5}$, R$^{b5}$, R$^{c5}$ and R$^{d5}$ are each independently selected from H, C$_{1-6}$ alkyl, C$_{1-6}$ haloalkyl, C$_{2-6}$ alkenyl, C$_{2-6}$ alkynyl, aryl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{1-6}$ haloalkyl, C$_{2-6}$ alkenyl, C$_{2-6}$ alkynyl C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a5}$, R$^{b5}$, R$^{c5}$ and R$^{d5}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

or R$^{c5}$ and R$^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

R$^{a6}$, R$^{b6}$, R$^{c6}$ and R$^{d6}$ are each independently selected from H, C$_{1-6}$ alkyl, C$_{1-6}$ haloalkyl, C$_{2-6}$ alkenyl, C$_{2-6}$ alkynyl, aryl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{1-6}$ haloalkyl, C$_{2-6}$ alkenyl, C$_{2-6}$ alkynyl C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a6}$, R$^{b6}$, R$^{c6}$ and R$^{d6}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

or R$^{c6}$ and R$^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy; and R$^{e1}$, R$^{e2}$, R$^{e3}$, R$^{e4}$, R$^{e5}$ and R$^{e6}$ are each, independently, H, CN or NO$_2$.

In some embodiments, Cy is unsubstituted or substituted C$_{3-7}$ cycloalkyl.

In some embodiments, Cy is unsubstituted or substituted 4-10 membered heterocycloalkyl.

In some embodiments, Cy is unsubstituted or substituted 4-7 membered heterocycloalkyl.

In some embodiments, Cy is unsubstituted or substituted heterocycloalkyl, the ring atoms of which consist of carbon atoms and 1 or 2 heteroatoms selected from N, O and S.

In some embodiments, Cy is unsubstituted or substituted heterocycloalkyl, the ring atoms of which consist of carbon atoms and 1 or 2 nitrogen atoms.

In some embodiments, Cy is unsubstituted or substituted heterocycloalkyl, the ring atoms of which consist of carbon atoms and 1 nitrogen atom.

In some embodiments, Cy is an unsubstituted or substituted pyrrolidine, piperidine or azepane ring.

In some embodiments, a nitrogen atom of Cy forms the bond between Cy and the remainder of the molecule.

In some embodiments, Cy is a piperidin-1-yl ring substituted at least by an amino group at the 3-position. Cy can be, e.g., 3-aminopiperidin-1-yl, 3-amino-4-hydroxypiperidinyl or 3-amino-4-hydroxy-5-methylpiperidinyl. In some embodiments, the configuration of the carbon atom at the 3-position of the piperidin-1-yl ring forming Cy is (S) when the carbon atom at the 2-position of the piperidin-1-yl ring forming Cy has a higher Cahn-Ingold-Prelog priority than the carbon atom at the 4-position and (R) when the carbon atom at the 4-position of the piperidin-1-yl ring forming Cy has a higher Cahn-Ingold-Prelog priority than the carbon atom at the 4-position. Cy can be, e.g., (3S)-aminopiperidin-1-yl, (3R,4R)-3-amino-4-hydroxypiperidinyl, (3R,4S)-3-amino-4-hydroxypiperidinyl, (3R,4R,5R)-3-amino-4-hydroxy-5-methylpiperidinyl, (3R,4R,5S)-3-amino-4-hydroxy-5-methylpiperidinyl, (3R,4S,5R)-3-amino-4-hydroxy-5-methylpiperidinyl or (3R,4S,5S)-3-amino-4-hydroxy-5-methylpiperidinyl. In other embodiments, the configuration of the carbon atom at the 3-position of the piperidin-1-yl ring forming Cy is (R) when the carbon atom at the 2-position of the piperidin-1-yl ring forming Cy has a higher Cahn-Ingold-Prelog priority than the carbon atom at the 4-position and (S) when the carbon atom at the 4-position of the piperidin-1-yl ring forming Cy has a higher Cahn-Ingold-Prelog priority than the carbon atom at the 4-position. Cy can be, e.g., (3R)-aminopiperidin-1-yl, (3S,4S)-3-amino-4-hydroxypiperidinyl, (3S,4R)-3-amino-4-hydroxypiperidinyl, (3S,4R,5R)-3-amino-4-hydroxy-5-methylpiperidinyl, (3S,4R,5S)-3-amino-4-hydroxy-5-methylpiperidinyl, (3S,4S,5R)-3-amino-4-hydroxy-5-methylpiperidinyl or (3S,4S,5S)-3-amino-4-hydroxy-5-methylpiperidinyl.

In some embodiments, Cy is unsubstituted.

In some embodiments, Cy is substituted. In some embodiments, Cy is substituted with 1, 2 or 3 substituents. In some embodiments, Cy is substituted with 1 substituent. In some embodiments, Cy is substituted with 2 substituents. In some embodiments, Cy is substituted with 2 substituents.

In some embodiments, Cy can be unsubstituted or substituted with 1 or 2 or 3 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, NR$^{c1}$R$^{d1}$, S(O)R$^{b1}$, S(O)NR$^{c1}$R$^{d1}$, S(O)$_2$R$^{b1}$ and S(O)$_2$NR$^{c1}$R$^{d1}$.

In some embodiments, Cy can be unsubstituted or substituted with 1 or 2 or 3 substituents independently selected from C$_{1-6}$ alkyl, e.g., methyl or ethyl, OR$^{a1}$, e.g., OH, OMe or OEt and NR$^{c1}$R$^{d1}$, e.g., NH$_2$, NHMe or NMe$_2$.

In some embodiments, Cy can be unsubstituted or substituted with 1 or 2 or 3 substituents independently selected from methyl, OH and NH$_2$.

In some embodiments, Cy can be substituted with 1 substituent.

In some embodiments, Cy is a group of the following formula (Cy-1):

(Cy-1)

wherein:
R$^x$ is H, C$_{1-6}$ alkyl or OC(O)C$_{1-6}$ alkyl;
R$^y$ is H or C$_{1-6}$ alkyl;
a is 1 or 2;
b is 0, 1 or 2; and
the sum of a and b is 1, 2 or 3.

In some embodiments, Cy is a group of the following formula (Cy-2):

(Cy-2)

wherein R$^x$, R$^y$, a and b are as defined for formula (Cy-1).

In some embodiments wherein Cy is a group of formula (Cy-1) or (Cy-2), $R^x$ is H.

In some embodiments wherein Cy is a group of formula (Cy-1) or (Cy-2), $R^y$ is H.

In some embodiments wherein Cy is a group of formula (Cy-1) or (Cy-2), a is 1.

In some embodiments wherein Cy is a group of formula (Cy-1) or (Cy-2), b is 1.

In some embodiments, Cy is a piperidin-1-yl ring substituted at the 3-position by an amino group. Cy can be, e.g., 3-aminopiperidin-1-yl, 3-amino-4-hydroxypiperidinyl or 3-amino-4-hydroxy-5-methylpiperidinyl.

In some embodiments, the configuration of the carbon atom at the 3-position of the piperidin-1-yl ring forming Cy is (S) when the carbon atom at the 2-position of the piperidin-1-yl ring forming Cy has a higher Cahn-Ingold-Prelog priority than the carbon atom at the 4-position and (R) when the carbon atom at the 4-position of the piperidin-1-yl ring forming Cy has a higher Cahn-Ingold-Prelog priority than the carbon atom at the 4-position. Cy can be, e.g., (3S)-aminopiperidin-1-yl, (3R,4R)-3-amino-4-hydroxypiperidinyl, (3R,4S)-3-amino-4-hydroxypiperidinyl, (3R,4R,5R)-3-amino-4-hydroxy-5-methylpiperidinyl, (3R,4R,5S)-3-amino-4-hydroxy-5-methylpiperidinyl, (3R,4S,5R)-3-amino-4-hydroxy-5-methylpiperidinyl or (3R,4S,5S)-3-amino-4-hydroxy-5-methylpiperidinyl.

In some embodiments, the configuration of the carbon atom at the 3-position of the piperidin-1-yl ring forming Cy is (R) when the carbon atom at the 2-position of the piperidin-1-yl ring forming Cy has a higher Cahn-Ingold-Prelog priority than the carbon atom at the 4-position and (S) when the carbon atom at the 4-position of the piperidin-1-yl ring forming Cy has a higher Cahn-Ingold-Prelog priority than the carbon atom at the 4-position. Cy can be, e.g., (3R)-aminopiperidin-1-yl, (3S,4S)-3-amino-4-hydroxypiperidinyl, (3S,4R)-3-amino-4-hydroxypiperidinyl, (3S,4R,5R)-3-amino-4-hydroxy-5-methylpiperidinyl, (3S,4R,5S)-3-amino-4-hydroxy-5-methylpiperidinyl, (3S,4S,5R)-3-amino-4-hydroxy-5-methylpiperidinyl or (3S,4S,5S)-3-amino-4-hydroxy-5-methylpiperidinyl.

In some embodiments, Cy is a group can be any of the following groups (Cy-3) to (Cy-25):

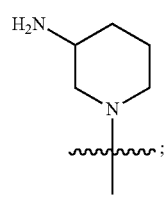
(Cy-3)

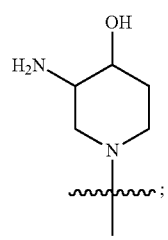
(Cy-4)

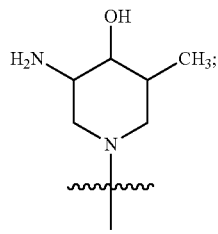
(Cy-5)

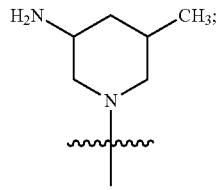
(Cy-6)

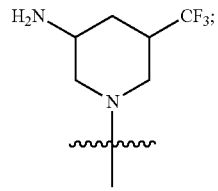
(Cy-7)

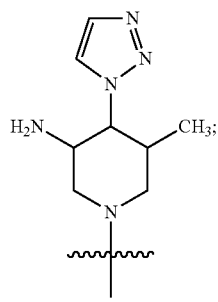
(Cy-8)

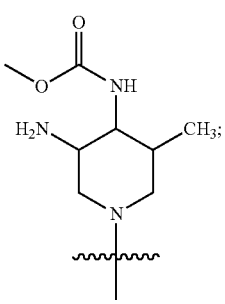
(Cy-9)

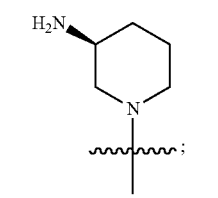
(Cy-10)

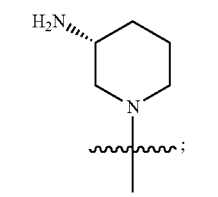
(Cy-11)

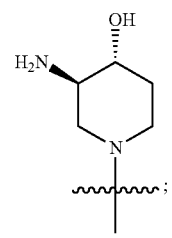 (Cy-12)
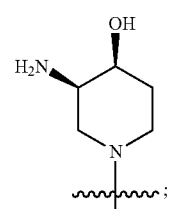 (Cy-13)
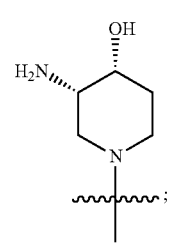 (Cy-14)
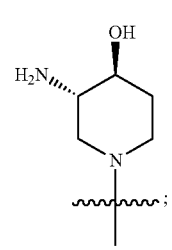 (Cy-15)
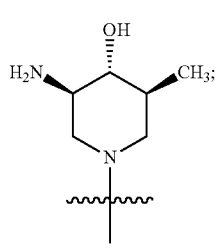 (Cy-16)
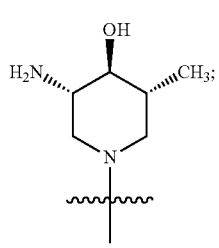 (Cy-17)
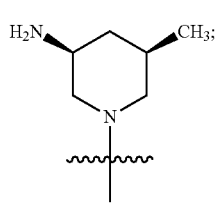 (Cy-18)
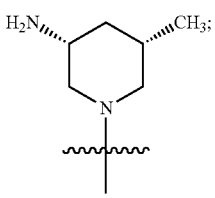 (Cy-19)
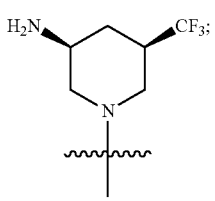 (Cy-20)
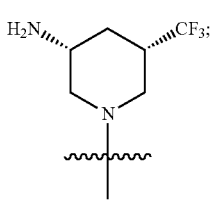 (Cy-21)
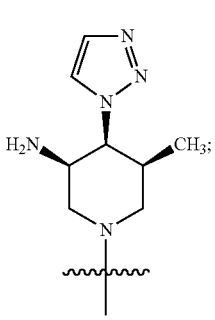 (Cy-22)
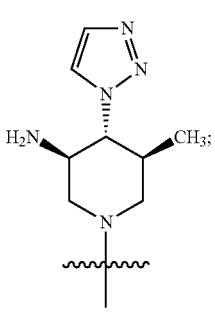 (Cy-23)
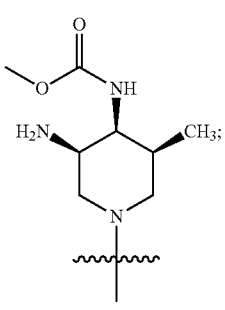 (Cy-24)

(Cy-25)

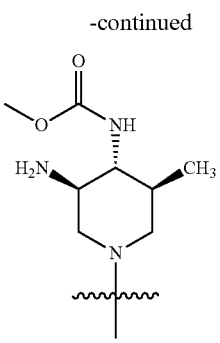

In some embodiments, $A^1$ is N.
In some embodiments, $A^1$ is $CR^1$.
In some embodiments, $R^1$ is H, halogen, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$.

In some embodiments, $R^1$ is H, halogen or $C_{1-6}$ alkyl.
In some embodiments, $R^1$ is H or $C_{1-6}$ alkyl.
In some embodiments, $R^1$ is H.
In some embodiments, $R^1$ is methyl or ethyl.
In some embodiments, $R^2$ is H, halogen, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$.

In some embodiments, $R^2$ is H, halogen, CN, $C_{1-6}$ alkyl or $C_{1-6}$ alkoxy.
In some embodiments, $R^2$ is H, F, CN, methyl, ethyl, methoxy or ethoxy.
In some embodiments, $R^2$ is H.
In some embodiments, $A^1$ and $R^2$ in combination, together with the carbon atom to which $R^2$ is attached, form a 5, 6 or 7-membered unsaturated or partially saturated carbocyclic or heterocyclic ring containing 3 to 7 ring carbon atoms and 0, 1 or 2 ring heteroatoms, each independently selected from N, O and S; wherein the ring formed by the combination of $A^1$ and $R^2$ is unsubstituted or substituted by 1, 2 or 3 substituents independently selected from halogen, $C_{1-6}$ alkyl, CN, $OR^{a2}$, $OC(O)R^{a2}$ and oxo.
In some embodiments, $A^1$ is $CR^1$, and $R^1$ and $R^2$ in combination form a $C_{3-5}$ alkylene that is unsubstituted or substituted by 1, 2 or 3 substituents independently selected from halogen, $C_{1-6}$ alkyl, CN, $OR^{a2}$, $OC(O)R^{a2}$ and oxo.
In some embodiments, $A^1$ is $CR^1$, and $R^1$ and $R^2$ in combination form a $C_{3-5}$ alkylene that is unsubstituted or substituted by $OR^{a2}$.
In some embodiments, $A^1$ is $CR^1$, and $R^1$ and $R^2$ in combination form a $C_{3-5}$ alkylene that is unsubstituted or substituted by OH.
In some embodiments, $R^3$ is $NH_2$.
In some embodiments, $R^3$ is H.
In some embodiments, $R^3$ is halogen.
In some embodiments, $R^3$ is F.
In some embodiments, $R^4$ is H.
In some embodiments, $R^4$ is halogen.
In some embodiments, $R^4$ is F.
In some embodiments, $A^5$ is N.

In some embodiments, $A^5$ is $CR^5$.
In some embodiments, $R^5$ is H.
In some embodiments, $R^5$ is halogen.
In some embodiments, $R^5$ is F.
In some embodiments, $A^6$ is N.
In some embodiments, $A^6$ is $CR^6$.
In some embodiments, $R^6$ is H.
In some embodiments, $R^6$ is halogen.
In some embodiments, $R^6$ is F.
In some embodiments, $A^7$ is N.
In some embodiments, $A^7$ is $CR^7$.
In some embodiments, $R^7$ is H, halogen, $C_{1-6}$ alkyl, $C_{2-6}$ alkenyl, $C_{2-6}$ alkynyl, $C_{1-6}$ haloalkyl, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, or $S(O)_2NR^{c3}R^{d3}$, wherein said $C_{1-6}$ alkyl, $C_{2-6}$ alkenyl or $C_{2-6}$ alkynyl forming $R^7$ are each unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$.

In some embodiments, $R^7$ is H, halogen, $C_{1-6}$ alkyl, $C_{2-6}$ alkenyl or $C_{2-6}$ alkynyl, wherein said $C_{1-6}$ alkyl, $C_{2-6}$ alkenyl or $C_{2-6}$ alkynyl forming $R^7$ are each unsubstituted or substituted with 1, 2 or 3 substituents independently selected from halogen, $C_{1-6}$ alkyl, $C_{2-6}$ alkenyl, $C_{2-6}$ alkynyl, CN, $OR^{a3}$, $OC(O)R^{b3}$, $NR^{c3}R^{d3}$, and $NR^{c3}C(O)R^{b3}$.

In some embodiments, $R^7$ is H, halogen or $C_{1-6}$ alkyl, wherein said $C_{1-6}$ alkyl forming $R^7$ is unsubstituted or substituted with 1, 2 or 3 substituents independently selected from halogen, CN, $OR^{a3}$, $OC(O)R^{b3}$, $NR^{c3}R^{d3}$, and $NR^{c3}C(O)R^{b3}$.

In some embodiments, $R^7$ is H, halogen or $C_{1-6}$ alkyl, wherein said $C_{1-6}$ alkyl forming $R^7$ is unsubstituted or substituted with a substituent selected from halogen, CN, $OR^{a3}$, $OC(O)R^{b3}$, $NR^{c3}R^{d3}$, and $NR^{c3}C(O)R^{b3}$.

In some embodiments, $R^7$ is H, halogen, $C_{1-6}$ alkyl, ($C_{1-6}$ alkylene)-CN, ($C_{1-6}$ alkylene)-OH, ($C_{1-6}$ alkylene)-O($C_{1-6}$ alkyl) or ($C_{1-6}$ alkylene)-$NR^{c3}R^{d3}$.

In some embodiments, $R^7$ is H, halogen, methyl, ethyl, isopropyl, $CH_2CN$, $CH(OH)CH_3$, $C(OH)(CH_3)_2$, $CFCH_3$ or $CH_2N(CH_3)_2$.

In some embodiments, $R^7$ is $Cy^7$.
In some embodiments, $R^7$ is $-L^7-Cy^7$.
In some embodiments, $Cy^7$ is unsubstituted or substituted $C_{6-10}$ aryl, unsubstituted or substituted 5-10 membered heteroaryl, unsubstituted or substituted $C_{3-6}$ cycloalkyl or unsubstituted or substituted 4-7 membered heterocycloalkyl, wherein the substituted $C_{6-10}$ aryl, 5-10 membered heteroaryl, $C_{3-6}$ cycloalkyl or 4-7 membered heterocycloalkyl forming $Cy^7$ is substituted with 1, 2, 3, 4 or 5 substituents each independently selected from halogen, $R^{Cy7}$, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$, wherein each $R^{Cy7}$ is $C_{1-6}$ alkyl, each of which is independently unsubstituted or substituted by 1, 2 or 3 substituents independently selected from halogen, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)$ NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted C$_{6-10}$ aryl or C$_{6-10}$ aryl substituted with 1, 2, 3, 4 or 5 substituents each independently selected from halogen, C$_{1-6}$ alkyl, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted phenyl or phenyl substituted with 1, 2, 3, 4 or 5 substituents each independently selected from halogen, R$^{Cy7}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$, wherein each R$^{Cy7}$ is C$_{1-6}$ alkyl, each of which is independently unsubstituted or substituted by 1, 2 or 3 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted phenyl or phenyl substituted with 1, 2, 3, 4 or 5 substituents each independently selected from halogen, C$_{1-6}$ alkyl, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted phenyl.

In some embodiments, Cy$^7$ is phenyl substituted with 1, 2, 3, 4 or 5 substituents each independently selected from halogen, R$^{Cy7}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$, wherein each R$^{Cy7}$ is C$_{1-6}$ alkyl, each of which is independently unsubstituted or substituted by 1, 2 or 3 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is phenyl substituted with 1, 2, 3, 4 or 5 substituents each independently selected from halogen, C$_{1-6}$ alkyl, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted 2,6-difluorophenyl, 2-carbamylphenyl, 2-carbamyl-6-fluorophenyl, 2-cyanophenyl, 2-cyano-6-fluorophenyl.

In some embodiments, Cy$^7$ is unsubstituted 5-10 membered heteroaryl or 5-10 membered heteroaryl substituted with 1, 2, 3, 4 or 5 substituents each independently selected from halogen, R$^{Cy7}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$, wherein each R$^{Cy7}$ is C$_{1-6}$ alkyl, each of which is independently unsubstituted or substituted by 1, 2 or 3 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted 5-10 membered heteroaryl or 5-10 membered heteroaryl substituted with 1, 2, 3, 4 or 5 substituents each independently selected from halogen, C$_{1-6}$ alkyl, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted pyrazolyl or pyrazolyl substituted with 1, 2 or 3 C$_{1-6}$ alkyl substituents.

In some embodiments, Cy$^7$ is 1-methyl-1H-pyrazol-3-yl.

In some embodiments, Cy$^7$ is unsubstituted C$_{3-7}$ cycloalkyl or C$_{3-7}$ cycloalkyl substituted with substituted with 1, 2, 3, 4 or 5 substituents each independently selected from halogen, R$^{Cy7}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$, wherein each R$^{Cy7}$ is C$_{1-6}$ alkyl, each of which is independently unsubstituted or substituted by 1, 2 or 3 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted C$_{3-7}$ cycloalkyl or C$_{3-7}$ cycloalkyl substituted with 1, 2, 3, 4 or 5 substituents each independently selected from halogen, C$_{1-6}$ alkyl, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted C$_{3-7}$ cycloalkyl.

In some embodiments, Cy$^7$ is unsubstituted 4-7 membered heterocycloalkyl or 4-7 membered heterocycloalkyl substituted with 1, 2, 3, 4 or 5 substituents each independently selected from halogen, R$^{Cy7}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$, wherein each R$^{Cy7}$ is C$_{1-6}$ alkyl, each of which is independently unsubstituted or substituted by 1, 2 or 3 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted 4-7 membered heterocycloalkyl or 4-7 membered heterocycloalkyl substituted with 1, 2, 3, 4 or 5 substituents each independently selected from halogen, C$_{1-6}$ alkyl, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments, Cy$^7$ is unsubstituted 4-7 membered heterocycloalkyl.

In some embodiments, Cy$^7$ is morpholinyl, piperidinyl, pyrrolidinyl or tetrahydropyranyl.

In some embodiments, Cy$^7$ is morpholin-4-yl, piperidin-4-yl, pyrrolidin-1-yl or tetrahydro-2H-pyran-4-yl.

In some embodiments, Cy$^7$ is piperazine-1-yl, 4-methyl-piperazin-1-yl, oxopiperazinyl, 3-oxopiperazin-1-yl, 4-methyl-3-oxopiperazin-1-yl, 1-methylpiperidin-4-yl, 2-oxopiperidin-1-yl, oxomorpholinyl or 3-oxomorpholin-4-yl.

In some embodiments, L$^7$ is unsubstituted C$_{1-6}$ alkylene.

In some embodiments, L$^7$ is CH$_2$.

In some embodiments, L$^7$ is C$_{1-6}$ alkylene substituted with 1, 2 or 3 substituents independently selected from F, Cl, CN, OH, O(C$_{1-6}$ alkyl), NH$_2$, NH(C$_{1-6}$ alkyl) and N(C$_{1-6}$ alkyl)$_2$.

In some embodiments, L$^7$ is C$_{1-6}$ alkylene substituted with 1 substituent selected from CN, OH, O(C$_{1-6}$ alkyl), NH$_2$, NH(C$_{1-6}$ alkyl) and N(C$_{1-6}$ alkyl)$_2$ or 1, 2 or 3 substituents independently selected from F and Cl.

In some embodiments, L$^7$ is —CH(OH)—.

In some embodiments, A$^8$ is N.

In some embodiments, A$^8$ is CR$^8$.

In some embodiments, R$^8$ is H.

In some embodiments, R$^8$ is halogen.

In some embodiments, R$^8$ is F.

In some embodiments, R$^8$ is CN.

In some embodiments, A$^5$ is CR$^5$, A$^6$ is CR$^6$, A$^7$ is CR$^7$ and A$^8$ is CR$^8$.

In some embodiments, A$^5$ is CH, A$^6$ is CR$^6$, A$^7$ is CR$^7$ and A$^8$ is CH.

In some embodiments, A$^1$ is CR$^1$, A$^5$ is CR$^5$, A$^6$ is CR$^6$, A$^7$ is CR$^7$ and A$^8$ is CR$^8$.

In some embodiments, A$^1$ is CH, A$^5$ is CH, A$^6$ is CR$^6$, A$^7$ is CR$^7$ and A$^8$ is CH.

In some embodiments, R$^3$ is H, R$^4$ is H, A$^8$ is CR$^5$, A$^6$ is CR$^6$, A$^7$ is CR$^7$ and A$^8$ is CR$^8$.

In some embodiments, R$^2$ is H, R$^3$ is H, R$^4$ is H, A$^8$ is CR$^5$, A$^6$ is CR$^6$, A$^7$ is CR$^7$ and A$^8$ is CR$^8$.

In some embodiments, R$^3$ is H, R$^4$ is H, A$^5$ is CH, A$^6$ is CR$^6$, A$^7$ is CR$^7$ and A$^8$ is CH.

In some embodiments, R$^2$ is H, R$^3$ is H, R$^4$ is H, A$^5$ is CH, A$^6$ is CR$^6$, A$^7$ is CR$^7$ and A$^8$ is CH.

In some embodiments, R$^3$ is H, R$^4$ is H, A$^1$ is CR$^1$, A$^5$ is CR$^5$, A$^6$ is CR$^6$, A$^7$ is CR$^7$ and A$^8$ is CR$^8$.

In some embodiments, R$^2$ is H, R$^3$ is H, R$^4$ is H, A$^1$ is CR$^1$, A$^5$ is CR$^5$, A$^6$ is CR$^6$, A$^7$ is CR$^7$ and A$^8$ is CR$^8$.

In some embodiments, R$^3$ is H, R$^4$ is H, A$^1$ is CH, A$^5$ is CH, A$^6$ is CR$^6$, A$^7$ is CR$^7$ and A$^8$ is CH.

In some embodiments, R$^2$ is H, R$^3$ is H, R$^4$ is H, A$^1$ is CH, A$^5$ is CH, A$^6$ is CR$^6$, A$^7$ is CR$^7$ and A$^8$ is CH.

In some embodiments, R$^3$ is NH$_2$, R$^4$ is H, A$^5$ is CR$^5$, A$^6$ is CR$^6$, A$^7$ is CR$^7$ and A$^8$ is CR$^8$.

In some embodiments, R$^2$ is H, R$^3$ is NH$_2$, R$^4$ is H, A$^5$ is CR$^5$, A$^6$ is CR$^6$, A$^7$ is CR$^7$ and A$^8$ is CR$^8$.

In some embodiments, R$^3$ is NH$_2$, R$^4$ is H, A$^5$ is CH, A$^6$ is CR$^6$, A$^7$ is CR$^7$ and A$^8$ is CH.

In some embodiments, R$^2$ is H, R$^3$ is NH$_2$, R$^4$ is H, A$^5$ is CH, A$^6$ is CR$^6$, A$^7$ is CR$^7$ and A$^8$ is CH.

In some embodiments, R$^3$ is NH$_2$, R$^4$ is H, A$^1$ is CR$^1$, A$^5$ is CR$^5$, A$^6$ is CR$^6$, A$^7$ is CR$^7$ and A$^8$ is CR$^8$.

In some embodiments, R$^2$ is H, R$^3$ is NH$_2$, R$^4$ is H, A$^1$ is CR$^1$, A$^5$ is CR$^5$, A$^6$ is CR$^6$, A$^7$ is CR$^7$ and A$^8$ is CR$^8$.

In some embodiments, R$^3$ is NH$_2$, R$^4$ is H, A$^1$ is CH, A$^5$ is CH, A$^6$ is CR$^6$, A$^7$ is CR$^7$ and A$^8$ is CH.

In some embodiments, R$^2$ is H, R$^3$ is NH$_2$, R$^4$ is H, A$^1$ is CH, A$^5$ is CH, A$^6$ is CR$^6$, A$^7$ is CR$^7$ and A$^8$ is CH.

In some embodiments, R$^3$ is H, R$^4$ is H, A$^5$ is CR$^5$, A$^6$ is CR$^6$, A$^7$ is CR$^7$ and A$^8$ is CR$^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, R$^2$ is H, R$^3$ is H, R$^4$ is H, A$^5$ is CR$^5$, A$^6$ is CR$^6$, A$^7$ is CR$^7$ and A$^8$ is CR$^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, R$^3$ is H, R$^4$ is H, A$^5$ is CH, A$^6$ is CR$^6$, A$^7$ is CR$^7$ and A$^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, R$^2$ is H, R$^3$ is H, R$^4$ is H, A$^5$ is CH, A$^6$ is CR$^6$, A$^7$ is CR$^7$ and A$^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, R$^3$ is H, R$^4$ is H, A$^1$ is CR$^1$, A$^5$ is CR$^5$, A$^6$ is CR$^6$, A$^7$ is CR$^7$ and A$^8$ is CR$^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, R$^2$ is H, R$^3$ is H, R$^4$ is H, A$^1$ is CR$^1$, A$^5$ is CR$^5$, A$^6$ is CR$^6$, A$^7$ is CR$^7$ and A$^8$ is CR$^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, R$^3$ is H, R$^4$ is H, A$^1$ is CH, A$^5$ is CH, A$^6$ is CR$^6$, A$^7$ is CR$^7$ and A$^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^2$ is H, $R^3$ is H, $R^4$ is H, $A^1$ is CH, $A^5$ is CH, $A^6$ is $CR^6$, $A^7$ is $CR^7$ and $A^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^3$ is $NH_2$, $R^4$ is H, $A^5$ is $CR^5$, $A^6$ is $CR^6$, $A^7$ is $CR^7$ and $A^8$ is $CR^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^2$ is H, $R^3$ is $NH_2$, $R^4$ is H, $A^5$ is $CR^5$, $A^6$ is $CR^6$, $A^7$ is $CR^7$ and $A^8$ is $CR^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^3$ is $NH_2$, $R^4$ is H, $A^5$ is CH, $A^6$ is $CR^6$, $A^7$ is $CR^7$ and $A^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^2$ is H, $R^3$ is $NH_2$, $R^4$ is H, $A^5$ is CH, $A^6$ is $CR^6$, $A^7$ is $CR^7$ and $A^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^3$ is $NH_2$, $R^4$ is H, $A^1$ is $CR^1$, $A^5$ is $CR^5$, $A^6$ is $CR^6$, $A^7$ is $CR^7$ and $A^8$ is $CR^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^2$ is H, $R^3$ is $NH_2$, $R^4$ is H, $A^1$ is $CR^1$, $A^5$ is $CR^5$, $A^6$ is $CR^6$, $A^7$ is $CR^7$ and $A^8$ is $CR^8$, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^3$ is $NH_2$, $R^4$ is H, $A^1$ is CH, $A^5$ is CH, $A^6$ is $CR^6$, $A^7$ is $CR^7$ and $A^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, $R^2$ is H, $R^3$ is $NH_2$, $R^4$ is H, $A^1$ is CH, $A^8$ is CH, $A^6$ is $CR^6$, $A^7$ is $CR^7$ and $A^8$ is CH, and Cy is a piperidin-1-yl ring that such as piperidinyl ring that can be substituted at least by an amino group the 3-position, e.g., 3-aminopiperidin-1-yl, 3-amino-4-hydroxypiperidinyl, 3-amino-4-hydroxypiperidinyl, 3-amino-4-hydroxy-5-methylpiperidinyl, or any of the stereoisomers thereof, as described above.

In some embodiments, any one or more of $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$ and $R^{d6}$ may each be independently selected from H and $C_{1-6}$ alkyl.

In some embodiments, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$ and $R^{d6}$ are each independently selected from H and $C_{1-6}$ alkyl.

In some embodiments, any one or more of $R^{e1}$, $R^{e2}$, $R^{e3}$, $R^{e4}$, $R^{e5}$ and $R^{e6}$ can be H.

In some embodiments, $R^{e1}$, $R^{e2}$, $R^{e3}$, $R^{e4}$, $R^{e5}$ and $R^{e6}$ are H.

In some embodiments, the compound according to formula (I) can be according to any of the following formulae (II-1), (II-2), (II-3) and (II-4):

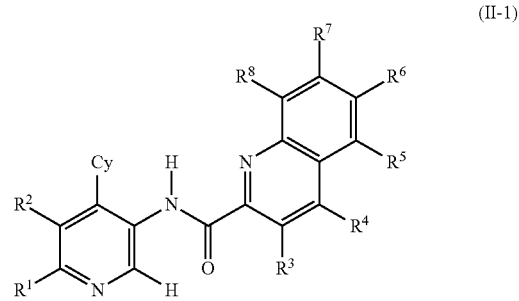

(II-1)

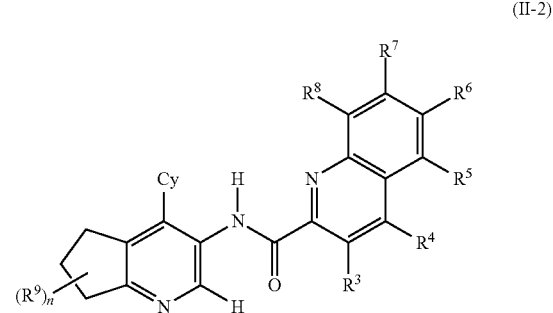

(II-2)

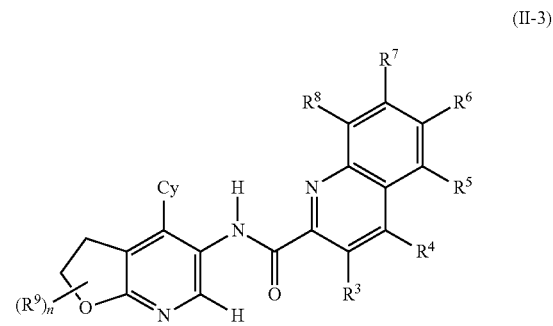

(II-3)

-continued (II-4)

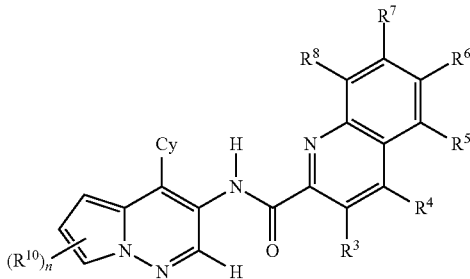

wherein $R^1$, $R^2$, $R^3$, $R^4$, $R^5$, $R^6$, $R^7$, $R^8$, and Cy are as defined above for formula (I) or any of the embodiments thereof;

each $R^9$ is independently selected from halogen, $C_{1-6}$ alkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$ and oxo;

each $R^{10}$ is independently selected from halogen, $C_{1-6}$ alkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, and $NR^{c2}C(O)OR^{a2}$ and n is 0, 1, 2 or 3.

In some embodiments of the compounds of formula (II-1), (II-2), (II-3) and (II-4), n is 0.

In some embodiments of the compounds of formula (II-1), (II-2), (II-3) and (II-4), n is 1.

The compounds of formula (I) include the following compounds, and pharmaceutically acceptable salts thereof:

3-amino-N-{4-[3-aminopiperidin-1-yl]pyridin-3-yl}-7-piperidin-4-ylquinoline-2-carboxamide;
3-amino-N-{4-[3-aminopiperidin-1-yl]pyridin-3-yl}-7-(tetrahydro-2H-pyran-4-yl)quinoline-2-carboxamide;
3-amino-N-{4-[3-aminopiperidin-1-yl]pyridin-3-yl}-7-(2,6-difluorophenyl)quinoline-2-carboxamide;
3-amino-N-{4-[3-aminopiperidin-1 1-yl]pyridin-3-yl}-7-(1-methyl-1H-pyrazol-5-yl)quinoline-2-carboxamide;
3-amino-N-{4-[3-aminopiperidin-1-yl]pyridin-3-yl}-7-(2-cyanophenyl)quinoline-2-carboxamide;
3-amino-7-[2-(aminocarbonyl)phenyl]-N-{4-[3-aminopiperidin-1-yl]pyridin-3-yl}quinoline-2-carboxamide;
3-amino-N-{4-[3-aminopiperidin-1-yl]pyridin-3-yl}-7-(2-cyano-6-fluorophenyl)quinoline-2-carboxamide;
3-amino-7-[2-(aminocarbonyl)-6-fluorophenyl]-N-{4-[3-aminopiperidin-1-yl]pyridin-3-yl}quinoline-2-carboxamide;
3-amino-N-{4-[3-aminopiperidin-1-yl]pyridin-3-yl}-7-isopropylquinoline-2-carboxamide;
3-amino-N-{4-[3-aminopiperidin-1-yl]pyridin-3-yl}-7-ethylquinoline-2-carboxamide;
3-amino-N-{4-[3-aminopiperidin-1-yl]pyridin-3-yl}quinoline-2-carboxamide;
3-amino-N-{4-[3-aminopiperidin-1-yl]pyridin-3-yl}-7-bromoquinoline-2-carboxamide;
3-amino-N-{4-[3-aminopiperidin-1-yl]pyridin-3-yl}-7-(cyanomethyl)quinoline-2-carboxamide;
3-amino-N-{4-[3-aminopiperidin-1-yl]pyridin-3-yl}-7-ethyl-6-fluoroquinoline-2-carboxamide;
3-amino-N-{4-[3-aminopiperidin-1-yl]pyridin-3-yl}-7-(1-hydroxyethyl)quinoline-2-carboxamide;
3-amino-N-{4-[3-aminopiperidin-1-yl]pyridin-3-yl}-7-(1-hydroxy-1-methylethyl)quinoline-2-carboxamide;
3-amino-N-{4-[3-aminopiperidin-1-yl]pyridin-3-yl}-7-[hydroxy(phenyl)methyl]quinoline-2-carboxamide;
3-amino-N-{4-[3-aminopiperidin-1-yl]pyridin-3-yl}-7-(1-fluoroethyl)quinoline-2-carboxamide;
3-amino-N-{4-[3-aminopiperidin-1-yl]pyridin-3-yl}-7-(pyrrolidin-1-ylmethyl)quinoline-2-carboxamide;
3-amino-N-{4-[3-aminopiperidin-1-yl]pyridin-3-yl}-7-[(dimethylamino)methyl]quinoline-2-carboxamide;
3-amino-N-{4-[3-aminopiperidin-1-yl]pyridin-3-yl}-7-(morpholin-4-ylmethyl)quinoline-2-carboxamide;
3-amino-N-{4-[3-aminopiperidin-1-yl]-7-hydroxy-6,7-dihydro-5H-cyclopenta[b]pyridin-3-yl}-7-ethylquinoline-2-carboxamide;
3-amino-N-[4-(3-aminocyclohexyl)pyridin-3-yl]-7-ethylquinoline-2-carboxamide;
3-amino-N-(4-(3-aminopiperidin-1-yl)-2,3-dihydrofuro[2,3-b]pyridin-5-yl)-7-ethylquinoline-2-carboxamide;
3-amino-N-{4-[3-aminopiperidin-1-yl]pyridin-3-yl}-7-ethoxy-1,8-naphthyridine-2-carboxamide;
3-amino-N-{4-[3-amino-4-hydroxy-5-methylpiperidin-1-yl]pyridin-3-yl}-7-ethoxy-1,8-naphthyridine-2-carboxamide;
3-amino-N-{4-[3-aminopiperidin-1-yl]pyridin-3-yl}-7-ethyl-1,6-naphthyridine-2-carboxamide;
3-amino-N-{4-[3-amino-4-hydroxy-5-methylpiperidin-1-yl]-5-methylpyridin-3-yl}-7-ethylquinoline-2-carboxamide;
3-amino-N-{4-[3-amino-4-hydroxy-5-methylpiperidin-1-yl]pyridin-3-yl}-7-ethylquinoline-2-carboxamide;
3-amino-N-{4-[3-aminopiperidin-1-yl]-5-methylpyridin-3-yl}-7-ethylquinoline-2-carboxamide;
3-amino-N-{4-[3-aminopiperidin-1-yl]-6-methoxypyridin-3-yl}-7-ethylquinoline-2-carboxamide;
3-amino-N-{4-[3-aminopiperidin-1-yl]-5-cyanopyridin-3-yl}-7-ethylquinoline-2-carboxamide;
3-amino-N-{4-[3-amino-4-hydroxy-5-methylpiperidin-1-yl]pyridin-3-yl}-7-morpholin-4-ylquinoline-2-carboxamide;
3-amino-N-{4-[3-amino-5-methylpiperidin-1-yl]pyridin-3-yl}-7-morpholin-4-ylquinoline-2-carb oxamide;
3-amino-N-{4-[3-amino-5-(trifluoromethyl)piperidin-1-yl]pyridin-3-yl}-7-morpholin-4-ylquinoline-2-carboxamide;
3-amino-N-{4-[3-amino-5-methylpiperidin-1-yl]pyridin-3-yl}-7-(4-methylpiperazin-1-yl)quinoline-2-carboxamide;
3-amino-N-{4-[3-amino-5-(trifluoromethyl)piperidin-1-yl]pyridin-3-yl}-7-(4-methylpiperazin-1-yl)quinoline-2-carboxamide;
3-amino-N-{4-[3-amino-4-hydroxy-5-methylpiperidin-1-yl]pyridin-3-yl}-7-(4-methylpiperazin-1-yl)quinoline-2-carboxamide;
3-amino-N-{4-[3-amino-5-(trifluoromethyl)piperidin-1-yl]pyridin-3-yl}-7-(tetrahydro-2H-pyran-4-yl)quinoline-2-carboxamide;
3-amino-N-{4-[3-amino-5-methylpiperidin-1-yl]pyridin-3-yl}-7-(tetrahydro-2H-pyran-4-yl)quinoline-2-carboxamide;
3-amino-N-{4-[3-amino-4-hydroxy-5-methylpiperidin-1-yl]pyridin-3-yl}-7-(tetrahydro-2H-pyran-4-yl)quinoline-2-carboxamide;
3-amino-N-{4-[3-amino-4-hydroxy-5-methylpiperidin-1-yl]pyridin-3-yl}-7-(1-methylpiperidin-4-yl)quinoline-2-carboxamide;
3-amino-N-{4-[3-amino-5-methylpiperidin-1-yl]pyridin-3-yl}-7-(1-methylpiperidin-4-yl)quinoline-2-carboxamide;
3-amino-N-{4-[3-amino-5-(trifluoromethyl)piperidin-1-yl]pyridin-3-yl}-7-(1-methylpiperidin-4-yl)quinoline-2-carboxamide;

3-amino-N-{4-[3-amino-5-methylpiperidin-1-yl]pyridin-3-yl}-7-(2-oxopiperidin-1-yl)quinoline-2-carboxamide;
3-amino-N-{4-[3-amino-5-methylpiperidin-1-yl]pyridin-3-yl}-7-(4-methyl-3-oxopiperazin-1-yl)quinoline-2-carboxamide;
3-amino-N-{4-[3-amino-5-methylpiperidin-1-yl]pyridin-3-yl}-7-(3-oxopiperazin-1-yl)quinoline-2-carboxamide;
3-amino-N-{4-[3-amino-4-hydroxy-5-methylpiperidin-1-yl]pyridin-3-yl}-7-(4-methyl-3-oxopiperazin-1-yl)quinoline-2-carboxamide;
3-amino-N-{4-[3-amino-4-hydroxy-5-methylpiperidin-1-yl]pyridin-3-yl}-7-(2-oxopiperidin-1-yl)quinoline-2-carboxamide;
3-amino-N-{4-[3-amino-5-methylpiperidin-1-yl]pyridin-3-yl}-7-(3-oxomorpholin-4-yl)quinoline-2-carboxamide;
3-amino-N-{4-[3-amino-4-hydroxy-5-methylpiperidin-1-yl]pyridin-3-yl}-7-(3-oxomorpholin-4-yl)quinoline-2-carboxamide;
3-amino-N-{4-[3-amino-5-methyl-4-(1H-1,2,3-triazol-1-yl)piperidin-1-yl]pyridin-3-yl}-7-(4-methyl-3-oxopiperazin-1-yl)quinoline-2-carboxamide;
3-amino-N-{4-[3-amino-5-methyl-4-(1H-1,2,3-triazol-1-yl)piperidin-1-yl]pyridin-3-yl}-7-(tetrahydro-2H-pyran-4-yl)quinoline-2-carboxamide;
3-amino-N-{4-[3-amino-5-methyl-4-(1H-1,2,3-triazol-1-yl)piperidin-1-yl]pyridin-3-yl}-7-(4-methylpiperazin-1-yl)quinoline-2-carboxamide;
3-amino-N-{4-[3-amino-5-methyl-4-(1H-1,2,3-triazol-1-yl)piperidin-1-yl]pyridin-3-yl}-7-morpholin-4-ylquinoline-2-carboxamide;
3-amino-N-{4-[3-amino-5-methyl-4-(1H-1,2,3-triazol-1-yl)piperidin-1-yl]pyridin-3-yl}-7-(1-methylpiperidin-4-yl)quinoline-2-carboxamide;
3-amino-N-{4-[3-amino-5-methyl-4-(1H-1,2,3-triazol-1-yl)piperidin-1-yl]pyridin-3-yl}-7-ethylquinoline-2-carboxamide;
methyl[3-amino-1-(3-{[(3-amino-7-ethylquinolin-2-yl)carbonyl]amino}pyridin-4-yl)-5-methylpiperidin-4-yl]carbamate;
methyl[3-amino-1-(3-{[(3-amino-7-morpholin-4-ylquinolin-2-yl)carbonyl]amino}pyridin-4-yl)-5-methylpiperidin-4-yl]carbamate;
methyl {3-amino-1-[3-({[3-amino-7-(4-methylpiperazin-1-yl)quinolin-2-yl]carbonyl}amino)pyridin-4-yl]-5-methylpiperidin-4-yl}carbamate;
methyl {3-amino-1-[3-({[3-amino-7-(tetrahydro-2H-pyran-4-yl)quinolin-2-yl]carbonyl}amino)pyridin-4-yl]-5-methylpiperidin-4-yl}carbamate; and
methyl {3-amino-1-[3-({[3-amino-7-(1-methylpiperidin-4-yl)quinolin-2-yl]carbonyl}amino)pyridin-4-yl]-5-methylpiperidin-4-yl}carbamate.

The compounds of formula (I) include the following compounds, and pharmaceutically acceptable salts thereof:
3-amino-N-{4-[(3S)-3-aminopiperidin-1-yl]pyridin-3-yl}-7-piperidin-4-ylquinoline-2-carboxamide;
3-amino-N-{4-[(3S)-3-aminopiperidin-1-yl]pyridin-3-yl}-7-(tetrahydro-2H-pyran-4-yl)quinoline-2-carboxamide;
3-amino-N-{4-[(3S)-3-aminopiperidin-1-yl]pyridin-3-yl}-7-(2,6-difluorophenyl)quinoline-2-carboxamide;
3-amino-N-{4-[(3S)-3-aminopiperidin-1-yl]pyridin-3-yl}-7-(1-methyl-1H-pyrazol-5-yl)quinoline-2-carboxamide;
3-amino-N-{4-[(3S)-3-aminopiperidin-1-yl]pyridin-3-yl}-7-(2-cyanophenyl)quinoline-2-carboxamide;
3-amino-7-[2-(aminocarbonyl)phenyl]-N-{4-[(3S)-3-aminopiperidin-1-yl]pyridin-3-yl}quinoline-2-carboxamide;
3-amino-N-{4-[(3S)-3-aminopiperidin-1-yl]pyridin-3-yl}-7-(2-cyano-6-fluorophenyl)quinoline-2-carboxamide;
3-amino-7-[2-(aminocarbonyl)-6-fluorophenyl]-N-{4-[(3S)-3-aminopiperidin-1-yl]pyridin-3-yl}quinoline-2-carboxamide;
3-amino-N-{4-[(3S)-3-aminopiperidin-1-yl]pyridin-3-yl}-7-isopropylquinoline-2-carboxamide;
3-amino-N-{4-[(3S)-3-aminopiperidin-1-yl]pyridin-3-yl}-7-ethylquinoline-2-carboxamide;
3-amino-N-{4-[(3S)-3-aminopiperidin-1-yl]pyridin-3-yl}quinoline-2-carboxamide;
3-amino-N-{4-[(3S)-3-aminopiperidin-1-yl]pyridin-3-yl}-7-bromoquinoline-2-carboxamide;
3-amino-N-{4-[(3S)-3-aminopiperidin-1-yl]pyridin-3-yl}-7-(cyanomethyl)quinoline-2-carboxamide;
3-amino-N-{4-[(3S)-3-aminopiperidin-1-yl]pyridin-3-yl}-7-ethyl-6-fluoroquinoline-2-carboxamide;
3-amino-N-{4-[(3S)-3-aminopiperidin-1-yl]pyridin-3-yl}-7-(1-hydroxyethyl)quinoline-2-carboxamide;
3-amino-N-{4-[(3S)-3-aminopiperidin-1-yl]pyridin-3-yl}-7-(1-hydroxy-1-methylethyl)quinoline-2-carboxamide;
3-amino-N-{4-[(3S)-3-aminopiperidin-1-yl]pyridin-3-yl}-7-[hydroxy(phenyl)methyl]quinoline-2-carboxamide;
3-amino-N-{4-[(3S)-3-aminopiperidin-1-yl]pyridin-3-yl}-7-(1-fluoroethyl)quinoline-2-carboxamide;
3-amino-N-{4-[(3S)-3-aminopiperidin-1-yl]pyridin-3-yl}-7-(pyrrolidin-1-ylmethyl)quinoline-2-carboxamide;
3-amino-N-{4-[(3S)-3-aminopiperidin-1-yl]pyridin-3-yl}-7-[(dimethylamino)methyl]quinoline-2-carboxamide;
3-amino-N-{4-[(3S)-3-aminopiperidin-1-yl]pyridin-3-yl}-7-(morpholin-4-ylmethyl)quinoline-2-carboxamide;
3-amino-N-{4-[(3S)-3-aminopiperidin-1-yl]-7-hydroxy-6,7-dihydro-5H-cyclopenta[b]pyridin-3-yl}-7-ethylquinoline-2-carboxamide;
3-amino-N-{4-[(3S)-3-aminopiperidin-1-yl]-(7R)-7-hydroxy-6,7-dihydro-5H-cyclopenta[b]pyridin-3-yl}-7-ethylquinoline-2-carboxamide;
3-amino-N-{4-[(3S)-3-aminopiperidin-1-yl]-(7S)-7-hydroxy-6,7-dihydro-5H-cyclopenta[b]pyridin-3-yl}-7-ethylquinoline-2-carboxamide;
3-amino-N-[4-(3-aminocyclohexyl)pyridin-3-yl]-7-ethylquinoline-2-carboxamide;
3-amino-N-[4-((3S)-3-aminocyclohexyl)pyridin-3-yl]-7-ethylquinoline-2-carboxamide;
3-amino-N-[4-((3R)-3-aminocyclohexyl)pyridin-3-yl]-7-ethylquinoline-2-carboxamide.
(S)-3-amino-N-(4-(3-aminopiperidin-1-yl)-2,3-dihydrofuro[2,3-b]pyridin-5-yl)-7-ethylquinoline-2-carboxamide;
3-amino-N-{4-[(3S)-3-aminopiperidin-1-yl]pyridin-3-yl}-7-ethoxy-1,8-naphthyridine-2-carboxamide;
3-amino-N-{4-[(3R,4R,5S)-3-amino-4-hydroxy-5-methylpiperidin-1-yl]pyridin-3-yl}-7-ethoxy-1,8-naphthyridine-2-carboxamide;
3-amino-N-{4-[(3S)-3-aminopiperidin-1-yl]pyridin-3-yl}-7-ethyl-1,6-naphthyridine-2-carboxamide;
3-amino-N-{4-[(3R,4R,5S)-3-amino-4-hydroxy-5-methylpiperidin-1-yl]-5-methylpyridin-3-yl}-7-ethylquinoline-2-carboxamide;
3-amino-N-{4-[(3R,4R,5S)-3-amino-4-hydroxy-5-methylpiperidin-1-yl]pyridin-3-yl}-7-ethylquinoline-2-carboxamide;
3-amino-N-{4-[(3S)-3-aminopiperidin-1-yl]-5-methylpyridin-3-yl}-7-ethylquinoline-2-carboxamide;
3-amino-N-{4-[(3S)-3-aminopiperidin-1-yl]-6-methoxypyridin-3-yl}-7-ethylquinoline-2-carboxamide;
3-amino-N-{4-[(3S)-3-aminopiperidin-1-yl]-5-cyanopyridin-3-yl}-7-ethylquinoline-2-carboxamide;

3-amino-N-{4-[(3R,4R,5S)-3-amino-4-hydroxy-5-methyl-piperidin-1-yl]pyridin-3-yl}-7-morpholin-4-ylquinoline-2-carboxamide;

3-amino-N-{4-[(3S,5R)-3-amino-5-methylpiperidin-1-yl]pyridin-3-yl}-7-morpholin-4-ylquinoline-2-carboxamide;

3-amino-N-{4-[(3S,5R)-3-amino-5-(trifluoromethyl)piperidin-1-yl]pyridin-3-yl}-7-morpholin-4-ylquinoline-2-carboxamide;

3-amino-N-{4-[(3S,5R)-3-amino-5-methylpiperidin-1-yl]pyridin-3-yl}-7-(4-methylpiperazin-1-yl)quinoline-2-carboxamide;

3-amino-N-{4-[(3S,5R)-3-amino-5-(trifluoromethyl)piperidin-1-yl]pyridin-3-yl}-7-(4-methylpiperazin-1-yl)quinoline-2-carboxamide;

3-amino-N-{4-[(3R,4R,5S)-3-amino-4-hydroxy-5-methyl-piperidin-1-yl]pyridin-3-yl}-7-(4-methylpiperazin-1-yl)quinoline-2-carboxamide;

3-amino-N-{4-[(3S,5R)-3-amino-5-(trifluoromethyl)piperidin-1-yl]pyridin-3-yl}-7-(tetrahydro-2H-pyran-4-yl)quinoline-2-carboxamide;

3-amino-N-{4-[(3S,5R)-3-amino-5-methylpiperidin-1-yl]pyridin-3-yl}-7-(tetrahydro-2H-pyran-4-yl)quinoline-2-carboxamide;

3-amino-N-{4-[(3R,4R,5S)-3-amino-4-hydroxy-5-methyl-piperidin-1-yl]pyridin-3-yl}-7-(tetrahydro-2H-pyran-4-yl)quinoline-2-carboxamide;

3-amino-N-{4-[(3R,4R,5S)-3-amino-4-hydroxy-5-methyl-piperidin-1-yl]pyridin-3-yl}-7-(1-methylpiperidin-4-yl)quinoline-2-carboxamide;

3-amino-N-{4-[(3S,5R)-3-amino-5-methylpiperidin-1-yl]pyridin-3-yl}-7-(1-methylpiperidin-4-yl)quinoline-2-carboxamide;

3-amino-N-{4-[(3S,5R)-3-amino-5-(trifluoromethyl)piperidin-1-yl]pyridin-3-yl}-7-(1-methylpiperidin-4-yl)quinoline-2-carboxamide;

3-amino-N-{4-[(3S,5R)-3-amino-5-methylpiperidin-1-yl]pyridin-3-yl}-7-(2-oxopiperidin-1-yl)quinoline-2-carboxamide;

3-amino-N-{4-[(3S,5R)-3-amino-5-methylpiperidin-1-yl]pyridin-3-yl}-7-(4-methyl-3-oxopiperazin-1-yl)quinoline-2-carboxamide;

3-amino-N-{4-[(3S,5R)-3-amino-5-methylpiperidin-1-yl]pyridin-3-yl}-7-(3-oxopiperazin-1-yl)quinoline-2-carboxamide;

3-amino-N-{4-[(3R,4R,5S)-3-amino-4-hydroxy-5-methyl-piperidin-1-yl]pyridin-3-yl}-7-(4-methyl-3-oxopiperazin-1-yl)quinoline-2-carboxamide;

3-amino-N-{4-[(3R,4R,5S)-3-amino-4-hydroxy-5-methyl-piperidin-1-yl]pyridin-3-yl}-7-(2-oxopiperidin-1-yl)quinoline-2-carboxamide;

3-amino-N-{4-[(3S,5R)-3-amino-5-methylpiperidin-1-yl]pyridin-3-yl}-7-(3-oxomorpholin-4-yl)quinoline-2-carboxamide;

3-amino-N-{4-[(3R,4R,5S)-3-amino-4-hydroxy-5-methyl-piperidin-1-yl]pyridin-3-yl}-7-(3-oxomorpholin-4-yl)quinoline-2-carboxamide;

3-amino-N-{4-[(3R,4S,5S)-3-amino-5-methyl-4-(1H-1,2,3-triazol-1-yl)piperidin-1-yl]pyridin-3-yl}-7-(4-methyl-3-oxopiperazin-1-yl)quinoline-2-carboxamide;

3-amino-N-{4-[(3R,4S,5S)-3-amino-5-methyl-4-(1H-1,2,3-triazol-1-yl)piperidin-1-yl]pyridin-3-yl}-7-(tetrahydro-2H-pyran-4-yl)quinoline-2-carboxamide;

3-amino-N-{4-[(3R,4S,5S)-3-amino-5-methyl-4-(1H-1,2,3-triazol-1-yl)piperidin-1-yl]pyridin-3-yl}-7-(4-methylpiperazin-1-yl)quinoline-2-carboxamide;

3-amino-N-{4-[(3R,4S,5S)-3-amino-5-methyl-4-(1H-1,2,3-triazol-1-yl)piperidin-1-yl]pyridin-3-yl}-7-morpholin-4-ylquinoline-2-carboxamide;

3-amino-N-{4-[(3R,4S,5S)-3-amino-5-methyl-4-(1H-1,2,3-triazol-1-yl)piperidin-1-yl]pyridin-3-yl}-7-(1-methylpiperidin-4-yl)quinoline-2-carboxamide;

3-amino-N-{4-[(3R,4S,5S)-3-amino-5-methyl-4-(1H-1,2,3-triazol-1-yl)piperidin-1-yl]pyridin-3-yl}-7-ethylquinoline-2-carboxamide;

methyl [(3R,4S,5S)-3-amino-1-(3-{[(3-amino-7-ethylquinolin-2-yl)carbonyl]amino}pyridin-4-yl)-5-methylpiperidin-4-yl]carbamate;

methyl [(3R,4S,5S)-3-amino-1-(3-{[(3-amino-7-morpholin-4-ylquinolin-2-yl)carbonyl]amino}pyridin-4-yl)-5-methylpiperidin-4-yl]carbamate;

methyl {(3R,4S,5S)-3-amino-1-[3-({[3-amino-7-(4-methyl-piperazin-1-yl)quinolin-2-yl]carbonyl}amino)pyridin-4-yl]-5-methylpiperidin-4-yl}carbamate;

methyl {(3R,4S,5S)-3-amino-1-[3-({[3-amino-7-(tetra-hydro-2H-pyran-4-yl)quinolin-2-yl]carbonyl}amino)pyridin-4-yl]-5-methylpiperidin-4-yl}carbamate; and methyl {(3R,4S,5S)-3-amino-1-[3-({[3-amino-7-(1-methyl-piperidin-4-yl)quinolin-2-yl]carbonyl}amino)pyridin-4-yl]-5-methylpiperidin-4-yl}carbamate.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1}halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl.

The term "heteroaryl" or "heteroaromatic", employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., C(O), S(O), C(S) or $S(O)_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected.

Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); aq. (aqueous); atm. (atmosphere(s)); Boc (t-butoxycarbonyl); BOP ((benzotriazol-1-yloxy)tris(dimethylamino)phosphonium hexafluorophosphate); Cbz (carboxybenzyl); calc. (calculated); d (doublet); dd (doublet of doublets); DCM (dichloromethane); DIAD (N,N'-diisopropyl azidodicarboxylate); DIC (N,N'-diisopropylcarbodiimide); DIPEA (N,N-diisopropylethylamine); DMF (N,N-dimethylformamide); Et (ethyl); EtOAc (ethyl acetate); Fmoc (9-fluorenylmethylmethoxycarbonyl); g (gram(s)); h (hour(s)); HATU (N,N,N',N'-tetramethyl-O-(7-azabenzotriazol-1-yl)uronium hexafluorophosphate); HCl (hydrochloric acid/hydrogen choride); HPLC (high performance liquid chromatography); Hz (hertz); J (coupling constant); $K_3PO_4$ (potassium phosphate); LCMS (liquid chromatography-mass spectrometry); $LiAlH_4$ (lithium tetrahydroaluminate); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaHCO_3$ (sodium bicarbonate); NaOH (sodium hydroxide); $Na_2SO_4$ (sodium sulfate); $NH_4OH$ (ammonium hydroxide); nM (nanomolar); NMR (nuclear magnetic resonance spectroscopy); Pd (palladium); pM (picomolar); RP-HPLC (reverse phase high performance liquid chromatography); t (triplet or tertiary); t-Bu (tert-butyl); TFA (trifluoroacetic acid); THF (tetrahydrofuran); μg (microgram(s)); μL (microliter(s)); μM (micromolar); wt % (weight percent).

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of formula (I) can be prepared, e.g., using a process as illustrated in Scheme 1. In the process shown in Scheme 1, a suitably substituted 2-amino-substituted aromatic carboxaldehyde 1-1 can be converted to a compound of formula 1-2 (R=alkyl), e.g., by heating with a suitable alkyl bromopyruvate in the presence of pyridine. The compound of formula 1-2 is then protected with a suitable protecting group, PG, such as a Cbz or Boc group using methods known to one skilled in the art. Wuts et al., *Protective Groups in Organic Synthesis*, 4$^{th}$ Ed. (Wiley, 2006). The resulting protected ester of formula 1-3 can be hydrolyzed to a corresponding acid 1-4 under standard saponification conditions also known to one skilled in the art. (Wuts et al). The carboxylic acid 1-4 can then be reacted with an appropriately substituted aminopyridine or aminopyridazine under conditions suitable for formation of an amide bond to form an amide of formula 1-6. Suitable combinations for forming the amide bond include, e.g., the methods used to form amide bonds in peptides as described, e.g., in Jones, *Amino Acid and Peptide Synthesis*, 2$^{nd}$ Ed., Oxford University Press, 2002; and Jones, *The Chemical Synthesis of Peptides* (*International Series of Monographs on Chemistry*) (Oxford University Press, 1994). An example of a suitable coupling agent is HATU/DIPEA. Deprotection of the compound of formula 1-6 then gives the compound of formula 1-7, which corresponds to the compound of formula (I) wherein $R^3$ is $NH_2$ and $R^4$ is hydrogen. The substitutions of compound 1-7 can be further transformed to desired functional groups.

Scheme 1

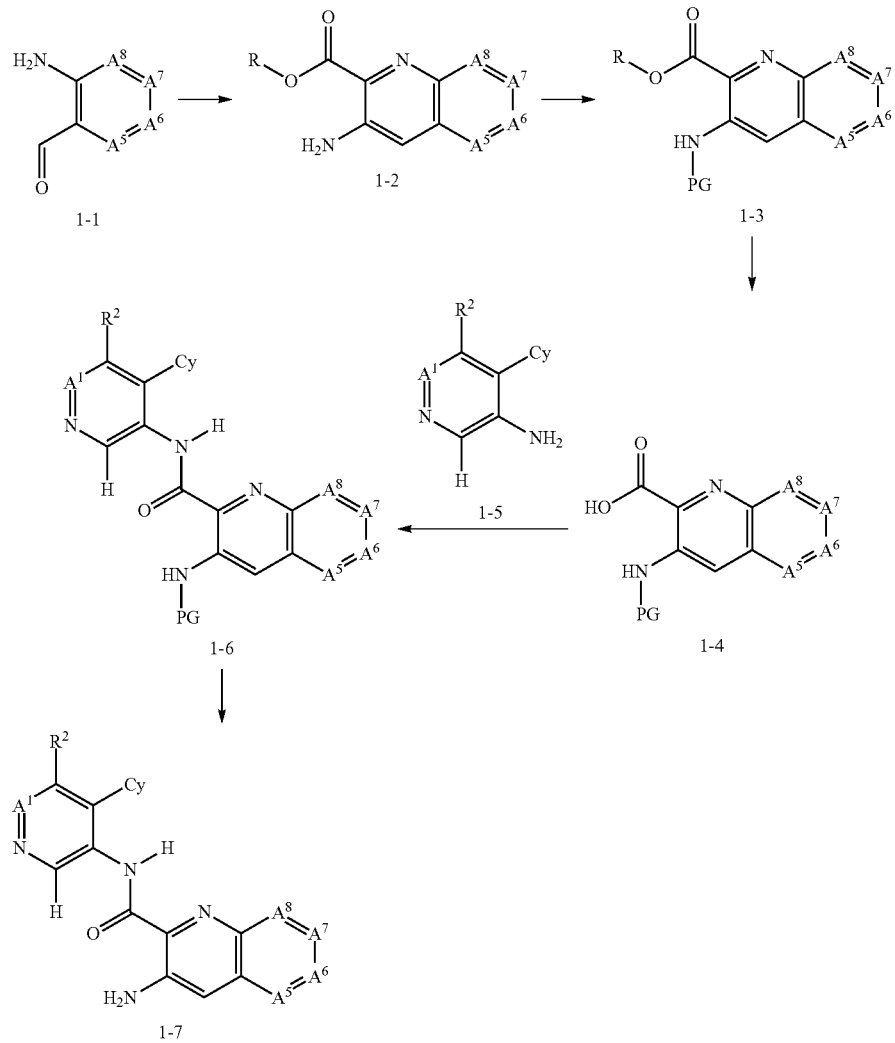

Other compounds of formula (I) can be prepared by appropriate modifications of the synthetic route described above. For example, compounds according to formula (I) wherein R³ is other than amino can be prepared by suitable functional group interconversion reactions known to one of ordinary skill in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996). Similarly, compounds group with a suitable protecting group (PG, e.g., Cbz or Boc), the resulting esters 2-3 is hydrolyzed to corresponding acids 2-4 and reacted with an appropriately substituted aminopyridine 2-5 under coupling conditions to afford an amides 2-6, which can be deprotected to give compound 2-7. The substitutions on 2-7 can be further transformed to desired functional groups in the final product, or in any of the steps of the synthesis, using methods know to one skilled in the art.

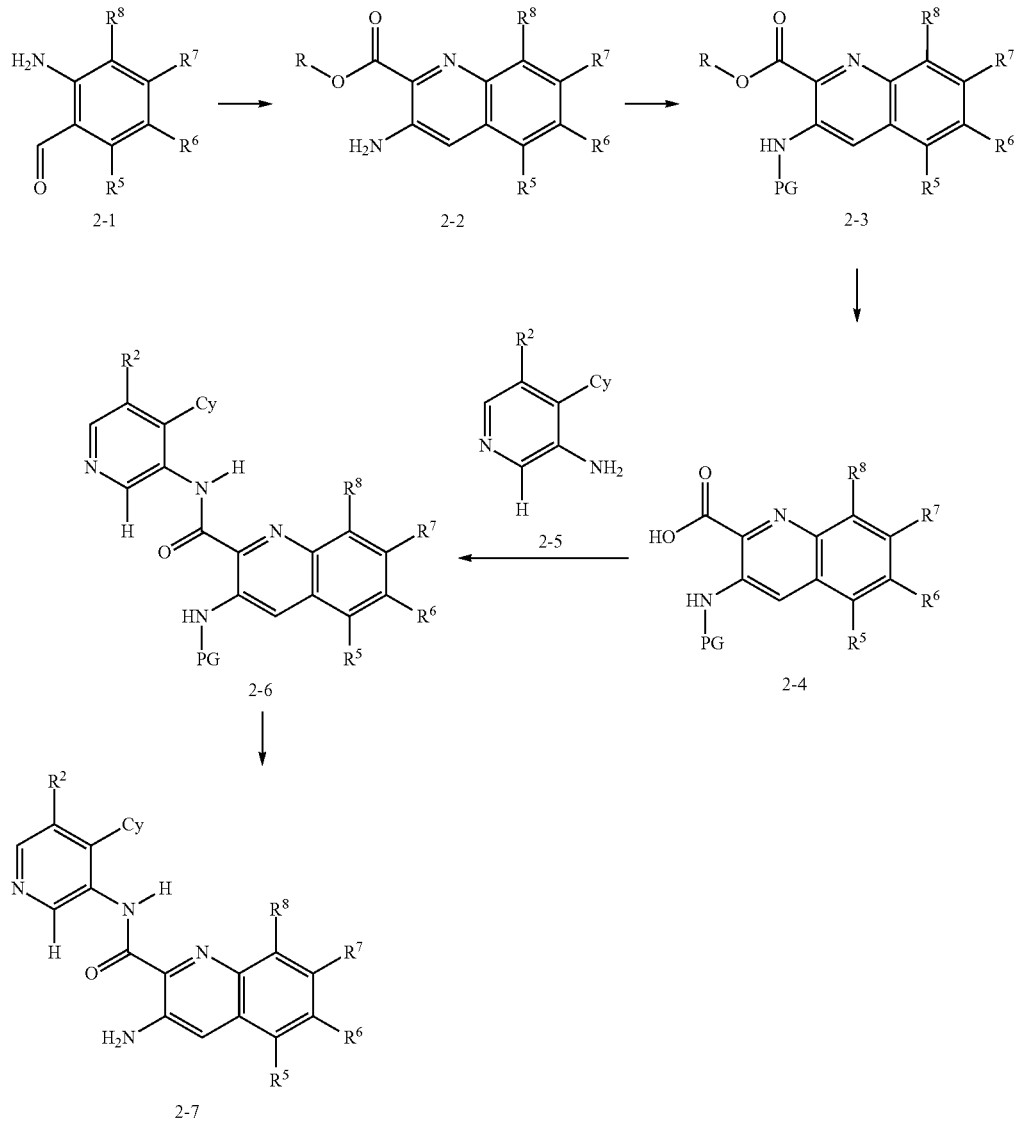

Scheme 2 with R³ groups other than hydrogen can be prepared, e.g., by electrophilic substitution of the 4-position of the quinolone directed by the amino group, followed by appropriate functional group transformations.

The synthetic method illustrated by Scheme 1 can be applied to the synthesis of quinoline compounds as shown in Scheme 2. A substituted 2-aminobezaldehyde 2-1 is heated with ethyl bromopyruvate in the presence of pyridine to provide aminoquinoline 2-2. After protection of amino Other compounds of formula (I) can be prepared as illustrated in Scheme 3. Commercially available 2,6-dichloronicotinic acid 3-1 can be treated with ammonia in elevated temperature to give 2-amino-6-chloronicotinic acid 3-2, which can be reacted with with N-hydroxylsuccinimide in the presence of a coupling agent (e.g., HATU or BOP) in and an organic base (e.g., DIPEA) to provide the activated exter 3-3. Compound 3-3 can be subjected to reaction with diethyl 2-oxosuccinate in the presence of potassium tert-butoxide to generated azaquinoline 3-4. Ester hydrolysis and in situ decarboxylation under acidic conditions (e.g., 6 N HCl, heat) to provide carboxylic acid 3-5. Compound 3-5 can be subjected to nitration conditions to provide nitro-acid 3-6 which can be coupled with an appropriately substituted aminopyridine (or aminopyridiazine) 3-7 in the presence of a suitable coupling reagents (e.g., HATU) to afford amide 3-8. The amide 3-8 can then be subjected to an appropriate functional group interconversion coupling reaction, e.g., Suzuki coupling to the desired $R^7$ group. To form a compound of formula (I) wherein $R^3$ is $NH_2$ and $R^4$ is H, the resulting compound of formula 3-9 can be converted to corresponding triflate 3-10, which subsequently can be transformed to compounds 3-11 by hydrogenation. The substitutions of 3-11 can be further transformed to desired functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Further compounds of formula (I) can be synthesized as illustrated in Scheme 4. Commercially available N-aminophthalimide 4-1 can be treated with 2,5-dimethoxy THF at elevated temperature to provide isoindolinedione compound 4-2. When treated with hydrazine monohydrate, 4-2 can be hydrolyzed to give 1-amino-pyrrole 4-3. The aminopyrrole 4-3 can be transformed to 4-4 through condensation with diethyl-2-(ethoxymethylene)malonate and removal of ethanol generated. Compound 4-4 can be cyclized in a high boiling solvent such as Dowtherm A under elevated temperature to generate the pyrrolopyridazine compound 4-5. Compound 4-5 can be reacted with $POCl_3$ to afford the corresponding chloropyrrolopyridazine 4-6. Coupling of 4-6 with an appropriate Cy can be achieved with methods known to one skilled in the art, such as direct coupling or Buchwald-Hartwig coupling when Cy is attached to pyrrolopyridazine through nitrogen; or Suzuki coupling when Cy is attached to pyrrolopyridazine through carbon. Saponification of the ester group of compound 4-7 to provide a carboxylic acid 4-8, followed by Curtius rearrangement to give a Boc-protected amino compound 4-9 and, deprotection of the Boc group can then give amino pyrrolopyridazines Scheme 3

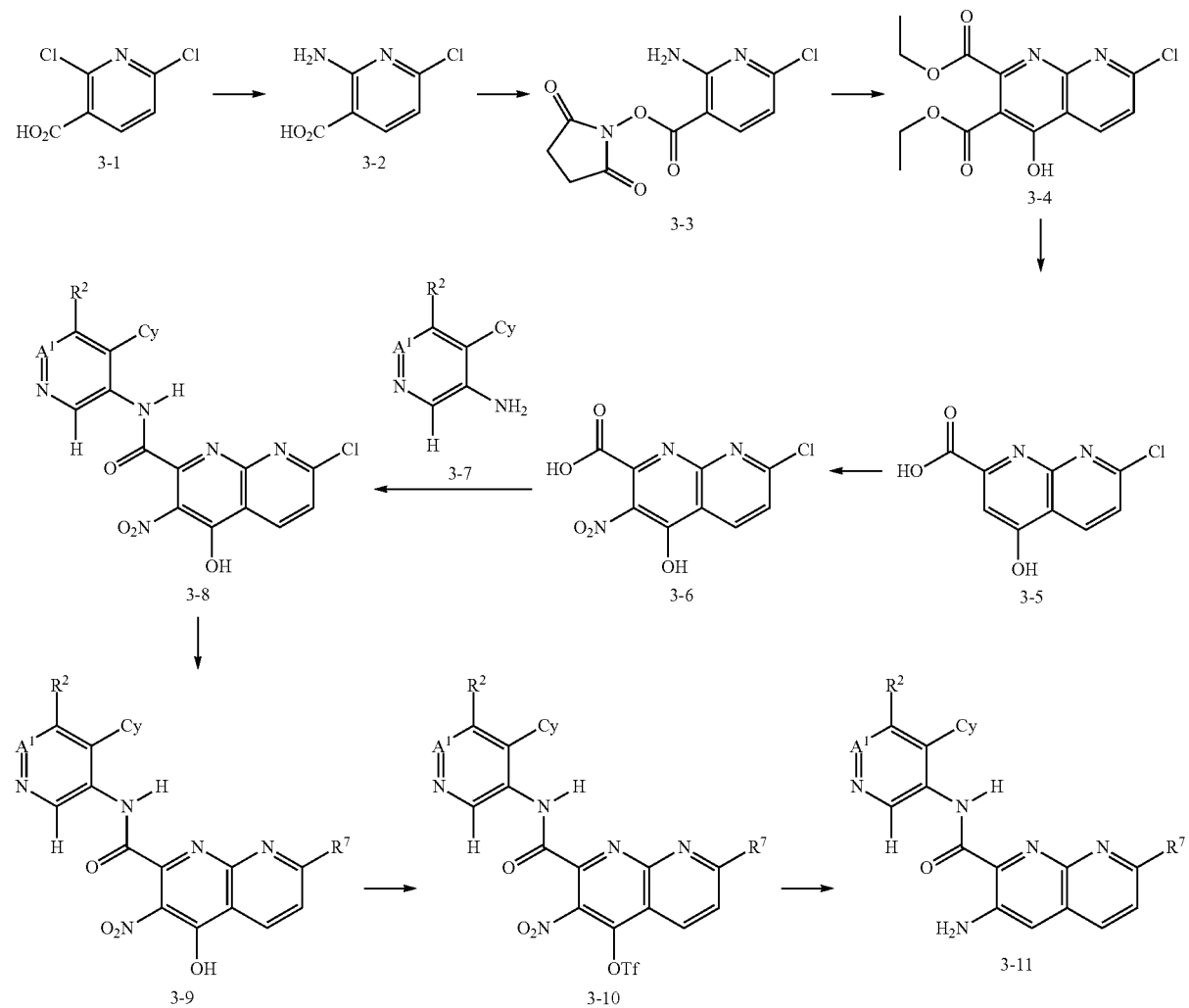

4-10. Finally, amide coupling of 4-10 with an acid such as 1-4 or 2-4 can yield desired compounds of formula 4-11. The substitutions on 4-11 can be further transformed to desired functional groups in the final product, or in any of the steps of the synthesis, using methods know to one skilled in the art.

Scheme 4

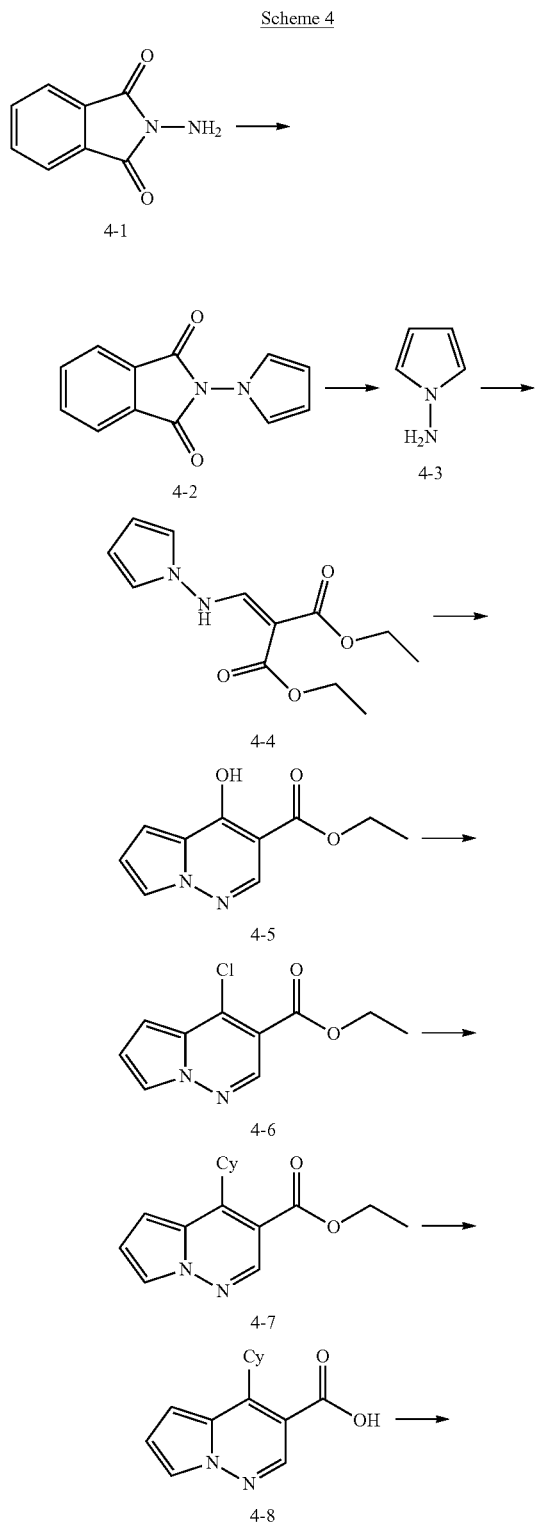

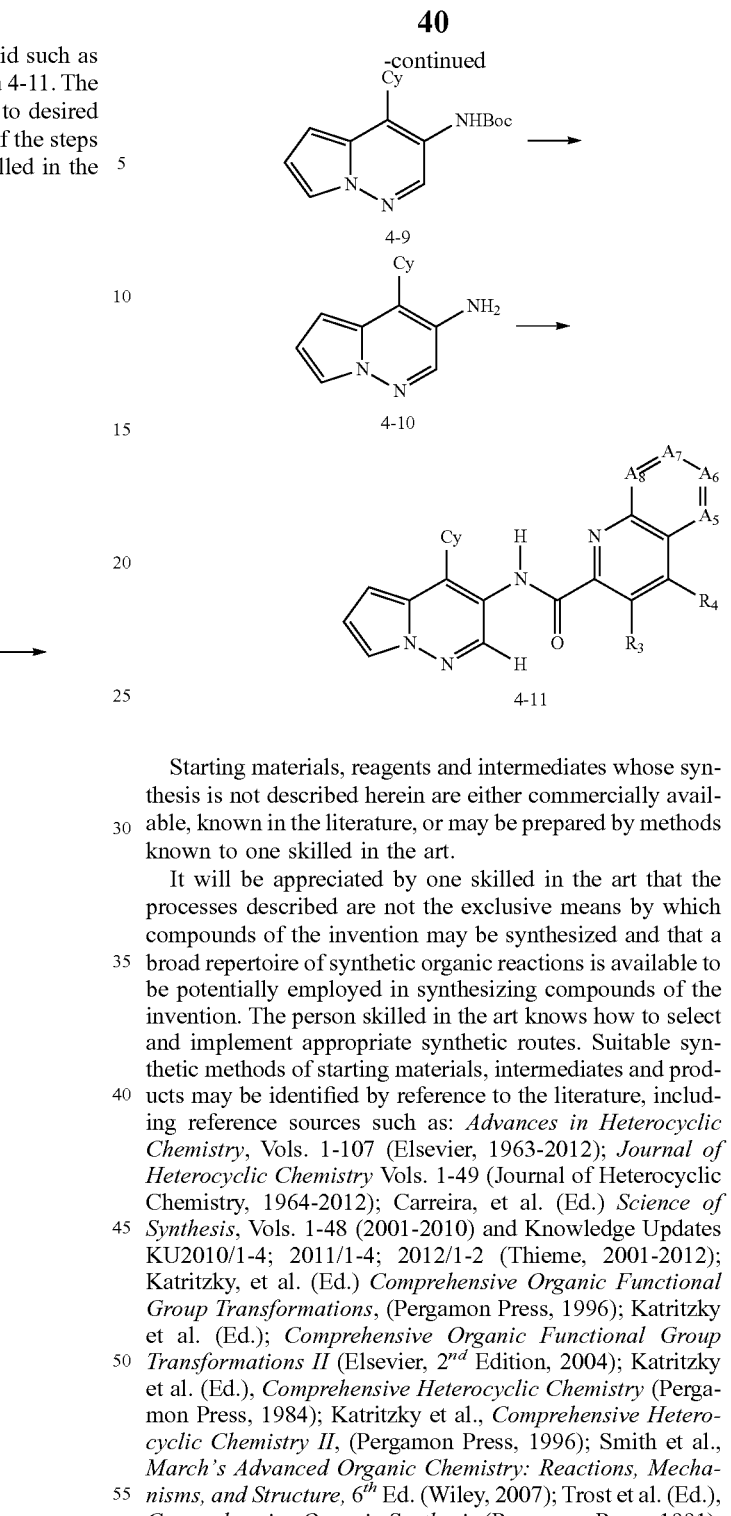

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of one or more members of the Pim kinase family and, thus, are useful in treating diseases and disorders associated with activity of Pim kinases. For the uses described herein, any of the compounds of the invention, including any of the embodiments thereof, may be used.

The compounds of the invention can inhibit one or more of Pim1, Pim2 and Pim3. In some embodiments the compounds are selective for one Pim kinase over another. "Selective" means that the compound binds to or inhibits a Pim kinase with greater affinity or potency, respectively, compared to a reference enzyme, such as another Pim kinase. For example, the compounds can be selective for Pim1 over Pim2 and Pim3, selective for Pim2 over Pim1 and Pim3, or selective for Pim3 over Pim1 and Pim2. In some embodiments, the compounds inhibit all of the Pim family members (e.g., Pim1, Pim2 and Pim3). In some embodiments, the compounds can be selective for Pim over other kinases such as receptor and non-receptor Ser/Thr kinases such as Akt1, Akt2, Akt3, TGF-βR, PKA, PKG, PKC, CaM-kinase, phosphorylase kinase, MEKK, ERK, MAPK and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK or ABL. In general, selectivity can be at least about 5-fold, at least about 10-fold, at least about 20-fold, at least about 50-fold, at least about 100-fold, at least about 200-fold, at least about 500-fold or at least about 1000-fold. The method of inhibiting a Pim1, Pim2 or Pim3 kinase includes contacting the appropriate enzyme with the compound of the invention, or any of the embodiments thereof, or a pharmaceutically acceptable salt thereof.

Thus, the present disclosure provides methods of treating a Pim kinase-associated disease or disorder in an individual (e.g., patient) by administering to the individual in need of such treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a Pim kinase-associated disease or disorder. Also provided is the use of a compound of the invention, or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated using the compounds of the invention include cancer, including, in particular, cancers in which Pim kinases are upregulated or an oncogene, e.g., Myc or Bcl2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated using the compounds of the invention also include myeloproliferative disorders such as polycythemia vera (PV), essential thrombocythemia (ET), chronic myelogenous leukemia (CML) and the like. The myeloproliferative disorder can be myelofibrosis such as primary myelofibrosis (PMF), myelofibrosis with myeloid metaplasia (MMM), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

Pim kinase-associated diseases that can be treated with compounds according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated with compounds according to the invention also include atherosclerosis.

The compounds of the invention can also be used to inhibit disease processes in which Pim-kinases are involved, including angiogenesis and tumor metastasis.

Due to the fact that Pim kinases are regulated by the JAK/STAT pathway, the compounds of the invention are useful to treat diseases in which modulating JAK/STAT signaling is beneficial. Thus, other diseases that can be treated using the compounds of the invention include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitus (type I).

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

The Pim inhibitors of the present invention can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

The Pim inhibitors of the present invention can further be used in combination with one or more anti-inflammatory agents, steroids, immunosuppressants or therapeutic antibodies.

When more than one pharmaceutical agent is administered to a patient, they can be administered simultaneously, sequentially, or in combination (e.g., for more than two agents).

IV. Formulation, Dosage Forms and Administration

When employed as pharmaceuticals, the compounds of the invention can be administered in the form of pharmaceutical compositions. Thus the present disclosure provides a composition comprising a compound formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 pig/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Pim kinases in tissue samples, including human, and for identifying Pim kinase ligands by inhibition binding of a labeled compound. Accordingly, the present invention includes Pim kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro Pim kinase labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a Pim-kinase by monitoring its concentration variation when contacting with the Pim kinase, through tracking of the labeling. For example, a test compound (labeled) can be evaluated for its ability to reduce binding of another compound which is known to bind to a Pim kinase (i.e., standard compound). Accordingly, the ability of a test compound to compete with the standard compound for binding to the Pim kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of Pim kinase-associated diseases or disorders, such as cancer, which include one or more containers containing a pharmaceutical composition comprising a therapeutically effective amount of a compound of formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be Pim-kinase inhibitors according to at least one assay described herein.

EXAMPLES

Experimental procedures for compounds of the invention are provided below. Open Access Prep LC-MS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, *J. Combi. Chem.*, 2002, 4, 295-301; Blom et al., "Optimizing Preparative LC-MS Configurations and Methods for Parallel Synthesis Purification", *J. Combi. Chem.*, 2003, 5, 670-83; and Blom et al., "Preparative LC-MS Purification: Improved Compound Specific Method Optimization", *J. Combi. Chem.*, 2004, 6, 874-883.

Example 1

3-Amino-N-{4-[(3S)-3-aminopiperidin-1-yl]pyridin-3-yl}-7-piperidin-4-ylquinoline-2-carboxamide

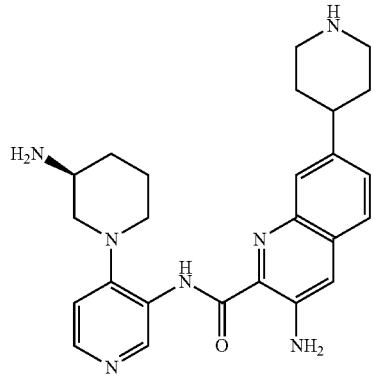 [SMILES: Nc1cc2ccc(C3CCNCC3)cc2nc1C(=O)Nc1cnccc1N1CCC[C@H](N)C1]

Step 1. Benzyl [(3S)-1-(3-nitropyridin-4-yl)piperidin-3-yl]carbamate

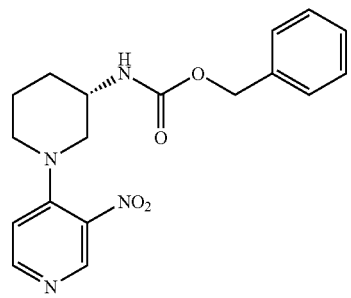

To a 20 mL microwave vial containing 4-chloro-3-nitropyridine (Aldrich, 1.373 g, 8.660 mmol) and benzyl (3S)-piperidin-3-ylcarbamate (MolBridge, 2.077 g, 8.865 mmol), 1-butanol (10.0 mL) was added followed by DIPEA (1.836 g, 14.20 mmol). The mixture was irradiated with microwaves at 130 OC for 1 h. The mixture was then concentrated under reduced pressure, and the resulting residue was purified by flash chromatography on silica gel (0-30% MeOH in DCM) to give the sub-title compound as a yellow solid (2.96 g, 96%). LCMS calc. for $C_{18}H_{21}N_4O_4$ (M+H)$^+$: m/z=357.2. found 357.1.

Step 2. Benzyl [(3S)-1-(3-aminopyridin-4-yl)piperidin-3-yl]carbamate

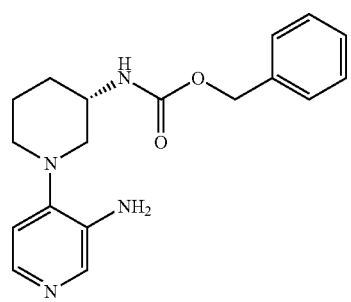 [SMILES: O=C(N[C@H]1CCCN(c2ccncc2[N+](=O)[O-])C1)OCc1ccccc1]

To a solution of benzyl [(3S)-1-(3-nitropyridin-4-yl)piperidin-3-yl]carbamate (2.96 g, 8.30 mmol) in AcOH (36.00 mL, 633.2 mmol), iron powder (2.703 g, 48.40 mmol) was added followed by water (5.00 mL, 278 mmol). After stirring at room temperature for 2 h, the reaction mixture was concentrated under reduced pressure. EtOAc (100 mL) was added to the resulting residue. The mixture was filtered through a pad of diatomaceous earth (CELITE®). The diatomaceous earth pad was washed with a 10 wt % aq. $K_3PO_4$ (150 mL) and EtOAc (100 mL). The organic layer was washed with brine (150 mL), dried over $Na_2SO_4$ and concentrated. The resulting residue was purified by flash chromatography on silica gel (0-20% MeOH in DCM) to give the sub-title compound as an off-white solid (2.24 g, 83%). LCMS calc. for $C_{18}H_{23}N_4O_2$ (M+H)$^+$: m/z=327.2. found 327.2.

Step 3. Ethyl 3-{[(benzyloxy)carbonyl]amino}-7-bromoquinoline-2-carboxylate

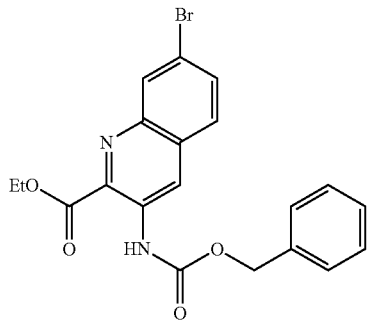

Pyridine (727.5 mg, 9.197 mmol) was added to a solution of ethyl 3-amino-7-bromoquinoline-2-carboxylate (Ark Pharm, 1069 mg, 3.622 mmol) in DCM (10.0 mL). The mixture was cooled to −10° C. A solution of benzyl chloroformate (816.5 mg, 4.547 mmol) in DCM (5.0 mL) was added slowly to the solution. The reaction mixture was allowed to warm to room temperature. After stirring at room temperature for 1 h, the reaction mixture was diluted with EtOAc (100 mL), washed with a saturated aqueous solution of $NaHCO_3$ (100 mL), brine (100 mL), dried over $Na_2SO_4$ and concentrated under reduced pressure. The resulting residue was purified by flash chromatography on silica gel (0-50% EtOAc in hexanes) to give the sub-title compound as an off-white solid (1.54 g, 99%). LCMS calc. for $C_{20}H_{18}BrN_2O_4$(M+H)$^+$: m/z=429.0. found 429.0.

Step 4. 3-{[(Benzyloxy)carbonyl]amino}-7-bromoquinoline-2-carboxylic acid

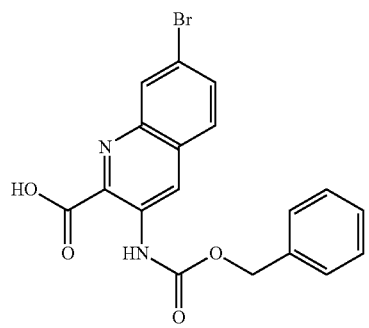 [SMILES: O=C(Nc1cc2ccc(Br)cc2nc1C(=O)O)OCc1ccccc1]

To a mixture of ethyl 3-{[(benzyloxy)carbonyl]amino}-7-bromoquinoline-2-carboxylate (887.5 mg, 2.067 mmol) and $K_3PO_4$ (1494 mg, 7.038 mmol), 1,4-dioxane (10.0 mL) was added, followed by water (10.0 mL). The mixture was heated at 100° C. for 3 h. After cooling to room temperature, the reaction mixture was diluted with water (50 mL). AcOH (1313 mg, 21.86 mmol) was added to adjust the pH to 5. The mixture was extracted with EtOAc (3×50 mL). The combined organic layer was washed with brine (100 mL), dried over $Na_2SO_4$ and concentrated under reduced pressure. The resulting residue was purified by flash chromatography on silica gel (0-15% MeOH in DCM) to give the sub-title compound as a yellow solid (632.0 mg, 76%). LCMS calc. for $C_{18}H_{14}BrN_2O_4$ (M+H)$^+$: m/z=401.0. found 401.0.

Step 5. Benzyl [(3S)-1-(3-{[(3-{[(benzyloxy)carbonyl]amino}-7-bromoquinolin-2-yl)carbonyl]amino}pyridin-4-yl)piperidin-3-yl]carbamate

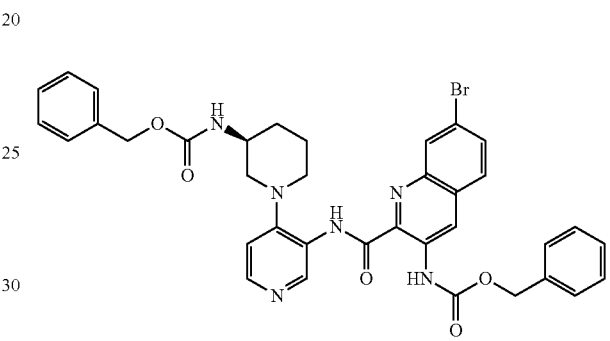

To a mixture of 3-{[(benzyloxy)carbonyl]amino}-7-bromoquinoline-2-carboxylic acid (632.0 mg, 1.575 mmol), benzyl [(3S)-1-(3-aminopyridin-4-yl)piperidin-3-yl]carbamate (559.9 mg, 1.715 mmol) and HATU (1822 mg, 4.792 mmol), DMF (15.0 mL) was added, followed by DIPEA (1854 mg, 14.34 mmol). The reaction mixture was stirred at room temperature for 2 h, then concentrated under reduced pressure. The residue was dissolved in EtOAc (100 mL), washed with brine (2×100 mL), dried over $Na_2SO_4$, and concentrated under reduced pressure. The residue was purified by flash chromatography on silica gel (0-10% MeOH in DCM) to afford the sub-title compound (912.7 mg, 82%). LCMS calc. for $C_{36}H_{34}BrN_6O_5$(M+H)$^+$: m/z=709.2. found 709.1.

Step 6. 3-Amino-N-{4-[(3S)-3-aminopiperidin-1-yl]pyridin-3-yl}-7-piperidin-4-ylquinoline-2-carboxamide To a screw-cap vial equipped with a magnetic stir bar was added benzyl [(3S)-1-(3-{[(3-{[(benzyloxy)carbonyl]amino}-7-bromoquinolin-2-yl)carbonyl]amino}pyridin-4-yl)piperidin-3-yl]carbamate (56.4 mg, 0.0795 mmol), benzyl 4-(4,4,5,5-tetramethyl-1,3,2-dioxaborolan-2-yl)-3,6-dihydropyridine-1(2H)-carboxylate (Ark Pharm, 48.2 mg, 0.140 mmol), chloro(2-dicyclohexylphosphino-2',4',6'-triisopropyl-1,1'-biphenyl) [2-(2'-amino-1,1'-biphenyl)]palladium(II) (Aldrich, 3.2 mg, 0.0041 mmol) and $K_3PO_4$ (53.4 mg, 0.252 mmol). The vial was sealed with a Teflon®-lined septum, and was then evacuated and backfilled with nitrogen three times. 1,4-Dioxane (1.00 mL) was added via a syringe, followed by deoxygenated water (0.50 mL). The mixture was heated at 60° C. for 1 h. After cooling to room temperature, the reaction mixture was filtered through a silica gel plug (eluted with MeCN), and concentrated under reduced pressure. The resulting residue was dissolved in MeOH (4.0 mL) and 10 wt % Pd on carbon (43.4 mg, 0.0408 mmol) was added. The mixture was stirred at room temperature under hydrogen (1 atm.) for 15 h. The reaction mixture was then filtered through a pad of diatomaceous earth (eluted with MeOH) and concentrated under reduced pressure. The resulting residue was purified using RP-HPLC (XBridge™ C18 column, eluting with a gradient of MeCN/water containing 0.05% TFA, at a flow rate of 30 mL/min.) to afford the title compound tetrakistrifluoroacetate salt as a yellow solid (13.1 mg, 18%). LCMS calc. for $C_{25}H_{32}N_7O$ (M+H)$^+$: m/z=446.3. found 446.2. $^1$H NMR (500 MHz, DMSO-d$_6$) δ 10.75 (s, 1H), 8.98 (s, 1H), 8.97-8.90 (m, 1H), 8.84-8.69 (m, 1H), 8.43 (d, J=6.6 Hz, 1H), 8.31 (s, 2H), 7.74-7.65 (m, 2H), 7.56 (s, 1H), 7.45-7.38 (m, 2H), 3.88-3.76 (m, 1H), 3.59-3.46 (m, 2H), 3.43 (d, J=11.5 Hz, 2H), 3.36-3.25 (m, 2H), 3.13-3.03 (m, 2H), 3.03-2.95 (m, 1H), 2.12-2.03 (m, 3H), 2.03-1.95 (m, 1H), 1.94-1.81 (m, 2H), 1.81-1.65 (m, 2H) ppm.

Example 2

3-Amino-N-{4-[(3S)-3-amino piperidin-1-yl]pyridin-3-yl}-7-(tetrahydro-2H-pyran-4-yl)quinoline-2-carboxamide

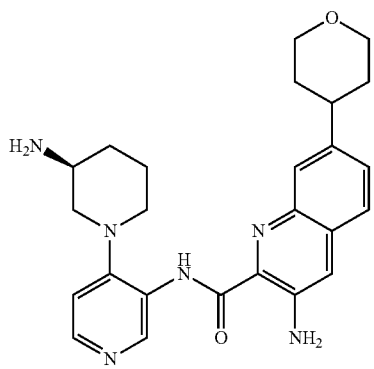 [SMILES: Nc1cc2ccc(C3CCOCC3)cc2nc1C(=O)Nc1cnccc1N1CCC[C@H](N)C1]

The title compound was prepared via a procedure analogous to that of Example 1 (step 6), using 3,6-dihydro-2H-pyran-4-boronic acid pinacol ester (Aldrich) instead of benzyl 4-(4,4,5,5-tetramethyl-1,3,2-dioxaborolan-2-yl)-3,6-dihydropyridine-1(2H)-carboxylate. The crude product was purified using RP-HPLC (XBridge™ C18 column, eluting with a gradient of MeCN/water containing 0.1% NH$_4$OH, at a flow rate of 30 mL/min.) to give the title product as a yellow solid. LCMS calc. for $C_{25}H_{31}N_6O_2$ (M+H)$^+$: m/z=447.2. found 447.2. $^1$H NMR (500 MHz, DMSO-d$_6$) δ 9.42 (s, 1H), 8.27 (d, J=5.3 Hz, 1H), 7.72-7.64 (m, 2H), 7.54 (s, 1H), 7.46 (d, J=8.6 Hz, 1H), 7.17 (d, J=5.3 Hz, 1H), 6.84 (s, 2H), 4.07-3.91 (m, 2H), 3.60-3.45 (m, 2H), 3.24-3.12 (m, 3H), 3.10-3.03 (m, 1H), 2.95-2.86 (m, 1H), 2.74-2.66 (m, 1H), 2.02-1.76 (m, 5H), 1.77-1.64 (m, 2H), 1.34-1.20 (m, 1H) ppm.

Example 3

3-Amino-N-{4-[(3S)-3-aminopiperidin-1-yl]pyridin-3-yl}-7-(2,6-difluorophenyl)quinoline-2-carboxamide

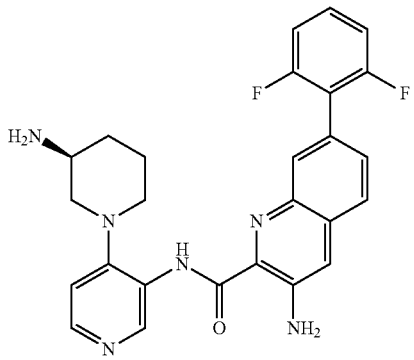 [SMILES: Nc1cc2ccc(-c3c(F)cccc3F)cc2nc1C(=O)Nc1cnccc1N1CCC[C@H](N)C1]

The title compound was prepared via a procedure analogous to that of Example 1 (step 6), using 2,6-difluorophenylboronic acid pinacol ester (Combi-Blocks) instead of benzyl 4-(4,4,5,5-tetramethyl-1,3,2-dioxaborolan-2-yl)-3,6-dihydropyridine-1(2H)-carboxylate. The crude product was purified using RP-HPLC (XBridge™ C18 column, eluting with a gradient of MeCN/water containing 0.1% NH$_4$OH, at a flow rate of 30 mL/min.) to give the title product as a yellow solid. LCMS calc. for $C_{26}H_{25}F_2N_6O$ (M+H)$^+$: m/z=475.2. found 475.2. $^1$H NMR (400 MHz, DMSO-d$_6$) δ 9.39 (s, 1H), 8.27 (d, J=5.3 Hz, 1H), 7.97 (s, 1H), 7.83 (d, J=8.7 Hz, 1H), 7.61 (s, 1H), 7.57 (d, J=9.9 Hz, 1H), 7.51 (dd, J=7.4, 6.5 Hz, 1H), 7.29 (t, J=8.2 Hz, 2H), 7.15 (d, J=5.3 Hz, 1H), 7.07 (s, 2H), 3.26-3.12 (m, 1H), 3.13-2.99 (m, 2H), 2.65 (d, J=6.0 Hz, 1H), 2.47-2.41 (m, 1H), 1.96-1.74 (m, 3H), 1.20 (s, 1H) ppm.

Example 4

3-Amino-N-{4-[(3S)-3-aminopiperidin-1-yl]pyridin-3-yl}-7-(1-methyl-1H-pyrazol-5-yl)quinoline-2-carboxamide

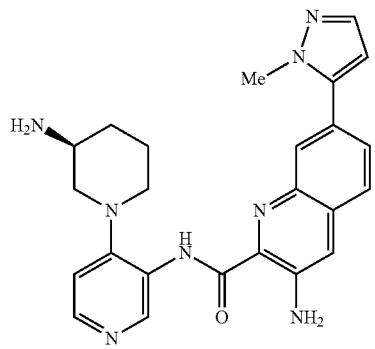 [SMILES: Cn1nccc1-c1ccc2cc(N)c(C(=O)Nc3cnccc3N3CCC[C@H](N)C3)nc2c1]

The title compound was prepared via a procedure analogous to that of Example 1 (step 6), using 1-methyl-1H-pyrazole-5-boronic acid pinacol ester (Aldrich) instead of benzyl 4-(4,4,5,5-tetramethyl-1,3,2-dioxaborolan-2-yl)-3,6-dihydropyridine-1(2H)-carboxylate. The crude product was purified using RP-HPLC (XBridge™ C18 column, eluting with a gradient of MeCN/water containing 0.1% NH$_4$OH, at a flow rate of 30 mL/min.) to give the title product as a yellow solid. LCMS calc. for C$_{24}$H$_{27}$N$_8$O (M+H)$^+$: m/z=443.2. found 443.2. $^1$H NMR (400 MHz, DMSO-d$_6$) δ 9.43 (s, 1H), 8.27 (d, J=5.3 Hz, 1H), 7.99 (s, 1H), 7.83 (d, J=8.7 Hz, 1H), 7.67 (d, J=10.1 Hz, 1H), 7.60 (s, 1H), 7.53 (d, J=1.8 Hz, 1H), 7.16 (d, J=5.3 Hz, 1H), 7.08 (s, 2H), 6.58 (d, J=1.8 Hz, 1H), 4.01 (s, 3H), 3.24-3.15 (m, 1H), 3.15-2.99 (m, 2H), 2.74-2.63 (m, 1H), 2.46-2.39 (m, 1H), 1.94-1.76 (m, 3H), 1.30-1.12 (m, 1H) ppm.

Example 5

3-Amino-N-{4-[(3S)-3-aminopiperidin-1-yl]pyridin-3-yl}-7-(2-cyanophenyl)quinoline-2-carboxamide

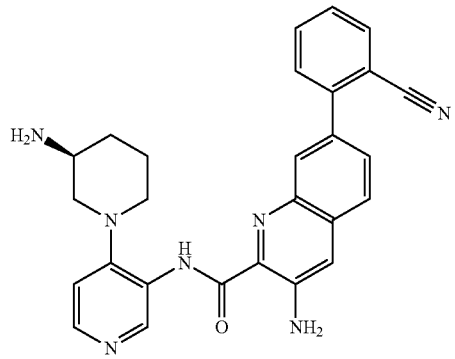 [SMILES: N#Cc1ccccc1-c1ccc2cc(N)c(C(=O)Nc3cnccc3N3CCC[C@H](N)C3)nc2c1]

The title compound was prepared via a procedure analogous to that of Example 1 (step 6), using 2-cyanophenylboronic acid pinacol ester (Aldrich) instead of benzyl 4-(4,4,5,5-tetramethyl-1,3,2-dioxaborolan-2-yl)-3,6-dihydropyridine-1(2H)-carboxylate. The crude product was purified using RP-HPLC (XBridge™ C18 column, eluting with a gradient of MeCN/water containing 0.1% NH$_4$OH, at a flow rate of 30 mL/min.) to give the title product as a yellow solid. LCMS calc. for C$_{27}$H$_{26}$N$_7$O (M+H)$^+$: m/z=464.2. found 464.2.

Example 6

3-Amino-7-[2-(aminocarbonyl)phenyl]-N-{4-[(3S)-3-aminopiperidin-1-yl]pyridin-3-yl}quinoline-2-carboxamide

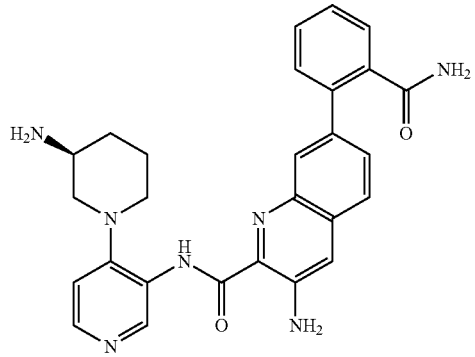 [SMILES: NC(=O)c1ccccc1-c1ccc2cc(N)c(C(=O)Nc3cnccc3N3CCC[C@H](N)C3)nc2c1]

The title compound was isolated as a byproduct during the preparation of 3-amino-N-{4-[(3S)-3-aminopiperidin-1-yl]pyridin-3-yl}-7-(2-cyanophenyl)quinoline-2-carboxamide (Example 5). A pure sample of the title compound was obtained as a yellow solid following purification using RP-HPLC (XBridge™ C18 column, eluting with a gradient of MeCN/water containing 0.1% NH$_4$OH, at a flow rate of 30 mL/min.). LCMS calc. for C$_{27}$H$_{28}$N$_7$O$_2$ (M+H)$^+$: m/z=482.2. found 482.2.

Example 7

3-Amino-N-{4-[(3S)-3-amino piperidin-1-yl]pyridin-3-yl}-7-(2-cyano-6-fluorophenyl)quinoline-2-carboxamide

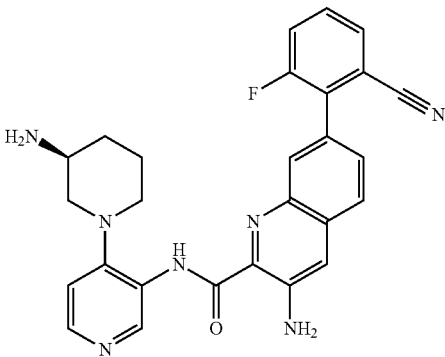 [SMILES: N#Cc1cccc(F)c1-c1ccc2cc(N)c(C(=O)Nc3cnccc3N3CCC[C@H](N)C3)nc2c1]

The title compound was prepared via a procedure analogous to that of Example 1 (step 6), using 2-fluoro-6-cyanophenylboronic acid pinacol ester (Combi-Blocks) instead of benzyl 4-(4,4,5,5-tetramethyl-1,3,2-dioxaborolan-2-yl)-3,6-dihydropyridine-1(2H)-carboxylate. The crude product was purified using RP-HPLC (XBridge™ C18 column, eluting with a gradient of MeCN/water containing 0.1% NH$_4$OH, at a flow rate of 30 mL/min.) to afford the title product as a yellow solid. LCMS calc. for C$_{27}$H$_{25}$FN$_7$O (M+H)$^+$: m/z=482.2. found 482.2.

Example 8

3-Amino-7-[2-(aminocarbonyl)-6-fluorophenyl]-N-{4-[(3S)-3-aminopiperidin-1-yl]pyridin-3-yl}quinoline-2-carboxamide

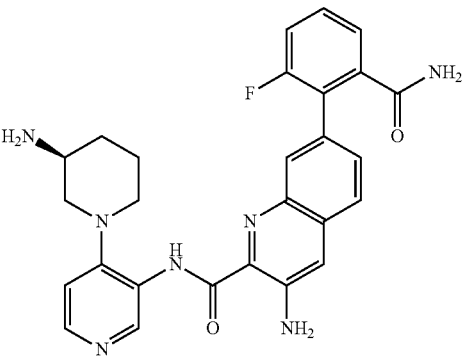 [SMILES: NC(=O)c1cccc(F)c1-c1ccc2cc(N)c(C(=O)Nc3cnccc3N3CCC[C@H](N)C3)nc2c1]

The title compound was isolated as a byproduct during the preparation of 3-amino-N-{4-[(3S)-3-aminopiperidin-1-yl]pyridin-3-yl}-7-(2-cyano-6-fluorophenyl)quinoline-2-carboxamide (Example 7). A pure sample of the title compound was obtained as a yellow solid following purification using RP-HPLC (XBridge™ C18 column, eluting with a gradient of MeCN/water containing 0.1% NH$_4$OH, at a flow rate of 30 mL/min.). LCMS calc. for C$_{27}$H$_{27}$FN$_7$O$_2$(M+H)$^+$: m/z=500.2. found 500.2.

Example 9

3-Amino-N-{4-[(3S)-3-aminopiperidin-1-yl]pyridin-3-yl}-7-isopropylquinoline-2-carboxamide

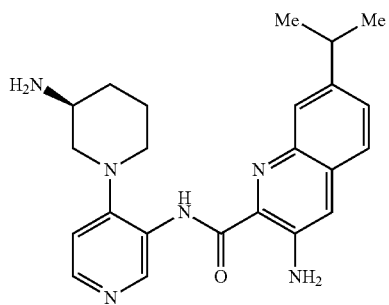 [SMILES: CC(C)c1ccc2cc(N)c(C(=O)Nc3cnccc3N3CCC[C@H](N)C3)nc2c1]

The title compound was prepared via a procedure analogous to that of Example 1 (step 6), using isopropenylboronic acid pinacol ester (Aldrich) instead of benzyl 4-(4,4,5,5-tetramethyl-1,3,2-dioxaborolan-2-yl)-3,6-dihydropyridine-1(2H)-carboxylate. The crude product was purified using RP-HPLC (XBridge™ C18 column, eluting with a gradient of MeCN/water containing 0.1% NH$_4$OH, at a flow rate of 30 mL/min.) to give the title product as a yellow solid. LCMS calc. for C$_{23}$H$_{89}$N$_6$O (M+H)$^+$: m/z=405.2. found 405.2. $^1$H NMR (500 MHz, DMSO-d$_6$) δ 9.43 (s, 1H), 8.26 (d, J=5.2 Hz, 1H), 7.69-7.62 (m, 2H), 7.53 (s, 1H), 7.44 (d, J=8.6 Hz, 1H), 7.16 (d, J=5.3 Hz, 1H), 6.82 (s, 2H), 3.23-3.17 (m, 1H), 3.17-3.11 (m, 1H), 3.09-2.96 (m, 2H), 2.73-2.64 (m, 1H), 2.48-2.42 (m, 1H), 2.01-1.82 (m, 3H), 1.31-1.28 (m, 6H), 1.27-1.19 (m, 1H) ppm.

Example 10

3-Amino-N-{4-[(3S)-3-aminopiperidin-1-yl]pyridin-3-yl}-7-ethylquinoline-2-carboxamide

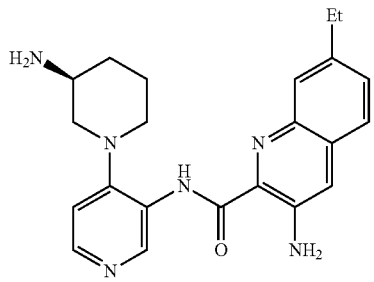 [SMILES: CCc1ccc2cc(N)c(C(=O)Nc3cnccc3N3CCC[C@H](N)C3)nc2c1]

The title compound was prepared via a procedure analogous to that of Example 1 (step 6), using vinylboronic acid pinacol ester (Aldrich) instead of benzyl 4-(4,4,5,5-tetramethyl-1,3,2-dioxaborolan-2-yl)-3,6-dihydropyridine-1(2H)-carboxylate. The crude product was purified using RP-HPLC (XBridge™ C18 column, eluting with a gradient of MeCN/water containing 0.1% NH$_4$OH, at a flow rate of 30 mL/min.) to afford the title product as a yellow solid. LCMS calc. for C$_{22}$H$_7$N$_6$O (M+H)$^+$: m/z=391.2. found 391.2. $^1$H NMR (500 MHz, CD$_3$CN): δ 9.46 (s, 1H), 8.23 (d, J=5.3 Hz, 1H), 7.66 (s, 1H), 7.52 (d, J=8.5 Hz, 1H), 7.42 (s, 1H), 7.32 (dd, J=8.5 and 1.6 Hz, 1H), 7.04 (d, J=5.3 Hz, 1H), 6.25 (s, 2H), 3.25-3.15 (m, 2H), 3.08-3.00 (m, 1H), 2.77 (q, J=7.5 Hz, 2H), 2.71-2.62 (m, 1H), 2.41 (dd, J=12.1, 10.0 Hz, 1H), 2.04-1.96 (m, 1H), 1.92-1.83 (m, 2H), 1.29 (t, J=7.6 Hz, 3H), 1.26-1.20 (m, 1H).

Example 11

3-Amino-N-{4-[(3S)-3-aminopiperidin-1-yl]pyridin-3-yl}quinoline-2-carboxamide

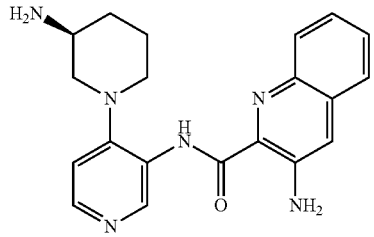 [SMILES: Nc1cc2ccccc2nc1C(=O)Nc1cnccc1N1CCC[C@H](N)C1]

To a solution of benzyl [(3S)-1-(3-{[(3-{[(benzyloxy)carbonyl]amino}-7-bromoquinolin-2-yl)carbonyl]amino}pyridin-4-yl)piperidin-3-yl]carbamate (from step 5 in Example 1, 51.3 mg, 0.0723 mmol) in MeOH (2.0 mL), 10 wt % Pd on carbon (8.3 mg, 0.0078 mmol) was added. The mixture was stirred at room temperature under hydrogen (1 atm.) for 15 h. The reaction mixture was then filtered through a pad of diatomaceous earth, eluted with MeOH and then concentrated under reduced pressure. The resulting residue was purified using RP-HPLC (XBridge™ C18 column, eluting with a gradient of MeCN/water containing 0.1% NH$_4$OH, at a flow rate of 30 mL/min.) to afford the title compound as a yellow solid (4.3 mg, 16%). LCMS calc. for C$_{20}$H$_{23}$N$_6$O (M+H)$^+$: m/z=363.2. found 363.2.

Example 12

3-Amino-N-{4-[(3S)-3-aminopiperidin-1-yl]pyridin-3-yl}-7-bromoquinoline-2-carboxamide

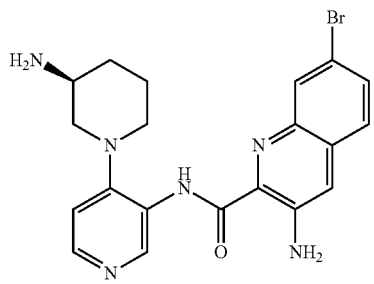

Step 1. tert-Butyl [(3S)-1-(3-nitropyridin-4-yl)piperidin-3-yl]carbamate

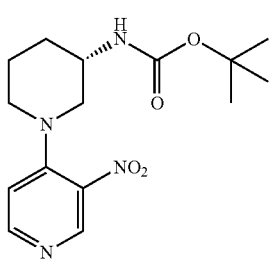 [SMILES: CC(C)(C)OC(=O)N[C@H]1CCCN(c2ccncc2[N+](=O)[O-])C1]

To a 20 mL microwave vial containing 4-chloro-3-nitropyridine (Aldrich, 1.350 g, 8.515 mmol) and tert-butyl (3S)-piperidin-3-ylcarbamate (Combi-Blocks, 1.922 g, 9.597 mmol), 1-butanol (13.0 mL) was added, followed by DIPEA (2.213 g, 17.12 mmol). The reaction mixture was irradiated with microwaves at 130° C. for 1 h. The reaction mixture was then allowed to cool and concentrated under reduced pressure. The resulting residue was purified by flash chromatography on silica gel (0-100% EtOAc in hexanes) to give the sub-title compound as a yellow solid (2.69 g, 98%). LCMS calc. for $C_{15}H_{23}N_4O_4$ (M+H)$^+$: m/z=323.2. found 323.2.

Step 2. tert-Butyl [(3S)-1-(3-aminopyridin-4-yl)piperidin-3-yl]carbamate

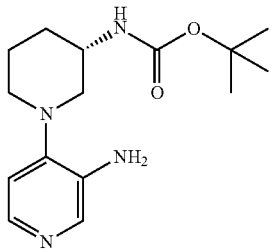 [SMILES: CC(C)(C)OC(=O)N[C@H]1CCCN(c2ccncc2N)C1]

To a solution of tert-butyl [(3S)-1-(3-nitropyridin-4-yl)piperidin-3-yl]carbamate (2.69 g, 8.34 mmol) in EtOH (30.0 mL), iron powder (2.335 g, 41.81 mmol) was added, followed by AcOH (7.04 g, 117 mmol) and water (7.00 mL, 388 mmol). The reaction mixture was stirred at room temperature for 3 h then concentrated under reduced pressure. EtOAc (100 mL) was added to the residue and the resulting mixture was filtered through a pad of diatomaceous earth. The diatomaceous earth pad was washed with 10 wt % aq. $K_3PO_4$ (150 mL) and EtOAc (100 mL). The organic layer was separated and was then washed with brine (150 mL), dried over $Na_2SO_4$ and concentrated under reduced pressure. The resulting residue was purified by flash chromatography on silica gel (0-30% MeOH in DCM) to give the sub-title compound as an off-white solid (2.13 g, 87%). LCMS calc. for $C_{15}H_{25}N_4O_2$ (M+H)$^+$: m/z=293.2. found 293.2.

Step 3. 3-Amino-7-bromoquinoline-2-carboxylic acid

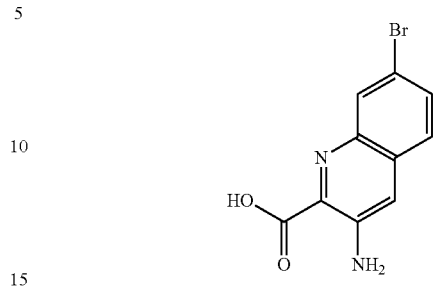

To a mixture of ethyl 3-amino-7-bromoquinoline-2-carboxylate (Ark Pharm, 113.9 mg, 0.3859 mmol) and lithium hydroxide monohydrate (82.8 mg, 1.97 mmol), THF (2.50 mL) was added, followed by water (0.50 mL). The resulting mixture was stirred at 50° C. for 2 h. The reaction mixture was then cooled to room temperature and water (25 mL) was then added, followed by AcOH (245.9 mg, 4.095 mmol) to adjust the pH to 5. The mixture was extracted with EtOAc (3×25 mL). The combined organic extract was washed with brine (50 mL), then dried over $Na_2SO_4$, and concentrated to yield a yellow solid (83.3 mg). The crude product was used directly in the next step without further purification. LCMS calc. for $C_{10}H_8BrN_2O_2$ (M+H)$^+$: m/z=267.0. found 267.0.

Step 4. 3-Amino-N-{4-[(3S)-3-aminopiperidin-1-yl]pyridin-3-yl}-7-bromoquinoline-2-carboxamide To a mixture of 3-amino-7-bromoquinoline-2-carboxylic acid (27.4 mg, 0.103 mmol), tert-butyl [(3S)-1-(3-aminopyridin-4-yl)piperidin-3-yl]carbamate (31.4 mg, 0.107 mmol) and HATU (78.2 mg, 0.206 mmol), DMF (1.00 mL) was added, followed by DIPEA (83.6 mg, 0.647 mmol). The mixture was stirred at room temperature. After 3 h, the reaction mixture was concentrated under reduced pressure. The resulting residue was dissolved in DCM (2.0 mL); then TFA (1.0 mL) was added. The mixture was stirred at room temperature for 30 min., and then concentrated under reduced pressure. The residue was purified using RP-HPLC (XBridge™ C18 column, eluting with a gradient of MeCN/water containing 0.1% $NH_4OH$, at a flow rate of 30 mL/min.) to give the title compound as a yellow solid (10.1 mg, 22%). LCMS calc. for $C_{20}H_{22}BrN_6O$ (M+H)$^+$: m/z=441.1. found 441.1.

Example 13

3-Amino-N-{4-[(3S)-3-aminopiperidin-1-yl]pyridin-3-yl}-7-(cyanomethyl)quinoline-2-carboxamide

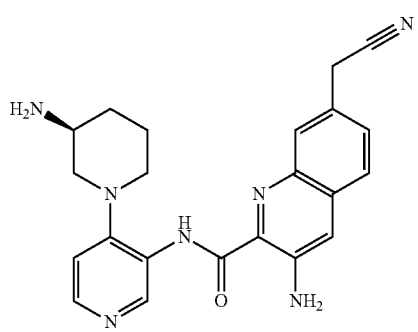 [SMILES: N#CCc1ccc2cc(N)c(C(=O)Nc3cnccc3N3CCC[C@H](N)C3)nc2c1]

Step 1. 3-{[(Benzyloxy)carbonyl]amino}-7-(cyanomethyl)quinoline-2-carboxylic acid

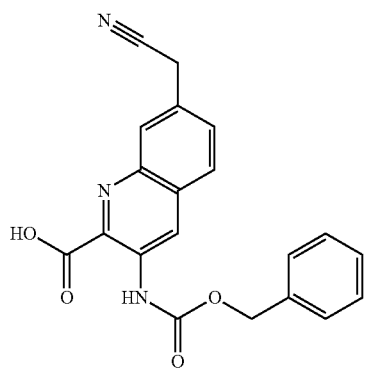 [SMILES: N#CCc1ccc2cc(NC(=O)OCc3ccccc3)c(C(=O)O)nc2c1]

To a screw-cap vial equipped with a magnetic stir bar, ethyl 3-{[(benzyloxy)carbonyl]amino}-7-bromoquinoline-2-carboxylate (105.9 mg, 0.2467 mmol), 4-isoxazoleboronic acid pinacol ester (Aldrich, 75.8 mg, 0.389 mmol), chloro(2-dicyclohexylphosphino-2',4',6'-triisopropyl-1,1'-biphenyl) [2-(2'-amino-1,1'-biphenyl)]palladium(II) (Aldrich, 20.5 mg, 0.0260 mmol) and cesium carbonate (257.9 mg, 0.7915 mmol) were added. The vial was sealed with a Teflon®-lined septum, and then evacuated and backfilled with nitrogen three times. 1,4-Dioxane (2.00 mL) was added via a syringe, followed by deoxygenated water (1.00 mL). The reaction mixture was heated at 90° C. for 2 h and was then allowed to cool to room temperature. After cooling, the reaction mixture was diluted with water (50 mL). AcOH (159 mg, 2.66 mmol) was added to adjust the pH to 5. The mixture was extracted with EtOAc (3×50 mL). The combined organic extract was washed with brine (100 mL), dried over Na$_2$SO$_4$ and concentrated under reduced pressure. The resulting residue was purified by flash chromatography on silica gel (0-10% MeOH in DCM) to give the sub-title compound as a brown solid (46.2 mg, 52%). LCMS calc. for C$_{20}$H$_{16}$N$_3$O$_4$ (M+H)$^+$: m/z=362.1. found 362.1.

Step 2. Benzyl {(3S)-1-[3-({[3-{[(benzyloxy)carbonyl]amino}-7-(cyanomethyl)quinolin-2-yl]carbonyl}amino)pyridin-4-yl]piperidin-3-yl}carbamate

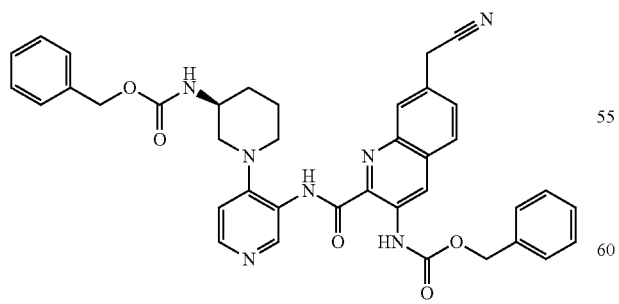

To a mixture of 3-{[(benzyloxy)carbonyl]amino}-7-(cyanomethyl)quinoline-2-carboxylic acid (46.2 mg, 0.128 mmol), benzyl [(3S)-1-(3-aminopyridin-4-yl)piperidin-3-yl]carbamate (46.6 mg, 0.143 mmol) and HATU (153.3 mg, 0.4032 mmol), DMF (2.00 mL) was added, followed by DIPEA (181.8 mg, 1.406 mmol). The reaction mixture was stirred at room temperature for 15 h, and was then concentrated under reduced pressure. The residue was purified by flash chromatography on silica gel (0-10% MeOH in DCM) to give the sub-title compound as a brown solid (65.8 mg, 77%). LCMS calc. for C$_{38}$H$_{36}$N$_7$O$_5$ (M+H)$^+$: m/z=670.3. found 670.3.

Step 3. 3-Amino-N-{4-[(3S)-3-aminopiperidin-1-yl]pyridin-3-yl}-7-(cyanomethyl)quinoline-2-carboxamide To a solution of benzyl {(3S)-1-[3-({[3-{[(benzyloxy)carbonyl]amino}-7-(cyanomethyl)quinolin-2-yl]carbonyl}amino)pyridin-4-yl]piperidin-3-yl}carbamate (65.8 mg, 0.0982 mmol) in MeOH (2.0 mL), 10 wt % Pd on carbon (15.4 mg, 0.0145 mmol) was added. The mixture was stirred at room temperature under hydrogen (1 atm.) for 15 h. The reaction mixture was filtered through a pad of diatomaceous earth (eluted with MeOH), and then concentrated under reduced pressure. The resulting residue was purified using RP-HPLC (XBridge™ C18 column, eluting with a gradient of MeCN/water containing 0.1% NH$_4$OH, at a flow rate of 30 mL/min.) to give the title compound as a yellow solid (3.4 mg, 9%). LCMS calc. for C$_{22}$H$_{24}$N$_7$O (M+H)$^+$: m/z=402.2. found 402.2. $^1$H NMR (400 MHz, DMSO-d$_6$) δ 9.41 (s, 1H), 8.27 (d, J=5.3 Hz, 1H), 7.85 (s, 1H), 7.75 (d, J=8.7 Hz, 1H), 7.57 (s, 1H), 7.41 (d, J=8.5 Hz, 1H), 7.17 (d, J=5.3 Hz, 1H), 6.98 (s, 2H), 4.23 (s, 2H), 3.25-3.18 (m, 1H), 3.18-3.03 (m, 2H), 2.78-2.58 (m, 1H), 2.47-2.41 (m, 1H), 2.08-1.95 (m, 1H), 1.95-1.76 (m, 2H), 1.22 (s, 1H) ppm.

Example 14

3-Amino-N-{4-[(3S)-3-aminopiperidin-1-yl]pyridin-3-yl}-7-ethyl-6-fluoroquinoline-2-carboxamide

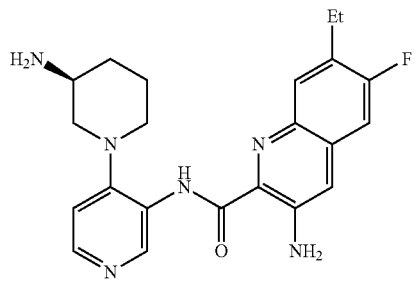 [SMILES: CCc1cc2nc(C(=O)Nc3cnccc3N3CCC[C@H](N)C3)c(N)cc2cc1F]

Step 1. Methyl 4-bromo-5-fluoro-2-nitrobenzoate

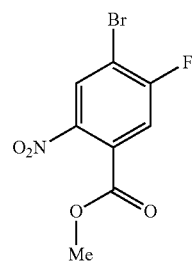 [SMILES: COC(=O)c1cc(F)c(Br)cc1[N+](=O)[O-]]

To a stirred solution of 4-bromo-5-fluoro-2-nitrobenzoic acid (Ark Pharm, 5.387 g, 20.40 mmol) in DMF (80.0 mL) at 0° C. was added potassium carbonate (5.870 g, 42.47 mmol), followed by methyl iodide (8.789 g, 61.92 mmol). After stirring at 0° C. for 15 min., the reaction was heated to 40° C. for 2 h. The mixture was filtered and concentrated. The residue was dissolved in EtOAc (150 mL), washed with water (2×100 mL), brine (100 mL), dried over $Na_2SO_4$, and concentrated under reduced pressure. The resulting residue was purified by flash chromatography on silica gel (0-50% EtOAc in hexanes) to give the sub-title compound as a pale yellow oil (5.348 g, 94%). LCMS calc. for $C_8H_6BrFNO_4$ $(M+H)^+$: m/z=277.9. found no ionization.

Step 2. 4-Bromo-5-fluoro-2-nitrobenzaldehyde

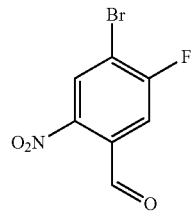 [SMILES: O=Cc1cc(F)c(Br)cc1[N+](=O)[O-]]

To a stirred solution of methyl 4-bromo-5-fluoro-2-nitrobenzoate (5.348 g, 19.24 mmol) in DCM (100 mL) at −78° C., a solution of diisobutylaluminum hydride in DCM (1.0 M, 25.0 mL, 25.0 mmol) was added dropwise over a period of 10 min. The mixture was stirred at −78° C. for 2 h. MeOH (10.0 mL) was then added. The reaction mixture was allowed to warm to room temperature. A 10 wt % aqueous solution of sodium tartrate (100 mL) was added to the mixture. The mixture was then stirred vigorously until a distinct bilayer was formed. The mixture was then diluted with DCM (100 mL), washed with water (2×100 mL), brine (2×100 mL), dried over $Na_2SO_4$ and concentrated under reduced pressure. The residue was purified by flash chromatography on silica gel (0-30% EtOAc in Hexanes) to give the sub-title compound as a pale yellow solid (4.19 g, 88%). LCMS calc. for $C_7H_4BrFNO_3$ $(M+H)^+$: m/z=247.9. found no ionization.

Step 3. 2-Amino-4-bromo-5-fluorobenzaldehyde

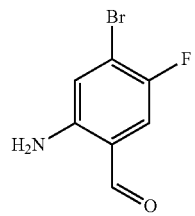

To a mixture of 4-bromo-5-fluoro-2-nitrobenzaldehyde (2.219 g, 8.947 mmol) and iron powder (2.535 g, 45.39 mmol), EtOH (30.0 mL) was added, followed by AcOH (10.0 mL) and water (5.0 mL). The reaction mixture was stirred at room temperature for 2 h, then concentrated under reduced pressure. EtOAc (150 mL) was added to the resulting residue. The mixture formed was filtered through a pad of diatomaceous earth. The diatomaceous earth pad was washed with 10 wt % aq. $K_3PO_4$ (150 mL) and EtOAc (100 mL). The organic layer was separated and then was washed with brine (150 mL), dried over $Na_2SO_4$ and concentrated under reduced pressure. The resulting residue was purified by flash chromatography on silica gel (0-30% EtOAc in hexanes) to give the sub-title compound as a yellow solid (1.518 g, 78%). LCMS calc. for $C_7H_6BrFNO$ $(M+H)^+$: m/z=218.0. found 217.9.

Step 4. Ethyl 3-amino-7-bromo-6-fluoroquinoline-2-carboxylate

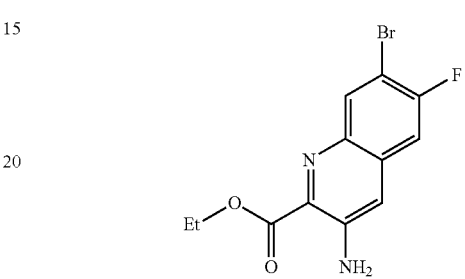

To a solution of pyridine (310.6 mg, 3.927 mmol) in EtOH (8.0 mL), a solution of ethyl bromopyruvate (752.1 mg, 3.857 mmol) in EtOH (8.0 mL) was added dropwise over a period of 20 min. The mixture was heated to 65° C. for 1 h, and then cooled to room temperature. 2-Amino-4-bromo-5-fluorobenzaldehyde (796.1 mg, 3.651 mmol) was added, followed by pyridine (690.6 mg, 8.731 mmol). The mixture was heated at 85° C. for 5 h. Pyrrolidine (640.1 mg, 9.000 mmol) was then added. After heating for an additional 3 h, the reaction mixture was allowed to cool and was then concentrated under reduced pressure. The residue was purified by flash chromatography on silica gel (0-100% EtOAc in hexanes) to give the sub-title compound as a yellow solid (882.5 mg, 77%). LCMS calc. for $C_{12}H_{11}BrFN_2O_2(M+H)^+$: m/z=313.0. found 313.0.

Step 5. Ethyl 3-{[(benzyloxy)carbonyl]amino}-7-bromo-6-fluoroquinoline-2-carboxylate

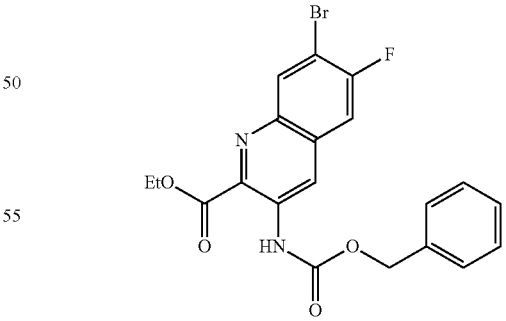

DCM (10.0 mL) was added to a mixture of ethyl 3-amino-7-bromo-6-fluoroquinoline-2-carboxylate (882.5 mg, 2.818 mmol) and pyridine (592.1 mg, 7.485 mmol). The mixture was cooled to −10° C. A solution of benzyl chloroformate (650.6 mg, 3.623 mmol) in DCM (5.0 mL) was added slowly over a period of 5 min. The mixture was then allowed to warm to room temperature and was stirred for 2 h. The reaction mixture was diluted with EtOAc (100 mL), washed with saturated aq. NaHCO₃ (100 mL) and brine (100 mL), then dried over Na₂SO₄ and concentrated under reduced pressure. The resulting residue was purified by flash chromatography on silica gel (0-30% EtOAc in hexanes) to give the sub-title compound as an off-white solid (854.9, 68%). LCMS calc. for C₂₀H₁₇BrFN₂O4 (M+H)⁺: m/z=447.0. found 447.0.

Step 6. 3-{[(Benzyloxy)carbonyl]amino}-6-fluoro-7-vinylquinoline-2-carboxylic acid

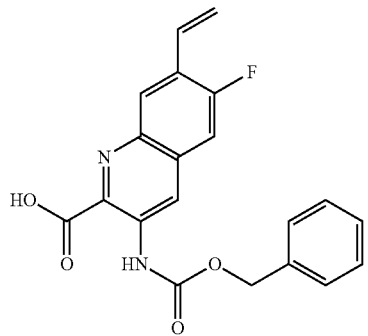 [SMILES: C=Cc1cc2nc(C(=O)O)c(NC(=O)OCc3ccccc3)cc2cc1F]

To a screw-cap vial equipped with a magnetic stir bar, ethyl 3-{[(benzyloxy)carbonyl]amino}-7-bromo-6-fluoroquinoline-2-carboxylate (252.8 mg, 0.5652 mmol), chloro(2-dicyclohexylphosphino-2',4',6'-triisopropyl-1,1'-biphenyl)[2-(2'-amino-1,1'-biphenyl)]palladium(II) (Aldrich, 22.8 mg, 0.0289 mmol) and K₃PO₄ (392.6 mg, 1.850 mmol) were added. The vial was sealed with a Teflon®-lined septum, and was then evacuated and backfilled with nitrogen three times. A solution of vinylboronic acid pinacol ester (146.9 mg, 0.9538 mmol) in 1,4-dioxane (4.0 mL) was added via a syringe, followed by deoxygenated water (2.0 mL). The resulting mixture was heated at 90° C. for 1 h, then allowed to cool to room temperature. Water (50 mL) was added followed by AcOH (379 mg, 6.32 mmol) to adjust the pH to 5. The mixture was extracted with EtOAc (3×50 mL). The combined organic extract was washed with brine (100 mL), dried over Na₂SO₄ and concentrated under reduced pressure. The resulting residue was purified by flash chromatography on silica gel (0-10% MeOH in DCM) to give the sub-title compound as a yellow solid (153.2 mg, 74%). LCMS calc. for C₂₀H₁₆FN₂O₄(M+H)⁺: m/z=367.1. found 367.1.

Step 7. Benzyl [(3S)-1-(3-{[(3-{[(benzyloxy)carbonyl]amino}-6-fluoro-7-vinylquinolin-2-yl)carbonyl]amino}pyridin-4-yl)piperidin-3-yl]carbamate

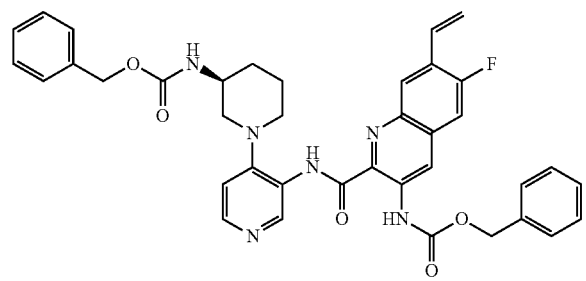 [SMILES: C=Cc1cc2nc(C(=O)Nc3cnccc3N3CCC[C@H](NC(=O)OCc4ccccc4)C3)c(NC(=O)OCc3ccccc3)cc2cc1F]

To a mixture of 3-{[(benzyloxy)carbonyl]amino}-6-fluoro-7-vinylquinoline-2-carboxylic acid (153.2 mg, 0.4182 mmol), benzyl [(3S)-1-(3-aminopyridin-4-yl)piperidin-3-yl]carbamate (151.1 mg, 0.4629 mmol) and HATU (485.8 mg, 1.278 mmol), DMF (4.0 mL) was added, followed by DIPEA (570.1 mg, 4.411 mmol). The reaction mixture was stirred at room temperature for 15 h, then concentrated under reduced pressure. The residue was purified by flash chromatography on silica gel (0-10% MeOH in DCM) to give the sub-title compound (242.7 mg, 86%). LCMS calc. for C₃₈H₃₆FN₆O₅(M+H)⁺: m/z=675.3. found 675.3.

Step 8. 3-Amino-N-{4-[(3S)-3-aminopiperidin-yl]pyridin-3-yl}-7-ethyl-6-fluoroquinoline-2-carboxamide To a solution of benzyl [(3S)-1-(3-{[(3-{[(benzyloxy)carbonyl]amino}-6-fluoro-7-vinylquinolin-2-yl)carbonyl]amino}pyridin-4-yl)piperidin-3-yl]carbamate (242.7 mg, 0.3597 mmol) in MeOH (7.00 mL), 10 wt % Pd on carbon (66.7 mg, 0.0627 mmol) was added. The mixture was then stirred at room temperature under hydrogen (1 atm.) for 15 h. The reaction mixture was filtered through a pad of diatomaceous earth (eluted with MeOH) and was then concentrated under reduced pressure. The resulting residue was purified using RP-HPLC (XBridge™ C18 column, eluting with a gradient of MeCN/water containing 0.1% NH₄OH, at a flow rate of 30 mL/min.) to give the title compound as a yellow solid (20.2 mg, 14%). LCMS calc. for C₂₂H₂₆FN₆O (M+H)⁺: m/z=409.2. found 409.2. ¹H NMR (500 MHz, DMSO-d₆) δ 9.38 (s, 1H), 8.28 (d, J=5.2 Hz, 1H), 7.73 (d, J=7.5 Hz, 1H), 7.53-7.44 (m, 2H), 7.17 (d, J=5.2 Hz, 1H), 6.95 (s, 2H), 3.56-3.13 (m, 2H), 3.13-3.01 (m, 1H), 2.82-2.67 (m, 3H), 2.55 (m, J=9.6 Hz, 1H), 2.03-1.94 (m, 1H), 1.94-1.79 (m, 2H), 1.37-1.32 (m, 1H), 1.29 (t, J=7.5 Hz, 3H) ppm.

Example 15

3-Amino-N-{4-[(3S)-3-aminopiperidin-1-yl]pyridin-3-yl}-7-(1-hydroxyethyl)quinoline-2-carboxamide

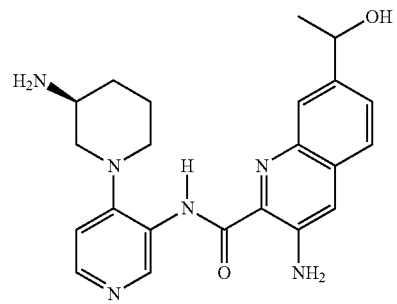 [SMILES: CC(O)c1ccc2cc(N)c(C(=O)Nc3cnccc3N3CCC[C@H](N)C3)nc2c1]

Step 1. Ethyl 3-{[(benzyloxy)carbonyl]amino}-7-bromoquinoline-2-carboxylate

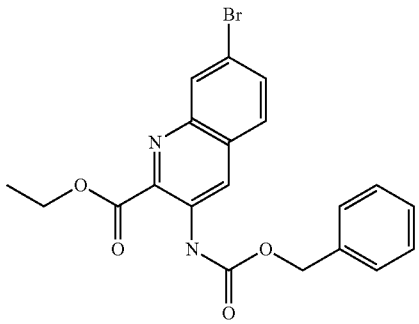 [SMILES: CCOC(=O)c1nc2cc(Br)ccc2cc1NC(=O)OCc1ccccc1]

DCM (20.0 mL) was added to a flask containing ethyl 3-amino-7-bromoquinoline-2-carboxylate (from commercial source, 1.38 g, 4.68 mmol) and pyridine (1.0 mL, 12 mmol). The reaction mixture was cooled to −10° C. Benzyl chloroformate (0.843 mL, 5.61 mmol) was added slowly. The mixture was then allowed to warm gradually to room temperature and stirred for an additional 1 h. The reaction mixture was concentrated under reduced pressure. The resulting residue was triturated with MeOH (10 mL) to form a precipitate that was collected by vacuum filtration and washed with cold MeOH to give the sub-title compound (1.73 g, 86%) as a white powder. LCMS calc. for $C_{20}H_{18}BrN_2O_4(M+H)^+$: m/z=429.2. Found: 429.1.

Step 2. 3-Amino-7-vinylquinoline-2-carboxylic acid

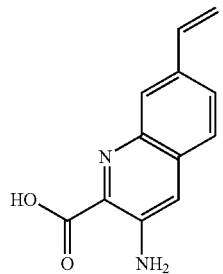 [SMILES: C=Cc1ccc2cc(N)c(C(=O)O)nc2c1]

Ethyl 3-{[(benzyloxy)carbonyl]amino}-7-bromoquinoline-2-carboxylate (1.50 g, 3.49 mmol), $K_3PO_4$ (1.48 g, 6.97 mmol), 1,4-dioxane (45 mL), water (7.5 mL) and 4,4,5,5-tetramethyl-2-vinyl-1,3,2-dioxaborolane (0.80 g, 5.2 mmol) were added to a flask. The reaction mixture was purged with nitrogen for 10 min., then dicyclohexyl(2',4',6'-triisopropylbiphenyl-2-yl)phosphine-(2'-aminobiphenyl-2-yl)(chloro)palladium (1:1) (0.18 g, 0.23 mmol) was added. The flask was then sealed and the reaction mixture was heated at 80° C. for 1 h, then allowed to cool to room temperature. After the reaction mixture was allowed to cool, aq. NaOH (2.5 M; 45 mL) was added, the resulting cloudy mixture was then heated at 95° C. for 3 h, and then allowed to cool. The crude product formed as a precipitate, which was collected by vacuum filtration and used in the next step without further purification. LCMS calc. for $C_{12}H_{11}N_2O_2$ $(M+H)^+$: m/z=215.2. Found: 215.0.

Step 3. 3-{[(Benzyloxy)carbonyl]amino}-7-vinylquinoline-2-carboxylic acid

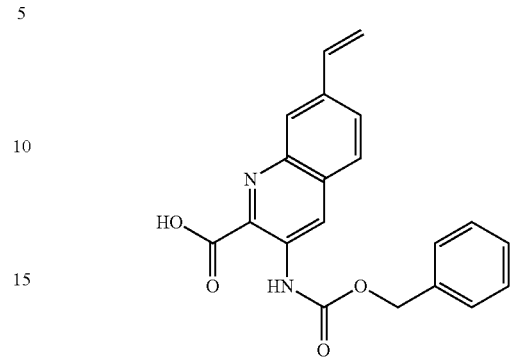

A vial containing the crude 3-amino-7-vinylquinoline-2-carboxylic acid (0.75 g, 3.5 mmol), water (60 mL) and NaOH (7.0 g, 180 mmol) was cooled to −10° C. Benzyl chloroformate (5.0 mL, 33 mmol) was added slowly to the mixture. The mixture was allowed to warm to room temperature and stirred for 1 h. The organic solvent was then removed under reduced pressure. The remaining aqueous layer was neutralized with aq. HCl. The yellow precipitate formed was collected by vacuum filtration, and washed with cold MeOH to give the sub-title compound (1.12 g, 92%) as light yellow powder. LCMS calc. for $C_{20}H_{17}N_2O_4$ $(M+H)^+$: m/z=349.1. Found: 349.1.

Step 4. Benzyl (2-{[(4-{(3S)-3-[(tert-butoxycarbonyl)amino]piperidin-1-yl}pyridin-3-yl)amino]carbonyl}-7-vinylquinolin-3-yl)carbamate

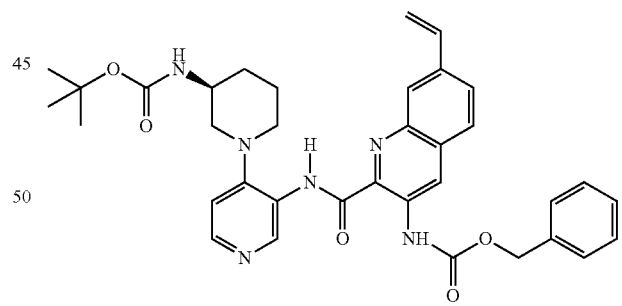

3-{[(Benzyloxy)carbonyl]amino}-7-vinylquinoline-2-carboxylic acid (0.55 g, 1.6 mmol) was mixed with tert-butyl [(3S)-1-(3-aminopyridin-4-yl)piperidin-3-yl]carbamate (0.46 g, 1.6 mmol), DMF (4.0 mL), HATU (1.2 g, 3.2 mmol) and DIPEA (1.1 mL, 6.3 mmol). The reaction mixture was stirred at room temperature for 16 h. Aq. NaOH (1 M, 20 mL) was then added to the reaction mixture. A precipitate formed, which was collected by vacuum filtration to give the sub-title compound (0.52 g, 53%) as light yellow powder. LCMS calc. for $C_{35}H_{39}N_6O_5$ $(M+H)^+$: m/z=623.2. Found: 623.3.

Step 5. Benzyl (2-{[(4-{(3S)-3-[(tert-butoxycarbonyl)amino]piperidin-1-yl}pyridin-3-yl)amino]carbonyl}-7-formylquinolin-3-yl)carbamate

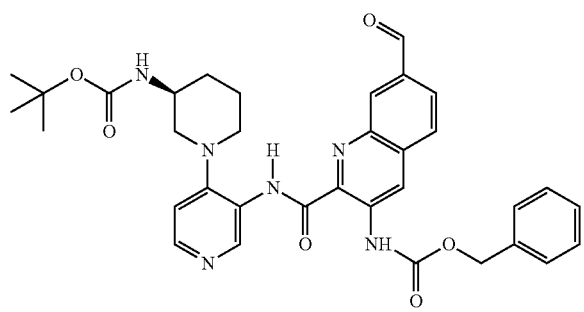 [SMILES: CC(C)(C)OC(=O)N[C@H]1CCCN(c2ccncc2NC(=O)c2nc3cc(C=O)ccc3cc2NC(=O)OCc2ccccc2)C1]

Benzyl (2-{[(4-{(3S)-3-[(tert-butoxycarbonyl)amino]piperidin-1-yl}pyridin-3-yl)amino]carbonyl}-7-vinylquinolin-3-yl)carbamate (520 mg, 0.84 mmol) was mixed with THF (20 mL), 0.25 M osmium tetroxide in water (1.0 mL, 0.3 mmol) and sodium metaperiodate (840 mg, 3.9 mmol) in water (2 mL). The reaction mixture was stirred at 70° C. for 2 h, then allowed to cool. After cooling, the mixture was filtered through a diatomaceous earth plug, which was rinsed with fresh THF. The filtrate was concentrated under reduced pressure. The residue was purified by silica gel column eluting with EtOAc in hexanes (0-100%) to give the sub-title compound (320 mg, 61%) as yellow powder. LCMS calc. for $C_{34}H_{37}N_6O_6$ (M+H)$^+$: m/z=625.2. Found: 625.1.

Step 6. Benzyl [2-{[(4-{(3S)-3-[(tert-butoxycarbonyl)amino]piperidin-1-yl}pyridin-3-yl)amino]carbonyl}-7-(1-hydroxyethyl)quinolin-3-yl]carbamate

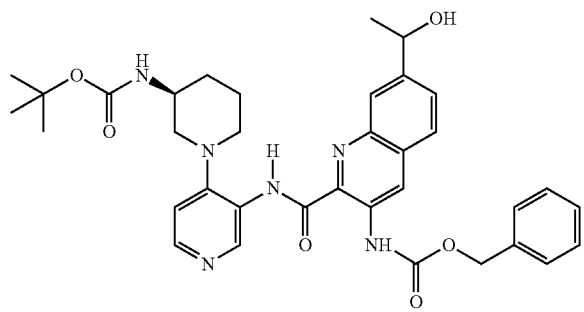 [SMILES: CC(O)c1ccc2cc(NC(=O)OCc3ccccc3)c(C(=O)Nc3cnccc3N3CCC[C@H](NC(=O)OC(C)(C)C)C3)nc2c1]

To a mixture of benzyl (2-{[(4-{(3S)-3-[(tert-butoxycarbonyl)amino]piperidin-1-yl}pyridin-3-yl)amino]carbonyl}-7-formylquinolin-3-yl)carbamate (0.200 g, 0.320 mmol) in THF (5.0 mL), methylmagnesium bromide in THF (3.0 M, 0.43 mL, 1.3 mmol) was added slowly at 0° C. under nitrogen. The reaction mixture was stirred at 0° C. for 1 h, then allowed to warm to room temperature. The reaction mixture was then diluted with EtOAc (10 mL), and 1 M HCl was slowly added to adjust the pH to 7. The aqueous layer was extracted twice with EtOAc. The organic extracts were combined, then dried over anhydrous $Na_2SO_4$, filtered and concentrated under reduced pressure to give the sub-title compound (201 mg, 98%). LCMS calc. for $C_{35}H_{41}N_6O_6$ (M+H)$^+$: m/z=641.2. Found: 641.1.

Step 7. 3-Amino-N-{4-[(3S)-3-aminopiperidin-1-yl]pyridin-3-yl}-7-(1-hydroxyethyl)quinoline-2-carboxamide A mixture of benzyl [2-{[(4-{(3S)-3-[(tert-butoxycarbonyl)amino]piperidin-1-yl}pyridin-3-yl)amino]carbonyl}-7-(1-hydroxyethyl)quinolin-3-yl]carbamate (0.020 g, 0.031 mmol) and 10% Pd on carbon (0.100 g, 0.0940 mmol) in MeOH (20 mL) was hydrogenated under 20 psi of $H_2$ for 2 h. The catalyst was removed by vacuum filtration, and the clear filtrate was concentrated under reduced pressure. To the residue, a mixture of DCM (1.0 mL) and TFA (1.0 mL, 13 mmol) was added. The resulting mixture was stirred at room temperature for 1 h. The mixture was then concentrated under reduced pressure and the residue was diluted with MeOH and neutralized with small amount of $NH_4OH$. The mixture was filtered and purified by prep LCMS (pH=10 method; XBridge™ preparative C18 5 μm OBD™ column, 30×10 mm, 60 mL/min., eluting with a gradient of MeCN and water with $NH_4OH$) to give the title compound as white powder. LCMS calc. for $C_{22}H_{27}N_6O_2$ (M+H)$^+$: m/z=407.3. Found: 407.2. $^1$H NMR (500 MHz, DMSO) δ 9.40 (s, 1H), 8.26 (d, J=5.3 Hz, 1H), 7.79 (s, 1H), 7.67 (d, J=8.6 Hz, 1H), 7.54 (s, 1H), 7.51 (dd, J=8.7, 1.5 Hz, 1H), 7.16 (d, J=5.3 Hz, 1H), 6.84 (s, 2H), 5.29 (d, J=3.8 Hz, 1H), 4.89-4.79 (m, 1H), 3.20 (d, J=10.9 Hz, 1H), 3.16 (d, J=4.2 Hz, 1H), 3.15-3.06 (m, 1H), 2.71-2.63 (m, 1H), 2.47-2.41 (m, 1H), 1.95 (d, J=12.9 Hz, 1H), 1.92-1.82 (m, 2H), 1.41 (d, 3H), 1.27-1.16 (m, 1H) ppm.

Example 16

3-Amino-N-{4-[(3S)-3-aminopiperidin-1-yl]pyridin-3-yl}-7-(1-hydroxy-1-methylethyl)quinoline-2-carboxamide

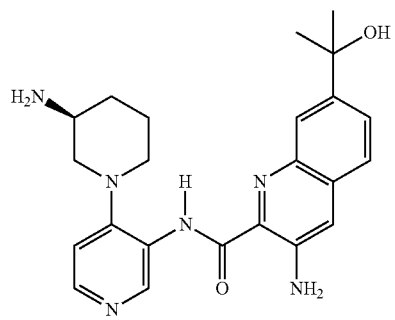 [SMILES: CC(C)(O)c1ccc2cc(N)c(C(=O)Nc3cnccc3N3CCC[C@H](N)C3)nc2c1]

Step 1. tert-Butyl [(3S)-1-(3-{[(7-acetyl-3-{[(benzyloxy)carbonyl]amino}quinolin-2-yl)carbonyl]amino}pyridin-4-yl)piperidin-3-yl]carbamate

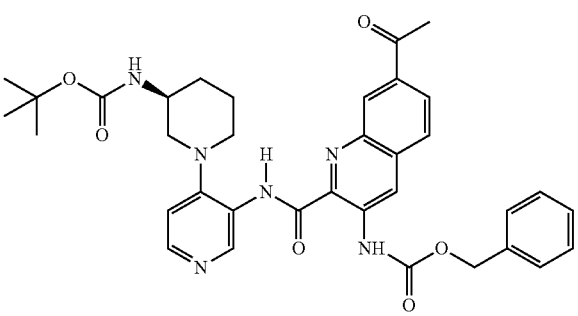 [SMILES: CC(=O)c1ccc2cc(NC(=O)OCc3ccccc3)c(C(=O)Nc3cnccc3N3CCC[C@H](NC(=O)OC(C)(C)C)C3)nc2c1]

A solution of benzyl [2-{[(4-{(3S)-3-[(tert-butoxycarbonyl)amino]piperidin-1-yl}pyridin-3-yl)amino]carbonyl}-7-(1-hydroxyethyl)quinolin-3-yl]carbamate (0.100 g, 0.156 mmol) (from Example 15, step 7) in DCM (0.50 mL) was mixed with a solution of Dess-Martin periodinane (0.099 g, 0.23 mmol) in DCM (0.50 mL, 7.8 mmol). The reaction mixture was stirred at room temperature for 18 h. The crude mixture was diluted with DCM and washed with aq. NaOH. The organic layer was dried over $Na_2SO_4$, filtered and concentrated under reduced pressure to give the sub-title compound (100 mg, 100%). LCMS calc. for $C_{35}H_{39}N_6O_6$ $(M+H)^+$: m/z=639.2. Found: 639.2.

Step 2. Benzyl [2-{[(4-{(3S)-3-[(tert-butoxycarbonyl)amino]piperidin-1-yl}pyridin-3-yl)amino]carbonyl}-7-(1-hydroxy-1-methylethyl)quinolin-3-yl]carbamate

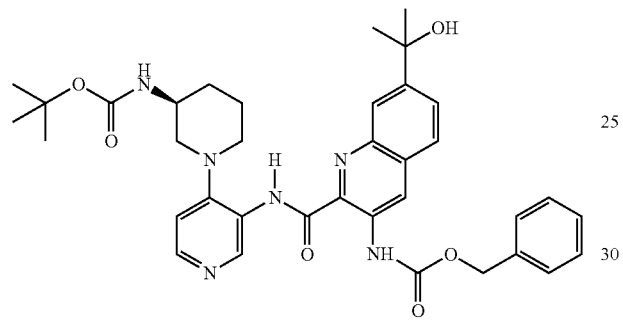

To a mixture of tert-butyl [(3S)-1-(3-{[(7-acetyl-3-{[(benzyloxy)carbonyl]amino}quinolin-2-yl)carbonyl]amino}pyridin-4-yl)piperidin-3-yl]carbamate (0.100 g, 0.156 mmol) in THF (4.0 mL), methylmagnesium bromide in THF (3.0 M, 0.43 mL, 1.3 mmol) was added slowly at 0° C. under nitrogen. The reaction mixture was stirred at 0° C. for 1 h and was then allowed to warm to room temperature. The reaction mixture was diluted with EtOAc (10 mL), and 1 M HCl was slowly added to adjust the pH to 7. The aqueous layer was extracted twice with EtOAc. The organic extracts were combined, dried over $Na_2SO_4$, filtered and concentrated under reduced pressure to give the sub-title compound (94 mg, 92%). LCMS calc. for $C_{36}H_{43}N_6O_6$ $(M+H)^+$: m/z=655.2. Found: 655.1.

Step 3. 3-Amino-N-{4-[(3S)-3-aminopiperidin-1-yl]pyridin-3-yl}-7-(1-hydroxy-1-methylethyl)quinoline-2-carboxamide A mixture of benzyl [2-{[(4-{(3S)-3-[(tert-butoxycarbonyl)amino]piperidin-1-yl}pyridin-3-yl)amino]carbonyl}-7-(1-hydroxy-1-methylethyl)quinolin-3-yl]carbamate (0.020 g, 0.030 mmol) and 10% Pd on carbon (0.100 g, 0.0940 mmol) in MeOH (20 mL) was hydrogenated under 20 psi of $H_2$ for 2 h. The catalyst was removed by vacuum filtration and the clear filtrate was concentrated under reduced pressure. To the residue was added a mixture of DCM (1.0 mL) and TFA (1.0 mL, 13 mmol). The resulting reaction mixture was stirred at room temperature for 1 h and then concentrated under reduced pressure. After concentration, the residue was diluted with MeOH and neutralized with a small amount of $NH_4OH$. The mixture was filtered and purified by preparative LC-MS (pH=10 method; XBridge™ preparative C18 5 μm OBD™ column, 30×10 mm, 60 mL/min., eluting with a gradient of MeCN and water with $NH_4OH$) to give the sub-title compound as white powder. LCMS calc. for $C_{23}H_{29}N_6O_2$ $(M+H)^+$: m/z=421.3. Found: 421.3. $^1H$ NMR (500 MHz, DMSO) δ 9.42 (s, 1H), 8.27 (d, J=5.2 Hz, 1H), 7.91 (s, 1H), 7.66 (s, 2H), 7.53 (s, 1H), 7.17 (d, J=5.3 Hz, 1H), 6.83 (s, 2H), 5.15 (s, 1H), 3.40-3.14 (m, 2H), 3.09 (d, J=11.4 Hz, 1H), 2.79-2.64 (m, 1H), 2.57-2.41 (m, 1H), 2.05-1.78 (m, 3H), 1.51 (s, 6H), 1.34-1.25 (n, 1H) ppm.

Example 17

3-Amino-N-{4-[(3S)-3-aminopiperidin-1-yl]pyridin-3-yl}-7-[hydroxy(phenyl)methyl]quinoline-2-carboxamide

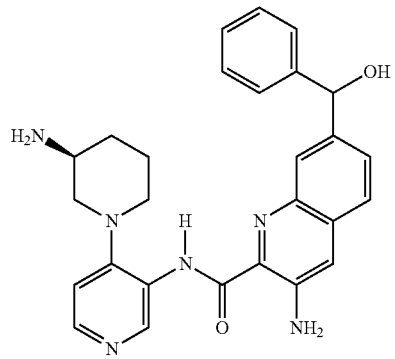 [SMILES: Nc1cc2ccc(C(O)c3ccccc3)cc2nc1C(=O)Nc1cnccc1N1CCC[C@H](N)C1]

To a mixture of benzyl (2-{[(4-{(3S)-3-[(tert-butoxycarbonyl)amino]piperidin-1-yl}pyridin-3-yl)amino]carbonyl}-7-formylquinolin-3-yl)carbamate (0.020 g, 0.032 mmol) (from Example 15, step 5) in THF (0.50 mL), phenylmagnesium bromide in THF (3.0 M, 0.032 mL, 0.096 mmol) was added slowly at 0° C. under nitrogen. The reaction mixture was stirred at 0° C. for 1 h, then allowed to warm to room temperature. The reaction mixture was diluted with EtOAc (10 mL), and 1 M HCl was slowly added to adjust the pH to 7. The aqueous layer was extracted twice with EtOAc. The organic layers were combined, dried over $Na_2SO_4$, filtered and concentrated under reduced pressure. The residue was dissolved in DCM (1 mL) and HBr in AcOH (8.0 M, 1.0 mL, 8.0 mmol) was added. The resulting reaction mixture was stirred at room temperature for 1 h and then concentrated under reduced pressure. To the residue was added 1 M NaOH, and the aqueous layer was extracted with DCM. The combined organic extracts were dried, filtered and concentrated under reduced pressure. The resulting crude product was purified by preparative LC-MS (pH=10 method; XBridge™ preparative C18 5 μm OBD™ column, 30×10 mm, 60 mL/min., eluting with a gradient of MeCN and water with $NH_4OH$) to give the title compound. LCMS calc. for $C_{27}H_{29}N_6O_2$ $(M+H)^+$: m/z=469.3. Found: 469.2.

Example 18

3-Amino-N-{4-[(3S)-3-aminopiperidin-1-yl]pyridin-3-yl}-7-(1-fluoroethyl)quinoline-2-carboxamide

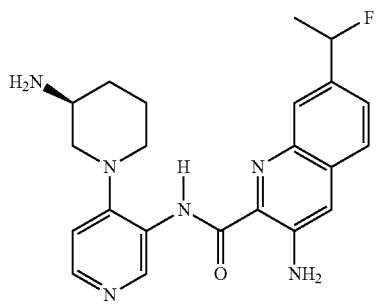 [SMILES: CC(F)c1ccc2cc(N)c(C(=O)Nc3cnccc3N3CCC[C@H](N)C3)nc2c1]

Benzyl [2-{[(4-{(3S)-3-[(tert-butoxycarbonyl)amino]piperidin-1-yl}pyridin-3-yl)amino]carbonyl}-7-(1-hydroxyethyl)quinolin-3-yl]carbamate (8.0 mg, 0.012 mmol) (from Example 15, step 6) was dissolved in DCM (0.3 mL), cooled to −78° C., and then treated with diethylaminosulfur trifluoride (50 mg, 0.3 mmol). The resulting reaction mixture allowed to warm to room temperature and stirred at room temperature for 2 h. The reaction mixture was poured into ice-water containing NaHCO$_3$, extracted three times with DCM, dried over Na$_2$SO$_4$, filtered and concentrated under reduced pressure. HBr in AcOH (8.0 M; 0.20 mL, 1.6 mmol) was added to the residue. The reaction mixture was stirred at room temperature for 30 min., and then concentrated under reduced pressure. The residue was diluted with MeOH and neutralized with small amounts of NH$_4$OH. The mixture was filtered and purified by preparative LC-MS (pH=10 method; XBridge™ preparative C18 5 μm OBD™ column, 30×10 mm, 60 mL/min., eluting with a gradient of MeCN and water with NH$_4$OH) to give the title compound. LCMS calc. for C$_{22}$H$_{26}$FN$_6$O (M+H)$^+$: m/z=409.1. Found: 409.0.

Example 19

3-Amino-N-{4-[(3S)-3-aminopiperidin-1-yl]pyridin-3-yl}-7-(pyrrolidin-1-ylmethyl)quinoline-2-carboxamide

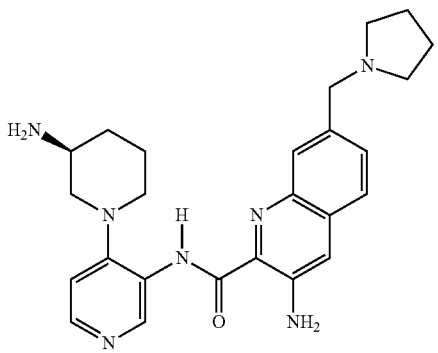 [SMILES: Nc1cc2ccc(CN3CCCC3)cc2nc1C(=O)Nc1cnccc1N1CCC[C@H](N)C1]

Benzyl (2-{[(4-{(3S)-3-[(tert-butoxycarbonyl)amino]piperidin-1-yl}pyridin-3-yl)amino]carbonyl}-7-formylquinolin-3-yl)carbamate (0.008 g, 0.01 mmol) (from Example 15, step 5) was mixed with pyrrolidine, DCM (0.20 mL) and sodium triacetoxyborohydride (0.020 g, 0.094 mmol). The reaction mixture was stirred at room temperature for 2 h. HBr in AcOH (8.0 M; 0.20 mL, 1.6 mmol) was added and the reaction mixture was stirred at room temperature for 30 min. After concentration to remove the solvent, the crude product was diluted with MeOH and neutralized with a small amount of NH$_4$OH. The mixture was filtered and purified by preparative LC-MS (pH=10 method; XBridge™ preparative C18 5 μm OBD™ column, 30×10 mm, 60 mL/min., eluting with a gradient of MeCN and water with NH$_4$OH) to give the title compound. LCMS calc. for C$_{25}$H$_{32}$N$_7$O (M+H)$^+$: m/z=446.2. Found: 446.1.

Example 20

3-Amino-N-{4-[(3S)-3-aminopiperidin-1-yl]pyridin-3-yl}-7-[(dimethylamino)methyl]quinoline-2-carboxamide

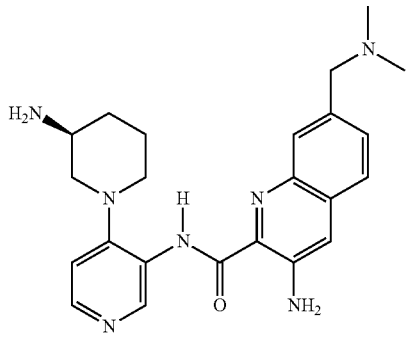 [SMILES: CN(C)Cc1ccc2cc(N)c(C(=O)Nc3cnccc3N3CCC[C@H](N)C3)nc2c1]

The title compound was prepared according to the procedure of Example 19 using benzyl (2-{[(4-{(3S)-3-[(tert-butoxycarbonyl)amino]piperidin-1-yl}pyridin-3-yl)amino]carbonyl}-7-formylquinolin-3-yl)carbamate and dimethylamine as the starting materials to give the title compound in 54% yield. LCMS calc. for C$_{23}$H$_{30}$N$_7$O (M+H)$^+$: m/z=420.4. Found: 420.3.

Example 21

3-Amino-N-{4-[(3S)-3-aminopiperidin-1-yl]pyridin-3-yl}-7-(morpholin-4-ylmethyl)quinoline-2-carboxamide

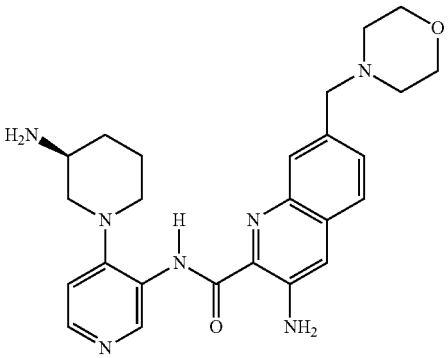 [SMILES: Nc1cc2ccc(CN3CCOCC3)cc2nc1C(=O)Nc1cnccc1N1CCC[C@H](N)C1]

The title compound was prepared according to the procedure of Example 19 using benzyl (2-{[(4-{(3S)-3-[(tert-butoxycarbonyl)amino]piperidin-1-yl}pyridin-3-yl)amino]carbonyl}-7-formylquinolin-3-yl)carbamate and morpholine as the starting materials to give the title compound in 40% yield. LCMS calc. for $C_{25}H_{32}N_7O_2$ (M+H)$^+$: m/z=462.3. Found: 462.2.

Example 22

3-Amino-N-{4-[(3S)-3-aminopiperidin-1-yl]-7-hydroxy-6,7-dihydro-5H-cyclopenta[b]pyridin-3-yl}-7-ethylquinoline-2-carboxamide

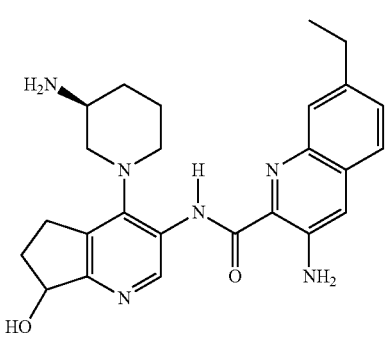 [SMILES: CCc1ccc2cc(N)c(C(=O)Nc3cnc4c(c3N3CCC[C@H](N)C3)CCC4O)nc2c1]

Step 1. 6,7-Dhydro-5H-cyclopenta[b]pyridine 1-oxide

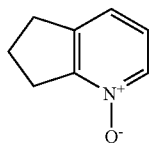

m-Chloroperbenzoic acid (10.0 g, 44.6 mmol) was added slowly to a mixture of 6,7-dihydro-5H-cyclopenta[b]pyridine (5.0 g, 42 mmol DCM (50 mL). The reaction mixture was stirred at room temperature for 2 h. The resulting solution was washed with aq. $Na_2S_2O_3$ (50 mL) and aq. 1 M NaOH (50 mL). The aqueous layer was extracted with DCM (70 mL×5). The combined organic extracts were dried, filtered and concentrated under reduced pressure to give the sub-title compound (4.5 g, 79%). LCMS calc. for $C_8H_{10}NO$ (M+H)$^+$: m/z=136.3. Found: 136.2.

Step 2. 4-Chloro-6,7-dihydro-5H-cyclopenta[b]pyridine

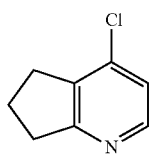

6,7-Dihydro-5H-cyclopenta[b]pyridine 1-oxide (2.5 g, 18 mmol) was mixed with phosphoryl chloride (20 mL, 200 mmol). The reaction mixture was stirred at 120° C. for 3 h. The excess POCl$_3$ was removed under reduced pressure. The residue was diluted in 80 mL of EtOAc and neutralized with Na$_2$CO$_3$ solution. After filtration, the aqueous layer was extracted with EtOAc twice. The combined organic extracts were dried, filtered and concentrated under reduced pressure to give the sub-title compound (2.6 g, 93%). LCMS calc. for $C_8H_9ClN$ (M+H)$^+$: m/z=154.2. Found: 154.3.

Step 3. 4-Methoxy-6,7-dihydro-5H-cyclopenta[b]pyridine

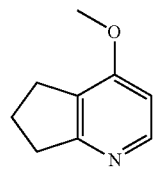

A mixture of 4-chloro-6,7-dihydro-5H-cyclopenta[b]pyridine (2.8 g, 18 mmol), MeOH (20 mL) and sodium methoxide (3.0 g, 56 mmol) was sealed in a pressurized flask and heated at 110 OC for 18 h. The mixture was diluted with EtOAc and neutralized with HCl to pH=1. The organic solvent was removed under reduced pressure. The resulting mixture was washed with ether twice, and neutralized with aq. Na$_2$CO$_3$. The aqueous layer was extracted twice with EtOAc. The combined organic extracts were dried, filtered and concentrated under reduced pressure to give the sub-title compound (1.20 g, 44%). LCMS calc. for $C_9H_{12}NO$ (M+H)$^+$: m/z=150.3. Found: 150.2.

Step 4. 4-Methoxy-3-nitro-6,7-dihydro-5H-cyclopenta[b]pyridine

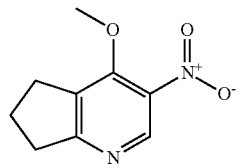

4-Methoxy-6,7-dihydro-5H-cyclopenta[b]pyridine (2.90 g, 19.4 mmol) was mixed with concentrated sulfuric acid (17.0 g, 173 mmol) at 0° C., then a mixture of potassium nitrate (5.3 g, 52 mmol) in another portion of concentrated sulfuric acid (26.5 g, 270 mmol) was added slowly. The reaction mixture was heated at 80° C. for 4 h. The crude mixture was slowly poured into ice (50 g), and neutralized carefully with 50% NaOH solution to pH 8-9. The resulting mixture was extracted six times with EtOAc. The organic extracts were combined, dried and concentrated under reduced pressure to give the sub-title compound as a brown gum (1.56 g, 41%). LCMS calc. for $C_9H_{11}N_2O_3$(M+H)$^+$: m/z=195.3. Found: 195.2.

Step 5.
3-Nitro-6,7-dihydro-5H-cyclopenta[b]pyridin-4-ol

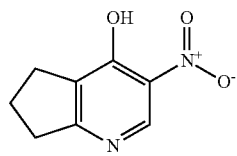 [SMILES: O=[N+]([O-])c1cnc2c(c1O)CCC2]

A mixture of 4-methoxy-3-nitro-6,7-dihydro-5H-cyclopenta[b]pyridine (1.535 g, 7.905 mmol) in AcOH (2.6 mL) was treated with 48% aq. HBr (2.6 mL, 23 mmol). The flask was sealed and heated at 130 OC for 40 min. then allowed to cool. The mixture was then concentrated under reduced pressure and the residue was neutralized to pH=7-8 using 50% NaOH in a cold bath. The mixture was then concentrated under reduced pressure and the residue was diluted with MeOH and THF, dried, filtered and concentrated to give the sub-title compound as a light brown powder. LCMS calc. for $C_8H_9N_2O_3(M+H)^+$: m/z=181.3. Found: 181.2.

Step 6. 4-Chloro-3-nitro-6,7-dihydro-5H-cyclopenta[b]pyridine

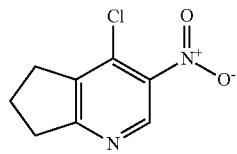 [SMILES: O=[N+]([O-])c1cnc2c(c1Cl)CCC2]

A solution of 3-nitro-6,7-dihydro-5H-cyclopenta[b]pyridin-4-ol (1.424 g, 7.904 mmol) in phosphoryl chloride (11.0 mL, 118 mmol) was heated at 110° C. in a sealed flask under nitrogen for 2 h. The mixture was cooled to room temperature, and concentrated under reduced pressure. The residue was carefully quenched with ice, and neutralized with 50% aq. NaOH to pH 7. The resulting mixture was extracted three times with EtOAc, dried, filtered and concentrated under reduced pressure to give the sub-title compound as a brown solid (0.82 g, 52%). LCMS calc. for $C_8H_8N_2O_2(M+H)^+$: m/z=199.3. Found: 199.2.

Step 7. tert-Butyl [(3S)-1-(3-nitro-6,7-dihydro-5H-cyclopenta[b]pyridin-4-yl)piperidin-3-yl]carbamate

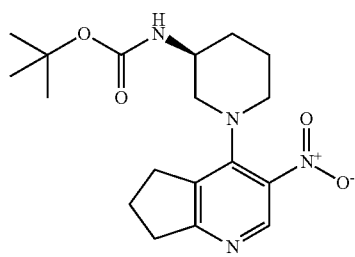 [SMILES: CC(C)(C)OC(=O)N[C@H]1CCCN(c2c([N+](=O)[O-])cnc3c2CCC3)C1]

A mixture of 4-chloro-3-nitro-6,7-dihydro-5H-cyclopenta[b]pyridine (40.0 mg, 0.201 mmol), tert-butyl (3S)-piperidin-3-ylcarbamate (80.7 mg, 0.403 mmol) and triethylamine (84.2 µL, 0.604 mmol) in isopropyl alcohol (0.462 mL) was stirred at 100° C. for 30 min. The mixture was concentrated and purified by flash chromatography on a silica gel column (12 g column, 0-40% EtOAc in hexanes) to give the sub-title compound as light yellow powder (43 mg, 59%). LCMS calc. for $C_{18}H_{27}N_4O_4$ $(M+H)^+$: m/z=363.3. Found: 363.2.

Step 8. tert-Butyl [(3S)-1-(3-nitro-1-oxido-6,7-dihydro-5H-cyclopenta[b]pyridin-4-yl)piperidin-3-yl]carbamate

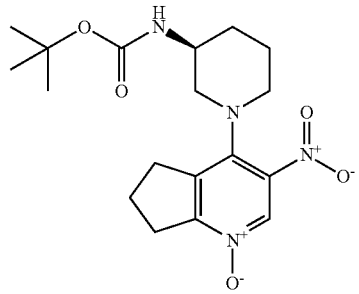 [SMILES: CC(C)(C)OC(=O)N[C@H]1CCCN(c2c([N+](=O)[O-])c[n+]([O-])c3c2CCC3)C1]

m-Chloroperbenzoic acid (198 mg, 0.883 mmol) was slowly added to a solution of tert-butyl [(3S)-1-(3-nitro-6,7-dihydro-5H-cyclopenta[b]pyridin-4-yl)piperidin-3-yl]carbamate (301.0 mg, 0.8305 mmol) in DCM (1.06 mL) at 0° C. The reaction mixture was stirred at room temperature for 67 h. The mixture was treated with aq, $Na_2S_2O_3$ and 1 M NaOH, and then stirred for 30 min. at room temperature. The reaction mixture was extracted three times with DCM. The combined organic extract was dried over $Na_2SO_4$, filtered and concentrated under reduced pressure to give the sub-title compound (277 mg, 88%) as light orange powder. LCMS calc. for $C_{18}H_{27}N_4O_5$ $(M+H)^+$: m/z=379.3. Found: 379.2.

Step 9. 4-{(3S)-3-[(tert-Butoxycarbonyl)amino]piperidin-1-yl}-3-nitro-6,7-dihydro-5H-cyclopenta[b]pyridin-7-yl acetate

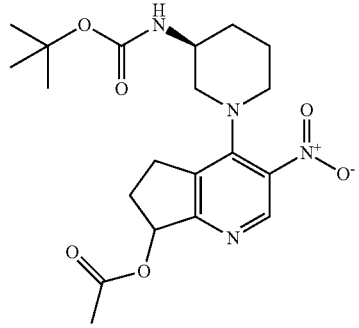 [SMILES: CC(=O)OC1CCc2c1ncc([N+](=O)[O-])c2N1CCC[C@H](NC(=O)OC(C)(C)C)C1]

A mixture of acetic anhydride (0.90 g, 8.8 mmol) and tert-butyl [(3S)-1-(3-nitro-1-oxido-6,7-dihydro-5H-cyclopenta[b]pyridin-4-yl)piperidin-3-yl]carbamate (270.0 mg, 0.7135 mmol) was sealed and heated at 90° C. for 1 h, then allowed to cool. After cooling, the excess acetic anhydride was removed under reduced pressure, the residue was dissolved in DCM, then poured into ice cold $Na_2CO_3$. The mixture was extracted twice with DCM, the combined extracts were dried, filtered and concentrated under reduced pressure to give the crude product, which was purified by preparative LCMS (pH=10 method; XBridge™ preparative C18 5 μm OBD™ column, 30×10 mm, 60 mL/min., eluting with a gradient of MeCN and water with NH₄OH) to provide the sub-title compound as yellow powder (65 mg, 22%). LCMS calc. for $C_{20}H_{29}N_4O_6$ (M+H)⁺: m/z=421.4. Found: 421.3.

Step 10. 3-Amino-4-{(3S)-3-[(tert-Butoxycarbonyl)amino]piperidin-1-yl}-6,7-dihydro-5H-cyclopenta[b]pyridin-7-yl acetate

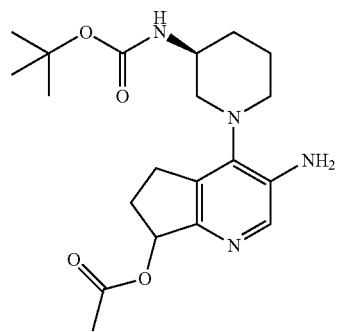 [SMILES: CC(=O)OC1CCc2c1ncc(N)c2N1CCC[C@H](NC(=O)OC(C)(C)C)C1]

A mixture of 4-{(3S)-3-[(tert-butoxycarbonyl)amino]piperidin-1-yl}-3-nitro-6,7-dihydro-5H-cyclopenta[b]pyridin-7-yl acetate (64.0 mg, 0.152 mmol), AcOH (0.90 mL), water (0.10 mL) and iron powder (149 mg, 2.66 mmol) was stirred at room temperature for 20 min. The mixture was diluted with EtOAc, and filtered through a short silica gel plug. The filtrate was concentrated under reduced pressure, diluted with EtOAc and washed with aq. Na₂CO₃. The combined organic extract was dried, filtered and concentrated under reduced pressure to give the sub-title compound as a yellow solid. LCMS calc. for $C_{20}H_{31}N_4O_4$ (M+H)⁺: m/z=391.2. Found: 391.1.

Step 11. 3-{[(3-{[(Benzyloxy)carbonyl]amino}-7-ethylquinolin-2-yl)carbonyl]amino}-4-{(3S)-3-[(tert-butoxycarbonyl)amino]piperidin-1-yl}-6,7-dihydro-5H-cyclopenta[b]pyridin-7-yl acetate

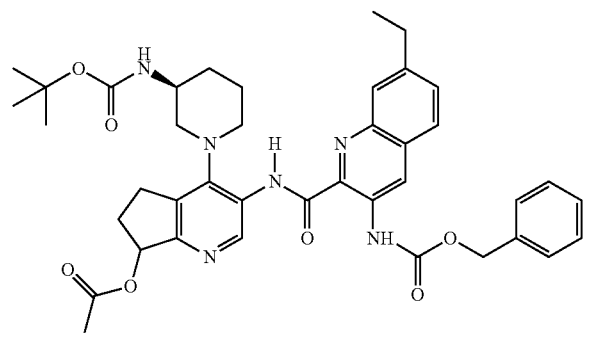 [SMILES: CCc1ccc2cc(NC(=O)OCc3ccccc3)c(C(=O)Nc3cnc4c(c3N3CCC[C@H](NC(=O)OC(C)(C)C)C3)CCC4OC(C)=O)nc2c1]

A mixture of 3-amino-4-{(3S)-3-[(tert-butoxycarbonyl)amino]piperidin-1-yl}-6,7-dihydro-5H-cyclopenta[b]pyridin-7-yl acetate (6.15 mg, 0.0158 mmol), 3-{[(benzyloxy)carbonyl]amino}-7-ethylquinoline-2-carboxylic acid (4.6 mg, 0.013 mmol), HATU (12.5 mg, 0.0328 mmol), DMF (0.0305 mL) and DIPEA (5.09 mg, 0.0394 mmol) was stirred at room temperature for 1 h. The reaction mixture was filtered, concentrated under reduced pressure and purified by preparative LC MS (pH=10 method; XBridge™ preparative C18 5 μm OBD™ column, 30×10 mm, 60 mL/min., eluting with a gradient of MeCN and water with NH₄OH) to give pure sub-title compound as a colorless gum (4 mg, 40%). LCMS calc. for $C_{40}H_{47}N_6O_7$ (M+H)⁺: m/z=723.4. Found: 723.3.

Step 12. 3-Amino-N-{4-[(3S)-3-aminopiperidin-1-yl]-7-hydroxy-6,7-dihydro-5H-cyclopenta[b]pyridin-3-yl}-7-ethylquinoline-2-carboxamide A mixture of 3-{[(3-{[(benzyloxy)carbonyl]amino}-7-ethylquinolin-2-yl)carbonyl]amino}-4-{(3S)-3-[(tert-butoxycarbonyl)amino]piperidin-1-yl}-6,7-dihydro-5H-cyclopenta[b]pyridin-7-yl acetate (4.0 mg, 0.0028 mmol) and 10% palladium on carbon (8.83 mg, 0.00830 mmol) in MeOH (2.0 mL) was hydrogenated at 20 psi for 2 h. The catalyst was removed by filtration and the filtrate was concentrated under reduced pressure to give a crude intermediate. MeOH (0.040 mL), THF (0.0202 mL) and aq. NaOH (1.0 M; 22 μL, 0.022 mmol) were added to the intermediate. The reaction mixture was stirred at room temperature for 30 min. The organic solvents were removed under reduced pressure. The aqueous layer was then extracted twice with EtOAc. The combined organic extracts were dried, filtered and concentrated to give the intermediate, which was treated with DCM (0.034 mL) and TFA (0.034 mL, 0.45 mmol). The resulting mixture was stirred at room temperature for 1 h, then concentrated under reduced pressure. After concentration, the residue was diluted with MeOH and neutralized with small amount of NH₄OH. The mixture was filtered and purified by preparative LCMS (pH=10 method; XBridge™ preparative C18 5 μm OBD™ column, 30×10 mm, 60 mL/min., eluting with a gradient of MeCN and water with NH₄OH) to separate both diastereomers of the title compound (0.7 mg for each isomer, 57% total yield). LCMS calc. for $C_{25}H_{31}N_6O_2$ (M+H)⁺: m/z=447.2. Found: 447.1.

The diastereoisomers are assigned as 3-amino-N-{4-[(3S)-3-aminopiperidin-1-yl]-(7R)-7-hydroxy-6,7-dihydro-5H-cyclopenta[b]pyridin-3-yl}-7-ethylquinoline-2-carboxamide and 3-amino-N-{4-[(3S)-3-aminopiperidin-1-yl]-(7S)-7-hydroxy-6,7-dihydro-5H-cyclopenta[b]pyridin-3-yl}-7-ethylquinoline-2-carboxamide.

Example 23

3-Amino-N-[4-(3-amino cyclohexyl)pyridin-3-yl]-7-ethylquinoline-2-carboxamide

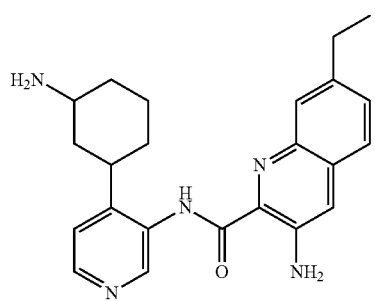 [SMILES: CCc1ccc2cc(N)c(C(=O)Nc3cnccc3C3CCCC(N)C3)nc2c1]

Step 1. 3-(4,4,5,5-Tetramethyl-1,3,2-dioxaborolan-2-yl)cyclohex-2-en-1-one

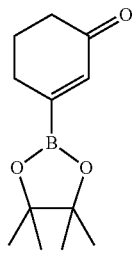 [SMILES: CC1(C)OB(C2=CC(=O)CCC2)OC1(C)C]

To a mixture of 1,3-cyclohexanedione (5.0 g, 44 mmol), sodium carbonate (4.7 g, 44 mmol) in DCM (75 mL), trifluoromethanesulfonic anhydride in DCM (1.0 M; 44 mL, 44 mmol) was added dropwise over 1 h at 0° C. under nitrogen. The reaction mixture was stirred at room temperature for 2 h. The solution was filtered and the filtrate was carefully washed with NaHCO$_3$ solution followed with brine. The combined organic layers were dried with Na$_2$SO$_4$, filtered through short silica gel plug and concentrated to give a triflate intermediate. The intermediate was dissolved in 1,4-dioxane (60 mL), and potassium acetate (6.6 g, 67 mmol), 4,4,5,5,4',4',5',5'-octamethyl-[2,2']bi[[1,3,2]dioxaborolanyl](11 g, 44 mmol) and [1,1'-bis(diphenylphosphino)ferrocene]dichloropalladium(II) complex with DCM (1:1) (1.8 g, 2.2 mmol) were added. The reaction mixture was deoxygenated with nitrogen, and then heated at 80° C. for 2 h. The reaction mixture was filtered and the crude sub-title compound was used for the next step without further purification. LCMS calc. for C$_{12}$H$_{20}$BO$_3$ (M+H)$^+$: m/z=223.1. Found: 223.1.

Step 2. 3-(3-Nitropyridin-4-yl)cyclohex-2-en-1-one

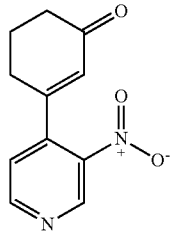

To a solution of 3-(4,4,5,5-tetramethyl-1,3,2-dioxaborolan-2-yl)cyclohex-2-en-1-one (6.0 g, 27 mmol) and 4-chloro-3-nitropyridine (2.4 g, 15 mmol) in 1,4-dioxane (60 mL), 2.0 N aq. Na$_2$CO$_3$ (12 mL, 24 mmol) and tetrakis(triphenylphosphine)palladium(0) (1.8 g, 1.5 mmol) were added. The reaction mixture was heated at 120° C. for 1 h. The reaction mixture was filtered through diatomaceous earth, which was washed with EtOAc. The filtrate was concentrated under reduced pressure and the residue was purified by silica gel column chromatography (eluting with 10-100% EtOAc in hexanes) to give the sub-title compound as a brown solid (1.97 g, 87%). LCMS calc. for C$_{11}$H$_{11}$N$_2$O$_3$ (M+H)$^+$: m/z=219.1. Found: 219.0.

Step 3. 3-(3-Nitropyridin-4-yl)cyclohex-2-en-1-ol

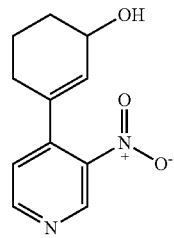

To a solution of 3-(3-nitropyridin-4-yl)cyclohex-2-en-1-one (1.9 g, 8.7 mmol) and cerium trichloride (4.2 g, 11 mmol) in EtOH (30 mL) at 0° C., sodium tetrahydroborate (0.43 g, 11 mmol) was slowly added. The reaction mixture was stirred at 0° C. for 2 h, then quenched with water (40 mL). After vacuum filtration, the residue was diluted with EtOAc. The aqueous layer was extracted three times with EtOAc. The combined organic layers were dried, filtered and concentrated under reduced pressure to give a crude product, which was further purified by silica gel column chromatography (eluting with 0-30% MeOH in EtOAc) to give the sub-title compound (1.06 g, 55%). LCMS calc. for C$_{11}$H$_{13}$NO$_3$ (M+H)$^+$: m/z=221.1. Found: 221.1.

Step 4. 2-[3-(3-Nitropyridin-4-yl)cyclohex-2-en-1-yl]-1H-isoindole-1,3(2H)-dione

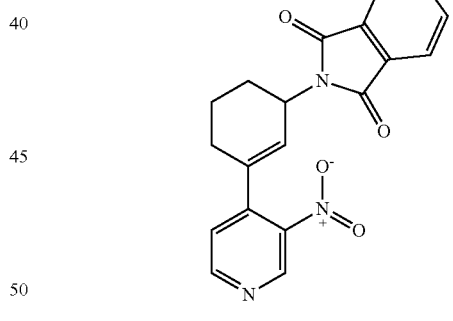

To a solution of 3-(3-nitropyridin-4-yl)cyclohex-2-en-1-ol (1.0 g, 4.5 mmol), phthalimide (1.0 g, 6.8 mmol) and triphenylphosphine (1.8 g, 6.8 mmol) in THF (20 mL), di-tert-butyl azodicarboxylate (1.6 g, 6.8 mmol) was added slowly at 0° C. The resulting mixture was stirred at 0° C. for 3 h. After concentrated concentrating under reduced pressure, the crude product was purified by silica gel column chromatography (eluting with 0-70% EtOAc in hexanes) to give a solid, which was further treated with DCM and hexanes to yield sub-title compound (1.55 g, 98%). LCMS calc. for C$_{19}$H$_{16}$N$_3$O$_4$ (M+H)$^+$: m/z=350.1. Found: 350.3.

Step 5. 2-[3-(3-Aminopyridin-4-yl)cyclohexyl]-1H-isoindole-1,3(2H)-dione

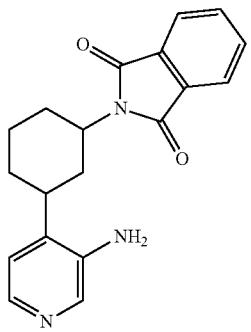 [SMILES: Nc1cnccc1C1CCCC(N2C(=O)c3ccccc3C2=O)C1]

A solution of 2-[3-(3-nitropyridin-4-yl)cyclohex-2-en-1-yl]-1H-isoindole-1,3(2H)-dione (0.100 g, 0.286 mmol) in AcOH (3.0 mL) was mixed with 10% Pd on carbon (0.046 g, 0.043 mmol) and hydrogenated at 30 psi for 16 h. The reaction mixture was diluted in MeOH (50 mL), filtered and concentrated under vacuum. The residue was dissolved in EtOAc and washed with 1 M NaOH. The organic layer was dried over $Na_2SO_4$, filtered and concentrated under reduced pressure to give the sub-title compound. LCMS calc. for $C_{19}H_{20}N_3O_2$ $(M+H)^+$: m/z=322.2. Found: 322.1.

Step 6. 3-Amino-N-[4-(3-aminocyclohexyl)pyridin-3-yl]-7-ethylquinoline-2-carboxamide A mixture of 3-amino-7-ethylquinoline-2-carboxylic acid (0.040 g, 0.18 mmol), 2-[3-(3-aminopyridin-4-yl)cyclohexyl]-1H-isoindole-1,3(2H)-dione (0.055 g, 0.17 mmol), HATU (0.22 g, 0.58 mmol), DMF (0.65 mL) and DIPEA (0.076 g, 0.59 mmol) was stirred at room temperature for 16 h. Aq. NaOH (1 M) was added to the reaction mixture, and a precipitate formed, which was collected by vacuum filtration. The collected solid was washed with 1 M NaOH, followed by water and dried under vacuum to afford an intermediate. The intermediate was dissolved in DMF (0.15 mL) and hydrazine (0.15 mL) was added. The resulting reaction mixture was stirred at room temperature for 16 h, diluted with MeOH, filtered and purified by preparative LC MS (XBridge™ preparative C18 5 μm 30×10 mm OBD™ column, flow rate 60 mL/min., eluting with a gradient of MeCN and water with 0.15% $NH_4OH$) to give title compound. LCMS calc. for $C_{23}H_{28}N_5O$ $(M+H)^+$: m/z=390.2. Found: 390.1.

The title compound is resolved to provide 3-amino-N-[4-((3S)-3-aminocyclohexyl)pyridin-3-yl]-7-ethylquinoline-2-carboxamide and 3-amino-N-[4-((3R)-3-aminocyclohexyl)pyridin-3-yl]-7-ethylquinoline-2-carboxamide.

Example 24

(S)-3-Amino-N-(4-(3-aminopiperidin-1-yl)-2,3-dihydrofuro[2,3-b]pyridin-5-yl)-7-ethylquinoline-2-carboxamide

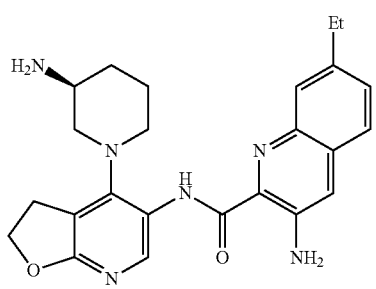 [SMILES: CCc1ccc2cc(N)c(C(=O)Nc3cnc4c(c3N3CCC[C@H](N)C3)CCO4)nc2c1]

Step 1. 2-(2-Fluoro-4-iodopyridin-3-yl)ethanol

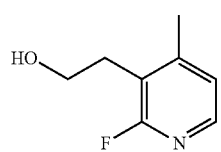

To a solution of 2-fluoro-3-iodopyridine (Ark Pharm, 2.989 g, 13.40 mmol) in THF (50 mL) at −78° C., a solution of lithium diisopropylanide in heptane/THF/ethylbenzene (2.0 M; 8.10 mL, 16.2 mmol) was added. The mixture was stirred at −78° C. for 90 min. A solution of 1,3,2-dioxathiolane 2,2-dioxide (2.206 g, 17.77 mmol) in THF (30 mL) was then added slowly to the mixture at −78° C., over a period of 20 min. After stirring at −78° C. for 20 min., the reaction mixture was allowed to warm to room temperature and stirred for 2 h. The mixture was then cooled to 0° C., and 12.0 M HCl in water (5.0 mL, 60 mmol) was added. The reaction was allowed to warm to room temperature and stirred for 3 h. Saturated aq. $NaHCO_3$ (250 mL) was added. The mixture was extracted with EtOAc (3×150 mL). The combined extracts were washed with brine (250 mL), dried over $Na_2SO_4$ and concentrated under reduced pressure. The residue was purified by flash chromatography on silica gel (0-100% EtOAc in hexanes) to give the sub-title compound as a white solid (3.13 g, 87%). LCMS calc. for $C_7H_8FINO$ $(M+H)^+$: m/z=268.0. found 268.0.

Step 2. 4-Iodo-2,3-dihydrofuro[2,3-b]pyridine

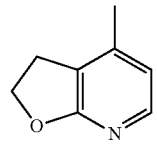

To a solution of 2-(2-fluoro-4-iodopyridin-3-yl)ethanol (3.13 g, 11.7 mmol) in 1,4-dioxane (100 mL), $K_3PO_4$ (10.0 g, 47.1 mmol) was added. The mixture was heated under reflux for 36 h. The reaction mixture was then filtered, the filter cake was washed with EtOAc, and the combined filtrates were concentrated under reduced pressure. The residue was dissolved in DCM (100 mL), washed with brine (2×100 mL), dried over $Na_2SO_4$ and concentrated. The resulting residue of the crude sub-title compound (2.55 g) was used in the next step directly without further purification. LCMS calc. for $C_7H_7INO$ $(M+H)^+$: m/z=247.9. found 248.0.

Step 3. 4-Iodo-5-nitro-2,3-dihydrofuro[2,3-b]pyridine

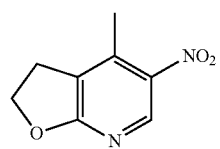

4-Iodo-2,3-dihydrofuro[2,3-b]pyridine (2.237 g, 9.055 mmol) in sulfuric acid (10.0 mL, 188 mmol) at −10° C. was added slowly to a stirred solution of a solution of fuming nitric acid (15.0 mL, 358 mmol) in sulfuric acid (15.0 mL, 281 mmol) slowly over a period of 15 min. The reaction mixture was allowed to warm to room temperature and stirred for 16 h. The reaction mixture was then quenched by addition onto crushed ice and the resulting mixture was extracted with EtOAc (6×100 mL). The combined organic extract was washed with saturated aq. NaHCO$_3$ (2×300 mL) and brine (300 mL), dried over Na$_2$SO$_4$ and concentrated under reduced pressure. The residue was purified by flash chromatography on silica gel (0-100% EtOAc in hexanes) to give the sub-title compound as a pale yellow solid (2.43 g, 92%). LCMS calc. for C$_7$H$_6$IN$_2$O$_3$(M+H)$^+$: m/z=292.9. found 293.0.

Step 4. tert-Butyl [(3S)-1-(5-nitro-2,3-dihydrofuro[2,3-b]pyridin-4-yl)piperidin-3-yl]carbamate

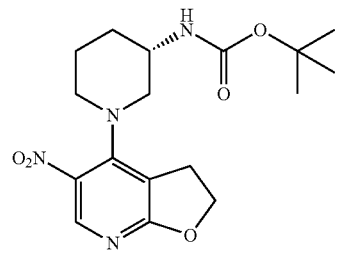 [SMILES: CC(C)(C)OC(=O)N[C@H]1CCCN(c2c([N+](=O)[O-])cnc3c2CCO3)C1]

A microwave vial containing 4-iodo-5-nitro-2,3-dihydrofuro[2,3-b]pyridine (2.05 g, 7.02 mmol), tert-butyl (3S)-piperidin-3-ylcarbamate (Combi-Blocks, 1.489 g, 7.435 mmol), DIPEA (1.836 g, 14.20 mmol) and EtOH (12.0 mL) was heated under microwave irradiation at 100° C. for 2 h. The reaction was then concentrated under reduced pressure. The resulting residue was purified by flash chromatography on silica gel (0-100% EtOAc in hexanes) to give the sub-title compound as a yellow solid (2.46 g, 96%). LCMS calc. for C$_{17}$H$_{25}$N$_4$O$_5$ (M+H)$^+$: m/z=365.2. found 365.1.

Step 5. tert-Butyl [(3S)-1-(5-amino-2,3-dihydrofuro[2,3-b]pyridin-4-yl)piperidin-3-yl]carbamate

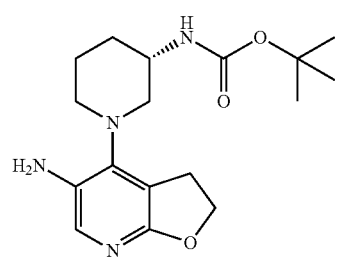

To a solution of tert-butyl [(3S)-1-(5-nitro-2,3-dihydrofuro[2,3-b]pyridin-4-yl)piperidin-3-yl]carbamate (411.2 mg, 1.128 mmol) in MeOH (5.00 mL) under a nitrogen atmosphere was added 10% Pd on carbon (108.7 mg, 0.1021 mmol). The reaction mixture was hydrogenated at 1 atm. for 14 h. The mixture was then filtered through a pad of diatomaceous earth (eluted with MeOH). The filtrate was concentrated under reduced pressure to give the sub-title compound as an off-white solid (387.9 mg) which was used directly in the next step without further purification. LCMS calc. for C$_{17}$H$_{27}$N$_4$O$_3$ (M+H)$^+$: m/z=335.2. found 335.2.

Step 6. 3-{[(Benzyloxy)carbonyl]amino}-7-vinylquinoline-2-carboxylic acid

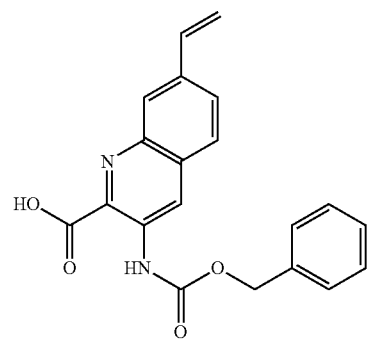 [SMILES: C=Cc1ccc2cc(NC(=O)OCc3ccccc3)c(C(=O)O)nc2c1]

To a screw-cap vial equipped with a magnetic stir bar, ethyl 3-{[(benzyloxy)carbonyl]amino}-7-bromoquinoline-2-carboxylate (Example 1, step 3, 971.6 mg, 2.263 mmol), chloro(2-dicyclohexylphosphino-2',4',6'-triisopropyl-1,1'-biphenyl)[2-(2'-amino-1,1'-biphenyl)]palladium(II) (Aldrich, 163.8 mg, 0.2082 mmol) and K$_3$PO$_4$ (1017.1 mg, 4.7916 mmol) were added. The vial was sealed with a Teflon-lined septum, evacuated and backfilled with nitrogen (this process was repeated a total of three times). A solution of vinylboronic acid pinacol ester (561.6 mg, 3.646 mmol) in 1,4-dioxane (10.0 mL) was added via a syringe, followed by deoxygenated water (8.0 mL). The mixture was then heated at 90° C. for 6 h. After the reaction was cooled to room temperature, water (50 mL) was added. AcOH (1.50 mL, 26.4 mmol) was added to adjust the pH to 5. The mixture was extracted with EtOAc (3×50 mL). The combined organic layer was washed with brine (100 mL), dried over Na$_2$SO$_4$ and concentrated under reduced pressure. The resulting residue was purified by flash chromatography on silica gel (0-10% MeOH in DCM) to give the title compound as a yellow solid (673.9 mg, 85%). LCMS calc. for C$_{20}$H$_{17}$N$_2$O$_4$ (M+H)$^+$: m/z=349.1. found 349.1.

Step 7. 3-Amino-7-ethylquinoline-2-carboxylic acid

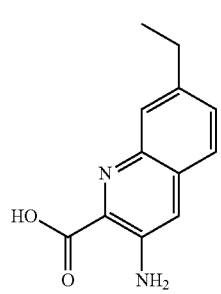 [SMILES: CCc1ccc2cc(N)c(C(=O)O)nc2c1]

To a solution of 3-{[(benzyloxy)carbonyl]amino}-7-vinylquinoline-2-carboxylic acid (673.9 mg, 1.934 mmol) in MeOH (25.0 mL) was added 10 wt % Pd on carbon (100.1 mg, 0.09406 mmol). The mixture was stirred at room Step 8. 3-Amino-N-{4-[(3S)-3-aminopiperidin-1-yl]-2,3-dihydrofuro[2,3-b]pyridin-5-yl}-7-ethylquinoline-2-carboxamide

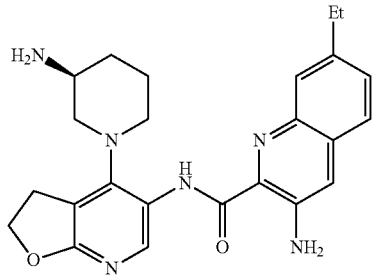 [SMILES: CCc1ccc2cc(N)c(C(=O)Nc3cnc4c(c3N3CCC[C@H](N)C3)CCO4)nc2c1]

3-Amino-7-ethylquinoline-2-carboxylic acid (24.5 mg, 0.113 mmol), tert-butyl [(3S)-1-(5-amino-2,3-dihydrofuro[2,3-b]pyridin-4-yl)piperidin-3-yl]carbamate (38.3 mg, 0.114 mmol) and HATU (136.1 mg, 0.3579 mmol), DMF (2.00 mL) was added, followed by DIPEA (152.9 mg, 1.183 mmol). The reaction mixture was stirred at room temperature for 3 h and then concentrated under reduced pressure. To the resulting residue DCM (2.0 mL) was added followed by T (2.0 mL). The mixture was stirred at room temperature for 30 min. and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a yellow solid (5.7 mg, 12%). LCMS calc. for C$_{24}$H$_{29}$N$_6$O$_2$ (M+H)$^+$: m/z=433.2. found 433.2. $^1$H NMR (500 MHz, DMSO-d$_6$) δ 8.82 (s, 1H), 7.65-7.61 (m, 2H), 7.51 (s, 1H), 7.37 (dd, J=8.6, 1.5 Hz, 1H), 6.81 (s, 2H), 4.52 (t, J=8.6 Hz, 2H), 3.46-3.39 (m, 2H), 3.22-3.17 (m, 1H), 3.17-3.10 (m, 1H), 3.07-3.00 (m, 1H), 2.88-2.81 (m, 1H), 2.76 (q, J=7.5 Hz, 2H), 2.67-2.59 (m, 1H), 2.00-1.92 (m, 1H), 1.92-1.79 (m, 2H), 1.28 (t, J=7.5 Hz, 3H), 1.26-1.20 (m, 1H) ppm.

Example 25

3-Amino-N-{4-[(3S)-3-aminopiperidin-1-yl]pyridin-3-yl}-7-ethoxy-1,8-naphthyridine-2-carboxamide

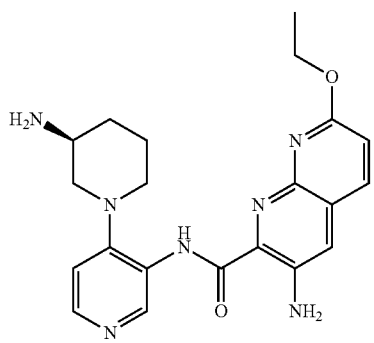 [SMILES: CCOc1ccc2cc(N)c(C(=O)Nc3cnccc3N3CCC[C@H](N)C3)nc2n1]

Step 1. 2-Amino-6-bromonicotinaldehyde

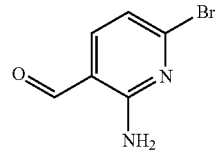

A solution of LiAlH$_4$ in THF (2.0 M, 1.7 mL, 3.4 mmol) was added dropwise to a solution of 2-amino-6-bromonicotinic acid (from Ark Pharm, 350 mg, 1.61 mmol) in anhydrous THF (8.2 mL) at 0° C., causing some effervescence. The solution was allowed to warm to ambient temperature gradually while stirring for 4 h. The reaction was quenched by the sequential addition of H$_2$O (129 μL), 15% aq. NaOH (129 μL) and H$_2$O (388 μL). The solution was stirred vigorously for 1 h, a precipitate was removed by filtration and the filtrate was concentrated under reduced pressure and used for the next reaction.

The crude alcohol prepared by the LiAlH$_4$ reduction was dissolved in hot DCM (25 mL) and then allowed to cool to ambient temperature prior to the addition of manganese(IV) oxide (743 mg, 8.55 mmol). The mixture was stirred for 16 h at ambient temperature. The crude reaction mixture was filtered through a pad of diatomaceous earth and the inorganics were washed thoroughly with EtOAc. The filtrate was concentrated under reduced pressure and the crude product was used directly in the next step without further purification. LCMS (ESI) calc. for C$_6$H$_6$BrN$_2$O [M+H]$^+$: m/z=201.0. found: 200.9.

Step 2. Ethyl 3-amino-7-ethoxy-1,8-naphthyridine-2-carboxylate

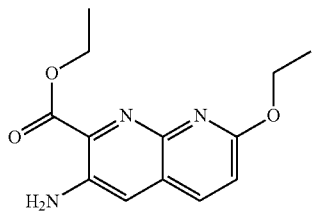 [SMILES: CCOC(=O)c1nc2nc(OCC)ccc2cc1N]

A solution of pyridine (0.13 mL, 1.6 mmol) and ethyl bromopyruvate (0.22 mL, 1.7 mmol) in EtOH (0.5 mL) was stirred at 70° C. in a sealed vial for 16 h. The reaction mixture was allowed to cool to ambient temperature and a solution of 2-amino-6-bromonicotinaldehyde (317 mg, 1.58 mmol) and pyridine (0.76 mL, 9.5 mmol) in EtOH (1 mL) was added. The reaction mixture then was heated at 100° C. in a sealed vial for 16 h. Pyrrolidine (0.26 mL, 3.2 mmol) was added, and stirring in the sealed vial was continued at 100° C. i for 16 h. The crude reaction mixture was purified by flash chromatography (40 g silica gel column, eluting with 0-100% EtOAc/hexanes) to afford the sub-title compound. LCMS (ESI) calc. for C$_{13}$H$_{16}$N$_3$O$_3$ [M+H]$^+$: m/z=262.1. found: 262.0.

Step 3. Ethyl 3-{[(benzyloxy)carbonyl]amino}-7-ethoxy-1,8-naphthyridine-2-carboxylate

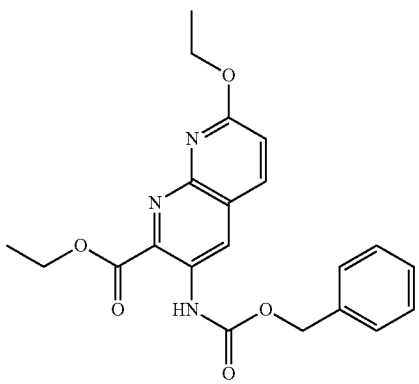 [SMILES: CCOC(=O)c1nc2nc(OCC)ccc2cc1NC(=O)OCc1ccccc1]

To a solution of ethyl 3-amino-7-ethoxy-1,8-naphthyridine-2-carboxylate (51 mg, 0.20 mmol) and DIPEA (100 µL, 0.58 mmol) in DCM (0.7 mL), benzyl chloroformate (84 µL, 0.58 mmol) was added and the reaction mixture was heated at 65° C. with stirring in a sealed vial for 16 h. The crude reaction mixture was concentrated under reduced pressure and the residue was purified by flash chromatography (24 g silica gel column, eluting with 0-40% EtOAc/hexanes) to afford the sub-title compound. LCMS (ESI) calc. for $C_{21}H_{22}N_3O_5$ [M+H]$^+$: m/z=396.2. found: 396.1.

Step 4. 3-{[(Benzyloxy)carbonyl]amino}-7-ethoxy-1,8-naphthyridine-2-carboxylic acid

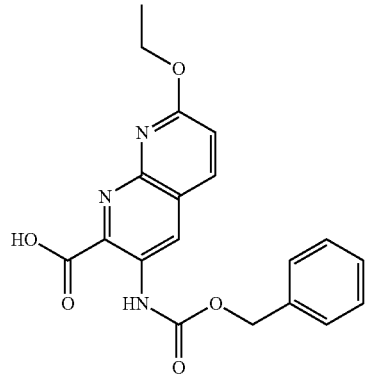 [SMILES: CCOc1ccc2cc(NC(=O)OCc3ccccc3)c(C(=O)O)nc2n1]

A solution containing ethyl 3-{[(benzyloxy)carbonyl]amino}-7-ethoxy-1,8-naphthyridine-2-carboxylate (47 mg, 0.12 mmol) and lithium hydroxide monohydrate (25 mg, 0.59 mmol) in THF (2.0 mL) and water (1.0 mL) was heated at 65° C. in a sealed vial for 2 h. A precipitate was filtered off and washed with EtOAc to afford the sub-title compound (11 mg). The filtrate was diluted with water (1 mL) and the solution was extracted with EtOAc (2×5 mL). The combined organic extract were washed with brine (3 mL), dried over $Na_2SO_4$, filtered and concentrated under reduced pressure to give additional sub-title compound (30 mg). The crude product was used directly in the subsequent reaction. LCMS (ESI) calc. for $C_{19}H_{18}N_3O_5$ [M+H]$^+$: m/z=368.1. found: 368.0.

Step 5. 3-Amino-N-{4-[(3S)-3-aminopiperidin-1-yl]pyridin-3-yl}-7-ethoxy-1,8-naphthyridine-2-carboxamide tert-Butyl [(3S)-1-(3-aminopyridin-4-yl)piperidin-3-yl]carbamate (9.6 mg, 0.033 mmol) and DMF (100 µL) were added to a stirred solution of 3-{[(benzyloxy)carbonyl]amino}-7-ethoxy-1,8-naphthyridine-2-carboxylic acid (11 mg, 0.030 mmol), HATU (17 mg, 0.045 mmol) and DIPEA (16 µL, 0.090 mmol) in 1,2-dichloroethane (0.6 mL), and the resulting solution was heated at 55° C. for 16 h. The crude reaction mixture was concentrated under reduced pressure and the residue was purified by flash chromatography (12 g silica gel column, eluting with 0-100% EtOAc/hexanes) to give a benzyloxycarbonyl/Boc-protected intermediate (18 mg, 95%).

The benzyl carbamate intermediate was stirred with 10% Pd on activated carbon (wet, Degussa type E101 NE/W) (13 mg) in MeOH (3 mL) under an atmosphere of hydrogen at atmospheric pressure (balloon) for 1.5 h. The crude reaction mixture was filtered through a pad of diatomaceous earth and the inorganics were washed thoroughly with EtOAc. The filtrate was concentrated under reduced pressure and the residue was used directly in the following Boc deprotection reaction.

The residue from the preceding reaction was stirred with TFA (1 mL) in DCM (3 mL). After 1 h, the crude reaction mixture was concentrated under reduced pressure and the residue was purified by preparative HPLC (XBridge™ C18 column, eluting with a gradient of MeCN/water containing 0.05% TFA, at a flow rate of 60 mL/min.) to afford the title compound as the tris-trifluoroacetate salt. LCMS (ESI) calc. for $C_{21}H_{26}N_7O_2$ [M+H]$^+$: m/z=408.2. found: 408.1.

Example 26

3-Amino-N-{4-[(3R,4R,5S)-3-amino-4-hydroxy-5-methylpiperidin-1-yl]pyridin-3-yl}-7-ethoxy-1,8-naphthyridine-2-carboxamide

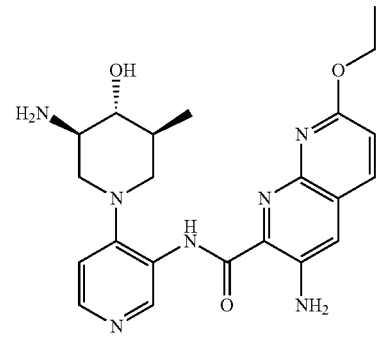 [SMILES: CCOc1ccc2cc(N)c(C(=O)Nc3cnccc3N3C[C@@H](N)[C@H](O)[C@@H](C)C3)nc2n1]

Step 1. tert-Butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate

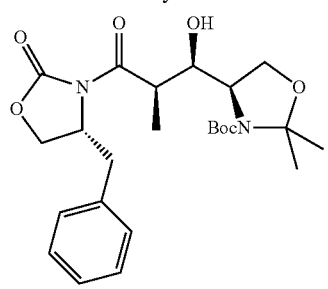

To a solution of (R)-3-(1-oxopropyl)-4-benzyl-2-oxazolidinone (Aldrich, 2.0 g, 8.6 mmol) in DCM (60 mL) at −40° C., a solution of TiCl$_4$ in DCM (1.0 M, 10.0 mL, 10.0 mmol) was added. The mixture was stirred at −40° C. for 10 min., then DIPEA (3.7 mL, 21 mmol) was added. The reaction mixture was allowed to warm to 0° C. and stirred for 20 min. A solution of tert-butyl (4R)-4-formyl-2,2-dimethyl-1,3-oxazolidine-3-carboxylate (Aldrich, 2.0 g, 8.7 mmol) in DCM (20 mL) was then added dropwise and the resulting mixture was stirred for 1.5 h. The reaction was quenched by the addition of a saturated aq. NH$_4$Cl and the mixture was extracted with EtOAc. The separated organic phase was washed with brine, dried over MgSO$_4$, and concentrated under reduced pressure. The residue was purified by flash chromatography on silica gel (eluting with 0-40% EtOAc in hexanes) to give the sub-title compound as the major product (5:2) in 87% yield (3.44 g). LCMS calc. for C$_{24}$H$_{34}$N$_2$NaO$_7$ (M+Na)$^+$: m/z=485.2. found 485.1.

Step 2. tert-Butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate

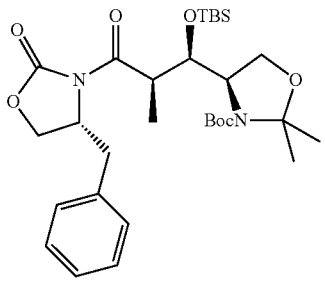 [SMILES: C[C@@H](C(=O)N1C(=O)OC[C@H]1Cc1ccccc1)[C@@H](O[Si](C)(C)C(C)(C)C)[C@H]1COC(C)(C)N1C(=O)OC(C)(C)C]

To a solution of tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate (2.0 g, 4.3 mmol) in DCM (40 mL) at −40° C., 2,6-lutidine (0.90 mL, 7.8 mmol) was added, followed by tert-butyieldimethylsilyltrifluoromethanesulfonate (1.4 mL, 6.0 mmol). The mixture was stirred at −40° C. for 2 h. The reaction mixture was diluted with EtOAc, washed with saturated aq. NaHCO$_3$ and brine, then dried over MgSO$_4$, and concentrated under reduced pressure. The residue was purified by flash chromatography on silica gel (0-20% EtOAc in hexanes) to afford the sub-title compound (2.2 g, 88%). LCMS calc. for C$_{30}$H$_{49}$N$_2$O$_7$Si (M+H)$^+$: m/z=577.3. found 577.3.

Step 3. tert-Butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate

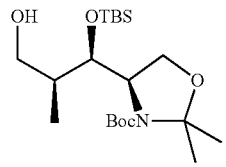 [SMILES: C[C@@H](CO)[C@@H](O[Si](C)(C)C(C)(C)C)[C@H]1COC(C)(C)N1C(=O)OC(C)(C)C]

LiBH$_4$ (0.25 g, 11 mmol) was added to a mixture of tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate (2.2 g, 3.8 mmol) and EtOH (0.67 mL, 11 mmol) in THF (40 mL) at −30 OC. The mixture was allowed to warm to 0° C. and stirred for 3 h. The reaction mixture was then diluted with Et$_2$O and 1 M NaOH was added. The resulting mixture was extracted with EtOAc. The separated organic extract was washed with brine, dried over MgSO$_4$, and concentrated under reduced pressure. The residue was purified by flash chromatography on silica gel (eluting with 0-20% EtOAc in hexanes) to give the sub-title compound (1.2 g, 78%). LCMS calc. for C$_{15}$H$_{34}$NO$_3$Si (M+H−Boc)$^+$: m/z=304.2. found 304.2.

Step 4. tert-Butyl (4R)-4-((1R,2S)-3-azido-1-{[tert-butyl(dimethyl)silyl]oxy}-2-methylpropyl)-2,2-dimethyl-1,3-oxazolidine-3-carboxylate

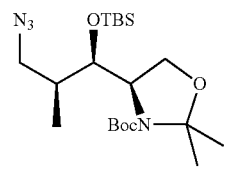 [SMILES: C[C@@H](CN=[N+]=[N-])[C@@H](O[Si](C)(C)C(C)(C)C)[C@H]1COC(C)(C)N1C(=O)OC(C)(C)C]

Diphenylphosphonic azide (1.3 mL, 5.9 mmol) was added to a mixture of tert-butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate (1.2 g, 3.0 mmol), diisopropyl azodicarboxylate (1.2 mL, 5.9 mmol) and PPh$_3$ (1.6 g, 5.9 mmol) in THF (20 mL). The mixture was stirred at room temperature overnight. The reaction mixture was then concentrated under reduced pressure. The residue was purified by flash chromatography on silica gel (eluting with 0-15% EtOAc in hexanes) to provide the sub-title compound (1.09 g, 86%). LCMS calc. for C$_{15}$H$_{33}$N$_4$O$_2$Si (M+H−Boc)$^+$: m/z=329.2. found 329.2.

Step 5. tert-Butyl [(1R,2R,3S)-4-azido-2-{[tert-butyl(dimethyl)silyl]oxy}-1-(hydroxymethyl)-3-methylbutyl]carbamate

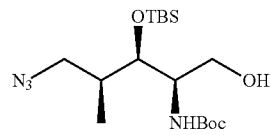 [SMILES: C[C@@H](CN=[N+]=[N-])[C@@H](O[Si](C)(C)C(C)(C)C)[C@@H](CO)NC(=O)OC(C)(C)C]

Pyridinium p-toluenesulfonate (1.3 g, 5.2 mmol) was added to a solution of tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate (1.09 g, 2.6 mmol) in EtOH (15 mL). The mixture was heated under reflux for 2 days. After cooling to room temperature, the reaction mixture was concentrated under reduced pressure. The residue was dissolved in DCM (25 mL), and DIPEA (0.67 mL, 3.8 mmol) was added followed by Boc$_2$O (0.67 g, 3.1 mmol). The mixture was stirred at room temperature for 5 h, and then concentrated under reduced pressure. The residue was purified by flash chromatography on silica gel (eluting with Step 6. (2R,3R,4S)-5-azido-2-[(tert-butoxycarbonyl) amino]-3-{[tert-butyl(dimethyl)silyl]oxy}-4-methyl-pentyl methanesulfonate

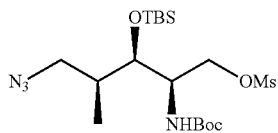 [SMILES: C[C@@H](CN=[N+]=[N-])[C@@H](O[Si](C)(C)C(C)(C)C)[C@@H](COS(C)(=O)=O)NC(=O)OC(C)(C)C]

To a stirred solution of tert-butyl [(1R,2R,3S)-4-azido-2-{[tert-butyl(dimethyl)silyl]oxy}-1-(hydroxymethyl)-3-methylbutyl]carbamate (0.56 g, 1.4 mmol) in pyridine (7.3 mL) at 0° C., methanesulfonyl chloride (0.14 mL, 1.9 mmol) was added followed by DMAP (0.04 g, 0.3 mmol). After stirring at 0° C. for 1 h, the mixture was diluted with EtOAc, washed with a saturated aq. NaHCO$_3$ and brine, dried over MgSO$_4$, and concentrated under reduced pressure. The residue was purified by flash chromatography on silica gel (eluting with 0-25% EtOAc in hexanes) to provide the sub-title compound (0.59 g, 88%). LCMS calc. for $C_{13}H_{31}N_4O_4SSi$ (M+H–Boc)$^+$: m/z=367.2. found 367.2.

Step 7. tert-butyl ((3R,4R,5S)-4-{[tert-butyl(dimethyl)silyl]oxy}-5-methylpiperidin-3-yl)carbamate

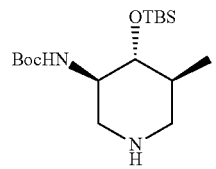

A solution of (2R,3R,4S)-5-azido-2-[(tert-butoxycarbonyl)amino]-3-{[tert-butyl(dimethyl)silyl]oxy}-4-methyl-pentyl methanesulfonate (0.59 g, 1.3 mmol) in MeOH (10 mL) was deoxygenated with nitrogen for 20 min. DIPEA (0.55 mL, 3.2 mmol) was added, followed by 10 wt % Pd on carbon (0.1 g, 0.1 mmol). The mixture was hydrogenated under hydrogen gas at 1 atm. for 2 h. The reaction mixture was then filtered and the filtrate was concentrated under reduced pressure to give the sub-title compound (0.43 g, 98%). LCMS calc. for $C_{17}H_{37}N_2O_3Si$ (M+H)$^+$: m/z=345.3. found: 345.2. $^1$H NMR (500 MHz, CDCl$_3$) δ 4.35 (bs, 1H), 3.32 (dt, J=13.1, 6.3 Hz, 1H), 3.25 (d, J=12.3 Hz, 1H), 3.04 (t, J=8.8 Hz, 1H), 2.94 (ddd, J=13.1, 4.1, 1.5 Hz, 1H), 2.33 (dd, J=12.6, 10.5 Hz, 1H), 2.24 (dd, J=13.1, 10.9 Hz, 1H), 1.76 (bs, 1H), 1.55 (tdd, J=8.9, 6.7, 4.2 Hz, 1H), 1.41 (s, 9H), 0.92 (d, J=6.6 Hz, 3H), 0.87 (s, 9H), 0.07 (d, J=10.3 Hz, 6H) ppm.

Step 8. tert-Butyl [(3R,4R,5S)-4-{[tert-butyl(dimethyl)silyl]oxy}-5-methyl-1-(3-nitropyridin-4-yl)piperidin-3-yl]carbamate

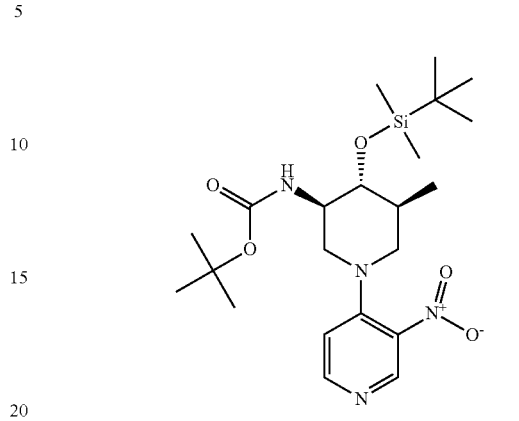

A mixture of 4-chloro-3-nitropyridine (96.6 mg, 0.609 mmol), tert-butyl ((3R,4R,5S)-4-{[tert-butyl(dimethyl)silyl]oxy}-5-methylpiperidin-3-yl)carbamate (300 mg, 0.609 mmol) and DIPEA (0.319 mL, 1.83 mmol) in isopropyl alcohol (20 mL) was stirred at 100° C. for 4 h. The reaction mixture was concentrated under reduced pressure. The resulting residue was purified by flash chromatography on silica using a CombiFlash® apparatus (eluting with 0 to 30% EtOAc in hexanes) to give the sub-title compound as a pale yellow powder (1.93 g). LCMS calc. for $C_{22}H_{39}N_4O_5Si$ (M+H)$^+$: m/z=467.3. found: 467.1.

Step 9. tert-Butyl ((3R,4R,5S)-1-(3-aminopyridin-4-yl)-4-{[tert-butyl(dimethyl)silyl]oxy}-5-methylpiperidin-3-yl)carbamate

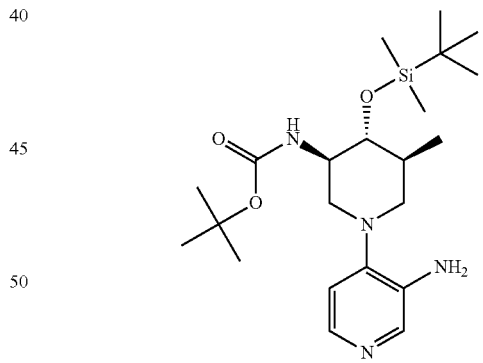

A mixture of tert-butyl [(3R,4R,5S)-4-{[tert-butyl(dimethyl)silyl]oxy}-5-methyl-1-(3-nitropyridin-4-yl)piperidin-3-yl]carbamate (130 mg, 0.279 mmol), AcOH (10.0 mL, 176 mmol) and iron powder (558 mg, 1.00 mmol) was stirred at room temperature for 2 h. The mixture was diluted with 30 mL of EtOAc and filtered through a pad of diatomaceous earth and the filtrate was then concentrated under reduced pressure. The resulting residue was diluted with EtOAc and then washed with aq. Na$_2$CO$_3$ solution and 0.2 M NaOH. The organic extract was concentrated under reduced pressure to give 0.622 g of the sub-title compound as a brown solid. LCMS calc. for $C_{22}H_{41}N_4O_3Si$ (M+H)$^+$: m/z=437.3. found: 437.1.

Step 10. 3-Amino-N-{4-[(3R,4R,5S)-3-amino-4-hydroxy-5-methylpiperidin-1-yl]pyridin-3-yl}-7-ethoxy-1,8-naphthyridine-2-carboxamide To a stirred solution of 3-{[(benzyloxy)carbonyl]amino}-7-ethoxy-1,8-naphthyridine-2-carboxylic acid (18 mg, 0.049 mmol), HATU (28 mg, 0.073 mmol) and DIPEA (21 µL, 0.12 mmol) in 1,2-dichloroethane (400 µL) and DMF (50 µL), a solution of tert-butyl ((3R,4R,5S)-1-(3-aminopyridin-4-yl)-4-{[tert-butyl(dimethyl)silyl]oxy}-5-methylpiperidin-3-yl)carbamate (22 mg, 0.050 mmol) in 1,2-dichloroethane (300 µL) and DMF (100 µL) was added. The resulting mixture was stirred at 55° C. for 2 h. The crude reaction mixture was purified by flash column chromatography (24 g silica gel column, eluting with 0-5% MeOH/DCM) to afford a benzyloxycarbonyl/Boc/TBS protected intermediate product (28 mg, 73%).

The benzyloxycarbamate intermediate was dissolved in MeOH (1.5 mL) and treated with 10% Pd on activated carbon (wet, Degussa type E101 NE/W) and hydrogenated under an atmosphere of hydrogen (1 atm.) (balloon) for 1 h. The crude reaction mixture was filtered through a pad of diatomaceous earth and the inorganics were washed thoroughly with EtOAc then the filtrate was concentrated under reduced pressure to give a Boc/TBS-protected intermediate.

The residue was dissolved in MeCN (1.5 mL) and 1.7 M fluorosilicic acid in water (500 µL, 0.8 mmol) and the resulting solution was heated at 50° C. for 1 h. The crude reaction mixture was purified by preparative HPLC (XBridge™ C18 column, eluting with a gradient of MeCN/water containing 0.05% TFA, at a flow rate of 60 mL/min.) to afford the title compound as the tris(trifluoroacetate) salt. LCMS (ESI) calc. for $C_{22}H_{28}N_7O_3$ [M+H]$^+$: m/z 438.2. found: 438.1.

Example 27

3-Amino-N-{4-[(3S)-3-aminopiperidin-1-yl]pyridin-3-yl}-7-ethyl-1,6-naphthyridine-2-carboxamide

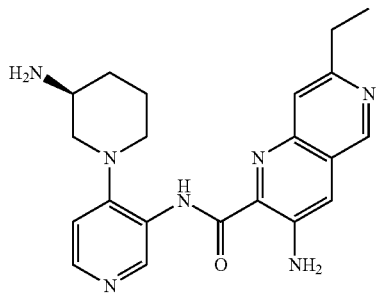 [SMILES: CCc1cc2nc(C(=O)Nc3cnccc3N3CCC[C@H](N)C3)c(N)cc2cn1]

Step 1. 4-Amino-6-bromonicotinaldehyde

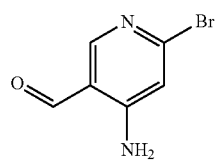

To a solution of 4-amino-6-bromonicotinic acid hydrochloride (from Anichem, 0.350 g, 1.38 mmol) at 0° C. in anhydrous THF (7 mL), LiAlH$_4$ in THF (2.0 M; 1.4 mL) was added dropwise, causing some effervescence. The solution was allowed to warm gradually to ambient temperature while stirring for 16 h. The reaction mixture was quenched by the sequential addition of H$_2$O (110 µL), 15% aq. NaOH (110 µL), and H$_2$O (330 µL). The solution was stirred vigorously for 1 h. The precipitate was filtered off, the inorganics were washed thoroughly with EtOAc and the filtrate was concentrated under reduced pressure.

The resulting residue was dissolved in DCM (7 mL) and manganese (IV) oxide (700 mg, 8.05 mmol) was added to the resulting solution. The reaction mixture was stirred at room temperature for 16 h. The crude reaction mixture was then filtered through a pad of diatomaceous earth and the inorganics were washed thoroughly with EtOAc. The filtrate was concentrated under reduced pressure and the crude aldehyde product was used directly in the subsequent reaction without further purification. LCMS (ESI) calc. for $C_6H_6BrN_2O$ [M+H]$^+$: m/z=201.0. found: 201.0.

Step 2. Ethyl 3-amino-7-bromo-1,6-naphthyridine-2-carboxylate

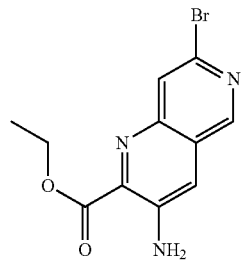 [SMILES: CCOC(=O)c1nc2cc(Br)ncc2cc1N]

A solution of pyridine (0.11 mL, 1.4 mmol) and ethyl bromopyruvate (0.19 mL, 1.5 mmol) in EtOH (2.2 mL) was stirred at 70° C. in a sealed vial for 16 h. The reaction mixture was allowed to cool to ambient temperature prior and a a solution of 4-amino-6-bromonicotinaldehyde (0.278 g, 1.38 mmol) and pyridine (0.67 mL, 8.3 mmol) in EtOH (1 mL) was then added. The resulting mixture was heated at 100° C. in a sealed vial for 16 h. Stirring was continued at 100° C. for an additional 24 h. Pyrrolidine (0.23 mL, 2.8 mmol) was added and stirring was continued at 100° C. for 5 h in a sealed vial. The crude reaction mixture was purified by flash chromatography (40 g silica gel column, eluting with 0-100% EtOAc/hexanes) to give the sub-title compound. LCMS (ESI) calc. for $C_{11}H_{11}BrN_3O_2$ [M+H]$^+$: m/z=296.0. found: 295.9.

Step 3. Ethyl 3-{[(benzyloxy)carbonyl]amino}-7-bromo-1,6-naphthyridine-2-carboxylate

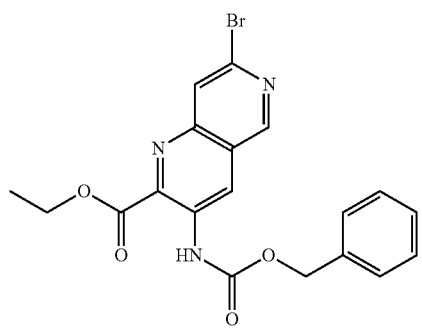 [SMILES: CCOC(=O)c1nc2cc(Br)ncc2cc1NC(=O)OCc1ccccc1]

To a solution of ethyl 3-amino-7-bromo-1,6-naphthyridine-2-carboxylate (47 mg, 0.16 mmol) and DIPEA (83 µL, 0.48 mmol) in DCM (1.5 mL), a solution of benzyl chloroformate (68 µL, 0.48 mmol) was added and the resulting mixture was heated at 60° C. in a sealed vial for 14 h. The crude reaction mixture was then concentrated under reduced pressure and the residue was purified by flash chromatography (24 g silica gel column, eluting with 0-60% EtOAc/hexanes) to afford the sub-title compound (41 mg, 60%). LCMS (ESI) calc. for $C_{19}H_{17}BrN_3O_4[M+H]^+$: m/z=430.0. found: 429.9.

Step 4. Ethyl 3-{[(benzyloxy)carbonyl]amino}-7-vinyl-1, 6-naphthyridine-2-carboxylate

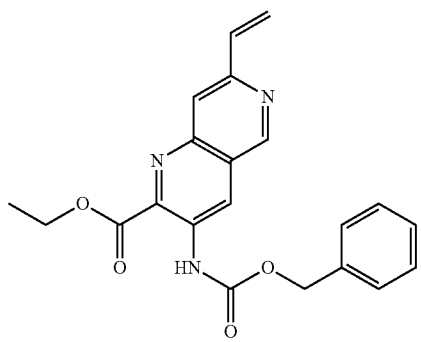 [SMILES: C=Cc1cc2nc(C(=O)OCC)c(NC(=O)OCc3ccccc3)cc2cn1]

A mixture of ethyl 3-{[(benzyloxy)carbonyl]amino}-7-bromo-1,6-naphthyridine-2-carboxylate (22 mg, 0.051 mmol), 4,4,5,5-tetramethyl-2-vinyl-1,3,2-dioxaborolane (43 µL, 0.26 mmol), tetrakis(triphenylphosphine)palladium(0) (4 mg, 0.004 mmol), and potassium carbonate (21 mg, 0.15 mmol) in 1,4-dioxane (500 µL) and water (50 µL) in a vial was deoxygenated and purged with nitrogen several times. The vial was sealed under nitrogen and then heated at 95° C. for 3 h. The crude reaction mixture was filtered through a pad of diatomaceous earth and the inorganics were washed thoroughly with EtOAc. The filtrate was concentrated under reduced pressure and the residue was purified by flash chromatography (24 g silica gel column, eluting with 0-50% EtOAc/hexanes) to afford the sub-title compound (10 mg, 50%). LCMS (ESI) calc. for $C_{21}H_{20}N_3O_4$ $[M+H]^+$: m/z=378.1. found: 378.1.

Step 5. 3-Amino-N-{4-[(3S)-3-aminopiperidin-1-yl]pyridin-3-yl}-7-ethyl-1, 6-naphthyridine-2-carboxamide A solution of 3-{[(benzyloxy)carbonyl]amino}-7-vinyl-1,6-naphthyridine-2-carboxylic acid (9.0 mg, 0.026 mmol), DIPEA (13 µL, 0.077 mmol), HATU (17 mg, 0.044 mmol), and tert-butyl [(3S)-1-(3-aminopyridin-4-yl)piperidin-3-yl]carbamate (15 mg, 0.052 mmol) in 1,2-dichloroethane (600 µL) was stirred at room temperature for 2 h. The crude reaction mixture was concentrated under reduced pressure and the residue was purified by flash chromatography (12 g silica gel column, eluting with 0-100% EtOAc/hexanes) to afford the an benzyloxycarbonyl/Boc protected intermediate (16 mg, 100% yield).

A mixture of the above intermediate compound and 10% Pd on activated carbon (wet, Degussa type E101 NE/W) (10 mg) in MeOH (3 mL) was stirred under an atmosphere of hydrogen for 1 h. The crude reaction mixture was filtered through a pad of diatomaceous earth and the inorganics were washed thoroughly with EtOAc.

The filtrate was concentrated under reduced pressure and the residue was dissolved in DCM (2 mL) and TFA (0.5 mL). The resulting solution was stirred at ambient temperature for 1.5 h. The crude reaction mixture was concentrated under reduced pressure and the residue was purified by preparative HPLC (XBridge™ C18 column, eluting with a gradient of MeCN/water containing 0.05% TFA, at a flow rate of 60 mL/min.) to give the title compound as its tris(trifluoroacetate) salt. LCMS (ESI) calc. for $C_{21}H_{26}N_7O$ $[M+H]^+$: m/z=392.2. found: 392.2.

Example 28

3-Amino-N-{4-[(3R,4R,5S)-3-amino-4-hydroxy-5-methylpiperidin-1-yl]-5-methylpyridin-3-yl}-7-ethylquinoline-2-carboxamide

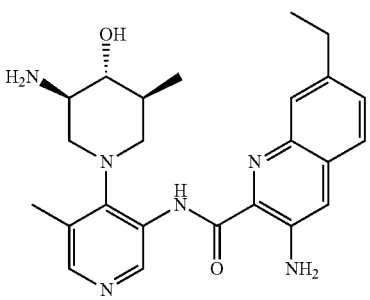 [SMILES: CCc1ccc2cc(N)c(C(=O)Nc3cncc(C)c3N3C[C@@H](N)[C@H](O)[C@@H](C)C3)nc2c1]

Step 1. tert-Butyl [(3R,4R,5S)-4-{[tert-butyl(dimethyl)silyl]oxy}-5-methyl-1-(3-methyl-5-nitropyridin-4-yl)piperidin-3-yl]carbamate

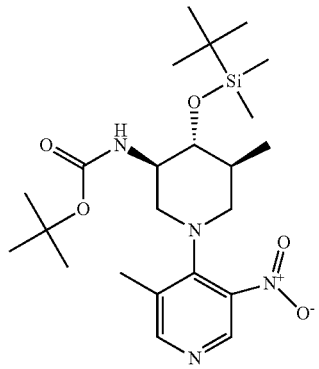 [SMILES: Cc1cncc([N+](=O)[O-])c1N1C[C@H](C)[C@@H](O[Si](C)(C)C(C)(C)C)[C@H](NC(=O)OC(C)(C)C)C1]

A solution of tert-butyl ((3R,4R,5S)-4-{[tert-butyl(dimethyl)silyl]oxy}-5-methylpiperidin-3-yl)carbamate (23 mg, 0.067 mmol, Example 26, Step 7), 4-chloro-3-methyl-5-nitropyridine (from ACES Pharma, 16 mg, 0.096 mmol), and triethylamine (37 µL, 0.27 mmol) in isopropyl alcohol (0.60 mL) was heated at 75° C. in a sealed vial for 16 h. Another portion of 4-chloro-3-methyl-5-nitropyridine (19 mg) was added and stirring was continued for 2 days at 100° C. The crude reaction mixture was purified by flash chromatography (24 g silica gel column, eluting with 0-100%

EtOAc/hexanes) to afford the sub-title compound (12 mg, 37% yield). LCMS (ESI) calc. for $C_{23}H_{41}N_4O_5Si$ [M+H]$^+$: m/z=481.3. found 481.3.

Step 2. tert-Butyl ((3R,4R,5S)-1-(3-amino-5-methylpyridin-4-yl)-4-{[tert-butyl(dimethyl)silyl]oxy}-5-methylpiperidin-3-yl)carbamate

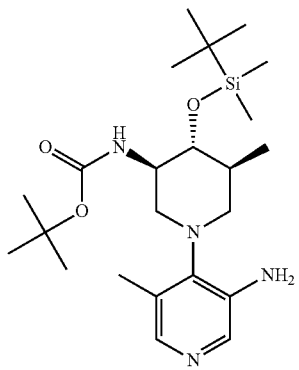 [SMILES: Cc1cncc(N)c1N1C[C@H](C)[C@@H](O[Si](C)(C)C(C)(C)C)[C@H](NC(=O)OC(C)(C)C)C1]

A mixture of tert-butyl [(3R,4R,5S)-4-{[tert-butyl(dimethyl)silyl]oxy}-5-methyl-1-(3-methyl-5-nitropyridin-4-yl)piperidin-3-yl]carbamate (12 mg, 0.025 mmol), iron powder (38 mg, 0.68 mmol) and ammonium chloride (55 mg, 1.0 mmol) in EtOH (0.9 mL) and water (0.2 mL) was stirred at room temperature for 16 h. A second aliquot of iron powder (380 mg), ammonium chloride (550 mg), and EtOH (1 mL) were added and stirring was continued at 55° C. for 3 h. The crude reaction mixture was filtered through a pad of diatomaceous earth and the inorganics were washed thoroughly with EtOAc. The filtrate was concentrated under reduced pressure to give the sub-title compound (11 mg, 100%), which was used directly in the subsequent reaction without further purification. LCMS (ESI) calc. for $C_{23}H_{43}N_4O_3Si$ [M+H]$^+$: m/z=451.3. found 451.2.

Step 3. 3-Amino-N-{4-[(3R,4R,5S)-3-amino-4-hydroxy-5-methylpiperidin-1-yl]-5-methylpyridin-3-yl}-7-ethylquinoline-2-carboxamide To a stirred solution of 3-{[(benzyloxy)carbonyl]amino}-7-vinylquinoline-2-carboxylic acid (16 mg, 0.046 mmol), HATU (18 mg, 0.049 mmol) and DIPEA (17 µL, 0.098 mmol) in 1,2-dichloroethane (400 µL), a solution of tert-butyl ((3R,4R,5S)-1-(3-amino-5-methylpyridin-4-yl)-4-{[tert-butyl(dimethyl)silyl]oxy}-5-methylpiperidin-3-yl)carbamate (11 mg, 0.024 mmol) in 1,2-dichloroethane (300 µL) was added, and the resulting solution was stirred at 50° C. for 16 h. The reaction mixture was concentrated under reduced pressure and the residue was purified by flash chromatography (24 g silica gel column, eluting with 0-60% EtOAc/hexanes) to afford an amide intermediate (10 mg, 52%).

The crude amide intermediate was dissolved in MeOH (2 mL) and treated with 10% Pd (dry basis) on activated carbon (wet, Degussa type E101 NE/W, 7.8 mg) under hydrogen (1 atm.) (balloon). The crude reaction mixture was filtered through a pad of diatomaceous earth and the inorganics were washed thoroughly with EtOAc. The filtrate was concentrated under reduced pressure to provide a Boc/TBS-protected intermediate.

The residue was dissolved in MeCN (1 mL) and heated at 55° C. with aq. fluorosilicic acid in water (1.7 M, 230 µL, 0.39 mmol) for 1 h. The crude reaction mixture was diluted with MeOH and was subjected to preparative HPLC (XBridge™ C18 column, eluting with a gradient of MeCN/water containing 0.05% TFA, at a flow rate of 60 mL/min.) to give the title compound as its trifluoroacetate salt. LCMS (ESI) calc. for $C_{24}H_{31}N_6O_2$ [M+H]$^+$: m/z=435.2. found: 435.3.

Example 29

3-Amino-N-{4-[(3R,4R,5S)-3-amino-4-hydroxy-5-methylpiperidin-1-yl]pyridin-3-yl}-7-ethylquinoline-2-carboxamide

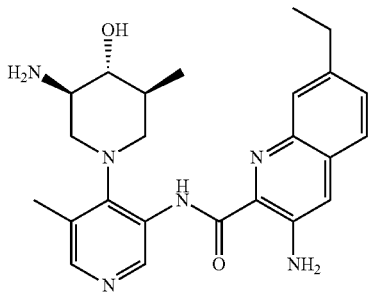 [SMILES: CCc1ccc2cc(N)c(C(=O)Nc3cncc(C)c3N3C[C@@H](N)[C@H](O)[C@@H](C)C3)nc2c1]

To a stirred solution of 3-{[(benzyloxy)carbonyl]amino}-7-vinylquinoline-2-carboxylic acid (19 mg, 0.055 mmol), HATU (16 mg, 0.041 mmol), and DIPEA (19 µL, 0.11 mmol) in 1,2-dichloroethane (0.5 mL), a solution of tert-butyl ((3R,4R,5S)-1-(3-aminopyridin-4-yl)-4-{[tert-butyl(dimethyl)silyl]oxy}-5-methylpiperidin-3-yl)carbamate (15 mg, 0.034 mmol, Example 26, Step 9) in 1,2-dichloroethane (300 µL) was and the resulting solution was stirred at 50° C. for 2.5 h. The reaction mixture was diluted DCM (40 mL) and water (3 mL). The layers were separated and the organic layer was washed with water (3×3 mL) and the combined aqueous phases were extracted with further DCM (3 mL). The combined organic layers were washed with brine (3 mL), dried over $Na_2SO_4$, filtered and concentrated under reduced pressure to give an amide intermediate.

The crude amide intermediate was dissolved in MeOH (2 mL) and treated with 10% Pd (dry basis) on activated carbon (wet, Degussa type E101 NE/W) under an atmosphere of hydrogen gas (1 atm.) (balloon) for 2 h. The crude reaction mixture was filtered through a pad of diatomaceous earth and the inorganics were washed thoroughly with EtOAc. The filtrate was concentrated under reduced pressure to provide a Boc/TBS-protected intermediate.

The residue was dissolved in AcCN (1.2 mL) and aq. fluorosilicic acid (1.7 M, 400 µL, 0.680 mmol) was added and the resulting solution was stirred at 50° C. for 3 h. The reaction mixture was diluted with MeOH and was purified by preparative HPLC (XBridge™ C18 column, eluting with a gradient of MeCN/water containing 0.05% TFA, at a flow rate of 60 mL/min.) to afford the title compound as a trifluoroacetate salt. LCMS (ESI) m/z calc. for $C_{23}H_{29}N_6O_2$ 421.2 [M+H]$^+$. found 421.2.

Example 30

3-Amino-N-{4-[(3S)-3-aminopiperidin-1-yl]-5-methylpyridin-3-yl}-7-ethylquinoline-2-carboxamide

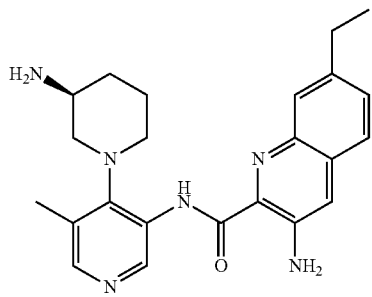 [SMILES: CCc1ccc2cc(N)c(C(=O)Nc3cncc(C)c3N3CCC[C@H](N)C3)nc2c1]

Step 1. tert-Butyl [(3S)-1-(3-methyl-5-nitropyridin-4-yl)piperidin-3-yl]carbamate

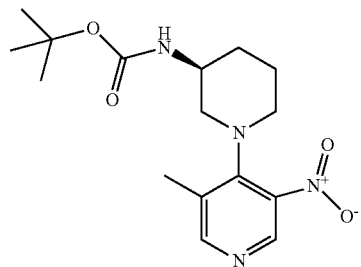 [SMILES: Cc1cncc([N+](=O)[O-])c1N1CCC[C@H](NC(=O)OC(C)(C)C)C1]

A mixture of 4-chloro-3-methyl-5-nitropyridine (0.300 g, 1.74 mmol) (from ACES Pharma Catalog No. 50630), tert-butyl (3S)-piperidin-3-ylcarbamate (0.42 g, 2.1 mmol) and triethylamine (0.73 mL, 5.2 mmol) in isopropyl alcohol (7 mL, dried over 4 Å molecular sieves) was heated at 100° C. for 16 h. Upon cooling to ambient temperature the solution was evaporated under reduced pressure and the crude product was purified by flash column chromatography (24 g column of silica gel, eluting with 20-30% EtOAc/hexanes) to give the sub-title compound (0.30 g). LCMS (ESI) calc. for $C_{16}H_{25}N_4O_4$ [M+H]$^+$: m/z=337.2. found 337.2.

Step 2. tert-Butyl [(3S)-1-(3-amino-5-methylpyridin-4-yl)piperidin-3-yl]carbamate

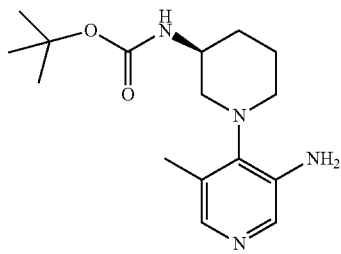 [SMILES: Cc1cncc(N)c1N1CCC[C@H](NC(=O)OC(C)(C)C)C1]

A mixture of tert-butyl [(3S)-1-(3-methyl-5-nitropyridin-4-yl)piperidin-3-yl]carbamate (0.300 g, 0.892 mmol), iron powder (0.12 g, 2.1 mmol) and ammonium chloride (0.5 g, 9 mmol) in EtOH (5 mL) and water (2 mL) was stirred at 85° C. for 2 h. After cooling to ambient temperature, the crude reaction mixture was filtered through a pad of diatomaceous earth and the inorganics were washed thoroughly with EtOH. The volatiles were removed under reduced pressure and the residue was re-dissolved in EtOAc (40 mL) and washed with saturated aq. NaHCO$_3$ (3 mL) and water (3×3 mL). The combined aqueous phases were extracted with further EtOAc (3 mL). The combined organic layers were washed with brine (3 mL), dried over Na$_2$SO$_4$, filtered and concentrated under reduced pressure to afford the sub-title compound (0.24 g), which was used in the subsequent reaction without further purification. LCMS (ESI) calc. for $C_{16}H_{27}N_4O_2$ [M+H]$^+$: m/z=307.2. found 307.1.

Step 3. 3-Amino-N-{4-[(3S)-3-aminopiperidin-1-yl]-5-methylpyridin-3-yl}-7-ethylquinoline-2-carboxamide A mixture of 3-{[(benzyloxy)carbonyl]amino}-7-vinylquinoline-2-carboxylic acid (0.030 g, 0.086 mmol), HATU (0.049 g, 0.13 mmol) and DIPEA (0.045 mL, 0.26 mmol) in anhydrous DMF (0.50 mL) was stirred for 10 min. A solution of tert-butyl [(3S)-1-(3-amino-5-methylpyridin-4-yl)piperidin-3-yl]carbamate (0.032 g, 0.10 mmol) in DMF (0.30 mL) was added and the resulting slurry was stirred at 44° C. for 1 h. The reaction mixture was diluted EtOAc (40 mL) and water (3 mL). The layers were separated and the organic layer was washed with water (3×3 mL). The combined aqueous phases were extracted with EtOAc (3 mL). The combined organic layers were washed with brine (3 mL), dried over Na$_2$SO$_4$, filtered and concentrated under reduced pressure to give an amide intermediate.

The crude product was dissolved in EtOH (3.5 mL) and treated with 10% Pd (dry basis) on activated carbon (wet, Degussa type E101 NE/W, 50 mg) under an atmosphere hydrogen (1 atm.) for 4 h. The crude reaction mixture was filtered through a pad of diatomaceous earth and the inorganics were washed thoroughly with EtOH. The filtrate was concentrated under reduced pressure and the residue containing of a further intermediate.

The residue was dissolved in DCM (0.6 mL) and TFA (40 µL), and the resulting mixture was stirred at room temperature for 1 h. The reaction mixture was diluted with MeOH and was purified by preparative HPLC (XBridge™ C18 column, eluting with a gradient of MeCN/water containing 0.1% NH$_4$OH, at a flow rate of 60 mL/min.) to afford the title compound. LCMS (ESI) calc. for $C_{23}H_{29}N_6O$ [M+H]$^+$: m/z=405.2. found 405.1.

Example 31

3-Amino-N-{4-[(3S)-3-aminopiperidin-1-yl]-6-methoxypyridin-3-yl}-7-ethylquinoline-2-carboxamide

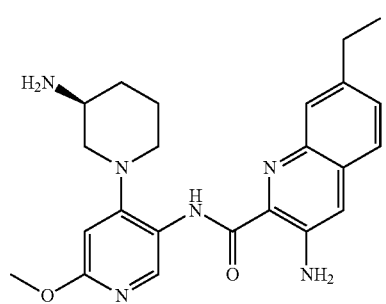 [SMILES: CCc1ccc2cc(N)c(C(=O)Nc3cnc(OC)cc3N3CCC[C@H](N)C3)nc2c1]

Step 1. tert-Butyl [(3S)-1-(2-chloro-5-nitropyridin-4-yl)piperidin-3-yl]carbamate

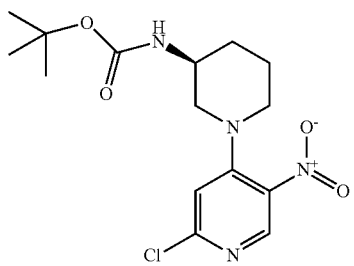 [SMILES: CC(C)(C)OC(=O)N[C@H]1CCCN(c2cc(Cl)ncc2[N+](=O)[O-])C1]

A solution of 2,4-dichloro-5-nitropyridine (from AstaTech, 0.500 g, 2.59 mmol), tert-butyl (3S)-piperidin-3-ylcarbamate (0.52 g, 2.6 mmol) and triethylamine (1.1 mL, 7.9 mmol) in isopropyl alcohol (10 mL) was heated at 65° C. for 2 h. The reaction mixture was concentrated under reduced pressure and the residue was re-dissolved in EtOAc (40 mL) and washed with saturated aq. NaHCO$_3$ and water (3×3 mL). The combined aqueous phases were extracted with EtOAc (3 mL). The combined organic layers were washed with brine (3 mL), then dried over Na$_2$SO$_4$, filtered and concentrated under reduced pressure to afford the sub-title compound (0.99 g), which was used in the subsequent reaction without further purification. LCMS (ESI) calc. for C$_{15}$H$_{22}$ClN$_4$O$_4$[M+H]$^+$: m/z=357.1. found 357.0.

Step 2. tert-Butyl [(3S)-1-(5-amino-2-methoxypyridin-4-yl)piperidin-3-yl]carbamate

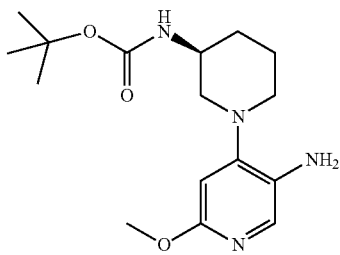 [SMILES: COc1cc(N2CCC[C@H](NC(=O)OC(C)(C)C)C2)c(N)cn1]

A mixture of tert-butyl [(3S)-1-(2-chloro-5-nitropyridin-4-yl)piperidin-3-yl]carbamate (0.100 g, 0.280 mmol) and sodium methoxide in MeOH (0.5 M; 2.8 mL, 1.4 mmol) was stirred at 60° C. for 45 min. The reaction was quenched by the addition of saturated aq. NH$_4$Cl and diluted with EtOAc (40 mL) and water (3 mL). The layers were separated and the organic layer was washed with water (3×3 mL). The combined aqueous phases were extracted with further EtOAc (3 mL). The combined organic layers were washed with brine (3 mL), dried over Na$_2$SO$_4$, filtered and concentrated under reduced pressure to afford a residue of an intermediate nitro compound (0.10 g).

The residue was dissolved in EtOH (4 mL) and treated with 10% Pd on activated carbon (wet, Degussa type E101 NE/W) under an atmosphere of hydrogen (1 atm.) (balloon) for 1 h. The crude reaction mixture was filtered through a pad of diatomaceous earth and the inorganics were washed thoroughly with EtOAc. The solvent were removed under reduced pressure to afford the sub-title compound (0.090 g), which was used in the subsequent reaction without further purification. LCMS (ESI) calc. for C$_{16}$H$_{27}$N$_4$O$_3$ [M+H]$^+$: m/z=323.2. found 323.2.

Step 3. 3-Amino-N-{4-[(3S)-3-aminopiperidin-1-yl]-6-methoxypyridin-3-yl}-7-ethylquinoline-2-carboxamide A mixture of 3-{[(benzyloxy)carbonyl]amino}-7-vinylquinoline-2-carboxylic acid (0.020 g, 0.057 mmol), HATU (0.033 g, 0.087 mmol) and DIPEA (0.030 mL, 0.17 mmol) in anhydrous DMF (0.30 mL) was stirred for 10 min. at 44° C. tert-Butyl [(3S)-1-(5-amino-2-methoxypyridin-4-yl)piperidin-3-yl]carbamate (0.022 g, 0.068 mmol) in DMF (0.30 mL) was then added and the solution was stirred at 44° C. for 2 h. The reaction mixture was then diluted with EtOAc (40 mL) and water (3 mL). The layers were separated and the organic layer was washed with water (3×3 mL) and the combined aqueous phases were extracted with EtOAc (3 mL). The combined organic layers were washed with brine (3 mL), dried over Na$_2$SO$_4$, filtered and concentrated under reduced pressure to give an amide intermediate.

The crude product was dissolved in EtOH (3.5 mL) and stirred overnight with 10% Pd (dry basis) on activated carbon (wet, Degussa type E101 NE/W, 40 mg) under an atmosphere hydrogen (1 atm.) (balloon). The crude reaction mixture was filtered through a pad of diatomaceous earth and the inorganics were washed thoroughly with EtOH. The filtrate was concentrated under reduced pressure to give a residue of a further intermediate.

The residue was dissolved in DCM (0.6 mL) and TFA (400 µL) and stirred at room temperature for 1 h. The reaction mixture was diluted with MeOH and was purified by preparative HPLC (XBridge™ C18 column, eluting with a gradient of MeCN/water containing 0.1% NH$_4$OH, at a flow rate of 60 mL/min.) to afford the title compound. LCMS (ESI) calc. for C$_{23}$H$_{29}$N$_6$O$_2$ [M+H]$^+$: m/z=421.2. found 421.1.

Example 32

3-Amino-N-{4-[(3S)-3-aminopiperidin-1-yl]-5-cyanopyridin-3-yl}-7-ethylquinoline-2-carboxamide

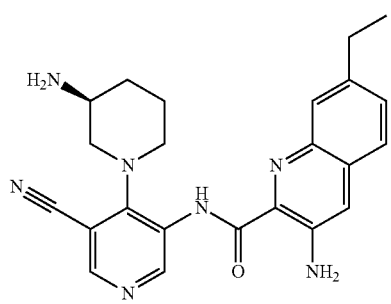 [SMILES: CCc1ccc2cc(N)c(C(=O)Nc3cncc(C#N)c3N3CCC[C@H](N)C3)nc2c1]

Step 1. Benzyl [(3S)-1-(3-bromo-5-nitropyridin-4-yl)piperidin-3-yl]carbamate

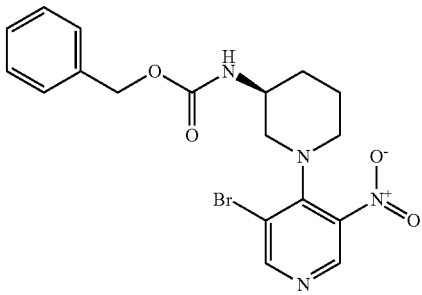 [SMILES: O=C(N[C@H]1CCCN(c2c(Br)cncc2[N+](=O)[O-])C1)OCc1ccccc1]

A mixture of 3-bromo-4-chloro-5-nitropyridine (from Ark Pharm, 0.050 g, 0.21 mmol), benzyl (3S)-piperidin-3-ylcarbamate (0.059 g, 0.25 mmol), and triethylamine (0.088 mL, 0.63 mmol) in isopropyl alcohol (0.8 mL) was heated at 90° C. in a sealed vial for 16 h. The reaction mixture was diluted with EtOAc (40 mL) and water (3 mL). The layers were separated and the organic layer was washed with water (3×3 mL) and the combined aqueous phases were extracted with EtOAc (3 mL). The combined organic layers were washed with brine (3 mL), dried over $Na_2SO_4$, filtered and concentrated under reduced pressure to afford the sub-title compound (0.084 g). The crude product was used without further purification in the subsequent reaction. LCMS (ESI) calc. for $C_{18}H_{20}BrN_4O_4[M+H]^+$: m/z=435.1. found 435.0/437.0.

Step 2. Benzyl [(3S)-1-(3-cyano-5-nitropyridin-4-yl)piperidin-3-yl]carbamate

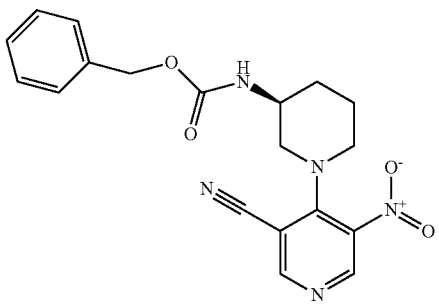 [SMILES: N#Cc1cncc([N+](=O)[O-])c1N1CCC[C@H](NC(=O)OCc2ccccc2)C1]

A mixture of benzyl [(3S)-1-(3-bromo-5-nitropyridin-4-yl)piperidin-3-yl]carbamate (0.082 g, 0.19 mmol), tris(dibenzylideneacetone)dipalladium(0) chloroform adduct (0.0097 g, 0.0094 mmol), (9,9-dimethyl-9H-xanthene-4,5-diyl)bis(diphenylphosphine) (0.0109 g, 0.0188 mmol), zinc cyanide (0.066 g, 0.56 mmol), N,N,N',N'-tetramethylethylenediamine (0.0114 mL, 0.0755 mmol) in DMF (1.40 mL) was in a vial was deoxygenated. The vial was purged with nitrogen several times, then sealed. The reaction mixture was heated in the sealed vial at 140° C. under microwave irradiation for 10 min. After cooling to ambient temperature, the crude reaction mixture was filtered through a pad of diatomaceous earth and the inorganics were washed thoroughly with EtOAc. The filtrate was diluted EtOAc (40 mL) and water (3 mL). The layers were separated and the organic layer was washed with water (3×3 mL). The combined aqueous phases were extracted with EtOAc (3 mL). The combined organic layers were washed with brine (3 mL), dried over $Na_2SO_4$, filtered and concentrated under reduced pressure to afford the sub-title compound (0.065 g). The crude product was used without further purification in the subsequent reaction. LCMS (ESI) calc. for $C_{19}H_{20}N_5O_4$ $[M+H]^+$: m/z=382.1. found 382.0.

Step 3. Benzyl [(3S)-1-(3-amino-5-cyanopyridin-4-yl)piperidin-3-yl]carbamate

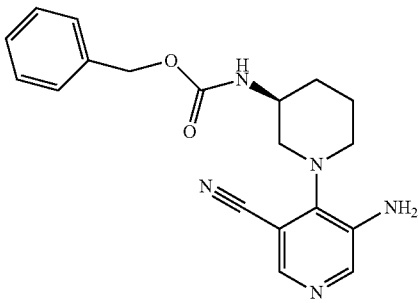 [SMILES: N#Cc1cncc(N)c1N1CCC[C@H](NC(=O)OCc2ccccc2)C1]

A mixture of benzyl [(3S)-1-(3-cyano-5-nitropyridin-4-yl)piperidin-3-yl]carbamate (0.065 g, 0.17 mmol), iron (0.084 g, 1.5 mmol), and ammonium chloride (0.091 g, 1.7 mmol) in EtOH (2 mL) and water (0.2 mL) was stirred at 85° C. for 15 min. The crude reaction mixture was filtered through a pad of diatomaceous earth and the inorganics were washed thoroughly with EtOH. The filtrate was concentrated under reduced pressure and the residue was partitioned between water and EtOAc. The organic fraction was washed with water, brine, dried over $Na_2SO_4$, filtered, and concentrated under reduced pressure to afford the sub-title compound (0.055 g). LCMS (ESI) calc. for $C_{19}H_{22}N_5O_2$ m/z=352.2 $[M+H]^+$. found 352.1.

Step 4. 3-Amino-N-{4-[(3S)-3-aminopiperidin-1-yl]-5-cyanopyridin-3-yl}-7-ethylquinoline-2-carboxamide

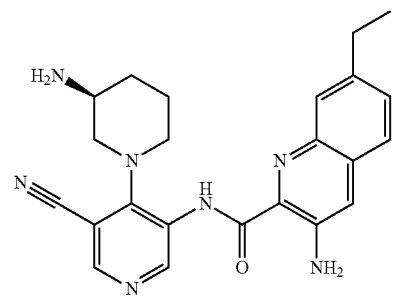 [SMILES: CCc1ccc2cc(N)c(C(=O)Nc3cncc(C#N)c3N3CCC[C@H](N)C3)nc2c1]

A mixture of 3-{[(benzyloxy)carbonyl]amino}-7-vinylquinoline-2-carboxylic acid (0.020 g, 0.057 mmol), HATU (0.033 g, 0.087 mmol) and DIPEA (0.030 mL, 0.17 mmol) in anhydrous DMF (0.50 mL) was stirred for 10 min. prior to the addition of a solution of benzyl [(3S)-1-(3-amino-5-cyanopyridin-4-yl)piperidin-3-yl]carbamate (0.024 g, 0.068 mmol) in DMF (0.15 mL). The reaction mixture was then stirred at 40° C. for 1 h. The reaction mixture was diluted EtOAc (40 mL) and water (3 mL). The layers were separated and the organic layer was washed with water (3×3 mL) and the combined aqueous phases were extracted with EtOAc (3 mL). The combined organic layers were washed with brine (3 mL), dried over Na₂SO₄, filtered and concentrated under reduced pressure to provide an amide intermediate.

The crude product was dissolved in EtOH (2 mL) and treated with 5% palladium on barium sulfate (10 mg) under an atmosphere of hydrogen (1 atm.) (balloon) for 4 h. The crude reaction mixture was filtered through a pad of diatomaceous earth and the inorganics were washed thoroughly with EtOH. The filtrate was purified by preparative HPLC (XBridge™ C18 column, eluting with a gradient of MeCN/water containing 0.1% ammonia hydroxide, at a flow rate of 60 mL/min.) to afford the title compound. LCMS (ESI) calc. for $C_{23}H_{26}N_7O$ $[M+H]^+$: m/z=416.2. found 416.2.

Example 33

3-Amino-N-{4-[(3R,4R,5S)-3-amino-4-hydroxy-5-methylpiperidin-1-yl]pyridin-3-yl}-7-morpholin-4-ylquinoline-2-carboxamide

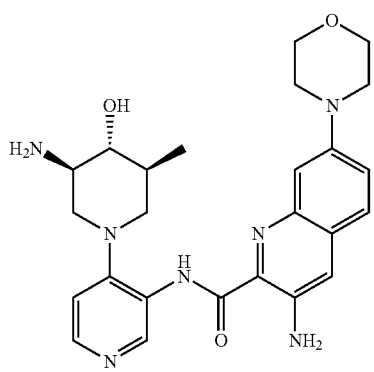 [SMILES: C[C@H]1CN(c2ccncc2NC(=O)c2nc3cc(N4CCOCC4)ccc3cc2N)C[C@@H](N)[C@@H]1O]

Step 1. Ethyl 3-{[(benzyloxy)carbonyl]amino}-7-morpholin-4-ylquinoline-2-carboxylate

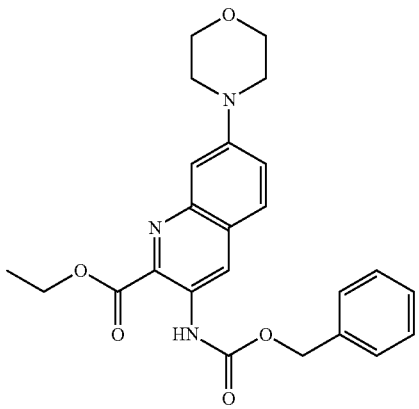 [SMILES: CCOC(=O)c1nc2cc(N3CCOCC3)ccc2cc1NC(=O)OCc1ccccc1]

A mixture of ethyl 3-{[(benzyloxy)carbonyl]amino}-7-bromoquinoline-2-carboxylate (300 mg, 0.7 mmol), morpholine (120 mg, 1.4 mmol), Pd(OAc)₂ (20 mg), dicyclohexyl(2',6'-diisopropoxybiphenyl-2-yl)phosphine (49 mg, 0.10 mmol), and K₃PO₄ (580 mg, 2.8 mmol) in tert-butanol (10 mL) in a sealed vial was purged with nitrogen then heated at 100° C. for 1 h. The solution was allowed to cool then and diluted with EtOAc, and the mixture was filtered through diatomaceous earth. The filtrate was concentrated under reduced pressure, and the resulting residue was purified by flash chromatography on 40 g of silica gel, eluting with 0-100% EtOAc in hexanes, to give the sub-title compound (0.3 g, 20%). LCMS (ESI) calc. for $C_{24}H_{26}N_3O_5$ $[M+H]^+$: m/z=436.2. found: 436.1.

Step 2. 3-{[(Benzyloxy)carbonyl]amino}-7-morpholin-4-ylquinoline-2-carboxylic acid

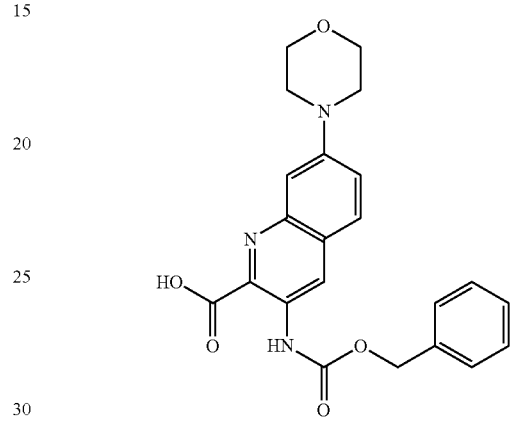

To a mixture of ethyl 3-{[(benzyloxy)carbonyl]amino}-7-morpholin-4-ylquinoline-2-carboxylate (0.065 g, 0.15 mmol) in 1,4-dioxane (2.0 mL) was added 2.5 M aq. NaOH (1.0 mL, 2.5 mmol). The reaction mixture was heated at 80° C. for 0.5 h, then cooled and neutralized with 2.5 mL 1 M HCl to pH=7. The precipitated solid was collected by filtration and air-dried overnight to yield the sub-title compound (0.042 g, 69%). LCMS (ESI) calc. for $C_{22}H_{22}N_3O_5$ $[M+H]^+$: m/z=408.2. found: 408.2.

Step 3. Benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-morpholin-4-ylquinolin-3-yl]carbamate

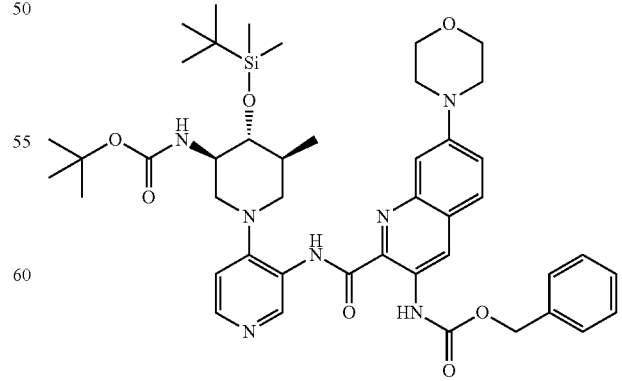

A mixture of 3-{[(benzyloxy)carbonyl]amino}-7-morpholin-4-ylquinoline-2-carboxylic acid (0.005 g, 0.01 mmol), tert-butyl ((3R,4R,5S)-1-(3-aminopyridin-4-yl)-4-{[tert-butyl(dimethyl)silyl]oxy}-5-methylpiperidin-3-yl)carbamate (0.0064 g, 0.015 mmol), and HATU (0.012 g, 0.031 mmol) in DMF (0.2 mL) and DIPEA (0.0064 mL, 0.037 mmol) was stirred at room temperature for 2 h. The mixture was quenched with 5 mL of EtOAc and 3 mL of 1 M NaOH. The resulting layers were separated and the aqueous layer was extracted with EtOAc. The combined organic extracts were concentrated under reduced pressure, then purified by preparative HPLC (XBridge™ C18 column, eluting with a gradient of MeCN/water containing 0.05% TFA, at a flow rate of 30 mL/min.) to afford the sub-title compound (0.0032 g, 30%). LCMS calc. for $C_{44}H_{60}N_7O_7Si$ $[M+H]^+$: m/z=826.4. found: 826.4.

Step 4. 3-Amino-N-{4-[(3R,4R,5S)-3-amino-4-hydroxy-5-methylpiperidin-1-yl]pyridin-3-yl}-7-morpholin-4-ylquinoline-2-carboxamide A mixture of benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-morpholin-4-ylquinolin-3-yl]carbamate (0.0035 g, 0.0042 mmol) in 3 mL of MeOH was hydrogenated under a balloon of hydrogen, in the presence of 3 mg of 10% Pd on carbon, at room temperature for 1 h. The reaction mixture was diluted with 5 mL of MeOH then filtered. The filtrate was concentrated under reduced pressure. The resulting residue was treated with 2 mL of MeOH and 2 mL of 4 M HCl in dioxane at room temperature for 1 h. The volatile solvents were removed under reduced pressure. The residue was dissolved in 4 mL of MeOH and treated with 0.5 mL of NH$_4$OH solution, then filtered. The filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for $C_{25}H_{32}N_7O_3$ $[M+H]^+$: m/z=478.3. found: 478.3.

Example 34

3-Amino-N-{4-[(3S,5R)-3-amino-5-methylpiperidin-1-yl]pyridin-3-yl}-7-morpholin-4-ylquinoline-2-carboxamide

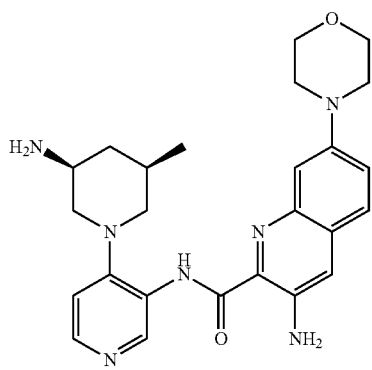 [SMILES: C[C@@H]1C[C@H](N)CN(c2ccncc2NC(=O)c2nc3cc(N4CCOCC4)ccc3cc2N)C1]

Step 1. 1-tert-Butyl 2-methyl (2S)-5-oxopyrrolidine-1, 2-dicarboxylate

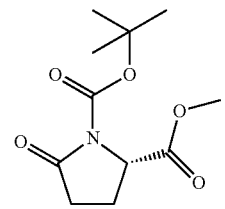 [SMILES: COC(=O)[C@@H]1CCC(=O)N1C(=O)OC(C)(C)C]

Thionyl chloride (5.6 mL, 77 mmol) was added dropwise over 10 min. to a solution of (2S)-5-oxopyrrolidine-2-carboxylic acid (Aldrich, 5.0 g, 39 mmol) in MeOH (30.0 mL) at 0° C. The mixture was allowed to warm to room temperature and stirred for 2 h. The reaction was concentrated under reduced pressure and the resulting residue was dissolved in EtOAc (25 mL). After slow addition of triethylamine (5.4 mL, 39 mmol), the mixture was filtered. DMAP (0.48 g, 3.9 mmol) was added to the filtrate, followed by di-tert-butyl dicarbonate (8.4 g, 39 mmol) and the mixture was stirred at room temperature for 2 h. The reaction mixture was then diluted with EtOAc (25 mL) and cooled to 0° C. 1 M HCl (50 mL) was added slowly. The organic layer was separated, washed with a saturated aq. NaHCO$_3$ (50 mL) and brine (50 mL), then dried over Na$_2$SO$_4$ and concentrated to give the sub-title compound as a white solid (8.08 g, 86%). LCMS calc. for $C_{11}H_{17}NNaO_5$ $(M+Na)^+$: m/z=266.1. found 266.1.

Step 2. 1-tert-Butyl 2-methyl (2S,4R)-4-methyl-5-oxopyrrolidine-1, 2-dicarboxylate

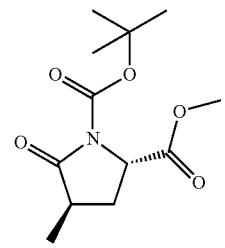 [SMILES: COC(=O)[C@@H]1C[C@@H](C)C(=O)N1C(=O)OC(C)(C)C]

This compound is prepared as described by Gu et al, *Tetrahedron Lett.*, 2003, 44, 3203-3205. Lithium hexamethyldisilazide in THF (1.0 M; 8.47 mL, 8.47 mmol) was added dropwise over 30 min. to a solution of 1-tert-butyl 2-methyl (2S)-5-oxopyrrolidine-1,2-dicarboxylate (2.0 g, 8.2 mmol) in THF (20 mL) at −78° C. The resulting mixture was stirred at −78° C. for 1 h. Methyl iodide (1.30 mL, 20.9 mmol) was then added dropwise over 10 min. After stirring at −78° C. for 2 h, the reaction mixture was allowed to warm to room temperature and stirred for 14 h. The reaction was then quenched with AcOH (1.00 mL, 17.6 mmol), and the reaction mixture was concentrated under reduced pressure. The residue was diluted with EtOAc (100 mL), washed with brine (100 mL), dried over Na$_2$SO$_4$, and concentrated under reduced pressure. The resulting residue was purified by flash chromatography on silica gel (0-50% EtOAc in hexanes) to give the sub-title compound (0.47 g, 22%). LCMS calc. for $C_{12}H_{19}NNaO_5$ $(M+Na)^+$: m/z=280.1. found 280.1. $^1$H NMR (CDCl$_3$, 400 MHz) δ 4.57 (1H, dd, J=1.6 and 9.6 Hz), 3.77 (3H, s), 2.68 (1H, m), 2.27 (1H, m), 1.93 (1H, m), 1.49 (9H, s), 1.21 (3H, d, J=6.8 Hz) ppm.

Step 3. tert-Butyl [(1S,3R)-4-hydroxy-1-(hydroxymethyl)-3-methylbutyl]carbamate

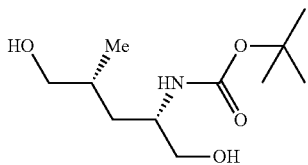 [SMILES: C[C@@H](CO)C[C@@H](CO)NC(=O)OC(C)(C)C]

To a solution of 1-tert-butyl 2-methyl (2S,4R)-4-methyl-5-oxopyrrolidine-1,2-dicarboxylate (0.47 g, 1.8 mmol) in THF (4.0 mL) at −10° C., NaBH$_4$ (0.207 g, 5.48 mmol) was added followed by EtOH (1.0 mL). After stirring at −10° C. for 1 h, the mixture was allowed to warm to room temperature and stirred for 15 h. The reaction mixture was then diluted with EtOAc (50 mL), washed with water (25 mL) and brine (30 mL), then dried over Na$_2$SO$_4$ and concentrated under reduced pressure. The resulting crude product (0.39 g, 92%) was used directly in the next step without further purification. LCMS calc. for C$_{11}$H$_{24}$NO$_4$ (M+H)$^+$: m/z=234.2. found no ionization.

Step 4. tert-Butyl [(3S,5R)-1-benzyl-5-methylpiperidin-3-yl]carbamate

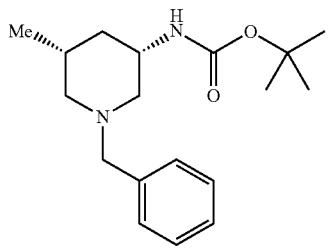 [SMILES: C[C@@H]1C[C@H](NC(=O)OC(C)(C)C)CN(Cc2ccccc2)C1]

Triethylamine (0.932 mL, 6.69 mmol) was added to a solution of tert-butyl [(1S,3R)-4-hydroxy-1-(hydroxymethyl)-3-methylbutyl]carbamate (0.39 g, 1.7 mmol) in DCM (7.5 mL) at 0° C. Methanesulfonyl chloride (0.388 mL, 5.01 mmol) was then added dropwise to the resulting solution. After stirring at 0° C. for 1 h, the mixture was diluted with DCM (50 mL), washed with saturated aq. NaHCO$_3$ (50 mL), dried over Na$_2$SO$_4$ and concentrated under reduced pressure. Benzylamine (3.65 mL, 33.4 mmol) was added to the resulting residue and mixture was stirred at 70° C. for 18 h, then cooled to room temperature. The reaction mixture was diluted with EtOAc (100 mL), washed with 10% aq. K$_3$PO$_4$ (50 mL) and brine (50 mL), dried over Na$_2$SO$_4$, and concentrated under reduced pressure. The residue was purified by flash chromatography on silica gel (0-30% EtOAc in hexanes) to give the sub-title compound as a white solid (0.34 g, 67%). LCMS calc. for C$_{18}$H$_{29}$N$_2$O$_2$ (M+H)$^+$: m/z=305.2. found 305.2.

Step 5. tert-Butyl [(3S,5R)-5-methylpiperidin-3-yl]carbamate

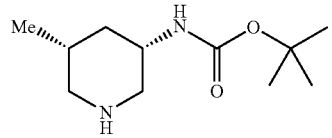

10 wt % Pd on carbon (120 mg, 0.11 mmol) was added to a solution of tert-butyl [(3S,5R)-1-benzyl-5-methylpiperidin-3-yl]carbamate (0.34 g, 1.1 mmol) in MeOH (15.0 mL). The mixture was stirred at room temperature under a hydrogen atmosphere (1 atm.) for 15 h. The reaction was filtered through a pad of diatomaceous earth (eluted with MeOH), and then concentrated under reduced pressure. The resulting crude product was used directly in the next step without further purification (0.21 g, 88%). LCMS calc. for C$_{11}$H$_{23}$N$_2$O$_2$ (M+H)$^+$: m/z=215.2. found: 215.2. $^1$H NMR (CDCl$_3$, 400 MHz) δ 4.33 (1H, m), 3.46 (1H, m), 3.25 (1H, m), 2.94 (1H, dd, J=3.6 and 12.8 Hz), 2.18-2.02 (3H, m), 1.60 (1H, m), 1.43 (9H, s), 0.85 (3H, d, J=6.8 Hz) ppm.

Step 6. tert-Butyl [(3S,5R)-5-methyl-1-(3-nitropyridin-4-yl)piperidin-3-yl]carbamate

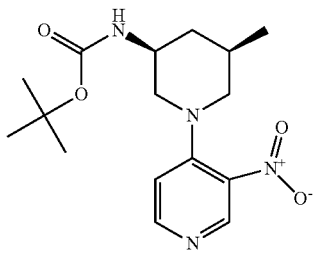 [SMILES: C[C@@H]1C[C@H](NC(=O)OC(C)(C)C)CN(c2ccncc2[N+](=O)[O-])C1]

A mixture of 4-chloro-3-nitropyridine (0.704 g, 4.44 mmol) and tert-butyl [(3S,5R)-5-methylpiperidin-3-yl]carbamate (1.0 g, 4.7 mmol) in isopropyl alcohol (8.7 mL) was stirred at 75° C. overnight. The mixture was concentrated under reduced pressure, and the resulting residue was diluted with water and extracted with EtOAc. The organic extracts were combined and evaporated under reduced pressure. The residue was purified by flash chromatography on 40 g silica gel, eluting with 0-90% EtOAc in hexanes, to give the sub-title compound as a yellow solid (1.14 g, 76.2%). LCMS calc. for C$_{16}$H$_{25}$N$_4$O$_4$ (M+H)$^+$: m/z=337.2. found: 337.3.

Step 7. tert-Butyl [(3S,5R)-1-(3-aminopyridin-4-yl)-5-methylpiperidin-3-yl]carbamate

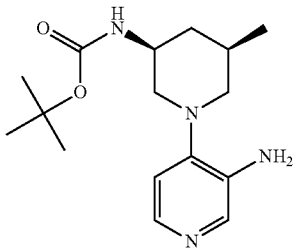 [SMILES: C[C@@H]1C[C@H](NC(=O)OC(C)(C)C)CN(c2ccncc2N)C1]

A mixture of tert-butyl [(3S,5R)-5-methyl-1-(3-nitropyridin-4-yl)piperidin-3-yl]carbamate (1.14 g, 3.39 mmol) in MeOH was hydrogenated in the presence of 10% Pd on carbon (0.14 g) under 45 psi of hydrogen overnight. The mixture was filtered through diatomaceous earth. The filtrate was concentrated under reduced pressure to give the sub-title compound (1.04 g, 100%). LCMS calc. for $C_{16}H_{27}N_4O_2$ (M+H)$^+$: m/z=307.2. found: 307.3.

Step 8. Benzyl {2-[({4-[(3S,5R)-3-amino-5-methyl-piperidin-1-yl]pyridin-3-yl}amino)carbonyl]-7-morpholin-4-ylquinolin-3-yl}carbamate

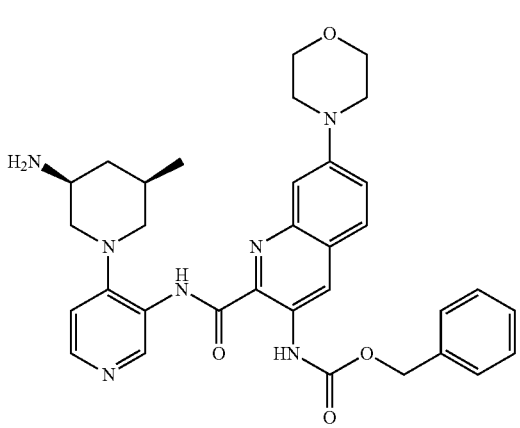 [SMILES: C[C@@H]1C[C@H](N)CN(c2ccncc2NC(=O)c2nc3cc(N4CCOCC4)ccc3cc2NC(=O)OCc2ccccc2)C1]

A mixture of 3-{[(benzyloxy)carbonyl]amino}-7-morpholin-4-ylquinoline-2-carboxylic acid (0.014 g, 0.034 mmol), tert-butyl [(3S,5R)-1-(3-aminopyridin-4-yl)-5-methylpiperidin-3-yl]carbamate (0.013 g, 0.041 mmol) and HATU (0.033 g, 0.086 mmol) in DMF (0.14 mL) and DIPEA (0.018 mL, 0.10 mmol) was stirred at room temperature for 2 h. The mixture was diluted with 5 mL of EtOAc and 3 mL of 1 M NaOH. The layers were separated and the aqueous layer was extracted with EtOAc. The organic layers were combined and concentrated under reduced pressure. The residue was purified by flash chromatography on 20 g silica gel column, eluting with 0-30% MeOH in EtOAc, to yield an amide intermediate, benzyl (2-{[(4-{(3S,5R)-3-[(tert-butoxycarbonyl)amino]-5-methylpiperidin-1-yl}pyridin-3-yl)amino]carbonyl}-7-morpholin-4-ylquinolin-3-yl)carbamate. LCMS calc. for $C_{38}H_{46}N_7O_6$ [M+H]$^+$: m/z=696.3. found: 696.5.

To the amide intermediate, 1 mL of 4 M HCl in dioxane and 1 mL of MeOH were added. The mixture was stirred at room temperature for 1 h, then concentrated under reduced pressure to give the sub-title compound as a HCl salt. LCMS calc. for $C_{33}H_{38}N_7O_4$ [M+H]$^+$: m/z=596.3. found: 596.3.

Step 9. 3-Amino-N-{4-[(3S,5R)-3-amino-5-methyl-piperidin-1-yl]pyridin-3-yl}-7-morpholin-4-ylquinoline-2-carboxamide A mixture of benzyl {2-[({4-[(3S,5R)-3-amino-5-methyl-piperidin-1-yl]pyridin-3-yl}amino)carbonyl]-7-morpholin-4-ylquinolin-3-yl}carbamate (0.002 g, 0.003 mmol) in 2 mL of 4 M HBr in AcOH solution was stirred at room temperature for 2 h. The solution was then concentrated under reduced pressure and the residue was treated with 4.5 mL of MeOH and 0.5 mL of NH$_4$OH solution. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for $C_{25}H_{32}N_7O_2$ [M+H]$^+$: m/z=462.3. found: 462.3.

Example 35

3-Amino-N-{4-[(3S,5R)-3-amino-5-(trifluoromethyl)piperidin-1-yl]pyridin-3-yl}-7-morpholin-4-ylquinoline-2-carboxamide

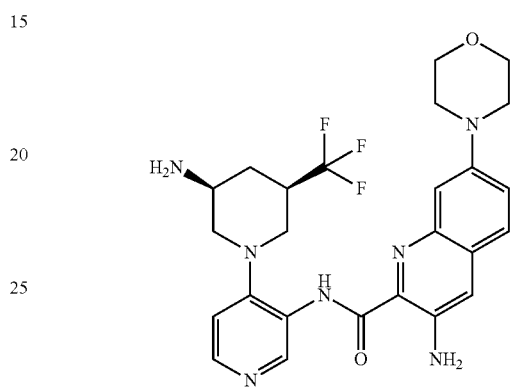

Step 1. Benzyl (3S,5R)-3-[(tert-butoxycarbonyl)amino]-5-(trifluoromethyl)piperidine-1-carboxylate

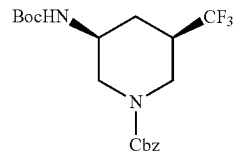 [SMILES: CC(C)(C)OC(=O)N[C@H]1C[C@@H](C(F)(F)F)CN(C(=O)OCc2ccccc2)C1]

To a round bottom flask containing cis-3-(Boc-amino)-5-(trifluoromethyl)piperidine (Molbridge, 10.00 g, 37.27 mmol) and sodium bicarbonate (18.8 g, 224 mmol), THF (200 mL) was added, followed by water (200 mL). Benzyl chloroformate (20.1, g, 112 mmol) was then added dropwise over a period of 30 min. via a syringe pump. The mixture was stirred at room temperature for 2 h. The mixture was then diluted with EtOAc and water. The layers were separated and the organic layer was washed with brine, dried over Na$_2$SO$_4$, filtered, and concentrated under reduced pressure. The resulting residue was purified by flash chromatography on silica gel (340 g, 15% EtOAc in hexanes) to give a white foamy solid which was subjected to chiral HPLC separation (Phenomenex Lux Cellulose C-1, 5 µm, 21.2×250 mm column, eluting with 15% EtOH in hexanes, at flow rate of 18 mL/min., with a loading of 100 mg in 1000 µL at 220 nm wavelength) to give the sub-title compound (retention time: 9.1 min.) as a white foamy solid (6.51 g, 43%). LCMS calc. for $C_{19}H_{25}F_3N_2NaO_4$ (M+Na)$^+$: m/z=425.2. found: 425.2. The sub-title compound is assigned as the (3S,5R) isomer. The alternative (3R,5S) isomer can be obtained from the same separation.

Step 2. tert-Butyl [(3S,5R)-5-(trifluoromethyl)piperidin-3-yl]carbamate

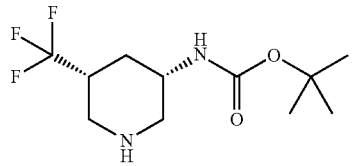 [SMILES: CC(C)(C)OC(=O)N[C@@H]1CNC[C@H](C(F)(F)F)C1]

A mixture of benzyl (3S,5R)-3-[(tert-butoxycarbonyl)amino]-5-(trifluoromethyl)piperidine-1-carboxylate (3.86 g, 9.59 mmol) in MeOH (50 mL) was hydrogenated in the presence of 10% Pd on carbon (0.30 g) under 25 psi of hydrogen for 2 h. The reaction mixture was filtered and the filtrate was concentrated under reduced pressure to give the sub-title compound (2.6 g, 100%). LCMS calc. for $C_{11}H_{20}F_3N_2O_2(M+H)^+$: m/z=269.1. found: 269.2.

Step 3. tert-Butyl [(3S,5R)-1-(3-nitropyridin-4-yl)-5-(trifluoromethyl)piperidin-3-yl]carbamate

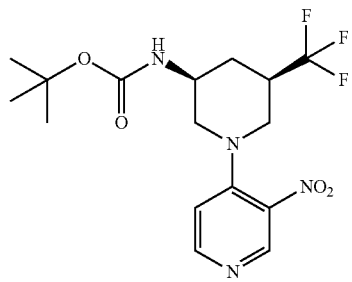

A mixture of 4-chloro-3-nitropyridine (580 mg, 3.6 mmol), tert-butyl [(3S,5R)-5-(trifluoromethyl)piperidin-3-yl]carbamate (800 mg, 3 mmol), isopropyl alcohol (5.0 mL) and DIPEA (1.0 mL, 6.0 mmol) was stirred at 80° C. overnight. The reaction mixture was concentrated under reduced pressure and the residue was purified by column chromatography on silica gel using CombiFlash® apparatus eluting with 50-100% EtOAc/hexanes. The purification gave 1.0 g (80% yield) of the sub-title compound as a yellow solid. LCMS calc. for $C_{16}H_{22}F_3N_4O_4(M+H)^+$: m/z=: 391.2. found: 391.1.

Step 4. tert-Butyl [(3S,5R)-1-(3-aminopyridin-4-yl)-5-(trifluoromethyl)piperidin-3-yl]carbamate

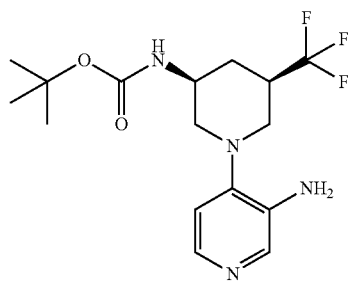 [SMILES: CC(C)(C)OC(=O)N[C@H]1C[C@@H](C(F)(F)F)CN(c2ccncc2[N+](=O)[O-])C1]

A mixture of tert-butyl [(3S,5R)-1-(3-nitropyridin-4-yl)-5-(trifluoromethyl)piperidin-3-yl]carbamate (1 g, 2 mmol), iron powder (0.57 g, 10 mmol), AcOH (16 mL) and water (2 mL) was stirred at room temperature for 1 h. The mixture was allowed to cool to room temperature, concentrated under reduced pressure and the resulting residue was diluted with EtOAc. The resulting mixture was filtered through a diatomaceous earth pad. The filtrate was concentrated under reduced pressure, and the residue was dissolved in 1 M NaOH aqueous solution and extracted with EtOAc (100 mL×3). The combined organic layers were washed with water and brine, dried over $Na_2SO_4$, filtered and concentrated under reduced pressure to give 0.9 g (100% yield) of the sub-title compound as a brown solid. LCMS calc. for $C_{16}H_{24}F_3N_4O_2$ $(M+H)^+$: m/z=: 361.2. found: 361.1.

Step 5. Benzyl {2-[({4-[(3S,5R)-3-amino-5-(trifluoromethyl)piperidin-1-yl]pyridin-3-yl}amino)carbonyl]-7-morpholin-4-ylquinolin-3-yl}carbamate

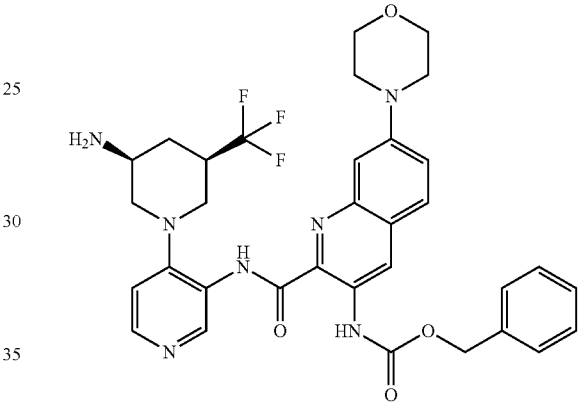

To a mixture of 3-{[(benzyloxy)carbonyl]amino}-7-morpholin-4-ylquinoline-2-carboxylic acid (0.014 g, 0.034 mmol), tert-butyl [(3S,5R)-1-(3-aminopyridin-4-yl)-5-(trifluoromethyl)piperidin-3-yl]carbamate (0.015 g, 0.041 mmol) and HATU (0.033 g, 0.086 mmol) in DMF (0.14 mL), DIPEA (0.018 mL, 0.10 mmol) was added. The mixture was stirred at room temperature for 2 h, then quenched with 5 mL of EtOAc and 3 mL of 1 M NaOH. The layers were separated and aqueous phase was extracted with EtOAc. The organic phases were combined and concentrated under vacuum. The residue was purified by flash chromatography on 20 g silica gel column, eluting with 0-30% MeOH in EtOAc, to yield an amide intermediate, benzyl {2-[({4-[(3S,5R)-3-[(tert-butoxycarbonyl)amino]-5-(trifluoromethyl)piperidin-1-yl]pyridin-3-yl}amino)carbonyl]-7-morpholin-4-ylquinolin-3-yl}carbamate.

To the amide intermediate, 1 mL of 4N HCl in dioxane and 1 mL of MeOH were added. The mixture was stirred at room temperature for 1 h, then concentrated under reduced pressure to give a crude product which was used directly in the next step without further purification.

Step 6. 3-Amino-N-{4-[(3S,5R)-3-amino-5-(trifluoromethyl)piperidin-1-yl]pyridin-3-yl}-7-morpholin-4-ylquinoline-2-carboxamide A mixture of benzyl {2-[({4-[(3S,5R)-3-amino-5-(trifluoromethyl)piperidin-1-yl]pyridin-3-yl}amino)carbonyl]-7-morpholin-4-ylquinolin-3-yl}carbamate (0.005 g, 0.008 mmol) in 2 mL of 4 M HBr in AcOH was stirred at room temperature for 2 h. The solution was then concentrated under reduced pressure and the residue was treated with 4.5 mL of MeOH and 0.5 mL of NH$_4$OH solution. The resulting mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for C$_{25}$H$_{29}$F$_3$N$_7$O$_2$[M+H]$^+$: m/z=516.2. found: 516.3.

The alternative enantiomer, 3-amino-N-{4-[(3R,5S)-3-amino-5-(trifluoromethyl)piperidin-1-yl]pyridin-3-yl}-7-morpholin-4-ylquinoline-2-carboxamide is obtained by an analogous route starting from benzyl (3R,5S)-3-[(tert-butoxycarbonyl)amino]-5-(trifluoromethyl)piperidine-1-carboxylate in step 1.

Example 36

3-Amino-N-{4-[(3S,5R)-3-amino-5-methylpiperidin-1-yl]pyridin-3-yl}-7-(4-methylpiperazin-1-yl)quinoline-2-carboxamide

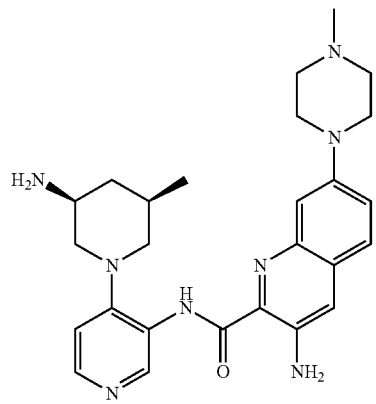 [SMILES: C[C@@H]1C[C@H](N)CN(c2ccncc2NC(=O)c2nc3cc(N4CCN(C)CC4)ccc3cc2N)C1]

Step 1. 3-{[(benzyloxy)carbonyl]amino}-7-(4-methylpiperazin-1-yl)quinoline-2-carboxylic acid

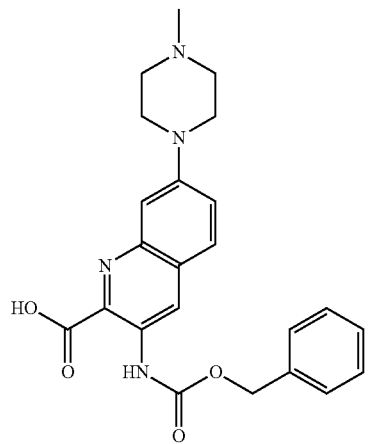 [SMILES: CN1CCN(c2ccc3cc(NC(=O)OCc4ccccc4)c(C(=O)O)nc3c2)CC1]

A mixture of ethyl 3-{[(benzyloxy)carbonyl]amino}-7-bromoquinoline-2-carboxylate (300 mg, 0.7 mmol), 1-methylpiperazine (200 mg, 2 mmol), Pd(OAc)$_2$ (20 mg), dicyclohexyl(2',6'-diisopropoxybiphenyl-2-yl)phosphine (49 mg, 0.10 mmol), and K$_3$PO$_4$ (580 mg, 2.8 mmol) in tert-butyl alcohol (10 mL) was purged with N$_2$ prior and then heated at 100° C. in a sealed vial for 2 h. The mixture was allowed to cool, diluted with EtOAc, and then filtered through a diatomaceous earth plug. The filtrate was concentrated under reduced pressure. To the resulting residue, 10 mL of dioxane and 4 mL of 2.5 M NaOH were added. The resulting mixture was heated at 80° C. for 30 min. then allowed to cool. The mixture was diluted with 80 mL of water then washed with EtOAc. The aqueous phase was neutralized with HCl to pH 8, then concentrated under reduced pressure until almost dry. The precipitated solid was collected by filtration, washed with MeOH and dried to yield pure product (28 mg, 10%). LCMS calc. for C$_{23}$H$_{25}$N$_4$O$_4$ [M+H]$^+$: m/z=421.2. found: 421.3.

Step 2. Benzyl [2-{[(4-{(3S,5R)-3-[(tert-butoxycarbonyl)amino]-5-methylpiperidin-1-yl}pyridin-3-yl)amino]carbonyl}-7-(4-methylpiperazin-1-yl)quinolin-3-yl]carbamate

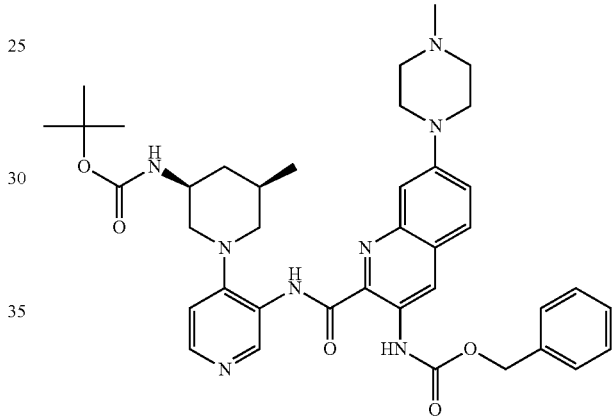

To a mixture of 3-{[(benzyloxy)carbonyl]amino}-7-(4-methylpiperazin-1-yl)quinoline-2-carboxylic acid (0.014 g, 0.034 mmol), tert-butyl [(3S,5R)-1-(3-aminopyridin-4-yl)-5-methylpiperidin-3-yl]carbamate (0.013 g, 0.041 mmol) and HATU (0.033 g, 0.086 mmol) in DMF (0.14 mL), DIPEA (0.018 mL, 0.10 mmol) was added. The mixture was stirred at room temperature for 2 h, then quenched with 5 mL of EtOAc and 3 mL of 1 M NaOH. The resulting layers were separated and the aqueous phase was further extracted with EtOAc. The combined organic phases were concentrated under reduced pressure. The residue was purified by preparative HPLC (XBridge™ C18 column, eluting with a gradient of MeCN/water containing 0.1% NH$_4$OH, at a flow rate of 30 mL/min.) to afford the sub-title compound. LCMS calc. for C$_{39}$H$_{49}$N$_8$O$_5$ [M+H]$^+$: m/z=709.4. found: 709.5.

Step 3. 3-Amino-N-{4-[(3S,5R)-3-amino-5-methylpiperidin-1-yl]pyridin-3-yl}-7-(4-methylpiperazin-1-yl)quinoline-2-carboxamide A mixture of benzyl [2-{[(4-{(3S,5R)-3-[(tert-butoxycarbonyl)amino]-5-methylpiperidin-1-yl}pyridin-3-yl)amino]carbonyl}-7-(4-methylpiperazin-1-yl)quinolin-3-yl]carbamate (0.006 g, 0.008 mmol) and 2 mL of 4.0 M HBr in AcOH was stirred at room temperature for 2 h. The solution was then concentrated under reduced pressure and the resulting residue was treated with 4.5 mL of MeOH and 0.5 mL of NH₄OH solution. The mixture was filtered and purified by preparative HPLC (XBridge™ C18 column, eluting with a gradient of MeCN/water containing 0.1% NH₄OH, at a flow rate of 30 mL/min.) to afford the title compound. LCMS calc. for $C_{26}H_{35}N_8O$ [M+H]⁺: m/z=475.3. found: 475.3.

Example 37

3-Amino-N-{4-[(3S,5R)-3-amino-5-(trifluoromethyl)piperidin-1-yl]pyridin-3-yl}-7-(4-methylpiperazin-1-yl)quinoline-2-carboxamide

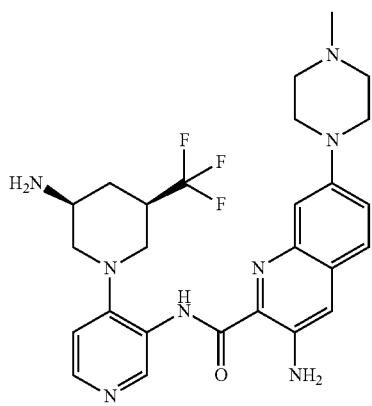 [SMILES: CN1CCN(c2ccc3cc(N)c(C(=O)Nc4cnccc4N4C[C@@H](N)C[C@@H](C(F)(F)F)C4)nc3c2)CC1]

Step 1. Benzyl [2-[({4-[(3S,5R)-3-[(tert-butoxycarbonyl)amino]-5-(trifluoromethyl)piperidin-1-yl]pyridin-3-yl}amino)carbonyl]-7-(4-methylpiperazin-1-yl)quinolin-3-yl]carbamate

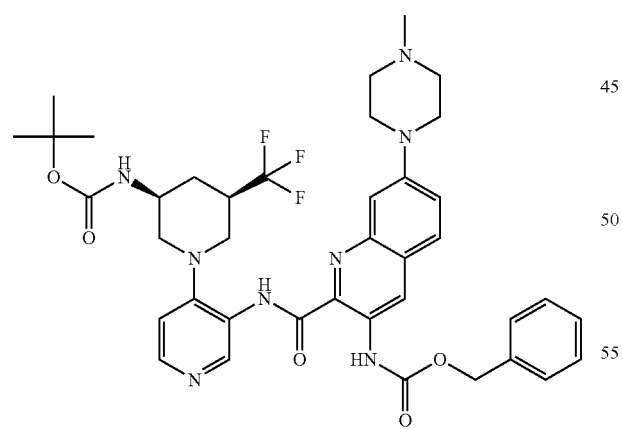

To a mixture of 3-{[(benzyloxy)carbonyl]amino}-7-(4-methylpiperazin-1-yl)quinoline-2-carboxylic acid (0.014 g, 0.034 mmol), tert-butyl [(3S,5R)-1-(3-aminopyridin-4-yl)-5-(trifluoromethyl)piperidin-3-yl]carbamate (0.015 g, 0.041 mmol) and HATU (0.033 g, 0.086 mmol) in DMF (0.14 mL), DIPEA (0.018 mL, 0.10 mmol) was added. The mixture was stirred at room temperature for 2 h, then quenched with 5 mL of EtOAc and 3 mL of 1 M NaOH. The layers were separated and the aqueous phase was extracted with EtOAc. The combined organic extracts were concentrated under reduced pressure. The resulting residue was purified by preparative HPLC (XBridge™ C18 column, eluting with a gradient of MeCN/water containing 0.1% NH₄OH, at a flow rate of 30 mL/min.) to afford the sub-title compound. LCMS calc. for $C_{39}H_{46}F_3N_8O_5$[M+H]⁺: m/z=763.4. found: 763.5.

Step 2. 3-Amino-N-{4-[(3S,5R)-3-amino-5-(trifluoromethyl)piperidin-1-yl]pyridin-3-yl}-7-(4-methylpiperazin-1-yl)quinoline-2-carboxamide A mixture of benzyl [2-[({4-[(3S,5R)-3-[(tert-butoxycarbonyl)amino]-5-(trifluoromethyl)piperidin-1-yl]pyridin-3-yl}amino)carbonyl]-7-(4-methylpiperazin-1-yl)quinolin-3-yl]carbamate (0.006 g, 0.008 mmol) and 2 mL of 4.0 M HBr in AcOH was stirred at room temperature for 2 h. The mixture was concentrated under reduced pressure, and the residue was then treated with 4.5 mL of MeOH and 0.5 mL of NH₄OH solution. The mixture was filtered and the filtrate was purified by preparative HPLC (XBridge™ C18 column, eluting with a gradient of MeCN/water containing 0.1% NH₄OH, at a flow rate of 30 mL/min.) to afford the title compound. LCMS calc. for $C_{26}H_{32}F_3N_8O$ [M+H]⁺: m/z=529.3. found: 529.3.

The alternative isomer 3-amino-N-{4-[(3R,5S)-3-amino-5-(trifluoromethyl)piperidin-1-yl]pyridin-3-yl}-7-(4-methylpiperazin-1-yl)quinoline-2-carboxamide is obtained beginning with tert-butyl [(3R,5S)-1-(3-aminopyridin-4-yl)-5-(trifluoromethyl)piperidin-3-yl]carbamate in step 1.

Example 38

3-Amino-N-{4-[(3R,4R,5S)-3-amino-4-hydroxy-5-methylpiperidin-1-yl]pyridin-3-yl}-7-(4-methylpiperazin-1-yl)quinoline-2-carboxamide

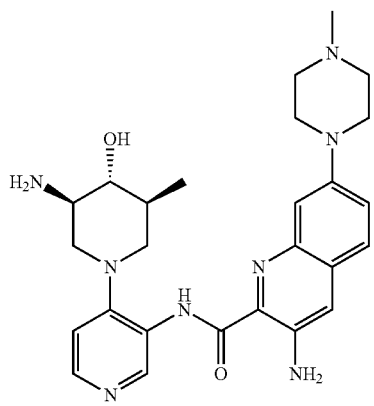 [SMILES: C[C@H]1CN(c2ccncc2NC(=O)c2nc3cc(N4CCN(C)CC4)ccc3cc2N)C[C@@H](N)[C@@H]1O]

121

Step 1. Benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-(4-methylpiperazin-1-yl)quinolin-3-yl]carbamate

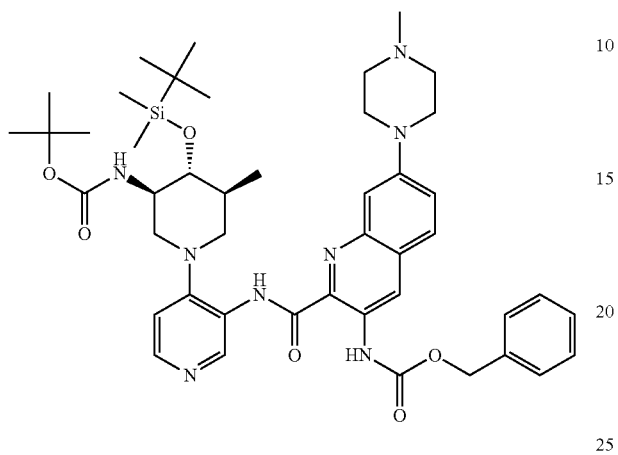

To a mixture of 3-{[(benzyloxy)carbonyl]amino}-7-(4-methylpiperazin-1-yl)quinoline-2-carboxylic acid (0.014 g, 0.034 mmol) tert-butyl ((3R,4R,5S)-1-(3-aminopyridin-4-yl)-4-{[tert-butyl(dimethyl)silyl]oxy}-5-methylpiperidin-3-yl)carbamate (0.018 g, 0.041 mmol) and HATU (0.033 g, 0.086 mmol) in DMF (0.4 mL), DIPEA (0.018 mL, 0.10 mmol) was added. The mixture was stirred at room temperature for 2 h, then quenched with 5 mL of EtOAc and 3 mL of 1 M NaOH. The resulting layers were separated and the aqueous phase was extracted with EtOAc. The combined organic layers were concentrated under reduced pressure. The resulting residue was dissolved in MeOH and filtered. The filtrate was preparative HPLC (XBridge™ C18 column, eluting with a gradient of MeCN/water containing 0.1% NH$_4$OH, at a flow rate of 60 mL/min.) to afford the sub-title compound (5.5 mg, 19%). LCMS calc. for C$_{45}$H$_{63}$N$_8$O$_6$Si [M+H]$^+$: m/z=839.5. found: 839.4.

Step 2. 3-Amino-N-{4-[(3R,4R,5S)-3-amino-4-hydroxy-5-methylpiperidin-1-yl]pyridin-3-yl}-7-(4-methylpiperazin-1-yl)quinoline-2-carboxamide A mixture of benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-(4-methylpiperazin-1-yl)quinolin-3-yl]carbamate (0.0055 g, 0.0066 mmol) in 3 mL of MeOH was hydrogenated in the presence of 3 mg of 10% Pd on carbon under a balloon of hydrogen at room temperature for 1 h. The mixture was diluted with 5 mL of MeOH then filtered. The filtrate was concentrated and the resulting residue was treated with 2 mL of MeOH and 2 mL of 4 M HCl in dioxane at room temperature for 1 h. The solution was concentrated under reduced pressure, the residue was dissolved in 4 mL of MeOH and 0.5 mL of NH$_4$OH solution, then filtered through a diatomaceous earth plug. The filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for C$_{26}$H$_{35}$N$_8$O$_2$ [M+H]$^+$: m/z=491.3. found: 491.3.

122

Example 39

3-Amino-N-{4-[(3S,5R)-3-amino-5-(trifluoromethyl)piperidin-1-yl]pyridin-3-yl}-7-(tetrahydro-2H-pyran-4-yl)quinoline-2-carboxamide

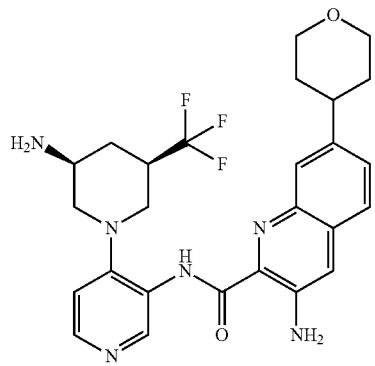 [SMILES: Nc1cc2ccc(C3CCOCC3)cc2nc1C(=O)Nc1cnccc1N1C[C@@H](N)C[C@@H](C(F)(F)F)C1]

Step 1. Benzyl {7-bromo-2-[({4-[(3S,5R)-3-[(tert-butoxycarbonyl)amino]-5-(trifluoromethyl)piperidin-1-yl]pyridin-3-yl}amino)carbonyl]quinolin-3-yl}carbamate

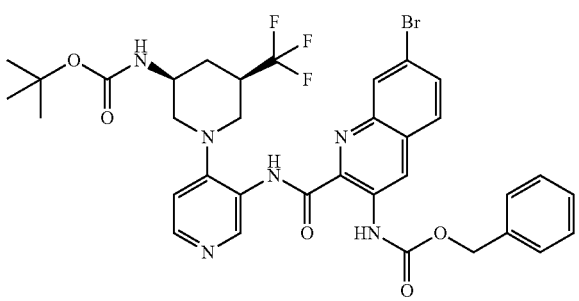 [SMILES: CC(C)(C)OC(=O)N[C@H]1C[C@@H](C(F)(F)F)CN(c2ccncc2NC(=O)c2nc3cc(Br)ccc3cc2NC(=O)OCc2ccccc2)C1]

To a mixture of 3-{[(benzyloxy)carbonyl]amino}-7-bromoquinoline-2-carboxylic acid (0.50 g, 1.2 mmol), tert-butyl [(3S,5R)-1-(3-aminopyridin-4-yl)-5-(trifluoromethyl)piperidin-3-yl]carbamate (0.45 g, 1.2 mmol) and HATU (1.2 g, 3.1 mmol) in DMF (4.9 mL), DIPEA (0.65 mL, 3.7 mmol) was added. The mixture was stirred at room temperature for 2 h, then quenched with 50 mL of EtOAc and 30 mL of 1 M NaOH. The layers were separated and the aqueous phase was extracted with EtOAc. The combined organics were concentrated under reduced pressure. The residue was purified by flash chromatography on a 40 g silica gel column, eluting with 0-100% EtOAc in hexanes, to give the sub-title compound (0.492 g, 53%). LCMS calc. for C$_{34}$H$_{35}$BrF$_3$N$_6$O$_5$[M+H]$^+$: m/z=743.2. found: 743.3.

Step 2. Benzyl [2-[({4-[(3S,5R)-3-[(tert-butoxycarbonyl)amino]-5-(trifluoromethyl)piperidin-1-yl]pyridin-3-yl}amino)carbonyl]-7-(3,6-dihydro-2H-pyran-4-yl)quinolin-3-yl]carbamate and tert-butyl [(3S,5R)-1-[3-({[3-amino-7-(3,6-dihydro-2H-pyran-4-yl)quinolin-2-yl]carbonyl}amino)pyridin-4-yl]-5-(trifluoromethyl)piperidin-3-yl]carbamate

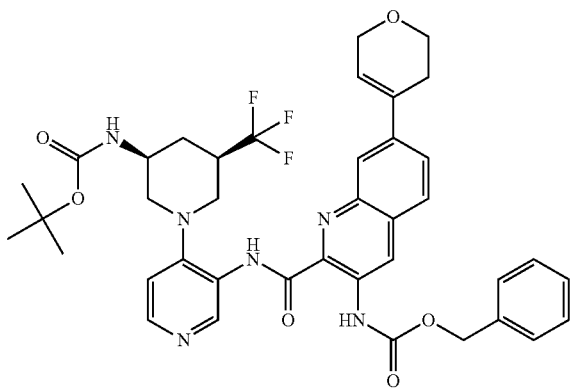

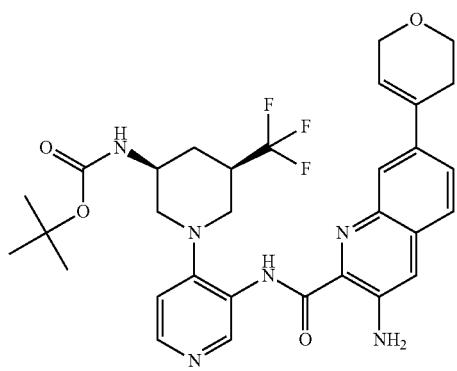

A pressure vial was charged with benzyl {7-bromo-2-[({4-[(3S,5R)-3-[(tert-butoxycarbonyl)amino]-5-(trifluoromethyl)piperidin-1-yl]pyridin-3-yl}amino)carbonyl]quinolin-3-yl}carbamate (0.032 g, 0.043 mmol), $K_3PO_4$ (0.0181 g, 0.0852 mmol), 1,4-dioxane (0.55 mL), water (0.092 mL) and 4-(4,4,5,5-tetramethyl-1,3,2-dioxaborolan-2-yl)-3,6-dihydro-2H-pyran (0.013 g, 0.063 mmol). The mixture was deoxygenated with nitrogen for 10 min. Dicyclohexyl(2',4',6'-triisopropylbiphenyl-2-yl)phosphine-(2'-aminobiphenyl-2-yl)(chloro)palladium (1:1) (0.0022 g, 0.0028 mmol) was added. The reaction mixture was sealed with a screw cap and heated at 80° C. for 1 h. The mixture was quenched with water and extracted with EtOAc. The combined organic extracts were dried and concentrated under reduced pressure. The residue was purified by flash chromatography on a 20 g silica gel column, eluting with 0-100% EtOAc in hexanes, to give benzyl [2-[({4-[(3S,5R)-3-[(tert-butoxycarbonyl)amino]-5-(trifluoromethyl)piperidin-1-yl]pyridin-3-yl}amino)carbonyl]-7-(3,6-dihydro-2H-pyran-4-yl)quinolin-3-yl]carbamate (0.16 g, 50%, LCMS calc. for $C_{39}H_{42}F_3N_6O_6[M+H]^+$: m/z=747.3. found: 747.4) and the corresponding benzyl carbamate deprotected product, tert-butyl [(3S,5R)-1-[3-({[3-amino-7-(3,6-dihydro-2H-pyran-4-yl)quinolin-2-yl]carbonyl}amino)pyridin-4-yl]-5-(trifluoromethyl)piperidin-3-yl]carbamate (0.13 g, 50%, LCMS calc. for $C_{31}H_{36}F_3N_6O_4$ $[M+H]^+$: m/z=613.3. found: 613.4).

Step 3. 3-Amino-N-{4-[(3S,5R)-3-amino-5-(trifluoromethyl)piperidin-1-yl]pyridin-3-yl}-7-(tetrahydro-2H-pyran-4-yl)quinoline-2-carboxamide A mixture of tert-butyl [(3S,5R)-1-[3-({[3-amino-7-(3,6-dihydro-2H-pyran-4-yl)quinolin-2-yl]carbonyl}amino)pyridin-4-yl]-5-(trifluoromethyl)piperidin-3-yl]carbamate (0.014 g, 0.023 mmol) in 1.5 mL of MeOH was hydrogenated in the presence of 10% Pd on carbon (20 mg) under a balloon of hydrogen at room temperature for 1 h. The mixture was filtered and the filtrate was concentrated to give the crude tert-butyloxycarbamate protected intermediate tert-butyl [(3S,5R)-1-[3-({[3-amino-7-(tetrahydro-2H-pyran-4-yl)quinolin-2-yl]carbonyl}amino)pyridin-4-yl]-5-(trifluoromethyl)piperidin-3-yl]carbamate (0.007 mg, 50%), LCMS calc. for $C_{31}H_{38}F_3N_6O_4[M+H]^+$: m/z=615.3. found: 615.3.

To the tert-butyloxycarbamate protected intermediate, 2 mL of 4 M HCl and 1 mL of MeOH were added. The mixture was stirred at room temperature for 1 h, evaporated under reduced pressure. The residue was dissolved in 4.5 mL of MeOH, and treated with 0.3 mL of $NH_4OH$ solution. The mixture was filtered and the filtrate was purified by preparative HPLC (XBridge™ C18 column, eluting with a gradient of MeCN/water containing 0.1% $NH_4OH$, at a flow rate of 30 mL/min.) to afford the title compound. LCMS calc. for $C26H_{30}F_3N_6O_2$ $[M+H]^+$: m/z=515.2. found: 515.4.

The alternative enantiomer 3-amino-N-{4-[(3R,5S)-3-amino-5-(trifluoromethyl)piperidin-1-yl]pyridin-3-yl}-7-(tetrahydro-2H-pyran-4-yl)quinoline-2-carboxamide is obtained by an analogous method using tert-butyl [(3R,5S)-1-(3-aminopyridin-4-yl)-5-(trifluoromethyl)piperidin-3-yl]carbamate in step 1.

Example 40

3-Amino-N-{4-[(3S,5R)-3-amino-5-methylpiperidin-1-yl]pyridin-3-yl}-7-(tetrahydro-2H-pyran-4-yl)quinoline-2-carboxamide

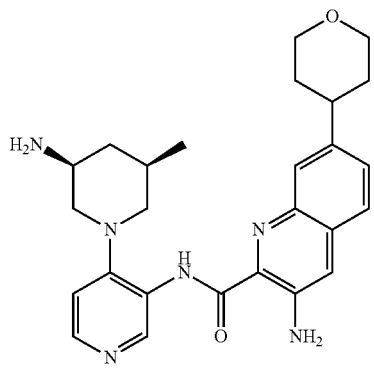 [SMILES: C[C@@H]1C[C@H](N)CN(c2ccncc2NC(=O)c2nc3cc(C4CCOCC4)ccc3cc2N)C1]

125

Step 1. Benzyl (7-bromo-2-{[(4-{(3S,5R)-3-[(tert-butoxycarbonyl)amino]-5-methylpiperidin-1-yl}pyridin-3-yl)amino]carbonyl}quinolin-3-yl)carbamate

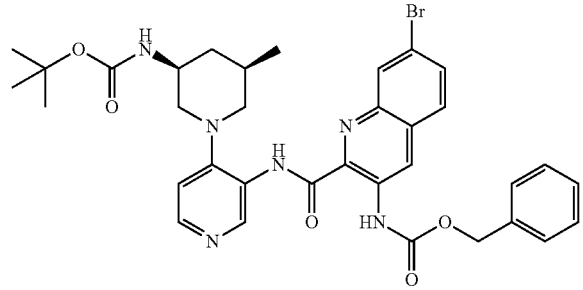 [SMILES: C[C@@H]1C[C@H](NC(=O)OC(C)(C)C)CN(c2ccncc2NC(=O)c2nc3cc(Br)ccc3cc2NC(=O)OCc2ccccc2)C1]

A mixture of 3-{[(benzyloxy)carbonyl]amino}-7-bromo-quinoline-2-carboxylic acid (0.50 g, 1.2 mmol), tert-butyl [(3S,5R)-1-(3-aminopyridin-4-yl)-5-methylpiperidin-3-yl]carbamate (0.38 g, 1.2 mmol), HATU (1.2 g, 3.1 mmol) in DMF (4.9 mL) and DIPEA (0.65 mL, 3.7 mmol) was stirred at room temperature for 2 h, then quenched with 50 mL of EtOAc and 30 mL of 1 M NaOH. The layers were separated and the aqueous phase was extracted with EtOAc. The combined organic extracts were concentrated under reduced pressure. The residue was purified by flash chromatography on 40 g silica gel column, eluting with 0-100% EtOAc in hexanes, to give the sub-title compound (0.435 g, 51%). LCMS calc. for $C_{34}H_{38}BrN_6O_5$ [M+H]$^+$: m/z=689.2. found: 689.3.

Step 2. Benzyl [2-{[(4-{(3S,5R)-3-[(tert-butoxycarbonyl)amino]-5-methylpiperidin-1-yl}pyridin-3-yl)amino]carbonyl}-7-(3,6-dihydro-2H-pyran-4-yl)quinolin-3-yl]carbamate and tert-butyl {(3S,5R)-1-[3-({[3-amino-7-(3,6-dihydro-2H-pyran-4-yl)quinolin-2-yl]carbonyl}amino)pyridin-4-yl]-5-methylpiperidin-3-yl}carbamate

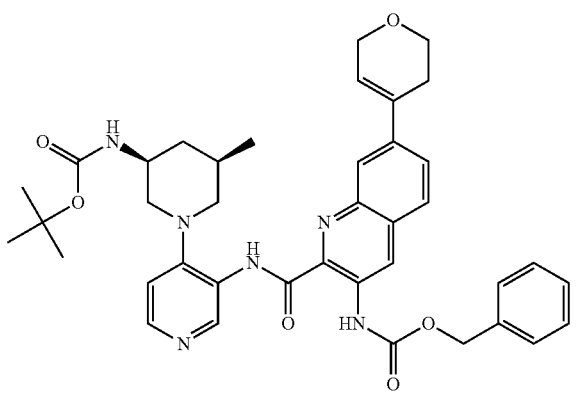

126

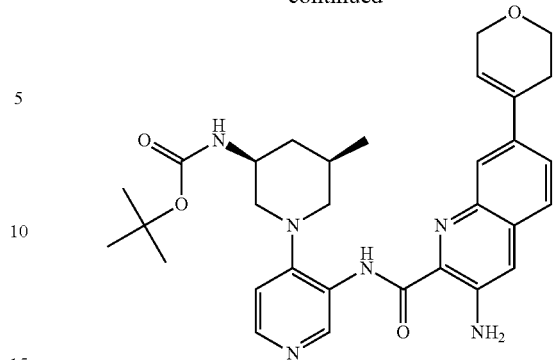

A pressure vial was charged with benzyl (7-bromo-2-{[(4-{(3S,5R)-3-[(tert-butoxycarbonyl)amino]-5-methylpiperidin-1-yl}pyridin-3-yl)amino]carbonyl}quinolin-3-yl)carbamate (0.029 g, 0.043 mmol), $K_3PO_4$ (0.0181 g, 0.0852 mmol), 1,4-dioxane (0.55 mL), water (0.092 mL) and 4-(4,4,5,5-tetramethyl-1,3,2-dioxaborolan-2-yl)-3,6-dihydro-2H-pyran (0.013 g, 0.063 mmol). The mixture was deoxygenated with nitrogen for 10 min. Dicyclohexyl(2',4',6'-triisopropylbiphenyl-2-yl)phosphine-(2'-aminobiphenyl-2-yl)(chloro)palladium (1:1) (0.0022 g, 0.0028 mmol) was added. The mixture was sealed with screw cap, then heated at 80° C. for 1 h. The reaction mixture was quenched with water and extracted with EtOAc. The combined organic extracts were dried and concentrated. The residue was purified by flash chromatography on 20 g silica gel, eluting with 0-100% EtOAc in hexanes, to yield benzyl [2-{[(4-{(3S,5R)-3-[(tert-butoxycarbonyl)amino]-5-methylpiperidin-1-yl}pyridin-3-yl)amino]carbonyl}-7-(3,6-dihydro-2H-pyran-4-yl)quinolin-3-yl]carbamate (0.017 g, 57%), LCMS calc. for $C_{39}H_{45}N_6O_6$ [M+H]$^+$: m/z=639.3. found: 693.3; and the corresponding benzyl carbamate deprotected product tert-butyl {(3S,5R)-1-[3-({[3-amino-7-(3,6-dihydro-2H-pyran-4-yl)quinolin-2-yl]carbonyl}amino)pyridin-4-yl]-5-methylpiperidin-3-yl}carbamate (0.010, 42%). LCMS calc. for $C_{31}H_{39}N_6O_4$ [M+H]$^+$: m/z=559.3. found: 559.3.

Step 3. 3-Amino-N-{4-[(3S,5R)-3-amino-5-methylpiperidin-1-yl]pyridin-3-yl}-7-(tetrahydro-2H-pyran-4-yl)quinoline-2-carboxamide A mixture of benzyl [2-{[(4-{(3S,5R)-3-[(tert-butoxycarbonyl)amino]-5-methylpiperidin-1-yl}pyridin-3-yl)amino]carbonyl}-7-(3,6-dihydro-2H-pyran-4-yl)quinolin-3-yl]carbamate (0.017 g, 0.024 mmol) in 1.5 mL of MeOH was hydrogenated in the presence of 10% Pd on carbon (10 mg) under a balloon of hydrogen at room temperature for 1 h. The mixture was filtered and the filtrate was concentrated under reduced pressure to give tert-butyl {(3S,5R)-1-[3-({[3-amino-7-(tetrahydro-2H-pyran-4-yl)quinolin-2-yl]carbonyl}amino)pyridin-4-yl]-5-methylpiperidin-3-yl}carbamate (0.012 g, 87%). LCMS calc. for $C_{31}H_{41}N_6O_4$ [M+H]$^+$: m/z=561.3. found: 561.4. To the intermediate made above was added 1 mL of 4 M HCl in dioxane and 1 mL of MeOH. The mixture was stirred at room temperature for 1 h, then evaporated under vacuum. The residue was dissolved in 4.5 mL of MeOH and treated with 0.3 mL of $NH_4OH$ solution. The mixture was filtered and the filtrate was purified by preparative HPLC (XBridge™ C18 column, eluting with a gradient of MeCN/water containing 0.1%

NH$_4$OH, at a flow rate of 30 mL/min.) to afford the title compound. LCMS calc. for C$_{26}$H$_{33}$N$_6$O$_2$ [M+H]$^+$: m/z=461.3. found: 461.3.

Example 41

3-Amino-N-{4-[(3R,4R,5S)-3-amino-4-hydroxy-5-methylpiperidin-1-yl]pyridin-3-yl}-7-(tetrahydro-2H-pyran-4-yl)quinoline-2-carboxamide

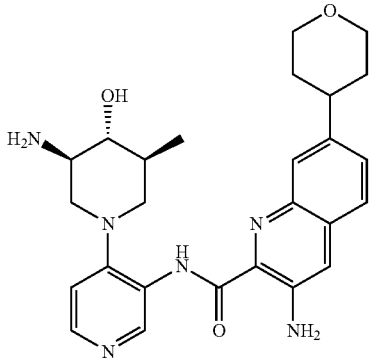 [SMILES: C[C@H]1CN(c2ccncc2NC(=O)c2nc3cc(C4CCOCC4)ccc3cc2N)C[C@@H](N)[C@@H]1O]

Step 1. Benzyl [7-bromo-2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)quinolin-3-yl]carbamate

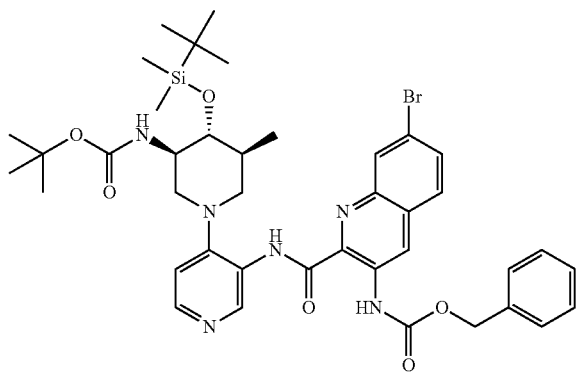 [SMILES: C[C@H]1CN(c2ccncc2NC(=O)c2nc3cc(Br)ccc3cc2NC(=O)OCc2ccccc2)C[C@@H](NC(=O)OC(C)(C)C)[C@@H]1O[Si](C)(C)C(C)(C)C]

A mixture of 3-{[(benzyloxy)carbonyl]amino}-7-bromoquinoline-2-carboxylic acid (0.50 g, 1.2 mmol), tert-butyl ((3R,4R,5S)-1-(3-aminopyridin-4-yl)-4-{[tert-butyl(dimethyl)silyl]oxy}-5-methylpiperidin-3-yl)carbamate (0.54 g, 1.2 mmol), and HATU (1.2 g, 3.1 mmol) in DMF (4.9 mL) and DIPEA (0.65 mL, 3.7 mmol) was stirred at room temperature for 2 h, then quenched with 50 mL of EtOAc and 30 mL of 1 M NaOH. The resulting layers were separated and the aqueous phase was extracted with EtOAc. The combined organic extracts were concentrated under reduced pressure. The residue was purified by flash chromatography on a 40 g silica gel column, eluting with 0-100% EtOAc in hexanes, to give the sub-title compound (0.565 g, 55%). LCMS calc. for C$_{40}$H$_{52}$BrN$_6$O$_6$Si [M+H]$^+$: m/z=919.3. found: 819.4.

Step 2. Benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-(3,6-dihydro-2H-pyran-4-yl)quinolin-3-yl]carbamate

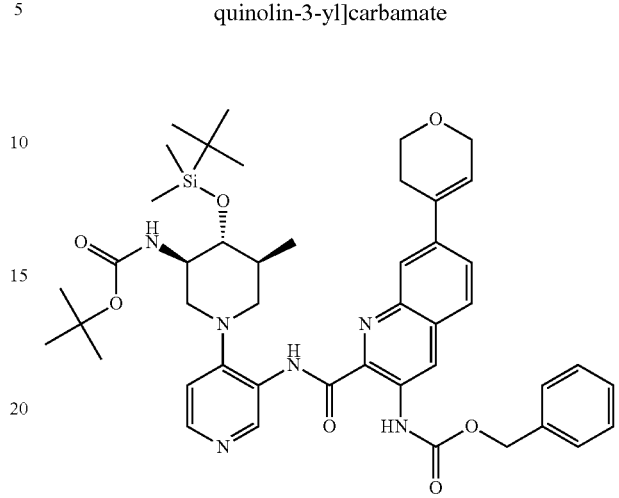

A pressure vial was charged with benzyl [7-bromo-2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)quinolin-3-yl]carbamate (0.035 g, 0.043 mmol), K$_3$PO$_4$ (0.0181 g, 0.0852 mmol), 1,4-dioxane (0.55 mL), water (0.092 mL) and 4-(4,4,5,5-tetramethyl-1,3,2-dioxaborolan-2-yl)-3,6-dihydro-2H-pyran (0.013 g, 0.063 mmol). The mixture was deoxygenated with nitrogen for 10 min. Dicyclohexyl(2',4',6'-triisopropylbiphenyl-2-yl)phosphine-(2'-aminobiphenyl-2-yl)(chloro)palladium (1:1) (0.0022 g, 0.0028 mmol) was added. The mixture was sealed with screw cap then heated at 90° C. for 1.5 h. The mixture was quenched with water and extracted with EtOAc. The combined organic extracts were dried and concentrated under reduced pressure. The residue was purified by flash chromatography on 20 g silica gel, eluting with 0-100% EtOAc in hexanes, to give the sub-title compound (0.023 g, 65%). LCMS calc. for C$_{45}$H$_{59}$N$_6$O$_7$Si [M+H]$^+$: m/z=823.4. found: 823.5.

Step 3. 3-Amino-N-{4-[(3R,4R,5S)-3-amino-4-hydroxy-5-methylpiperidin-1-yl]pyridin-3-yl}-7-(tetrahydro-2H-pyran-4-yl)quinoline-2-carboxamide A mixture of benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-(3,6-dihydro-2H-pyran-4-yl)quinolin-3-yl]carbamate (0.023 g, 0.028 mmol) in 1.5 mL of MeOH was hydrogenated in the presence of 10% Pd on carbon (10 mg) under a balloon of hydrogen at room temperature for 1 h. The mixture was filtered and the filtrate was concentrated under reduced pressure to afford a hydrogenated intermediate tert-butyl ((3R,4R,5S)-1-[3-({[3-amino-7-(tetrahydro-2H-pyran-4-yl)quinolin-2-yl]carbonyl}amino)pyridin-4-yl]-4-{[tert-butyl(dimethyl)silyl]oxy}-5-methylpiperidin-3-yl)carbamate (0.012 g, 62%). LCMS calc. for C$_{37}$H$_{55}$N$_6$O$_5$Si [M+H]$^+$: m/z=691.4. found: 691.5.

To the hydrogenated intermediate was added 1 mL of 4 M HCl in dioxane and 1 mL of MeOH. The mixture was stirred at room temperature for 1 h then concentrated under reduced pressure. The resulting residue was dissolved in 4.5 mL of MeOH, and treated with 0.3 mL of NH₄OH solution. The mixture was filtered and the filtrate was purified by preparative HPLC (XBridge™ C18 column, eluting with a gradient of MeCN/water containing 0.1% NH₄OH, at a flow rate of 30 mL/min.) to afford the title compound. LCMS calc. for $C_{26}H_{33}N_6O_3$ [M+H]⁺: m/z=477.3. found: 477.2.

Example 42

3-Amino-N-{4-[(3R,4R,5S)-3-amino-4-hydroxy-5-methylpiperidin-1-yl]pyridin-3-yl}-7-(1-methylpiperidin-4-yl)quinoline-2-carboxamide

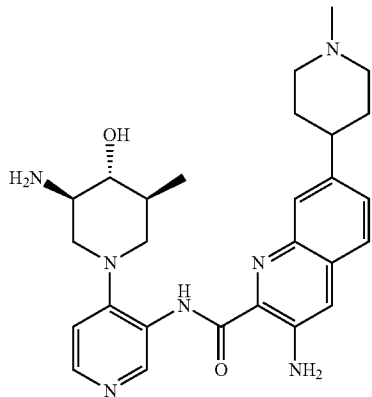 [SMILES: C[C@H]1CN(c2ccncc2NC(=O)c2nc3cc(C4CCN(C)CC4)ccc3cc2N)C[C@@H](N)[C@@H]1O]

Step 1. Benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-(1-methyl-1,2,3,6-tetrahydropyridin-4-yl)quinolin-3-yl]carbamate

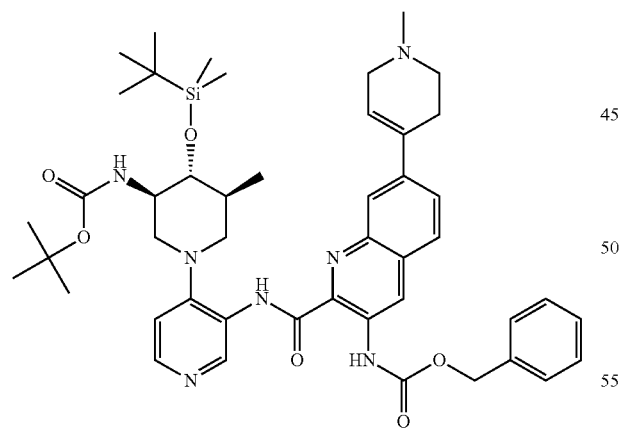

A pressure vial was charged with benzyl [7-bromo-2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)quinolin-3-yl]carbamate (0.035 g, 0.043 mmol), K₃PO₄ (0.0181 g, 0.0852 mmol), 1,4-dioxane (0.55 mL), water (0.092 mL) and 1-methyl-4-(4,4,5,5-tetramethyl-1,3,2-dioxaborolan-2-yl)-1,2,3,6-tetrahydropyridine (0.014 g, 0.063 mmol). The mixture was deoxygenated with nitrogen for 10 min. Dicyclohexyl(2',4',6'-triisopropylbiphenyl-2-yl)phosphine-(2'-aminobiphenyl-2-yl)(chloro)palladium (1:1) (0.0022 g, 0.0028 mmol) was added. The mixture was sealed with screw cap, then heated at 90° C. for 1.5 h. The mixture was quenched with water, extracted with EtOAc. The combined organic extracts were dried and concentrated under reduced pressure. The residue was purified by flash chromatography on 20 g silica gel, eluting with 0-100% EtOAc in hexanes, to give the sub-title compound (0.013 g, 36%). LCMS calc. for $C_{46}H_{62}N_7O_6Si$ [M+H]⁺: m/z=836.5. found: 836.6.

Step 2. 3-Amino-N-{4-[(3R,4R,5S)-3-amino-4-hydroxy-5-methylpiperidin-1-yl]pyridin-3-yl}-7-(1-methylpiperidin-4-yl)quinoline-2-carboxamide A mixture of benzyl [2-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-7-(1-methyl-1,2,3,6-tetrahydropyridin-4-yl)quinolin-3-yl]carbamate (0.013 g, 0.016 mmol) in 1.5 mL of MeOH was hydrogenated in the presence of 10% Pd on carbon (10 mg) under a balloon of hydrogen at room temperature for 1 h. The reaction mixture was filtered and the filtrate was evaporated to dryness under reduced pressure to yield the protected intermediate tert-butyl ((3R,4R,5S)-1-[3-({[3-amino-7-(1-methylpiperidin-4-yl)quinolin-2-yl]carbonyl}amino)pyridin-4-yl]-4-{[tert-butyl(dimethyl)silyl]oxy}-5-methylpiperidin-3-yl)carbamate (0.0075 g, 68%). LCMS calc. for $C_{38}H_{58}N_7O_4Si$ [M+H]⁺: m/z=704.4. found: 704.6.

To the protected intermediate were added 1 mL of 4 M HCl in dioxane and 1 mL of MeOH. The mixture was stirred at room temperature for 1 h, then evaporated under reduced pressure. The residue was dissolved in 4.5 mL of MeOH and treated with 0.3 mL of NH₄OH solution. The mixture was filtered and the filtrate was purified by preparative HPLC (XBridge™ C18 column, eluting with a gradient of MeCN/water containing 0.1% NH₄OH, at a flow rate of 30 mL/min.) to afford the title compound. LCMS calc. for $C_{27}H_{36}N_7O_2$ [M+H]⁺: m/z=490.3. found: 490.3.

Example 43

3-Amino-N-{4-[(3S,5R)-3-amino-5-methylpiperidin-1-yl]pyridin-3-yl}-7-(1-methylpiperidin-4-yl)quinoline-2-carboxamide

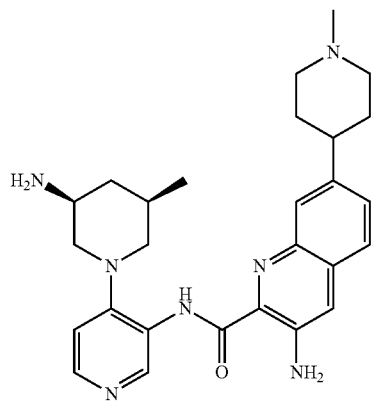 [SMILES: C[C@@H]1C[C@H](N)CN(c2ccncc2NC(=O)c2nc3cc(C4CCN(C)CC4)ccc3cc2N)C1]

Step 1. Benzyl [2-{[(4-{(3S,5R)-3-[(tert-butoxycarbonyl)amino]-5-methylpiperidin-1-yl}pyridin-3-yl)amino]carbonyl}-7-(1-methyl-1,2,3,6-tetrahydropyridin-4-yl)quinolin-3-yl]carbamate

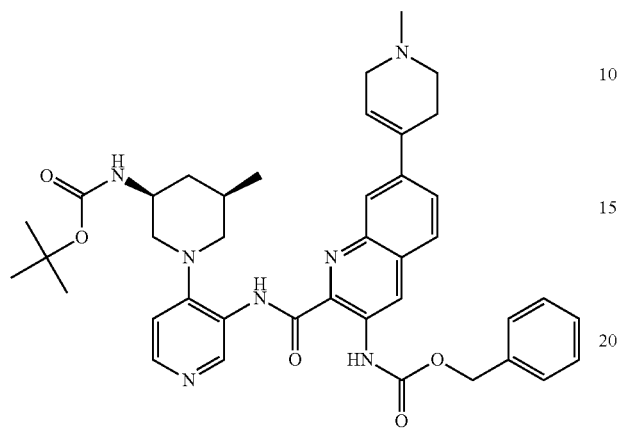

A pressure vial was charged with benzyl (7-bromo-2-{[(4-{(3S,5R)-3-[(tert-butoxycarbonyl)amino]-5-methylpiperidin-1-yl}pyridin-3-yl)amino]carbonyl}quinolin-3-yl)carbamate (0.029 g, 0.043 mmol), K$_3$PO$_4$ (0.0181 g, 0.0852 mmol), 1,4-dioxane (0.55 mL), water (0.092 mL) and 1-methyl-4-(4,4,5,5-tetramethyl-1,3,2-dioxaborolan-2-yl)-1,2,3,6-tetrahydropyridine (0.014 g, 0.063 mmol). The mixture was deoxygenated with nitrogen for 10 min. Dicyclohexyl(2',4',6'-triisopropylbiphenyl-2-yl)phosphine-(2'-aminobiphenyl-2-yl)(chloro)palladium (1:1) (0.0022 g, 0.0028 mmol) was added. The mixture was sealed with screw cap, then heated at 90° C. for 1.5 h. The mixture was quenched with water and extracted with EtOAc. The combined organic extracts were dried and concentrated under reduced pressure. The residue was purified by flash chromatography on 20 g silica gel, eluting with 0-30% MeOH in EtOAc, to yield the sub-title compound (0.009 g, 30%). LCMS calc. for C$_{40}$H$_{48}$N$_7$O$_5$ [M+H]$^+$: m/z=706.4. found: 706.5.

Step 2. 3-Amino-N-{4-[(3S,5R)-3-amino-5-methylpiperidin-1-yl]pyridin-3-yl}-7-(1-methylpiperidin-4-yl)quinoline-2-carboxamide A mixture of benzyl [2-{[(4-{(3S,5R)-3-[(tert-butoxycarbonyl)amino]-5-methylpiperidin-1-yl}pyridin-3-yl)amino]carbonyl}-7-(1-methyl-1,2,3,6-tetrahydropyridin-4-yl)quinolin-3-yl]carbamate (0.009 g, 0.01 mmol), in 1.5 mL of MeOH was hydrogenated, in the presence of 10% Pd on carbon (3.5 mg), under a hydrogen balloon at room temperature for 1 h. The mixture was filtered and the filtrate was evaporated under vacuum to give tert-butyl {(3S,5R)-1-[3-({[3-amino-7-(1-methylpiperidin-4-yl)quinolin-2-yl]carbonyl}amino)pyridin-4-yl]-5-methylpiperidin-3-yl}carbamate (0.0065 g, 90%). LCMS calc. for C$_{32}$H$_{44}$N$_7$O$_3$ [M+H]$^+$: m/z=574.3. found: 574.5.

To the intermediate tert-butyl {(3S,5R)-1-[3-({[3-amino-7-(1-methylpiperidin-4-yl)quinolin-2-yl]carbonyl}amino)pyridin-4-yl]-5-methylpiperidin-3-yl})carbamate, 1 mL of 4 M HCl in dioxane and 1 mL of MeOH were added. The mixture was stirred at room temperature for 1 h then concentrated under reduced pressure. The resulting residue was dissolved in 4.5 mL of MeOH and treated with 0.3 mL of NH$_4$OH solution. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for C$_{27}$H$_{36}$N$_7$O [M+H]$^+$: m/z=474.3. found: 474.4.

Example 44

3-Amino-N-{4-[(3S,5R)-3-amino-5-(trifluoromethyl)piperidin-1-yl]pyridin-3-yl}-7-(1-methylpiperidin-4-yl)quinoline-2-carboxamide

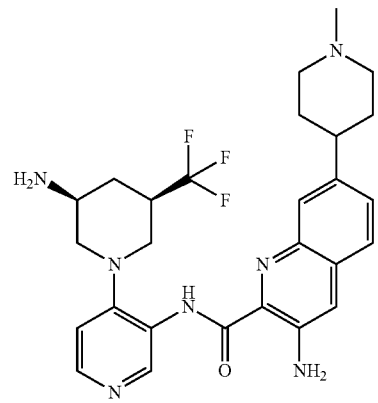 [SMILES: CN1CCC(c2ccc3cc(N)c(C(=O)Nc4cnccc4N4C[C@@H](N)C[C@@H](C(F)(F)F)C4)nc3c2)CC1]

Step 1. Benzyl [2-[({4-[(3S,5R)-3-[(tert-butoxycarbonyl)amino]-5-(trifluoromethyl)piperidin-1-yl]pyridin-3-yl}amino)carbonyl]-7-(1-methyl-1,2,3,6-tetrahydropyridin-4-yl)quinolin-3-yl]carbamate

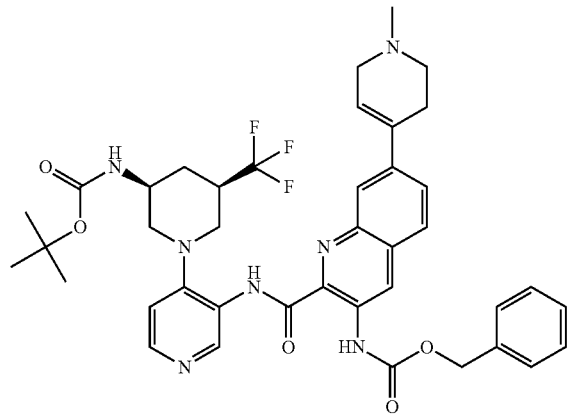 [SMILES: CN1CC=C(c2ccc3cc(NC(=O)OCc4ccccc4)c(C(=O)Nc4cnccc4N4C[C@@H](NC(=O)OC(C)(C)C)C[C@@H](C(F)(F)F)C4)nc3c2)CC1]

A pressure vial was charged with benzyl {7-bromo-2-[({4-[(3S,5R)-3-[(tert-butoxycarbonyl)amino]-5-(trifluoromethyl)piperidin-1-yl]pyridin-3-yl}amino)carbonyl]quinolin-3-yl}carbamate (0.032 g, 0.043 mmol), K$_3$PO$_4$ (0.0181 g, 0.0852 mmol), 1,4-dioxane (0.55 mL), water (0.092 mL) and 1-methyl-4-(4,4,5,5-tetramethyl-1,3,2-dioxaborolan-2-yl)-1,2,3,6-tetrahydropyridine (0.014 g, 0.063 mmol). The mixture was purged with nitrogen for 10 min. Dicyclohexyl(2',4',6'-triisopropylbiphenyl-2-yl)phosphine-(2'-aminobiphenyl-2-yl)(chloro)palladium (1:1) (0.0022 g, 0.0028 mmol) was added. The mixture was sealed with screw cap, then heated at 90° C. for 1.5 h. The mixture was quenched with water, then extracted with EtOAc. The combined organic layers were dried and concentrated under reduced pressure. The residue was purified by flash chromatography on 20 g silica gel, eluting with 0-30% MeOH in EtOAc, to yield the sub-title compound. LCMS calc. for $C_{40}H_{45}F_3N_7O_5[M+H]^+$: m/z=760.3. found: 760.4.

Step 2. 3-Amino-N-{4-[(3S,5R)-3-amino-5-(trifluoromethyl)piperidin-1-yl]pyridin-3-yl}-7-(1-methylpiperidin-4-yl)quinoline-2-carboxamide

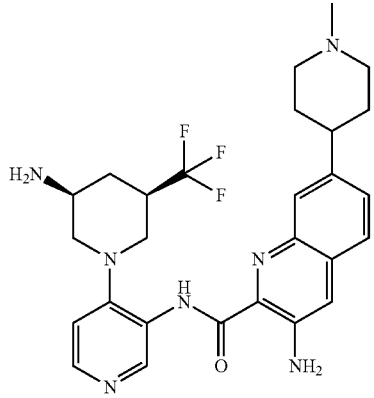 [SMILES: CN1CCC(c2ccc3cc(N)c(C(=O)Nc4cnccc4N4C[C@@H](N)C[C@@H](C(F)(F)F)C4)nc3c2)CC1]

A mixture of benzyl [2-[({4-[(3S,5R)-3-[(tert-butoxycarbonyl)amino]-5-(trifluoromethyl)piperidin-1-yl]pyridin-3-yl}amino)carbonyl]-7-(1-methyl-1,2,3,6-tetrahydropyridin-4-yl)quinolin-3-yl]carbamate (0.010 g, 0.013 mmol) in 1.5 mL of MeOH was hydrogenated in the presence of 10% Pd on carbon (3.5 mg) under a balloon of hydrogen at room temperature for 1 h. The mixture was filtered and the filtrate was concentrated under reduced pressure to give tert-butyl [(3S,5R)-1-[3-({[3-amino-7-(1-methylpiperidin-4-yl)quinolin-2-yl]carbonyl}amino)pyridin-4-yl]-5-(trifluoromethyl)piperidin-3-yl]carbamate (0.0065 g, 79%). LCMS calc. for $C_{32}H_{41}F_3N_7O_3[M+H]^+$: m/z=628.3. found: 628.3.

To the tert-butyl [(3S,5R)-1-[3-({[3-amino-7-(1-methylpiperidin-4-yl)quinolin-2-yl]carbonyl}amino)pyridin-4-yl]-5-(trifluoromethyl)piperidin-3-yl]carbamate, 1 mL of 4 M HCl in dioxane and 1 mL of MeOH were added. The mixture was stirred at room temperature for 1 h, then evaporated under vacuum. The resulting residue was dissolved in 4.5 mL of MeOH and treated with 0.3 mL of NH$_4$OH solution. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for $C_{27}H_{33}F_3N_7O$ $[M+H]^+$: m/z=528.3. found: 528.3.

The alternative enantiomer 3-amino-N-{4-[(3R,5S)-3-amino-5-(trifluoromethyl)piperidin-1-yl]pyridin-3-yl}-7-(1-methylpiperidin-4-yl)quinoline-2-carboxamide is prepared by an analogous route using benzyl {7-bromo-2-[({4-[(3R,5S)-3-[(tert-butoxycarbonyl)amino]-5-(trifluoromethyl)piperidin-1-yl]pyridin-3-yl}amino)carbonyl]quinolin-3-yl}) carbamate in step 1.

Example 45

3-Amino-N-{4-[(3S,5R)-3-amino-5-methylpiperidin-1-yl]pyridin-3-yl}-7-(2-oxopiperidin-1-yl)quinoline-2-carboxamide

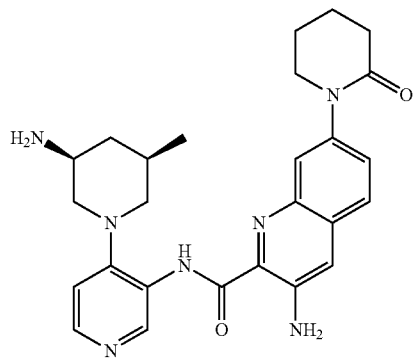 [SMILES: C[C@@H]1C[C@H](N)CN(c2ccncc2NC(=O)c2nc3cc(N4CCCCC4=O)ccc3cc2N)C1]

Step 1. 3-{[(Benzyloxy)carbonyl]amino}-7-(2-oxopiperidin-1-yl)quinoline-2-carboxylic acid

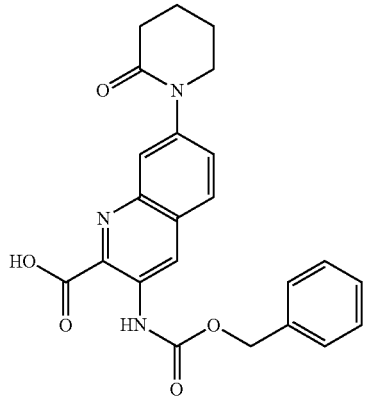 [SMILES: O=C(Nc1cc2ccc(N3CCCCC3=O)cc2nc1C(=O)O)OCc1ccccc1]

A mixture of ethyl 3-{[(benzyloxy)carbonyl]amino}-7-bromoquinoline-2-carboxylate (300 mg, 0.7 mmol), 2-piperidinone (90 mg, 0.91 mmol), Pd(OAc)$_2$ (0.010 mg, 0.064 mmol), 4,5-bis(diphenylphosphino)-9,9-dimethylxanthene (0.020 g, 0.049 mmol), and Cs$_2$CO$_3$ (0.28 g, 0.86 mmol) in dioxane (1 mL) was purged with nitrogen and then heated at 100° C. in a sealed vial for 1 h. The solution was allowed to cool and NH$_4$Cl solution and EtOAc were added. The resulting layers were separated and the aqueous phase was extracted twice with EtOAc. The combined organic extracts were concentrated to dryness under reduced pressure. To the resulting residue, 1 mL of dioxane, 2 mL of THF, and 2 mL of 2 M NaOH were added. The reaction mixture was heated at 80° C. for 0.5 h. The mixture was neutralized with HCl and extracted with DCM. The combined organic extracts were evaporated under reduced pressure. The residue was dissolved in 20 mL of DMF and purified by preparative HPLC (XBridge™ C18 column, eluting with a gradient of MeCN/water containing 0.1% NH$_4$OH, at a flow rate of 60 mL/min.) to afford the title compound (88 mg, 30%). LCMS calc. for $C_{23}H_{22}N_3O_5$ $[M+H]^+$: m/z=420.2. found: 420.2.

135

Step 2. Benzyl [2-{[(4-{(3S,5R)-3-[(tert-butoxycarbonyl)amino]-5-methylpiperidin-1-yl}pyridin-3-yl)amino]carbonyl}-7-(2-oxopiperidin-1-yl)quinolin-3-yl]carbamate

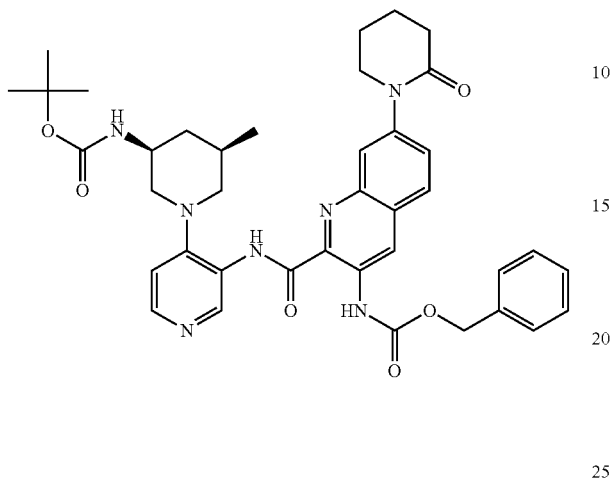

To a mixture of 3-{[(benzyloxy)carbonyl]amino}-7-(2-oxopiperidin-1-yl)quinoline-2-carboxylic acid (0.015 g, 0.036 mmol), tert-butyl [(3S,5R)-1-(3-aminopyridin-4-yl)-5-methylpiperidin-3-yl]carbamate (0.013 g, 0.043 mmol) and HATU (0.034 g, 0.089 mmol) in DMF (0.3 mL), DIPEA (0.019 mL, 0.11 mmol) was added. The mixture was stirred at room temperature for 2 h, then quenched with 5 mL of EtOAc and 3 mL of 1 M NaOH. The resulting layers were separated and the aqueous phase was extracted with EtOAc. The combined organic extracts were concentrated under reduced pressure, then purified by preparative HPLC (XBridge™ C18 column, eluting with a gradient of MeCN/water containing 0.1% NH$_4$OH, at a flow rate of 60 mL/min.) to afford the sub-title compound (0.005 g, 20%). LCMS calc. for C$_{39}$H$_{46}$N$_7$O$_6$ [M+H]$^+$: m/z=708.3. found: 708.4.

Step 3. 3-Amino-N-{4-[(3S,5R)-3-amino-5-methyl-piperidin-1-yl]pyridin-3-yl}-7-(2-oxopiperidin-1-yl)quinoline-2-carboxamide A mixture of benzyl [2-{[(4-{(3S,5R)-3-[(tert-butoxycarbonyl)amino]-5-methylpiperidin-1-yl}pyridin-3-yl)amino]carbonyl}-7-(2-oxopiperidin-1-yl)quinolin-3-yl]carbamate (0.005 g, 0.007 mmol) in 2 mL of 33% HBr in AcOH was stirred at room temperature for 2 h. The mixture was evaporated to dryness under reduced pressure. The resulting residue was dissolved in 4 mL of MeOH and treated with 0.5 mL of NH$_4$OH solution. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for C$_{26}$H$_{32}$N$_7$O$_2$ [M+H]$^+$: m/z=474.3. found: 474.6.

136

Example 46

3-Amino-N-{4-[(3S,5R)-3-amino-5-methylpiperidin-1-yl]pyridin-3-yl}-7-(4-methyl-3-oxopiperazin-1-yl)quinoline-2-carboxamide

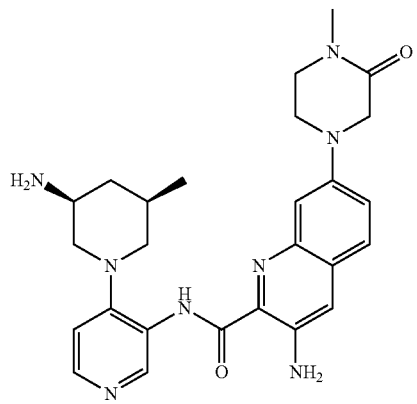 [SMILES: C[C@@H]1C[C@H](N)CN(c2ccncc2NC(=O)c2nc3cc(N4CCN(C)C(=O)C4)ccc3cc2N)C1]

Step 1. 3-{[(Benzyloxy)carbonyl]amino}-7-(4-methyl-3-oxopiperazin-1-yl)quinoline-2-carboxylic acid

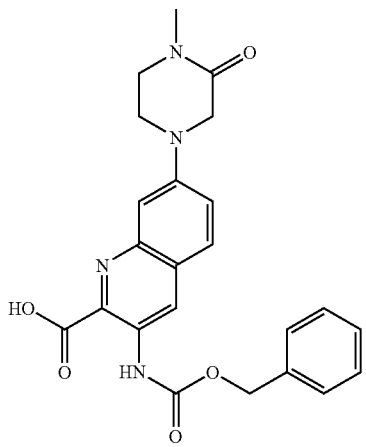 [SMILES: CN1CCN(c2ccc3cc(NC(=O)OCc4ccccc4)c(C(=O)O)nc3c2)CC1=O]

A mixture of ethyl 3-{[(benzyloxy)carbonyl]amino}-7-bromoquinoline-2-carboxylate (250 mg, 0.58 mmol), 1-methylpiperazin-2-one (130 mg, 1.2 mmol), Pd(OAc)$_2$ (20 mg), dicyclohexyl(2',6'-diisopropoxybiphenyl-2-yl)phosphine (41 mg, 0.087 mmol), and K$_3$PO$_4$ (490 mg, 2.3 mmol) in tert-butyl alcohol (8 mL) was purged with nitrogen then heated at 100° C. in a sealed vial for 3 h. The mixture was then allowed to cool and EtOAc and water were added. The resulting layers were separated and organic layer was concentrated under reduced pressure. To the resulting bright-yellow solid, 2 mL of dioxane, 2 mL of 2 M NaOH were added. The mixture was heated in 80° C. oil bath with stirring for 0.5 h, then allowed to cooled and neutralized with 4 mL of with 1 M HCl. The red solid formed was collected by filtration and air-dried overnight to give the sub-title compound (24 mg, 9.5%). LCMS calc. for C$_{26}$H$_{33}$N$_8$O$_2$ [M+H]$^+$: m/z=489.3. found: 435.2.

137

Step 2. Benzyl [2-{[(4-{(3S,5R)-3-[(tert-butoxycarbonyl)amino]-5-methylpiperidin-1-yl}pyridin-3-yl)amino]carbonyl}-7-(4-methyl-3-oxopiperazin-1-yl)quinolin-3-yl]carbamate

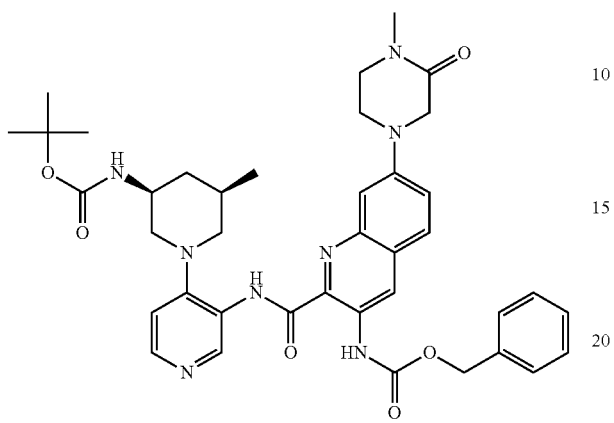

To a mixture of 3-{[(benzyloxy)carbonyl]amino}-7-(4-methyl-3-oxopiperazin-1-yl)quinoline-2-carboxylic acid (0.012 g, 0.028 mmol), tert-butyl [(3S,5R)-1-(3-aminopyridin-4-yl)-5-methylpiperidin-3-yl]carbamate (0.013 g, 0.043 mmol) and HATU (0.034 g, 0.089 mmol) in DMF (0.30 mL), DIPEA (0.019 mL, 0.11 mmol) was added. The resulting mixture was stirred at room temperature for 2 h, then quenched with 5 mL of EtOAc and 3 mL of 1 M NaOH. The resulting layers were separated and the aqueous phase was extracted with EtOAc. The combined organic extracts were concentrated under reduced pressure, then purified by preparative HPLC (XBridge™ C18 column, eluting with a gradient of MeCN/water containing 0.1% NH$_4$OH, at a flow rate of 60 mL/min.) to afford the sub-title compound as a yellow solid (0.005 g, 20%). LCMS calc. for $C_{39}H_{46}N_8O_6$ [M+H]$^+$: m/z=723.4. found: 723.4.

Step 3. 3-Amino-N-{4-[(3S,5R)-3-amino-5-methylpiperidin-1-yl]pyridin-3-yl}-7-(4-methyl-3-oxopiperazin-1-yl)quinoline-2-carboxamide A mixture of benzyl [2-{[(4-{(3S,5R)-3-[(tert-butoxycarbonyl)amino]-5-methylpiperidin-1-yl}pyridin-3-yl)amino]carbonyl}-7-(4-methyl-3-oxopiperazin-1-yl)quinolin-3-yl]carbamate (0.005 g, 0.007 mmol) in 1 mL of MeOH and 2 mL of 33% HBr in AcOH was stirred at room temperature for 2 h. The mixture was evaporated to dryness under reduced pressure. The resulting residue was dissolved in 4 mL of MeOH and treated with 0.5 mL of NH$_4$OH solution. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for $C_{26}H_{33}N_8O_2$ [M+H]$^+$: m/z=489.3. found: 489.3.

138

Example 47

3-Amino-N-{4-[(3S,5R)-3-amino-5-methylpiperidin-1-yl]pyridin-3-yl}-7-(3-oxopiperazin-1-yl)quinoline-2-carboxamide

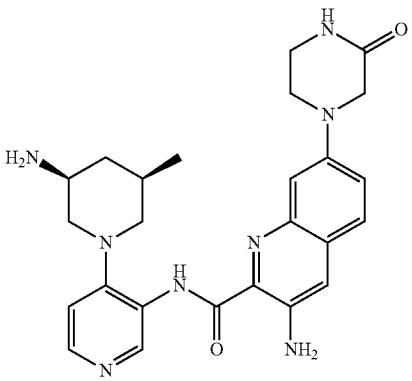 [SMILES: C[C@@H]1C[C@H](N)CN(c2ccncc2NC(=O)c2nc3cc(N4CCNC(=O)C4)ccc3cc2N)C1]

Step 1. 3-{[(Benzyloxy)carbonyl]amino}-7-(3-oxopiperazin-1-yl)quinoline-2-carboxylic acid

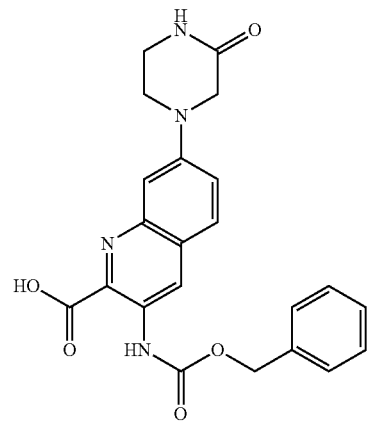 [SMILES: O=C1CN(c2ccc3cc(NC(=O)OCc4ccccc4)c(C(=O)O)nc3c2)CCN1]

A mixture of ethyl 3-{[(benzyloxy)carbonyl]amino}-7-bromoquinoline-2-carboxylate (250 mg, 0.58 mmol), piperazin-2-one (120 mg, 1.2 mmol), Pd(OAc)$_2$ (20 mg), dicyclohexyl(2',6'-diisopropoxybiphenyl-2-yl)phosphine (41 mg, 0.087 mmol), and K$_3$PO$_4$ (490 mg, 2.3 mmol) in tert-butyl alcohol (8 mL) was deoxygenated and purged with nitrogen then heated at 100° C. in a sealed vial for 3 h. To the mixture resulting mixture, 20 mL of EtOAc and 20 mL of water were added. The precipitates collected by filtration and purified by preparative HPLC (XBridge™ C18 column, eluting with a gradient of MeCN/water containing 0.1% NH$_4$OH, at a flow rate of 60 mL/min.) to afford the sub-title compound (0.017 g, 6.9%). LCMS calc. for $C_{22}H_{21}N_4O_5$ [M+H]$^+$: m/z=421.1. found: 421.2.

Step 2. Benzyl [2-[({4-[(3S,5R)-3-amino-5-methyl-piperidin-1-yl]pyridin-3-yl}amino)carbonyl]-7-(3-oxopiperazin-1-yl)quinolin-3-yl]carbamate

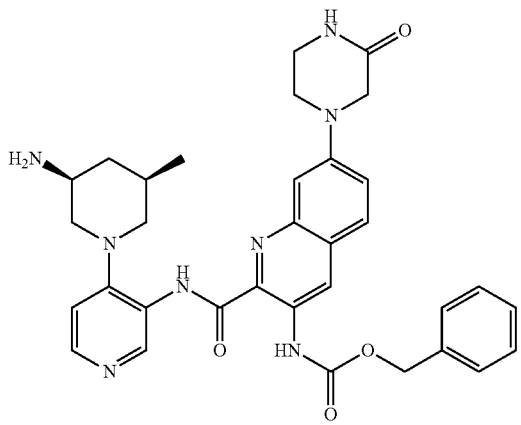 [SMILES: C[C@@H]1C[C@H](N)CN(c2ccncc2NC(=O)c2nc3cc(N4CCNC(=O)C4)ccc3cc2NC(=O)OCc2ccccc2)C1]

To a mixture of 3-{[(benzyloxy)carbonyl]amino}-7-(3-oxopiperazin-1-yl)quinoline-2-carboxylic acid (0.014 g, 0.033 mmol), tert-butyl [(3S,5R)-1-(3-aminopyridin-4-yl)-5-methylpiperidin-3-yl]carbamate (0.014 g, 0.046 mmol) and HATU (0.034 g, 0.089 mmol) in DMF (0.3 mL), DIPEA (0.020 mL, 0.11 mmol) was added. The mixture was stirred at room temperature for 2 h. The mixture was then diluted with 5 mL of EtOAc and 3 mL of 1 M NaOH. The layers were separated and the aqueous layer was extracted with EtOAc. The organic layers were combined and concentrated under reduced pressure. To the resulting residue, 2 mL of 4 M HCl in dioxane and 1 mL of MeOH were added. The mixture was stirred at room temperature for 1 h, then concentrated under reduced pressure. The resulting residue was purified by preparative HPLC (XBridge™ C18 column, eluting with a gradient of MeCN/water containing 0.1% NH$_4$OH, at a flow rate of 60 mL/min.) to afford the sub-title compound (0.0088 g, 43%). LCMS calc. for C$_{33}$H$_{37}$N$_8$O$_4$ [M+H]$^+$: m/z=609.3. found: 609.3.

Step 3. 3-Amino-N-{4-[(3S,5R)-3-amino-5-methyl-piperidin-1-yl]pyridin-3-yl}-7-(3-oxopiperazin-1-yl)quinoline-2-carboxamide A mixture of benzyl [2-[({4-[(3S,5R)-3-amino-5-methyl-piperidin-1-yl]pyridin-3-yl}amino)carbonyl]-7-(3-oxopiperazin-1-yl)quinolin-3-yl]carbamate (0.0086 g, 0.014 mmol) in 3.0 mL of MeOH was hydrogenated in the presence of 8 mg of 10% Pd on carbon under a balloon of hydrogen at room temperature for 1 h. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for C$_{25}$H$_{31}$N$_8$O$_2$ [M+H]$^+$: m/z=475.3. found: 475.4.

Example 48

3-Amino-N-{4-[(3R,4R,5S)-3-amino-4-hydroxy-5-methylpiperidin-1-yl]pyridin-3-yl}-7-(4-methyl-3-oxopiperazin-1-yl)quinoline-2-carboxamide

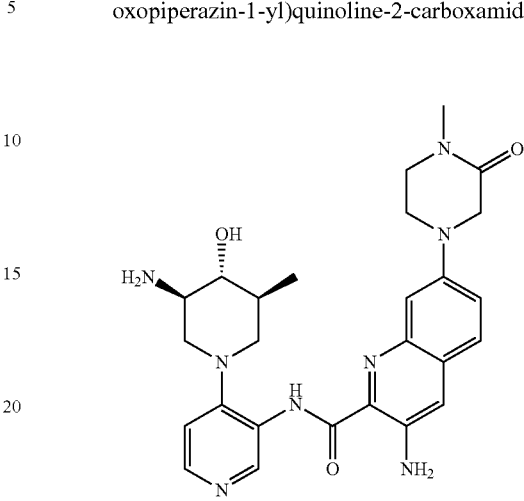

Step 1. Benzyl [2-[({4-[(3R,4R,5S)-3-amino-4-hydroxy-5-methylpiperidin-1-yl]pyridin-3-yl}amino)carbonyl]-7-(4-methyl-3-oxopiperazin-1-yl)quinolin-3-yl]carbamate

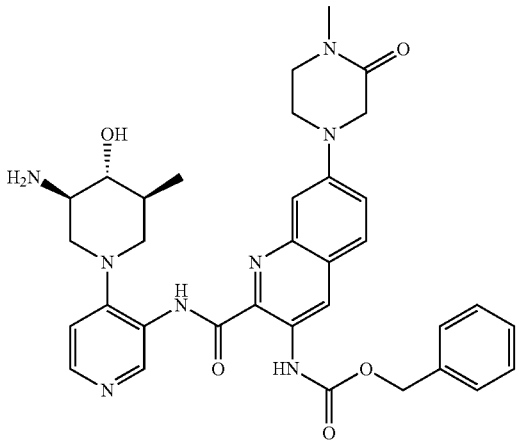 [SMILES: C[C@H]1CN(c2ccncc2NC(=O)c2nc3cc(N4CCN(C)C(=O)C4)ccc3cc2NC(=O)OCc2ccccc2)C[C@@H](N)[C@@H]1O]

To a mixture of 3-{[(benzyloxy)carbonyl]amino}-7-(4-methyl-3-oxopiperazin-1-yl)quinoline-2-carboxylic acid (0.012 g, 0.028 mmol), tert-butyl ((3R,4R,5S)-1-(3-aminopyridin-4-yl)-4-{[tert-butyl(dimethyl)silyl]oxy}-5-methyl-piperidin-3-yl)carbamate (0.019 g, 0.043 mmol) and HATU (0.034 g, 0.089 mmol) in DMF (0.30 mL) was added DIPEA (0.019 mL, 0.11 mmol). The mixture was stirred at room temperature for 2 h. The mixture was diluted with 5 mL of EtOAc and 3 mL of 1 M NaOH. The resulting layers were separated and the aqueous layer was extracted with EtOAc. The organic layers were combined and concentrated under reduced pressure. To the resulting residue, 1 mL of 4 M HCl in dioxane and 1 mL of MeOH were added. The mixture was stirred at room temperature for 1 h, then concentrated under reduced pressure. The resulting residue was purified by preparative HPLC (XBridge™ C18 column, eluting with a gradient of MeCN/water containing 0.1% NH₄OH, at a flow rate of 60 mL/min.) to afford the sub-title compound (0.007 g, 40%). LCMS calc. for C₃₄H₃₉N₈O₅ [M+H]⁺: m/z=639.3. found: 639.3.

Step 2. 3-Amino-N-{4-[(3R,4R,5S)-3-amino-4-hydroxy-5-methylpiperidin-1-yl]pyridin-3-yl}-7-(4-methyl-3-oxopiperazin-1-yl)quinoline-2-carboxamide A mixture of benzyl [2-[({4-[(3R,4R,5S)-3-amino-4-hydroxy-5-methylpiperidin-1-yl]pyridin-3-yl}amino)carbonyl]-7-(4-methyl-3-oxopiperazin-1-yl)quinolin-3-yl]carbamate (0.0070 g, 0.011 mmol) in 3.0 mL of MeOH was hydrogenated in the presence of 8 mg of 10% Pd on carbon under a balloon of hydrogen at room temperature for 1 h. The mixture was then filtered and the filtrate was purified by preparative HPLC (XBridge™ C18 column, eluting with a gradient of MeCN/water containing 0.1% NH₄OH, at a flow rate of 30 mL/min.) to afford the title compound. LCMS calc. for C₂₆H₃₃N₈O₃ [M+H]⁺: m/z=505.3. found: 505.3.

Example 49

3-Amino-N-{4-[(3R,4R,5S)-3-amino-4-hydroxy-5-methylpiperidin-1-yl]pyridin-3-yl}-7-(2-oxopiperidin-1-yl)quinoline-2-carboxamide

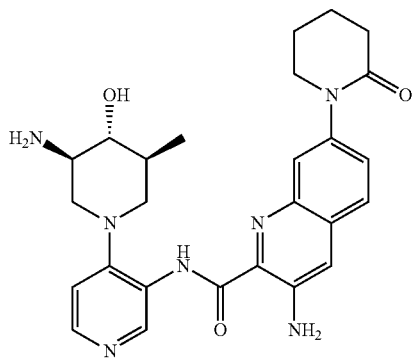 [SMILES: C[C@H]1CN(c2ccncc2NC(=O)c2nc3cc(N4CCCCC4=O)ccc3cc2N)C[C@@H](N)[C@@H]1O]

Step 1. Benzyl [2-[({4-[(3R,4R,5S)-3-amino-4-hydroxy-5-methylpiperidin-1-yl]pyridin-3-yl}amino)carbonyl]-7-(2-oxopiperidin-1-yl)quinolin-3-yl]carbamate

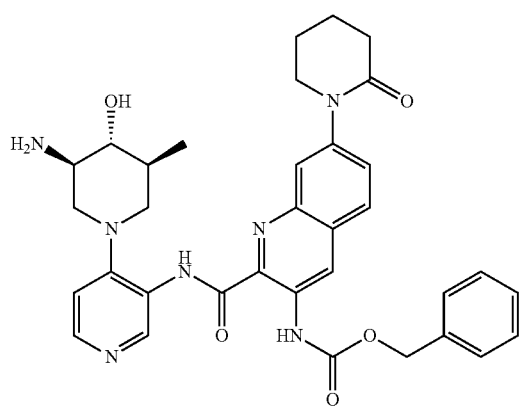 [SMILES: C[C@H]1CN(c2ccncc2NC(=O)c2nc3cc(N4CCCCC4=O)ccc3cc2NC(=O)OCc2ccccc2)C[C@@H](N)[C@@H]1O]

To a mixture of 3-{[(benzyloxy)carbonyl]amino}-7-(2-oxopiperidin-1-yl)quinoline-2-carboxylic acid (0.015 g, 0.036 mmol), tert-butyl ((3R,4R,5S)-1-(3-aminopyridin-4-yl)-4-{[tert-butyl(dimethyl)silyl]oxy}-5-methylpiperidin-3-yl)carbamate (0.019 g, 0.043 mmol) and HATU (0.034 g, 0.089 mmol) in DMF (0.30 mL), DIPEA (0.019 mL, 0.11 mmol) was added. The mixture was stirred at room temperature for 2 h. The mixture was then diluted with 5 mL of EtOAc and 3 mL of 1 M NaOH. The resulting layers were separated and the aqueous layer was extracted with EtOAc. The organic extracts were combined and concentrated under reduced pressure. To the resulting residue, 2 mL of 4 M HCl in dioxane and 1 mL of MeOH were added. The mixture was stirred at room temperature for 1 h, then concentrated under reduced pressure. The resulting residue was purified by preparative HPLC (XBridge™ C18 column, eluting with a gradient of MeCN/water containing 0.1% NH₄OH, at a flow rate of 60 mL/min.) to afford the sub-title compound (0.0072 g, 32%). LCMS calc. for C₃₄H₃₈N₇O₅ [M+H]⁺: m/z=624.3. found: 624.3.

Step 2. 3-Amino-N-{4-[(3R,4R,5S)-3-amino-4-hydroxy-5-methylpiperidin-1-yl]pyridin-3-yl}-7-(2-oxopiperidin-1-yl)quinoline-2-carboxamide A mixture of benzyl [2-[({4-[(3R,4R,5S)-3-amino-4-hydroxy-5-methylpiperidin-1-yl]pyridin-3-yl}amino)carbonyl]-7-(2-oxopiperidin-1-yl)quinolin-3-yl]carbamate (0.004 g, 0.007 mmol) in 3.0 mL of MeOH was hydrogenated in the presence of 5 mg of 10% Pd on carbon under a balloon of hydrogen at room temperature for 1 h. The mixture was filtered and the filtrate was purified by preparative HPLC (XBridge™ C18 column, eluting with a gradient of MeCN/water containing 0.1% NH₄OH, at a flow rate of 30 mL/min.) to afford the title compound. LCMS calc. for C₂₆H₃₁N₇O₃ [M+H]⁺: m/z=490.3. found: 490.2.

Example 50

3-Amino-N-{4-[(3S,5R)-3-amino-5-methylpiperidin-1-yl]pyridin-3-yl}-7-(3-oxomorpholin-4-yl)quinoline-2-carboxamide

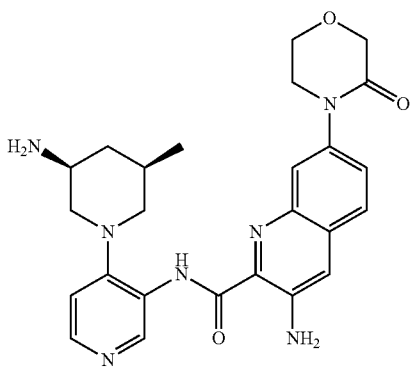 [SMILES: C[C@@H]1C[C@H](N)CN(c2ccncc2NC(=O)c2nc3cc(N4CCOCC4=O)ccc3cc2N)C1]

Step 1. 3-{[(Benzyloxy)carbonyl]amino}-7-(3-oxo-morpholin-4-yl)quinoline-2-carboxylic acid

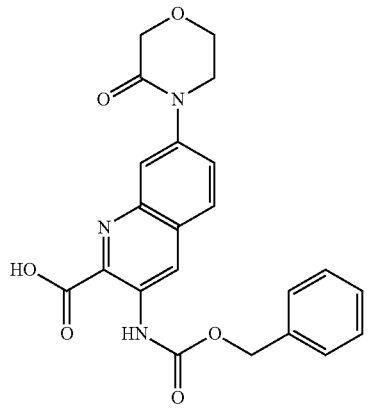 [SMILES: O=C(Nc1cc2ccc(N3CCOCC3=O)cc2nc1C(=O)O)OCc1ccccc1]

A mixture of ethyl 3-{[(benzyloxy)carbonyl]amino}-7-bromoquinoline-2-carboxylate (316 mg, 0.736 mmol), morpholin-3-one (100 mg, 1 mmol), Pd(OAc)$_2$ (20 mg), 4,5-bis(diphenylphosphino)-9,9-dimethylxanthene (0.041 g, 0.071 mmol), and Cs$_2$CO$_3$ (0.31 g, 0.95 mmol) in dioxane (1.0 mL) was purged with nitrogen and then heated at 100° C. in a sealed vial for 3 h. To the cooled mixture, 5 mL of MeOH and 2 mL of 2 M NaOH were added. The resulting mixture was heated at 80° C. for 30 min. The solution was allowed to cool and NH$_4$Cl solution and 10 mL of MeOH were added. The resulting mixture was filtered and the filtrate was purified by preparative HPLC (XBridge™ C18 column, eluting with a gradient of MeCN/water containing 0.1% NH$_4$OH, at a flow rate of 60 mL/min.) to afford the sub-title compound (0.080 g, 20%). LCMS calc. for C$_{22}$H$_{20}$N$_3$O$_6$ [M+H]$^+$: m/z=422.1. found: 422.2.

Step 2. Benzyl [2-[({4-[(3S,5R)-3-amino-5-methyl-piperidin-1-yl]pyridin-3-yl}amino)carbonyl]-7-(3-oxomorpholin-4-yl)quinolin-3-yl]carbamate

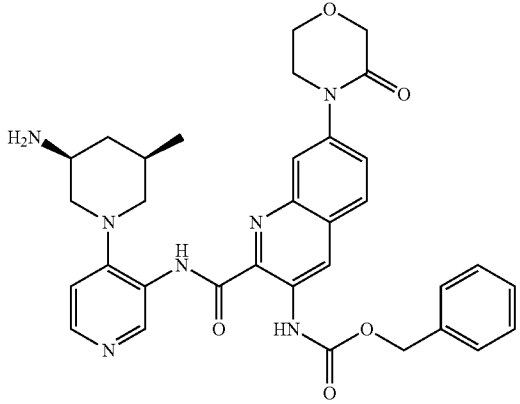 [SMILES: C[C@@H]1C[C@H](N)CN(c2ccncc2NC(=O)c2nc3cc(N4CCOCC4=O)ccc3cc2NC(=O)OCc2ccccc2)C1]

To a mixture of 3-{[(benzyloxy)carbonyl]amino}-7-(3-oxomorpholin-4-yl)quinoline-2-carboxylic acid (0.014 g, 0.033 mmol), tert-butyl [(3S,5R)-1-(3-aminopyridin-4-yl)-5-methylpiperidin-3-yl]carbamate (0.013 g, 0.043 mmol), HATU (0.034 g, 0.089 mmol) in DMF (0.30 mL), DIPEA (0.019 mL, 0.11 mmol) was added. The mixture was stirred at room temperature for 2 h. The mixture was diluted with 5 mL of EtOAc and 3 mL of 1 M NaOH. The layers were separated and the aqueous layer was extracted with EtOAc. The organic layers were combined and concentrated under reduced pressure. To the resulting residue, 1 mL of 4 M HCl in dioxane and 1 mL of MeOH were added. The mixture was stirred at room temperature for 1 h, then concentrated under reduced pressure. The resulting residue was purified by preparative HPLC (XBridge™ C18 column, eluting with a gradient of MeCN/water containing 0.1% NH$_4$OH, at a flow rate of 60 mL/min.) to afford the sub-title compound (0.0063 g, 31%). LCMS calc. for C$_{33}$H$_{36}$N$_7$O$_5$ [M+H]$^+$: m/z=610.3. found: 610.3.

Step 3. 3-Amino-N-{4-[(3S,5R)-3-amino-5-methyl-piperidin-1-yl]pyridin-3-yl}-7-(3-oxomorpholin-4-yl)quinoline-2-carboxamide A mixture of benzyl [2-[({4-[(3S,5R)-3-amino-5-methyl-piperidin-1-yl]pyridin-3-yl}amino)carbonyl]-7-(3-oxomorpholin-4-yl)quinolin-3-yl]carbamate (0.0067 g, 0.011 mmol) in 3.0 mL of MeOH was hydrogenated in the presence of 8 mg of 10% Pd on carbon under a balloon of hydrogen at room temperature for 1 h. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for C$_{25}$H$_{30}$N$_7$O$_3$ [M+H]$^+$: m/z=476.2. found: 476.3.

Example 51

3-Amino-N-{4-[(3R,4R,5S)-3-amino-4-hydroxy-5-methylpiperidin-1-yl]pyridin-3-yl}-7-(3-oxomorpholin-4-yl)quinoline-2-carboxamide

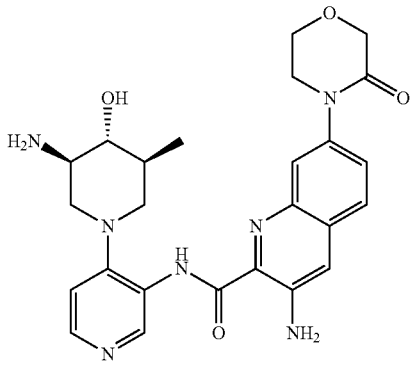 [SMILES: C[C@H]1CN(c2ccncc2NC(=O)c2nc3cc(N4CCOCC4=O)ccc3cc2N)C[C@@H](N)[C@@H]1O]

Step 1. Benzyl [2-[({4-[(3R,4R,5S)-3-amino-4-hydroxy-5-methylpiperidin-1-yl]pyridin-3-yl}amino)carbonyl]-7-(3-oxomorpholin-4-yl)quinolin-3-yl]carbamate

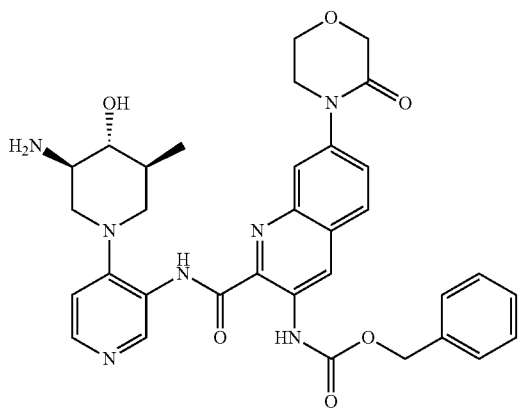 [SMILES: C[C@H]1CN(c2ccncc2NC(=O)c2nc3cc(N4CCOCC4=O)ccc3cc2NC(=O)OCc2ccccc2)C[C@@H](N)[C@@H]1O]

To a mixture of 3-{[(benzyloxy)carbonyl]amino}-7-(3-oxomorpholin-4-yl)quinoline-2-carboxylic acid (0.014 g, 0.033 mmol), tert-butyl ((3R,4R,5S)-1-(3-aminopyridin-4-yl)-4-{[tert-butyl(dimethyl)silyl]oxy}-5-methylpiperidin-3-yl)carbamate (0.019 g, 0.043 mmol) and HATU (0.034 g, 0.089 mmol) in DMF (0.30 mL), DIPEA (0.019 mL, 0.11 mmol) was added. The mixture was stirred at room temperature for 2 h. The mixture was diluted with 5 mL of EtOAc and 3 mL of 1 M NaOH. The resulting layers were separated and the aqueous layer was extracted with EtOAc. The organic extracts were combined and concentrated under reduced pressure. To the resulting residue, 1 mL of 4 M HCl in dioxane and 1 mL of MeOH were added. The mixture was stirred at room temperature for 1 h, then concentrated. The resulting residue was purified by preparative HPLC (XBridge™ C18 column, eluting with a gradient of MeCN/water containing 0.1% NH$_4$OH, at a flow rate of 60 mL/min.) to afford the sub-title compound. LCMS calc. for C$_{33}$H$_{36}$N$_7$O$_6$ [M+H]$^+$: m/z=626.3. found: 626.3.

Step 2. 3-Amino-N-{4-[(3R,4R,5S)-3-amino-4-hydroxy-5-methylpiperidin-1-yl]pyridin-3-yl}-7-(3-oxomorpholin-4-yl)quinoline-2-carboxamide A mixture of benzyl [2-[({4-[(3R,4R,5S)-3-amino-4-hydroxy-5-methylpiperidin-1-yl]pyridin-3-yl}amino)carbonyl]-7-(3-oxomorpholin-4-yl)quinolin-3-yl]carbamate (0.0068 g, 0.011 mmol) in of 3.0 mL of MeOH was hydrogenated in the presence of 8 mg of 10% Pd on carbon under a balloon of hydrogen at room temperature for 1 h. The mixture was filtered and the filtrate was purified by preparative HPLC (XBridge™ C18 column, eluting with a gradient of MeCN/water containing 0.1% NH$_4$OH, at a flow rate of 30 mL/min.) to afford the title compound. LCMS calc. for C$_{25}$H$_{30}$N$_7$O$_4$ [M+H]$^+$: m/z=492.2. found: 492.4.

Example 52

3-Amino-N-{4-[(3R,4S,5S)-3-amino-5-methyl-4-(1H-1,2,3-triazol-1-yl)piperidin-1-yl]pyridin-3-yl}-7-(4-methyl-3-oxopiperazin-1-yl)quinoline-2-carboxamide

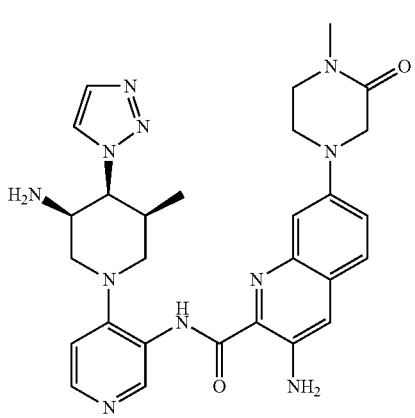 [SMILES: C[C@H]1CN(c2ccncc2NC(=O)c2nc3cc(N4CCN(C)C(=O)C4)ccc3cc2N)C[C@@H](N)[C@H]1n1ccnn1]

Step 1. tert-Butyl [(3R,4R,5S)-4-{[tert-butyl(dimethyl)silyl]oxy}-5-methyl-1-(3-nitropyridin-4-yl)piperidin-3-yl]carbamate

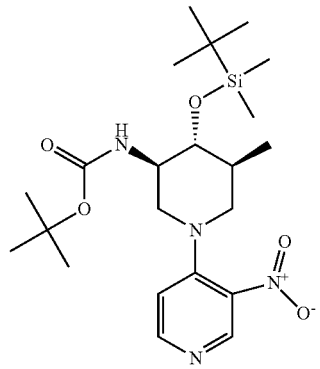 [SMILES: C[C@H]1CN(c2ccncc2[N+](=O)[O-])C[C@@H](NC(=O)OC(C)(C)C)[C@@H]1O[Si](C)(C)C(C)(C)C]

A mixture of 4-chloro-3-nitropyridine (5.11 g, 32.2 mmol), tert-butyl ((3R,4R,5S)-4-{[tert-butyl(dimethyl)silyl]oxy}-5-methylpiperidin-3-yl)carbamate[0.5]-oxalic acid (13.2 g, 33.8 mmol) in isopropyl alcohol (63.0 mL) was stirred at 90° C. for 3 h. The mixture was concentrated, and diluted with EtOAc and water. The layers were separated and the aqueous layer was extracted with EtOAc (×3). The combined organic layers were dried, filtered and concentrated under reduced pressure. The resulting residue was purified by silica gel column chromatography (eluting with 0-50% EtOAc in hexanes) to give the sub-title compound as a yellow powder (13.4 g, 89%). LCMS calc. for C$_{22}$H$_{39}$N$_4$O$_5$Si (M+H)$^+$: m/z=467.3. Found: 467.3.

Step 2. tert-Butyl ((3R,4R,5S)-1-(3-Aminopyridin-4-yl)-4-{[tert-butyl(dimethyl)silyl]oxy}-5-methylpiperidin-3-yl)carbamate

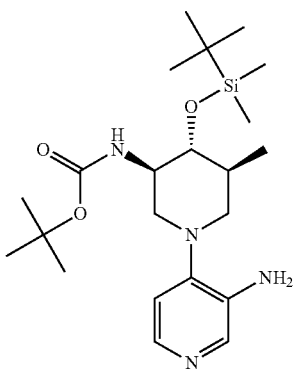 [SMILES: C[C@H]1CN(c2ccncc2N)C[C@@H](NC(=O)OC(C)(C)C)[C@@H]1O[Si](C)(C)C(C)(C)C]

A mixture of tert-butyl [(3R,4R,5S)-4-{[tert-butyl(dimethyl)silyl]oxy}-5-methyl-1-(3-nitropyridin-4-yl)piperidin-3-yl]carbamate (13.4 g, 28.7 mmol) in MeOH (80 mL) was hydrogenated in the presence of 10% palladium on carbon (4.6 g) under 60 psi of hydrogen for 16 h. The reaction mixture was filtered through diatomaceous earth and the filtrate was concentrated under reduced pressure to give the sub-title compound (12.5 g, 99%). LCMS calc. for C$_{22}$H$_{41}$N$_4$O$_3$Si (M+H)$^+$: m/z=437.3. Found: 437.4.

Step 3. Di-tert-butyl[4-((3R,4R,5S)-3-[(tert-butoxycarbonyl)amino]-4-{[tert-butyl(dimethyl)silyl]oxy}-5-methylpiperidin-1-yl)pyridin-3-yl]imidodicarbonate

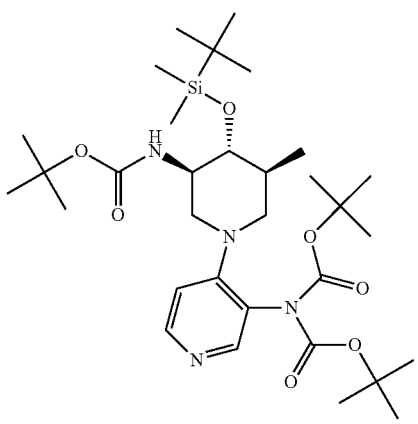 [SMILES: C[C@H]1CN(c2ccncc2N(C(=O)OC(C)(C)C)C(=O)OC(C)(C)C)C[C@@H](NC(=O)OC(C)(C)C)[C@@H]1O[Si](C)(C)C(C)(C)C]

To a solution of tert-butyl ((3R,4R,5S)-1-(3-aminopyridin-4-yl)-4-{[tert-butyl(dimethyl)silyl]oxy}-5-methylpiperidin-3-yl)carbamate (1.20 g, 2.75 mmol) in DCM (5.5 mL) at room temperature, di-tert-butyldicarbonate (3.60 g, 16.5 mmol) was added followed by 4-dimethylaminopyridine (0.671 g, 5.50 mmol). The reaction mixture was stirred at room temperature for 6 h. The solution was diluted with EtOAc and water, the layers were separated, and the organic layer was washed with brine, dried over $Na_2SO_4$, and then concentrated under reduced pressure. The residue was purified by flash chromatography on silica using CombiFlash® apparatus (eluting with 0-50% EtOAc in hexanes) to give the sub-title compound as a brown gum (1.05 g, 60%). LCMS calc. for $C_{32}H_{57}N_4O_7Si$ $(M+H)^+$: m/z=637.4. Found: 637.3.

Step 4. Di-tert-butyl (4-{(3R,4R, S)-3-[(tert-butoxycarbonyl)amino]-4-hydroxy-5-methylpiperidin-1-yl}pyridin-3-yl)imidodicarbonate

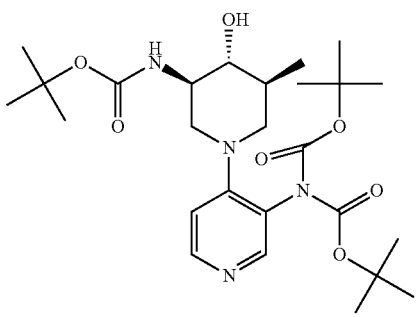 [SMILES: C[C@H]1CN(c2ccncc2N(C(=O)OC(C)(C)C)C(=O)OC(C)(C)C)C[C@@H](NC(=O)OC(C)(C)C)[C@@H]1O]

To a solution of di-tert-butyl[4-((3R,4R,5S)-3-[(tert-butoxycarbonyl)amino]-4-{[tert-butyl(dimethyl)silyl]oxy}-5-methylpiperidin-1-yl)pyridin-3-yl]imidodicarbonate (1.01 g, 1.58 mmol) in THF (7.9 mL) at room temperature 1.0 M tetra-n-butylammonium fluoride in THF (1.66 mL, 1.66 mmol) was added. The reaction mixture was stirred at room temperature for 2 h. The mixture was then diluted with EtOAc and water and the layers were separated. The organic layer was washed with brine, dried, and concentrated under reduced pressure. The residue was purified by flash chromatography on silica using CombiFlash® apparatus (0 to 80% EtOAc in hexanes) to give the sub-title compound (771 mg, 93%). LCMS calc. for $C_{26}H_{43}N_4O_7$ $(M+H)^+$: m/z=523.3. Found: 523.2.

Step 5. (3R,4R,5S)-1-{3-[Bis(tert-butoxycarbonyl)amino]pyridin-4-yl}-3-[(tert-butoxycarbonyl)amino]-5-methylpiperidin-4-yl methanesulfonate

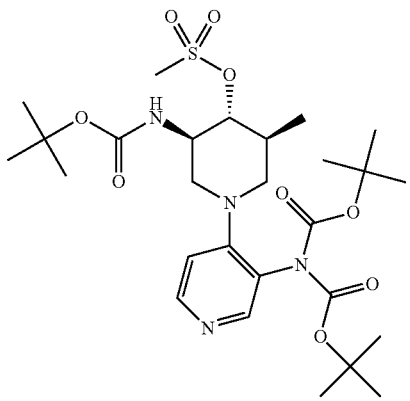 [SMILES: C[C@H]1CN(c2ccncc2N(C(=O)OC(C)(C)C)C(=O)OC(C)(C)C)C[C@@H](NC(=O)OC(C)(C)C)[C@@H]1OS(C)(=O)=O]

To a solution of di-tert-butyl (4-{(3R,4R,5S)-3-[(tert-butoxycarbonyl)amino]-4-hydroxy-5-methylpiperidin-1-yl}pyridin-3-yl)imidodicarbonate (500 mg, 0.957 mmol) in DCM (4.5 mL), triethylamine (0.227 mL, 1.63 mmol) was added followed by methanesulfonyl chloride (0.096 mL, 1.24 mmol). The capped solution was stirred at room temperature for 1 h. The reaction mixture was quenched with aq. $NaHCO_3$, extracted with EtOAc. The organic layer was washed with brine, dried, filtered and concentrated under reduced pressure to give the sub-title compound as a light yellow powder (574 mg, 100%). LCMS calc. for $C_{27}H_{45}N_4O_9S$ $(M+H)^+$: m/z=601.3. Found: 601.2.

Step 6. Di-tert-butyl (4-{(3R,4S,5S)-4-azido-3-[(tert-butoxycarbonyl)amino]-5-methylpiperidin-1-yl}pyridin-3-yl)imidodicarbonate

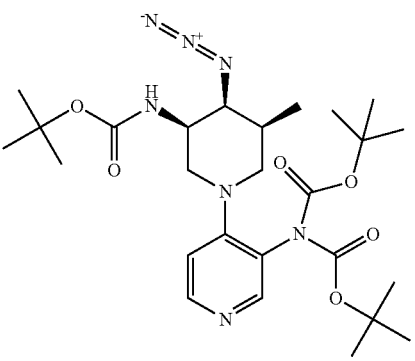

To a solution of (3R,4R,5S)-1-{3-[bis(tert-butoxycarbonyl)amino]pyridin-4-yl}-3-[(tert-butoxycarbonyl)amino]-5-methylpiperidin-4-yl methanesulfonate (0.57 g, 0.96 mmol) in DMF (5.0 mL), sodium azide (0.31 g, 4.8 mmol) was added. The reaction mixture was heated at 90° C. for 5 h then allowed to cool. The solution was then partitioned between EtOAc and water. The layers were separated organic layer was washed with aq. Na$_2$CO$_3$ and brine, then dried, filtered and concentrated under reduced pressure to give the sub-title compound (0.52 g, 99%). LCMS calc. for C$_{26}$H$_{42}$N$_7$O$_6$ (M+H)$^+$: m/z=548.3. Found: 548.4.

Step 7. Di-tert-butyl {4-[(3R,4S,5S)-3-[(tert-butoxycarbonyl)amino]-5-methyl-4-(1H-1,2,3-triazol-1-yl)piperidin-1-yl]pyridin-3-yl}imidodicarbonate

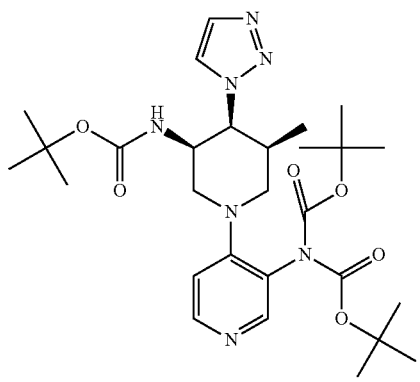 [SMILES: C[C@H]1CN(c2ccncc2N(C(=O)OC(C)(C)C)C(=O)OC(C)(C)C)C[C@@H](NC(=O)OC(C)(C)C)[C@H]1n1ccnn1]

A solution of di-tert-butyl (4-{(3R,4S,5S)-4-azido-3-[(tert-butoxycarbonyl)amino]-5-methylpiperidin-1-yl}pyridin-3-yl)imidodicarbonate (0.37 g, 0.67 mmol) in acetic acid ethenyl ester (5.50 mL, 59.7 mmol) in a sealed flask was heated at 115° C. for 40 h. The reaction mixture was concentrated under reduced pressure and the residue was purified by chromatography on silica using a CombiFlash® apparatus (50 to 100% EtOAc in hexanes) to give the sub-title compound (81 mg, 21%). LCMS calc. for C$_{28}$H$_{44}$N$_7$O$_6$ (M+H)$^+$: m/z=574.3. Found: 574.4.

Step 8. tert-Butyl [(3R,4S,5S)-1-(3-aminopyridin-4-yl)-5-methyl-4-(1H-1,2,3-triazol-1-yl)piperidin-3-yl]carbamate

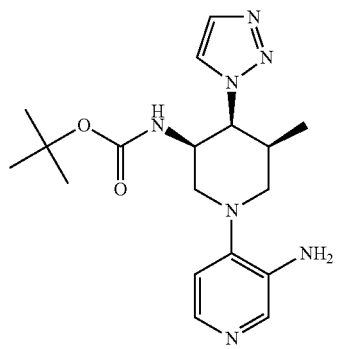 [SMILES: C[C@H]1CN(c2ccncc2N)C[C@@H](NC(=O)OC(C)(C)C)[C@H]1n1ccnn1]

To di-tert-butyl {4-[(3R,4S,5S)-3-[(tert-butoxycarbonyl)amino]-5-methyl-4-(1H-1,2,3-triazol-1-yl)piperidin-1-yl]pyridin-3-yl}imidodicarbonate (77 mg, 0.13 mmol), 4.0 M HCl in dioxane (1.0 mL, 4.0 mmol) was added. After 1 h, the volatile solvents were removed under reduced pressure then the residue (HCl salt) was dried under high vacuum for 20 min. The residue was dissolved in DCM (0.9 mL) at 0° C. and DIPEA (0.35 mL, 2.0 mmol) and 1-[(tert-butoxycarbonyl)oxy]pyrrolidine-2,5-dione (28.9 mg, 0.134 mmol) were added. The mixture was stirred at room temperature for 90 min., then quenched with aq. NaHCO$_3$ and diluted with EtOAc. The aqueous layer was separated and extracted with EtOAc (×2). The combined organic layers were dried, then concentrated under reduced pressure to give a yellow residue. The residue was purified by chromatography on silica using a CombiFlash®apparatus (0 to 25% MeOH in hexanes) to give the sub-title compound as a light yellow powder (36 mg, 72%). LCMS calc. for C$_{18}$H$_{28}$N$_7$O$_2$ (M+H)$^+$: m/z=374.2. Found: 374.2.

Step 9. Benzyl [2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-(4-methyl-3-oxopiperazin-1-yl)quinolin-3-yl]carbamate

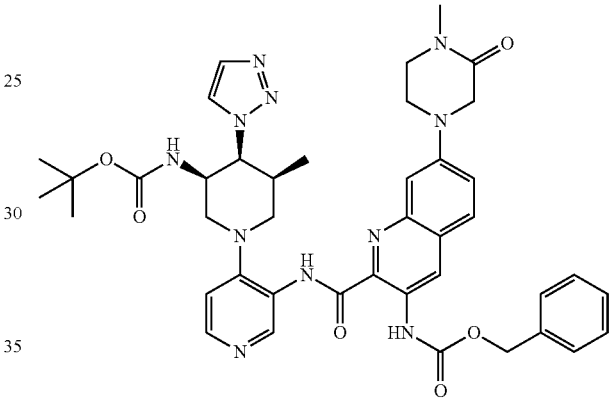

To a mixture of 3-{[(benzyloxy)carbonyl]amino}-7-(4-methyl-3-oxopiperazin-1-yl)quinoline-2-carboxylic acid (12.2 mg, 0.028 mmol), tert-butyl [(3R,4S,5S)-1-(3-aminopyridin-4-yl)-5-methyl-4-(1H-1,2,3-triazol-1-yl)piperidin-3-yl]carbamate (10.0 mg, 0.027 mmol), HATU (33 mg, 0.087 mmol), in DMF (0.29 mL), DIPEA (0.018 mL, 0.10 mmol) was added. The reaction mixture was stirred at room temperature for 2 h. The mixture was diluted with MeOH and H$_2$O, filtered and the filtrate was purified by preparative LCMS (XBridge™ C18 column, eluting with a gradient of MeCN/water containing 0.1% NH$_4$OH, at a flow rate of 60 mL/min.) to give the sub-title compound as a bright yellow powder (12 mg, 57%). LCMS calc. for C$_{41}$H$_{48}$N$_{11}$O$_6$(M+H)$^+$: m/z=790.4. Found: 790.3.

Step 10. 3-Amino-N-{4-[(3R,4S,5S)-3-amino-5-methyl-4-(1H-1,2,3-triazol-1-yl)piperidin-1-yl]pyridin-3-yl}-7-(4-methyl-3-oxopiperazin-1-yl)quinoline-2-carboxamide A solution of benzyl [2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-(4-methyl-3-oxopiperazin-1-yl)quinolin-3-yl]carbamate (12.0 mg, 0.015 mmol) in MeOH (1.0 mL) was hydrogenated in the presence of 10% palladium on carbon (6.0 mg) under a balloon of hydrogen for 1 h. The reaction mixture was filtered and the filtrate was concentrated under reduced pressure to give a benzyl carbamate deprotected intermediate. The intermediate was treated with 4.0 M HCl in dioxane (0.15 mL, 0.6 mmol) at room temperature for 1 h. The solution was concentrated under reduced pressure and the resulting residue was diluted with MeOH and NH$_4$OH, filtered. The filtrate was purified by preparative LCMS (XBridge™ C18 column, eluting with a gradient of MeCN/water containing 0.1% NH$_4$OH, at a flow rate of 30 mL/min.) to give the title compound as a yellow powder (5.1 mg, 60%). LCMS calc. for C$_{28}$H$_{34}$N$_{11}$O$_2$(M+H)$^+$: m/z=556.3. Found: 556.3.

Example 53

3-Amino-N-{4-[(3R,4S,5S)-3-amino-5-methyl-4-(1H-1,2,3-triazol-1-yl)piperidin-1-yl]pyridin-3-yl}-7-(tetrahydro-2H-pyran-4-yl)quinoline-2-carboxamide

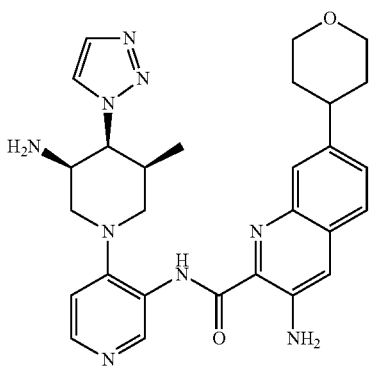 [SMILES: C[C@H]1CN(c2ccncc2NC(=O)c2nc3cc(C4CCOCC4)ccc3cc2N)C[C@@H](N)[C@H]1n1ccnn1]

Step 1. Benzyl {7-bromo-2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]quinolin-3-yl}carbamate

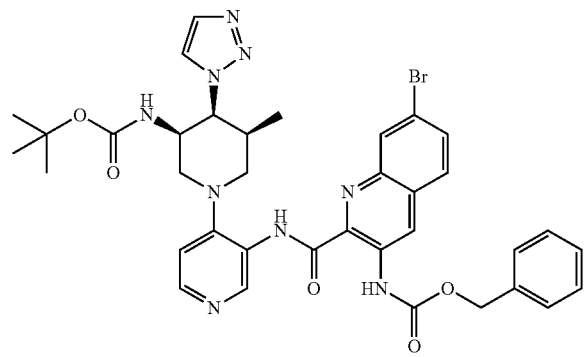 [SMILES: C[C@H]1CN(c2ccncc2NC(=O)c2nc3cc(Br)ccc3cc2NC(=O)OCc2ccccc2)C[C@@H](NC(=O)OC(C)(C)C)[C@H]1n1ccnn1]

To a mixture of 3-{[(benzyloxy)carbonyl]amino}-7-bromoquinoline-2-carboxylic acid (47 mg, 0.12 mmol), tert-butyl [(3R,4S,5S)-1-(3-aminopyridin-4-yl)-5-methyl-4-(1H-1,2,3-triazol-1-yl)piperidin-3-yl]carbamate (40 mg, 0.11 mmol), and HATU (100 mg, 0.27 mmol), in DMF (0.4 mL), DIPEA (0.056 mL, 0.32 mmol) was added. The reaction mixture was stirred at room temperature for 2 h then concentrated under reduced pressure. After concentration, the residue was purified by flash chromatography on silica using a CombiFlash® apparatus (0-100% EtOAc in hexanes) to give the sub-title compound as a light yellow powder (109 mg). LCMS calc. for C$_{36}$H$_{39}$BrN$_9$O$_5$(M+H)$^+$: m/z=756.2. Found: 756.3.

Step 2. Benzyl [2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-(3,6-dihydro-2H-pyran-4-yl)quinolin-3-yl]carbamate

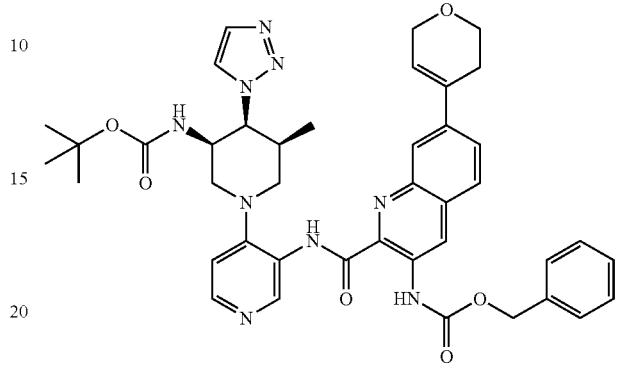

A pressure tube was charged with benzyl {7-bromo-2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]quinolin-3-yl}carbamate (15 mg, 0.020 mmol), K$_3$PO$_4$ (8.4 mg, 0.04 mmol), 1,4-dioxane (0.3 mL), water (0.04 mL) and 4-(4,4,5,5-tetramethyl-1,3,2-dioxaborolan-2-yl)-3,6-dihydro-2H-pyran (6.3 mg, 0.03 mmol). The reaction mixture was purged with nitrogen for 10 min., then dicyclohexyl(2',4',6'-triisopropylbiphenyl-2-yl)phosphine-(2'-aminobiphenyl-2-yl)(chloro)palladium (1:1) (1.6 mg, 0.002 mmol) was added. The pressure tube was sealed and the reaction mixture was heated at 90° C. for 30 min then allowed to cool. The mixture was then filtered and purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the sub-title compound as a light yellow powder (4 mg, 27%). LCMS calc. for C$_{41}$H$_{46}$N$_9$O$_6$ (M+H)$^+$: m/z=760.4. Found: 760.5.

Step 3. 3-Amino-N-{4-[(3R,4S,5S)-3-amino-5-methyl-4-(1H-1,2,3-triazol-1-yl)piperidin-1-yl]pyridin-3-yl}-7-(tetrahydro-2H-pyran-4-yl)quinoline-2-carboxamide To a solution of benzyl [2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-(3,6-dihydro-2H-pyran-4-yl)quinolin-3-yl]carbamate (4.0 mg, 0.005 mmol) in MeOH (0.3 mL) and THF (0.3 mL) 10% Pd on carbon (2 mg) was added. The reaction mixture was deoxygenated under reduced pressure and hydrogen was introduced via a balloon. The reaction mixture was stirred at room temperature under hydrogen for 1 h. The mixture was filtered and concentrated under reduced pressure to give an intermediate. The intermediate was treated with 4.0 M HCl in dioxane (0.053 mL, 0.21 mmol) and stirred at room temperature for 30 min. then concentrated under reduced pressure. The residue was diluted with MeOH and NH$_4$OH, filtered and purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the title compound as a yellow powder (1.8 mg, 65%). LCMS calc. for C$_{28}$H$_{34}$N$_9$O$_2$ (M+H)$^+$: m/z=528.3. Found: 528.3.

Example 54

3-Amino-N-{4-[(3R,4S,5S)-3-amino-5-methyl-4-(1H-1,2,3-triazol-1-yl)piperidin-1-yl]pyridin-3-yl}-7-(4-methylpiperazin-1-yl)quinoline-2-carboxamide

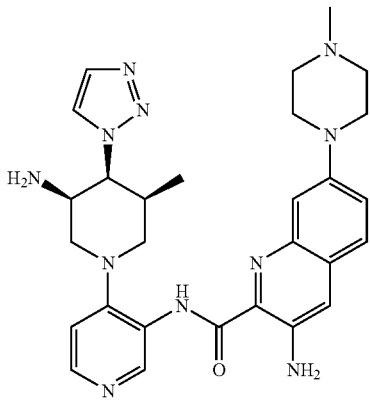 [SMILES: C[C@H]1CN(c2ccncc2NC(=O)c2nc3cc(N4CCN(C)CC4)ccc3cc2N)C[C@@H](N)[C@H]1n1ccnn1]

Step 1. Benzyl [2-[({4-[(3R,4S,5S)-3-[(tert-Butoxycarbonyl)amino]-5-methyl-4-(1H-1, 2,3-triazol-1-yl)piperidin-1-yl]pyridin-3-yl}amino)carbonyl]-7-(4-methylpiperazin-1-yl)quinolin-3-yl]carbamate

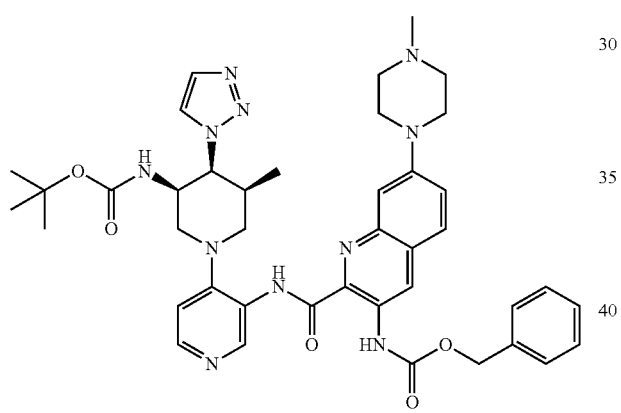

To a mixture of 3-{[(benzyloxy)carbonyl]amino}-7-(4-methylpiperazin-1-yl)quinoline-2-carboxylic acid (9.9 mg, 0.024 mmol), tert-butyl [(3R,4S,5S)-1-(3-aminopyridin-4-yl)-5-methyl-4-(1H-1,2,3-triazol-1-yl)piperidin-3-yl]carbamate (8.0 mg, 0.021 mmol), and HATU (26 mg, 0.069 mmol), in DMF (0.23 mL) and THF (0.5 mL), DIPEA (0.014 mL, 0.083 mmol) was added. The reaction mixture was stirred at room temperature for 2 h. The mixture was diluted with MeOH and H$_2$O, filtered and purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the sub-title compound as bright yellow powder (8.0 mg, 48%). LCMS calc. for C$_{41}$H$_{50}$N$_{11}$O$_5$(M+H)$^+$: m/z=776.4. Found: 776.3.

Step 2. 3-Amino-N-{4-[(3R,4S,5S)-3-amino-5-methyl-4-(1H-1,2,3-triazol-1-yl)piperidin-1-yl]pyridin-3-yl}-7-(4-methylpiperazin-1-yl)quinoline-2-carboxamide To a solution of benzyl [2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-(4-methylpiperazin-1-yl)quinolin-3-yl]carbamate (8.0 mg, 0.01 mmol) in MeOH (0.4 mL) and THF (0.4 mL), 10% Pd on carbon (4 mg) was added. The reaction mixture was deoxygenated under reduced pressure and hydrogen was introduced via a balloon. The reaction mixture was stirred at room temperature under hydrogen for 1 h. The mixture was filtered and concentrated under reduced pressure to give an intermediate. The intermediate was treated with 4.0 M HCl in dioxane (0.1 mL, 0.4 mmol) with stirring at room temperature for 30 min., then concentrated under reduced pressure. The residue was diluted with MeOH and NH$_4$OH, filtered and purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the title compound as a yellow powder (3.0 mg, 54%). LCMS calc. for C$_{28}$H$_{36}$N$_{11}$O (M+H)$^+$: m/z=542.3. Found: 542.3.

Example 55

3-Amino-N-{4-[(3R,4S,5S)-3-amino-5-methyl-4-(1H-1,2,3-triazol-1-yl)piperidin-1-yl]pyridin-3-yl}-7-morpholin-4-ylquinoline-2-carboxamide

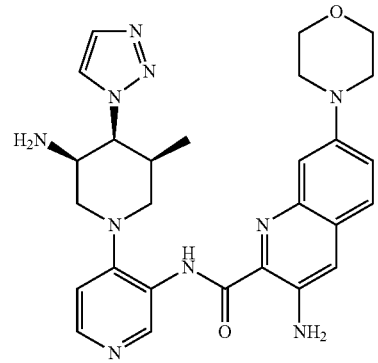 [SMILES: C[C@H]1CN(c2ccncc2NC(=O)c2nc3cc(N4CCOCC4)ccc3cc2N)C[C@@H](N)[C@H]1n1ccnn1]

Step 1. Benzyl {2-[({4-[(3R,4S,5S)-3-[(tert-butoxycarbonyl)amino]-5-methyl-4-(H-1,2,3-triazol-1-yl)piperidin-1-yl]pyridin-3-yl}amino)carbonyl]-7-morpholin-4-ylquinolin-3-yl}carbamate

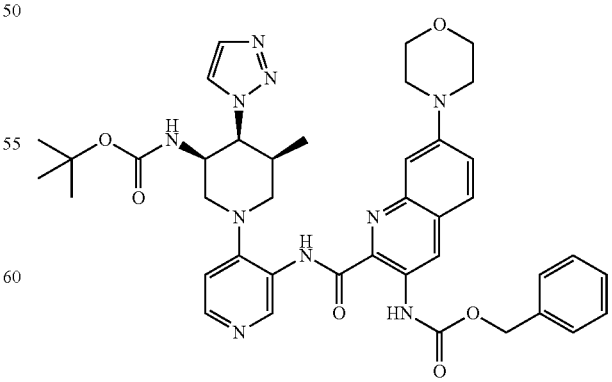

To a mixture of 3-{[(benzyloxy)carbonyl]amino}-7-morpholin-4-ylquinoline-2-carboxylic acid (9.6 mg, 0.024 mmol), tert-butyl [(3R,4S,5S)-1-(3-aminopyridin-4-yl)-5-methyl-4-(1H-1,2,3-triazol-1-yl)piperidin-3-yl]carbamate (8.0 mg, 0.021 mmol), and HATU (26 mg, 0.07 mmol) in DMF (0.23 mL), DIPEA (0.014 mL, 0.083 mmol) was added. The reaction mixture was stirred at room temperature for 2 h. The mixture was diluted with MeOH and H$_2$O, then filtered and purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the sub-title compound as a bright yellow powder (5.4 mg, 33%). LCMS calc. for $C_{40}H_{47}N_{10}O_6(M+H)^+$: m/z=763.4. Found: 763.3.

Step 2. 3-Amino-N-{4-[(3R,4S,5S)-3-amino-5-methyl-4-(1H-1,2,3-triazol-1-yl)piperidin-1-yl]pyridin-3-yl}-7-morpholin-4-ylquinoline-2-carboxamide To a solution of benzyl {2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-morpholin-4-ylquinolin-3-yl}carbamate (5.4 mg, 0.007 mmol) in MeOH (0.27 mL) and THF (0.14 mL) 10% Pd on carbon (2.8 mg) was added. The reaction mixture was deoxygenated under reduced pressure and hydrogen was introduced via a balloon. The reaction mixture was stirred at room temperature under hydrogen for 1 h. The mixture was filtered and concentrated under reduced pressure to give an intermediate. The intermediate was treated with 4.0 M HCl in dioxane (0.0701 mL, 0.28 mmol), stirred at room temperature for 30 min. then concentrated under reduced pressure. The residue was diluted with MeOH and NH$_4$OH, filtered and purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the title compound as a yellow powder (2.4 mg, 64%). LCMS calc. for $C_{27}H_{33}N_{10}O_2(M+H)^+$: m/z=529.3. Found: 529.3.

Example 56

3-Amino-N-{4-[(3R,4S,5S)-3-amino-5-methyl-4-(1H-1,2,3-triazol-1-yl)piperidin-1-yl]pyridin-3-yl}-7-(1-methylpiperidin-4-yl)quinoline-2-carboxamide

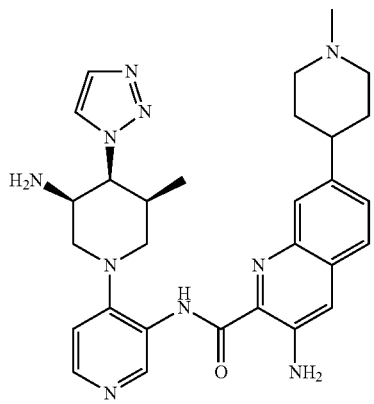 [SMILES: C[C@H]1CN(c2ccncc2NC(=O)c2nc3cc(C4CCN(C)CC4)ccc3cc2N)C[C@@H](N)[C@H]1n1ccnn1]

Step 1. Benzyl [2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-(1-methyl-], 2,3,6-tetrahydropyridin-4-yl)quinolin-3-yl]carbamate

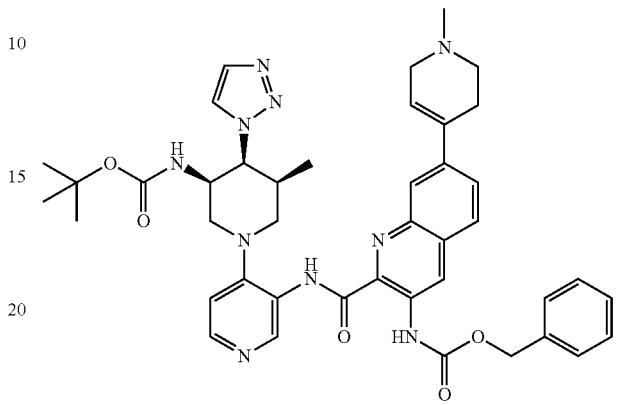

A pressure tube was charged with benzyl {7-bromo-2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]quinolin-3-yl}carbamate (15 mg, 0.020 mmol), K$_3$PO$_4$ (8.4 mg, 0.034 mmol), 1,4-dioxane (0.3 mL), water (0.04 mL) and 1-methyl-4-(4,4,5,5-tetramethyl-1,3,2-dioxaborolan-2-yl)-1,2,3,6-tetrahydropyridine (6.6 mg, 0.03 mmol). The reaction mixture was purged with nitrogen for 5 min., then dicyclohexyl(2',4',6'-triisopropylbiphenyl-2-yl)phosphine-(2'-aminobiphenyl-2-yl)(chloro)palladium (1:1) (1.6 mg, 0.002 mmol) was added. The reaction mixture was sealed and heated at 90° C. for 30 min., then allowed to cool to room temperature. The crude mixture was filtered and purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the title compound as a light yellow powder (4.7 mg, 33%). LCMS calc. for $C_{42}H_{49}N_{10}O_5(M+H)^+$: m/z=773.4. Found: 773.4.

Step 2. 3-Amino-N-{4-[(3R,4S,5S)-3-amino-5-methyl-4-(1H-1,2,3-triazol-1-yl)piperidin-1-yl]pyridin-3-yl}-7-(1-methylpiperidin-4-yl)quinoline-2-carboxamide To a solution of benzyl [2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-(1-methyl-1,2,3,6-tetrahydropyridin-4-yl)quinolin-3-yl]carbamate (4.7 mg, 0.006 mmol) in MeOH (0.24 mL) and THF (0.24 mL), 10% Pd on carbon (2.4 mg) was added. The reaction mixture was deoxygenated under reduced pressure and hydrogen was introduced via a balloon. The reaction mixture was stirred at room temperature under hydrogen for 2 h. The mixture was filtered and concentrated under reduced pressure to give an intermediate. The intermediate was treated with 4.0 M HCl in dioxane (0.061 mL, 0.24 mmol) and stirred at room temperature for 30 min. The solution was concentrated under reduced pressure. The residue resulting residue was diluted with MeOH and NH$_4$OH, filtered and purified by preparative LCMS (pH=10 method; XBridge™ preparative C18 5 μm OBD™ column, 30×10 mm, 60 mL/min., eluting with a gradient of MeCN and water with 0.1% NH₄OH) to give the title compound as a yellow powder (2.0 mg, 61%). LCMS calc. for $C_{29}H_{37}N_{10}O$ (M+H)⁺: m/z=541.3. Found: 541.3.

Example 57

3-Amino-N-{4-[(3R,4S,5S)-3-amino-5-methyl-4-(1H-1,2,3-triazol-1-yl)piperidin-1-yl]pyridin-3-yl}-7-ethylquinoline-2-carboxamide

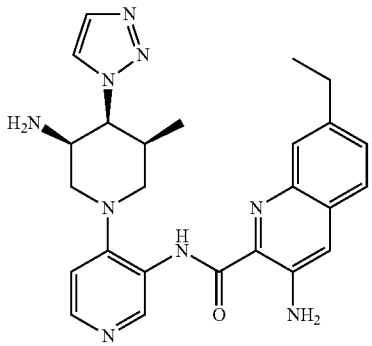 [SMILES: CCc1ccc2cc(N)c(C(=O)Nc3cnccc3N3C[C@@H](N)[C@@H](n4ccnn4)[C@@H](C)C3)nc2c1]

Step 1. Benzyl {2-[({4-[(3R,4S,5S)-3-[(tert-butoxycarbonyl)amino]-5-methyl-4-(H-1,2,3-triazol-1-yl)piperidin-1-yl]pyridin-3-yl}amino)carbonyl]-7-vinylquinolin-3-yl}carbamate

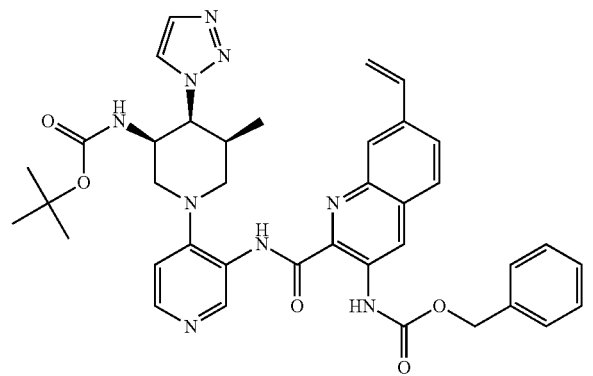 [SMILES: C=Cc1ccc2cc(NC(=O)OCc3ccccc3)c(C(=O)Nc3cnccc3N3C[C@H](C)[C@H](n4ccnn4)[C@H](NC(=O)OC(C)(C)C)C3)nc2c1]

A pressure tube charged with benzyl {7-bromo-2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]quinolin-3-yl}carbamate (15 mg, 0.020 mmol), K₃PO₄ (8.4 mg, 0.04 mmol), 1,4-dioxane (0.26 mL), water (0.042 mL) and 4,4,5,5-tetramethyl-2-vinyl-1,3,2-dioxaborolane (5.5 mg, 0.036 mmol). The reaction mixture was purged with nitrogen for 5 min., then dicyclohexyl(2',4',6'-triisopropylbiphenyl-2-yl)phosphine-(2'-aminobiphenyl-2-yl)(chloro)palladium (1:1) (1.6 mg, 0.002 mmol) was added. The pressure tube was sealed and the reaction mixture was heated at 90° C. for 30 min. then allowed to cool. The crude mixture was filtered and purified by preparative LCMS (pH=10 method; XBridge™ preparative C18 5 μm OBD™ column, 30×10 mm, 60 mL/min., eluting with a gradient of MeCN and water with 0.1% NH₄OH) to give the sub-title compound as a light yellow powder (5.2 mg, 37%). LCMS calc. for $C_{38}H_{42}N_9O_5$ (M+H)⁺: m/z=704.3. Found: 704.3.

Step 2. 3-Amino-N-{4-[(3R,4S,5S)-3-amino-5-methyl-4-(1H-1,2,3-triazol-1-yl)piperidin-1-yl]pyridin-3-yl}-7-ethylquinoline-2-carboxamide To a solution of benzyl {2-[({4-[(3R,4S,5S)-3-[(tert-butoxycarbonyl)amino]-5-methyl-4-(1H-1,2,3-triazol-1-yl)piperidin-1-yl]pyridin-3-yl}amino)carbonyl]-7-vinylquinolin-3-yl}carbamate (5.2 mg, 0.007 mmol) in MeOH (0.29 mL) and THF (0.29 mL) was added a mixture of palladium (2.9 mg) (10% Pd on carbon). The reaction mixture was deoxygenated under reduced pressure and hydrogen was introduced via a balloon. The reaction mixture was stirred at room temperature under hydrogen for 1 h. The mixture was filtered and concentrated under vacuum to give an intermediate. The intermediate was treated with 4.0 M HCl in dioxane (0.074 mL, 0.30 mmol) and stirred at room temperature for 30 min. The solution was then concentrated under reduced pressure. The residue was diluted with MeOH and NH₄OH, filtered and purified by preparative LCMS (pH=10 method; XBridge™ preparative C18 5 μm OBD™ column, 30×10 mm, 60 mL/min., eluting with a gradient of MeCN and water with 0.1% NH₄OH) to give the desired product as yellow powder (2.3 mg, 66%). LCMS calc. for $C_{25}H_{30}N_9O$ (M+H)⁺: m/z=472.3. Found: 472.3.

Example 58

Methyl [(3R,4S,5S)-3-amino-1-(3-{[(3-amino-7-ethylquinolin-2-yl)carbonyl]amino}pyridin-4-yl)-5-methylpiperidin-4-yl]carbamate

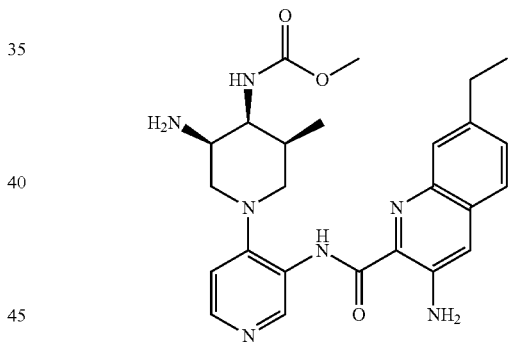

Step 1. Di-tert-butyl (4-{(3R,4S,5S)-4-amino-3-[(tert-butoxycarbonyl)amino]-5-methylpiperidin-1-yl}pyridin-3-yl)imidodicarbonate

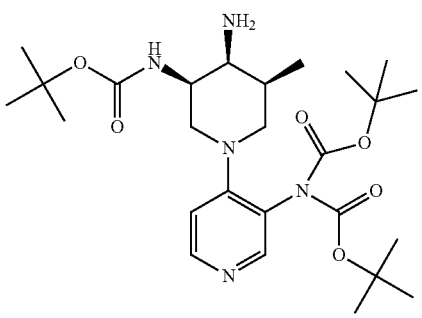 [SMILES: C[C@H]1CN(c2ccncc2N(C(=O)OC(C)(C)C)C(=O)OC(C)(C)C)C[C@@H](NC(=O)OC(C)(C)C)[C@H]1N]

To a solution of di-tert-butyl (4-{(3R,4S,5S)-4-azido-3-[(tert-butoxycarbonyl)amino]-5-methylpiperidin-1-yl}pyridin-3-yl)imidodicarbonate (1.337 g, 2.441 mmol) in THF (20 mL), water (1.00 mL, 55.5 mmol) was added, followed by trimethylphosphine (383 mg, 5.03 mmol). The mixture was stirred at 50° C. for 15 h. The mixture was then concentrated under reduced pressure. The residue was diluted with EtOAc, washed with brine, dried over $Na_2SO_4$, filtered, and concentrated under reduced pressure to give the sub-title compound as a white foamy solid (1.336 g, 105%). LCMS calc. for $C_{26}H_{44}N_5O_6$ $(M+H)^+$: m/z=522.3. Found: 522.3.

Step 2. Di-tert-butyl (4-{(3R,4S,5S)-3-[(tert-butoxycarbonyl)amino]-4-[(methoxycarbonyl)amino]-5-methylpiperidin-1-yl}pyridin-3-yl)imidodicarbonate

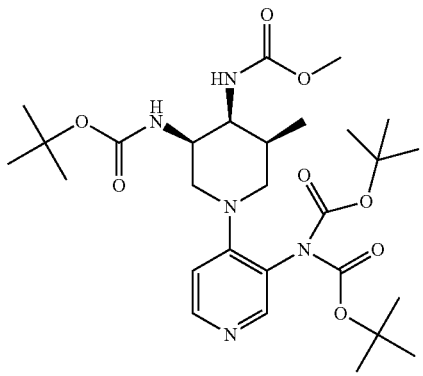 [SMILES: COC(=O)N[C@H]1[C@@H](C)CN(c2ccncc2N(C(=O)OC(C)(C)C)C(=O)OC(C)(C)C)C[C@H]1NC(=O)OC(C)(C)C]

To a solution of di-tert-butyl (4-{(3R,4S,5S)-4-amino-3-[(tert-butoxycarbonyl)amino]-5-methylpiperidin-1-yl}pyridin-3-yl)imidodicarbonate (1.27 g, 2.43 mmol) in DCM (50.0 mL) at 0° C., DIPEA (983 mg, 7.60 mmol) was added followed by a solution of methyl chloroformate (244 mg, 2.59 mmol) in DCM (10 mL). The solution was stirred at 0° C. for 30 min., then at room temperature for additional 30 min., then the reaction was quenched with 1.0 M aq. $Na_2CO_3$ in water (75.0 mL, 75.0 mmol). The organic layer was separated, washed with brine, then dried over $Na_2SO_4$, filtered and concentrated to give the crude sub-title compound as a yellow foamy solid (1.545 g, 109%). The crude product was used directly in the next step without further purification. LCMS calc. for $C_{28}H_{46}N_5O_8$ $(M+H)^+$: m/z=580.3. Found: 580.3.

Step 4. tert-Butyl methyl [(3R,4S,5S)-1-(3-aminopyridin-4-yl)-5-methylpiperidine-3, 4-diyl]biscarbamate

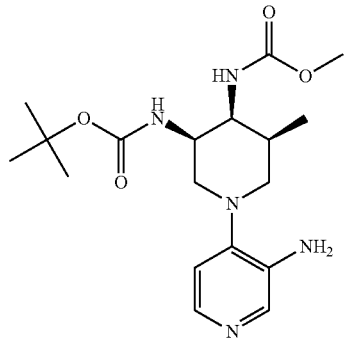 [SMILES: COC(=O)N[C@H]1[C@@H](C)CN(c2ccncc2N)C[C@H]1NC(=O)OC(C)(C)C]

A mixture of di-tert-butyl (4-{(3R,4S,5S)-3-[(tert-butoxycarbonyl)amino]-4-[(methoxycarbonyl)amino]-5-methylpiperidin-1-yl}pyridin-3-yl)imidodicarbonate (1.41 g, 2.43 mmol) and 4.0 M HCl in dioxane (40.0 mL, 1.60E2 mmol) was stirred at room temperature for 1 h. The reaction mixture was concentrated under reduced pressure and the solid was dried under high vacuum for 10 min. DCM (25.0 mL) was added to the residue, followed by DIPEA (1.94 g, 15.0 mmol) and 1-[(tert-butoxycarbonyl)oxy]pyrrolidine-2,5-dione (579 mg, 2.69 mmol). The mixture was then stirred room temperature for 16 h, then concentrated under reduced pressure. The residue was dissolved in EtOAc, washed with saturated aq. $Na_2CO_3$ and brine, dried over $Na_2SO_4$, filtered and concentrated under reduced pressure. The residue was purified by flash chromatography on silica gel (40 g, eluting with 100% EtOAc, then 10% MeOH in DCM with 1% $Et_3N$) to give the sub-title compound as a yellow foamy solid (701 mg, 76%). LCMS calc. for $C_{18}H_{30}N_5O_4$ $(M+H)^+$: m/z=380.2. Found: 380.3.

Step 5. tert-Butyl methyl [(3R,4S,5S)-1-(3-{[(3-{[(benzyloxy)carbonyl]amino}-7-bromoquinolin-2-yl)carbonyl]amino}pyridin-4-yl)-5-methylpiperidine-3, 4-diyl]biscarbamate

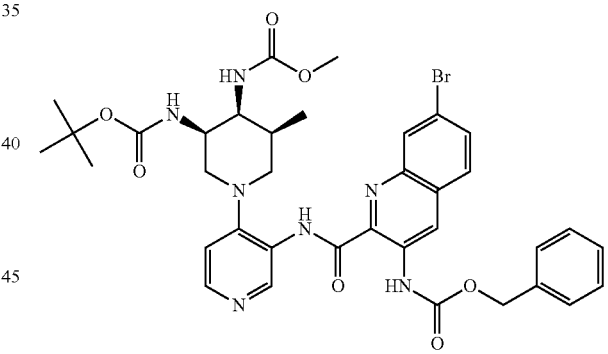

To a mixture of 3-{[(benzyloxy)carbonyl]amino}-7-bromoquinoline-2-carboxylic acid (360 mg, 0.897 mmol), tert-butyl methyl [(3R,4S,5S)-1-(3-aminopyridin-4-yl)-5-methylpiperidine-3,4-diyl]biscarbamate (303 mg, 0.799 mmol) and HATU (914.8 mg, 2.406 mmol) in DMF (5.0 mL), DIPEA (539 mg, 4.17 mmol) was added. The mixture was stirred at room temperature for 3 h. The volatile solvents were removed under reduced pressure, and the residue was purified by flash chromatography (40 g, 0-100% EtOAc in hexanes) to give the sub-title compound as a red viscous oil (1.120 g, 184%). The product was used in the next step without further purification. LCMS calc. for $C_{36}H_{41}BrN_7O_7$ $(M+H)^+$: m/z=762.2. Found: 762.3.

Step 6. tert-Butyl methyl [(3R,4S,5S)-1-(3-{[(3-{[(benzyloxy)carbonyl]amino}-7-vinylquinolin-2-yl)carbonyl]amino}pyridin-4-yl)-5-methylpiperidine-3,4-diyl]biscarbamate

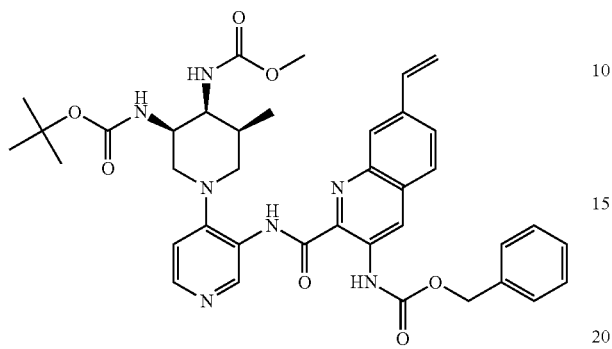

A vial was charged with dicyclohexyl(2',4',6'-triisopropylbiphenyl-2-yl)phosphine-(2'-aminobiphenyl-2-yl)(chloro)palladium (1:1) (40 mg, 0.051 mmol), and $K_3PO_4$ (179 mg, 0.844 mmol) were added. The vial was sealed with a septum, then purged with nitrogen three times. A mixture of tert-butyl methyl [(3R,4S,5S)-1-(3-{[(3-{[(benzyloxy)carbonyl]amino}-7-bromoquinolin-2-yl)carbonyl]amino}pyridin-4-yl)-5-methylpiperidine-3,4-diyl]biscarbamate (200 mg, 0.262 mmol) and 4,4,5,5-tetramethyl-2-vinyl-1,3,2-dioxaborolane (87 mg, 0.56 mmol) in 1,4-dioxane (2.0 mL) was added, followed by deoxygenated water (0.50 mL, 28 mmol). The resulting reaction mixture was heated at 60° C. for 2 h. The mixture was purified by preparative LCMS (pH=10 method; XBridge™ preparative C18 5 μm OBD™ column, 30×10 mm, 60 mL/min., eluting with a gradient of MeCN and water with 0.1% $NH_4OH$) to give the sub-title compound as a yellow solid (92 mg, 49%). LCMS calc. for $C_{38}H_{44}N_7O_7$ $(M+H)^+$: m/z=710.3. Found: 710.3.

Step 7. Methyl [(3R,4S,5S)-3-amino-1-(3-{[(3-amino-7-ethylquinolin-2-yl)carbonyl]amino}pyridin-4-yl)-5-methylpiperidin-4-yl]carbamate To a solution of tert-butyl methyl [(3R,4S,5S)-1-(3-{[(3-{[(benzyloxy)carbonyl]amino}-7-vinylquinolin-2-yl)carbonyl]amino}pyridin-4-yl)-5-methylpiperidine-3,4-diyl]biscarbamate (92 mg, 0.13 mmol) in MeOH (4.0 mL), 10% Pd on carbon (21 mg) was added. The reaction mixture was deoxygenated under reduced pressure and hydrogen was introduced via a balloon. The reaction mixture was stirred at room temperature under hydrogen for 1 h. The mixture was then filtered and concentrated under reduced pressure. The resulting residue was dissolved in DCM (2 mL), and TFA (2 mL) was added. The mixture then was stirred at room temperature for 1 h before being concentrated under reduced pressure. The residue was purified by preparative LCMS (pH=10 method; XBridge™ preparative C18 5 μm OBD™ column, 30×10 mm, 60 mL/min., eluting with a gradient of MeCN and water with 0.1% $NH_4OH$) to give the title compound as a yellow powder (45 mg, 73%). LCMS calc. for $C_{25}H_{32}N_7O_3$ $(M+H)^+$: m/z=478.3. Found: 478.3.

Example 59

Methyl [(3R,4S,5S)-3-amino-1-(3-{[(3-amino-7-morpholin-4-ylquinolin-2-yl)carbonyl]amino}pyridin-4-yl)-5-methylpiperidin-4-yl]carbamate

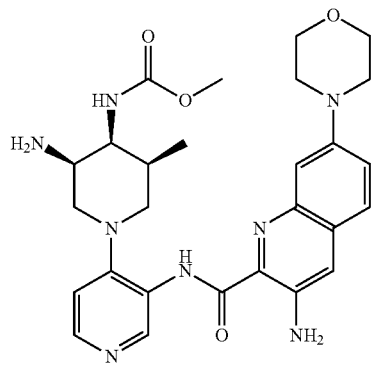

Step 1. tert-Butyl methyl [(3R,4S,5S)-1-(3-{[(3-{[(benzyloxy)carbonyl]amino}-7-morpholin-4-ylquinolin-2-yl)carbonyl]amino}pyridin-4-yl)-5-methylpiperidine-3,4-diyl]biscarbamate

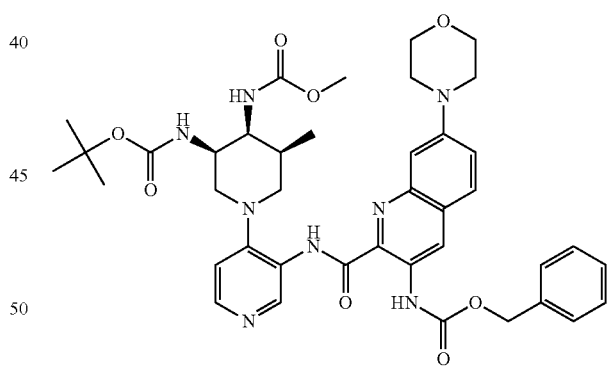

To a mixture of 3-{[(benzyloxy)carbonyl]amino}-7-morpholin-4-ylquinoline-2-carboxylic acid (31 mg, 0.075 mmol), tert-butyl methyl [(3R,4S,5S)-1-(3-aminopyridin-4-yl)-5-methylpiperidine-3,4-diyl]biscarbamate (30 mg, 0.079 mmol) and HATU (92 mg, 0.24 mmol) in DMF (1.0 mL), DIPEA (90 μL, 0.52 mmol) was added. The reaction mixture was stirred at room temperature overnight. The mixture was then purified by preparative LCMS (pH=10 method; XBridge™ preparative C18 5 μm OBD™ column, 30×10 mm, 60 mL/min., eluting with a gradient of MeCN and water with 0.1% $NH_4OH$) to give the sub-title compound as a yellow solid (30 mg, 51%). LCMS calc. for $C_{40}H_{49}N_8O_8$ $(M+H)^+$: m/z=769.4. Found: 769.4.

Step 2. Methyl [(3R,4S,5S)-3-amino-1-(3-{[(3-amino-7-morpholin-4-ylquinolin-2-yl)carbonyl]amino}pyridin-4-yl)-5-methylpiperidin-4-yl]carbamate

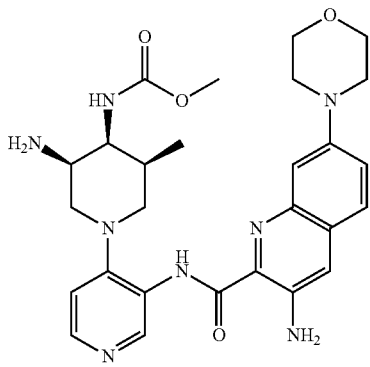 [SMILES: COC(=O)N[C@@H]1[C@H](N)CN(c2ccncc2NC(=O)c2nc3cc(N4CCOCC4)ccc3cc2N)C[C@@H]1C]

To a solution of tert-butyl methyl [(3R,4S,5S)-1-(3-{[(benzyloxy)carbonyl]amino}-7-morpholin-4-ylquinolin-2-yl)carbonyl]amino}pyridin-4-yl)-5-methylpiperidine-3,4-diyl]biscarbamate (30 mg, 0.039 mmol) in MeOH (2.0 mL) and THF (1.0 mL), 10% Pd on carbon (6.9 mg) was added. The reaction mixture was deoxygenated under reduced pressure and hydrogen was introduced via a balloon. The reaction mixture was stirred at room temperature under hydrogen for 90 min. The mixture was then filtered and concentrated under reduced pressure. The resulting residue was dissolved in DCM (2 mL), and TFA (2 mL) was added. The mixture was stirred at room temperature for 1 h, then concentrated under reduced pressure. The residue was purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the title compound as a yellow powder (11 mg, 52%). LCMS calc. for $C_{27}H_{35}N_8O_4$ (M+H)$^+$: m/z=535.3. Found: 535.4.

Example 60

Methyl {(3R,4S,5S)-3-amino-1-[3-({[3-amino-7-(4-methylpiperazin-1-yl)quinolin-2-yl]carbonyl}amino)pyridin-4-yl]-5-methylpiperidin-4-yl}carbamate

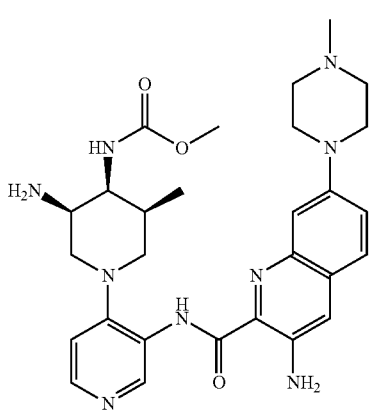

Step 1. tert-Butyl methyl {(3R,4S,5S)-1-[3-({[3-{[(benzyloxy)carbonyl]amino}-7-(4-methylpiperazin-1-yl)quinolin-2-yl]carbonyl}amino)pyridin-4-yl]-5-methylpiperidine-3, 4-diyl}biscarbamate

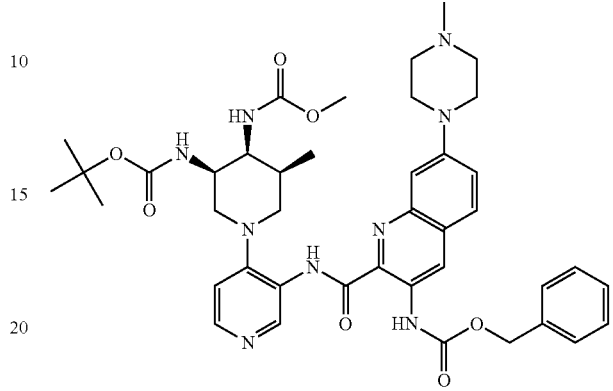

To a mixture of 3-{[(benzyloxy)carbonyl]amino}-7-(4-methylpiperazin-1-yl)quinoline-2-carboxylic acid (68 mg, 0.16 mmol), tert-butyl methyl [(3R,4S,5S)-1-(3-aminopyridin-4-yl)-5-methylpiperidine-3,4-diyl]biscarbamate (62 mg, 0.16 mmol) and HATU (190 mg, 0.500 mmol) in 2 mL of DMF, DIPEA (180 μL, 1.03 mmol) was added. The reaction mixture was stirred at room temperature overnight. The mixture was purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the sub-title compound as a yellow solid (62.4 mg, 49%). LCMS calc. for $C_{41}H_{52}N_9O_7$ (M+H)$^+$: m/z=782.4. Found: 782.4.

Step 2. Methyl {(3R,4S,5S)-3-amino-1-[3-({[3-amino-7-(4-methylpiperazin-1-yl)quinolin-2-yl]carbonyl}amino)pyridin-4-yl]-5-methylpiperidin-4-yl}carbamate To a solution of tert-butyl methyl {(3R,4S,5S)-1-[3-({[3-{[(benzyloxy)carbonyl]amino}-7-(4-methylpiperazin-1-yl)quinolin-2-yl]carbonyl}amino)pyridin-4-yl]-5-methylpiperidine-3,4-diyl}biscarbamate (62 mg, 0.080 mmol) in MeOH (3.0 mL), 10% Pd on carbon (15 mg) was added. The reaction mixture was deoxygenated under reduced pressure and hydrogen was introduced via a balloon. The reaction mixture was stirred at room temperature under the hydrogen balloon for 1 h. The mixture was filtered and concentrated under reduced pressure. The resulting residue was dissolved in DCM (2 mL), and TFA (2 mL) was added. The resulting mixture was stirred at room temperature for 1 h, then concentrated under reduced pressure. The residue was purified by preparative LCMS (pH=10 method; XBridge™ preparative C18 5 μm OBD™ column, 30×10 mm, 60 mL/min., eluting with a gradient of MeCN and water with 0.1% NH$_4$OH) to give the title compound as a yellow powder (29 mg, 65%). LCMS calc. for $C_{28}H_{38}N_9O_3$ (M+H)$^+$: m/z=548.3. Found: 548.4.

Example 61

Methyl {(3R,4S,5S)-3-amino-1-[3-({[3-amino-7-(tetrahydro-2H-pyran-4-yl)quinolin-2-yl]carbonyl}amino)pyridin-4-yl]-5-methylpiperidin-4-yl}carbamate

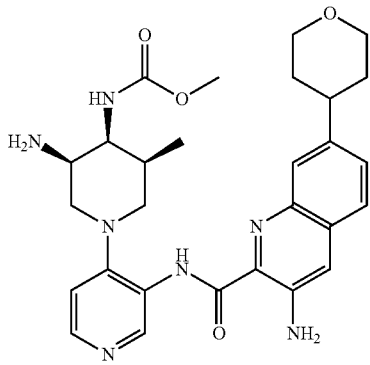 [SMILES: COC(=O)N[C@@H]1[C@H](N)CN(c2ccncc2NC(=O)c2nc3cc(C4CCOCC4)ccc3cc2N)C[C@@H]1C]

Step 1. tert-Butyl methyl {(3R,4S,5S)-1-[3-({[3-{[(benzyloxy)carbonyl]amino}-7-(3,6-dihydro-2H-pyran-4-yl)quinolin-2-yl]carbonyl}amino)pyridin-4-yl]-5-methylpiperidine-3, 4-diyl}biscarbamate

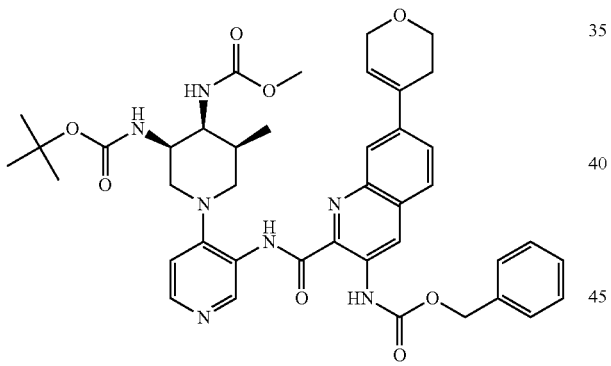

A vial was charged with 4-(4,4,5,5-tetramethyl-1,3,2-dioxaborolan-2-yl)-3,6-dihydro-2H-pyran (104 mg, 0.493 mmol), dicyclohexyl(2',4',6'-triisopropylbiphenyl-2-yl)phosphine-(2'-aminobiphenyl-2-yl)(chloro)palladium (1:1) (35 mg, 0.045 mmol), and $K_3PO_4$ (180 mg, 0.849 mmol). The vial was sealed with a septum and purged with nitrogen three times). A solution of tert-butyl methyl [(3R,4S,5S)-1-(3-{[(3-{[(benzyloxy)carbonyl]amino}-7-bromoquinolin-2-yl)carbonyl]amino}pyridin-4-yl)-5-methylpiperidine-3,4-diyl]biscarbamate (200 mg, 0.262 mmol) in 1,4-dioxane (2.0 mL) was added, followed by deoxygenated water (0.50 mL, 28 mmol). The reaction was heated at 60° C. for 2 h. The mixture was purified by preparative LCMS (pH=10 method; XBridge™ preparative C18 5 μm OBD™ column, 30×10 mm, 60 mL/min., eluting with a gradient of MeCN and water with 0.1% $NH_4OH$) to give the sub-title compound as a yellow solid (63.0 mg, 31%). LCMS calc. for $C_{41}H_{48}N_7O_8$ $(M+H)^+$: m/z=766.4. Found: 766.4.

Step 2. Methyl {(3R,4S,5S)-3-amino-1-[3-({[3-amino-7-(tetrahydro-2H-pyran-4-yl)quinolin-2-yl]carbonyl}amino)pyridin-4-yl]-5-methylpiperidin-4-yl}carbamate To a solution of tert-butyl methyl {(3R,4S,5S)-1-[3-({[3-{[(benzyloxy)carbonyl]amino}-7-(3,6-dihydro-2H-pyran-4-yl)quinolin-2-yl]carbonyl}amino)pyridin-4-yl]-5-methylpiperidine-3,4-diyl}biscarbamate (63 mg, 0.082 mmol) in MeOH (2.0 mL) and THF (1.0 mL), 10% Pd on carbon (16 mg) was added. The reaction mixture was deoxygenated under reduced pressure and hydrogen was introduced via a balloon. The reaction mixture was stirred at room temperature under hydrogen for 20 h. The mixture was filtered and the filtrate concentrated under reduced pressure. The resulting residue was dissolved in DCM (2 mL), and TFA (2 mL) was added. The mixture was stirred at room temperature for 30 min. then concentrated under reduced pressure. The residue was purified by preparative LCMS (pH=10 method; XBridge™ preparative C18 5 ™ OBD™ column, 30×10 mm, 60 mL/min., eluting with a gradient of MeCN and water with 0.1% $NH_4OH$) to give the title compound as a yellow powder (26 mg, 58%). LCMS calc. for $C_{28}H_{36}N_7O_4$ $(M+H)^+$: m/z=534.3. Found: 534.4.

Example 62

Methyl {(3R,4S,5S)-3-amino-1-[3-({[3-amino-7-(1-methylpiperidin-4-yl)quinolin-2-yl]carbonyl}amino)pyridin-4-yl]-5-methylpiperidin-4-yl}carbamate

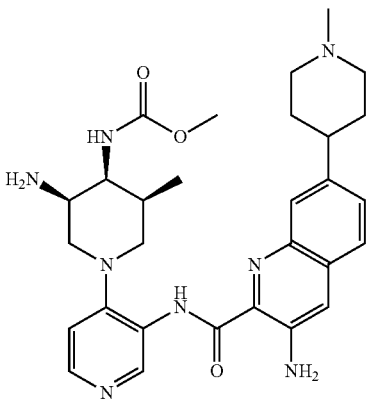 [SMILES: COC(=O)N[C@@H]1[C@H](N)CN(c2ccncc2NC(=O)c2nc3cc(C4CCN(C)CC4)ccc3cc2N)C[C@@H]1C]

Step 1. tert-Butyl methyl {(3R,4S,5S)-1-[3-({[3-{[(benzyloxy)carbonyl]amino}-7-(1-methyl-1,2,3,6-tetrahydropyridin-4-yl)quinolin-2-yl]carbonyl}amino)pyridin-4-yl]-5-methylpiperidine-3, 4-diyl}biscarbamate

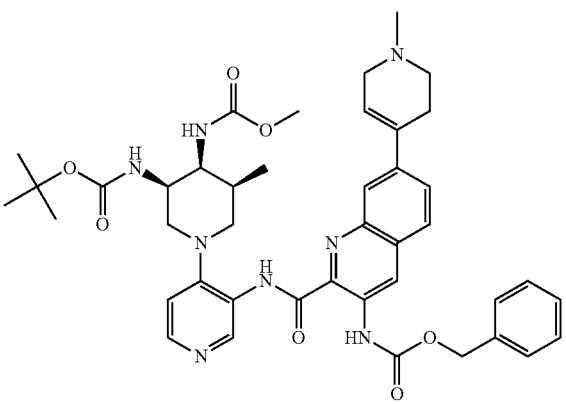 [SMILES: COC(=O)N[C@H]1[C@@H](C)CN(c2ccncc2NC(=O)c2nc3cc(C4=CCN(C)CC4)ccc3cc2NC(=O)OCc2ccccc2)C[C@H]1NC(=O)OC(C)(C)C]

A vial was charged with 1-methyl-4-(4,4,5,5-tetramethyl-1,3,2-dioxaborolan-2-yl)-1,2,3,6-tetrahydropyridine (107 mg, 0.477 mmol), dicyclohexyl(2',4',6'-triisopropylbiphenyl-2-yl)phosphine-(2'-aminobiphenyl-2-yl)(chloro)palladium (1:1) (36 mg, 0.046 mmol), and $K_3PO_4$ (175 mg, 0.824 mmol). The vial was sealed with a septum and purged with nitrogen three times. A solution of tert-butyl methyl [(3R,4S,5S)-1-(3-{[(3-{[(benzyloxy)carbonyl]amino}-7-bromo-quinolin-2-yl)carbonyl]amino}pyridin-4-yl)-5-methylpiperidine-3,4-diyl]biscarbamate (200 mg, 0.262 mmol) in 1,4-dioxane (2.0 mL) was added, followed by deoxygenated water (0.50 mL). The reaction mixture was heated at 60° C. for 2 h. The mixture was purified by preparative LCMS (pH=10 method; XBridge™ preparative C18 5 μm OBD™ column, 30×10 mm, 60 mL/min., eluting with a gradient of MeCN and water with 0.1% $NH_4OH$) to give the sub-title compound as a yellow solid (40 mg, 19%). LCMS calc. for $C_{42}H_{51}N_8O_7$ $(M+H)^+$: m/z=779.4. Found: 779.4.

Step 2. Methyl {(3R,4S,5S)-3-amino-1-[3-({[3-amino-7-(1-methylpiperidin-4-yl)quinolin-2-yl]carbonyl}amino)pyridin-4-yl]-5-methylpiperidin-4-yl}carbamate To a solution of tert-butyl methyl {(3R,4S,5S)-1-[3-({[3-{[(benzyloxy)carbonyl]amino}-7-(1-methyl-1,2,3,6-tetrahydropyridin-4-yl)quinolin-2-yl]carbonyl}amino)pyridin-4-yl]-5-methylpiperidine-3,4-diyl}biscarbamate (40 mg, 0.051 mmol) in MeOH (3.0 mL), 10% Pd on carbon (9 mg). The reaction mixture was deoxygenated under reduced pressure and hydrogen was introduced via a balloon. The reaction mixture was stirred at room temperature under hydrogen for 16 h. The mixture was filtered and concentrated under reduced pressure. The resulting residue was dissolved in DCM (2 mL), and TFA (2 mL) was added. The mixture was stirred at room temperature for 30 min. then concentrated under reduced pressure. The residue was purified by preparative LCMS (pH=10 method; XBridge™ preparative C18 5 μm OBD™ column, 30×10 mm, 60 mL/min., eluting with a gradient of MeCN and water with 0.1% $NH_4OH$) to give the title compound as a yellow powder (18 mg, 66%). LCMS calc. for $C_{29}H_{39}N_8O_3$ $(M+H)^+$: m/z=547.3. Found: 547.4.

Example A. Pim Enzyme Assays

Pim-1 and Pim-3 kinase assays-20 μL reactions were run in white 384 well polystyrene plates dotted with 0.8 μL compound/DMSO in the assay buffer (50 mM Tris, pH 7.5, 0.01% Tween-20, 5 mM $mgCl_2$, 0.01% BSA, 5 mM DTT), containing 0.05 μM Biotin-labeled BAD peptide substrate (AnaSpec 62269), 1 mM ATP, and 2.5 μM (Pim-1, Invitrogen PV3503) or 1.25 pM (Pim-3, Millipore 14-738) enzyme for 1 h at 25° C. Reactions were stopped by addition of 10 μL STOP Buffer (150 mM Tris, pH=7.5, 150 mM NaCl, 75 mM EDTA, 0.01% Tween-20, 0.3% BSA,) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 g/mL each. Supplementation of the STOP buffer with beads and stopping the reactions were done under reduced light. Prior to the stopping reactions STOP buffer with beads was preincubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay-20 μL reactions were run in white 384 well polystyrene plates dotted with 0.8 μL compound/DMSO in the assay buffer (50 mM Tris, pH 7.5, 0.01% Tween-20, 5 mM $mgCl_2$, 0.01% BSA, 5 mM DTT), containing 0.05 M Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 μL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an $IC_{50}$ of 2 μM or less when tested for PIM kinase activity under the assay conditions disclosed above are considered active.

Although the above in vitro assays are conducted at 1 mM ATP compounds can also be evaluated for potency and in vitro activity against PIM targets utilizing $K_m$ conditions, where the concentration of ATP is set to the $K_m$ value and the assay is more sensitive to PIM inhibition activity.

Example B. Pim Cellular Assays

One or more compounds of the invention were tested for inhibitory activity of PIM according to at least one of the following cellular assays. Compounds of the invention having an $IC_{50}$ of 10 μM or less when tested for PIM kinase activity under the cellular assay conditions disclosed below would be and were considered active.

Pim Cell Proliferation Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the anti-proliferation activity of test compounds, both cell lines are plated with the culture medium ($2 \times 10^3$ cells/well/in 200 μL) into 96-well polystyrene ultralow binding (Costar,) in the presence or absence of a concentration range of test compounds. After 4 days, [$^3$H]-thymidine, 1 μCi/10 μL/well (PerkinElmer, Boston, Mass.) in culture medium is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). $IC_{50}$ determination is performed by fitting the curve of percent inhibition versus the log of the inhibitor concentration using the GraphPad Prism 5.0 software.

Pim pBAD Signaling Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium ($1 \times 10^6$/well/100 μL for KG1A and $4 \times 10^5$ cells/well/in 100 μL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS.12.BM cells and 4 h for KG1-A cells. Plates are centrifuged at 2000 RPM for 10 min. and supernatants aspirated. 100 μL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80° C. To measure the pBAD activity, a Cell Signaling ELISA kit (Cell Signaling Path Scan phosphor pBAD ELISA) is utilized. 50 μL of the lysate is tested per the ELISA protocol and the data analysis is performed by software on a SpectrMax5 plate reader (Molecular Devices, Sunnyvale, Calif.). $IC_{50}$ determination is performed by fitting the curve of percent inhibition versus the log of the inhibitor concentration using the GraphPad Prism 5.0 software.

Data obtained for the Example compounds, obtained using the methods described in Example A, are provided in Table 1.

TABLE 1

| Pim Enzyme Assay Data | | | |
|---|---|---|---|
| Example | Pim1 $IC_{50}$ (nM) | Pim2 $IC_{50}$ (nM) | Pim3 $IC_{50}$ (nM) |
| 1 | + | ++ | + |
| 2 | + | ++ | + |
| 3 | + | ++ | + |
| 4 | + | +++ | + |
| 5 | + | + | + |
| 6 | >40 | >2000[†] | >40 |
| 7 | + | + | + |
| 8 | >40 | >2000 | + |
| 9 | + | + | + |
| 10 | + | + | + |
| 11 | + | ++ | + |
| 12 | + | ++ | + |
| 13 | + | ++ | + |
| 14 | + | ++ | + |
| 15 | + | ++ | + |
| 16 | + | ++ | + |
| 17 | + | >2000 | + |
| 18 | + | ++ | + |
| 19 | + | >2000 | + |
| 20 | + | >2000 | + |
| 21 | + | ++ | + |
| 22 isomer 1 | >40 | >2000[‡] | >40 |
| 22 isomer 2 | + | >2000 | + |
| 23 | + | ++ | + |
| 24 | + | ++ | + |
| 25 | + | | + |
| 26 | + | | + |
| 27 | + | | + |
| 28 | + | + | + |
| 29 | + | + | + |
| 30 | + | + | + |
| 31 | >40 | >2000 | + |
| 32 | + | >2000 | + |
| 33 | + | ++ | + |
| 34 | + | + | + |
| 35 | + | ++ | + |
| 36 | + | + | + |
| 37 | + | ++ | + |
| 38 | + | + | + |
| 39 | + | + | + |
| 40 | + | + | + |
| 41 | + | + | + |
| 42 | + | + | + |
| 43 | + | + | + |
| 44 | + | + | + |
| 45 | + | ++ | + |
| 46 | + | ++ | + |
| 47 | + | ++ | + |
| 48 | + | + | + |
| 49 | + | ++ | + |
| 50 | + | ++ | + |
| 51 | + | +++ | + |
| 52 | + | >2000 | + |
| 53 | + | +++ | + |
| 54 | + | >2000 | + |
| 55 | + | >2000 | + |

TABLE 1-continued

| Pim Enzyme Assay Data | | | |
|---|---|---|---|
| Example | Pim1 $IC_{50}$ (nM) | Pim2 $IC_{50}$ (nM) | Pim3 $IC_{50}$ (nM) |
| 56 | + | +++ | + |
| 57 | + | ++ | + |
| 58 | + | ++ | + |
| 59 | + | +++ | + |
| 60 | + | +++ | + |
| 61 | + | ++ | + |
| 62 | + | +++ | + |

1000 nM < $IC_{50}$ ≤ 10000 nM: +++;
100 nM < $IC_{50}$ ≤ 1000 nM: ++;
$IC_{50}$ ≤ 100 nM: +
[†]Compound was active ($IC_{50}$ < 100 nM) as a Pim2 inhibitor in an assay analogous to Example A performed under $K_m$ ATP conditions rather than at 1 mM ATP concentration.
[‡]Compound was active (100 nM < $IC_{50}$ ≤ 1000 nM) as a Pim2 inhibitor in an assay analogous to Example A performed under $K_m$ ATP conditions rather than at 1 mM ATP concentration.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of treating cancer, wherein the cancer is lymphoma, leukemia, multiple myeloma or myeloproliferative disorders, comprising administering to a patient in need of such treatment a therapeutically effective amount of a compound of Formula (I):

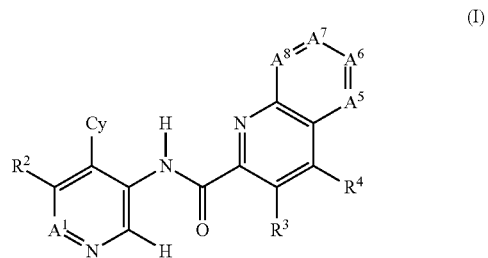

or a pharmaceutically acceptable salt thereof, wherein:
Cy is a group of the following formula (Cy-2):

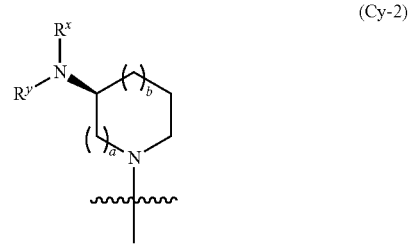

wherein:
$R^x$ is H;
$R^y$ is H;
a is 1; and
b is 1;
wherein the substituted piperidin-1-yl ring forming Cy is substituted with 1, 2, 3, 4 or 5 substituents each independently selected from halogen, $R^{Cy1}$, $C_{1-6}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $OC(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$, wherein each $R^{Cy1}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-7}$ cycloalkyl and 4-7 membered heterocycloalkyl, each of which is independently unsubstituted or substituted with 1, 2 or 3 substituents independently selected from halogen, $R^{Cy2}$, $C_{1-6}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$, and wherein each $R^{Cy2}$ is independently $C_{1-6}$ alkyl, $C_{2-6}$ alkenyl, $C_{2-6}$ alkynyl, $C_{6-10}$ aryl, 5-10 membered heteroaryl, $C_{3-7}$ cycloalkyl and 4-7 membered heterocycloalkyl, each of which is independently unsubstituted or substituted with 1, 2 or 3 substituents independently selected from halogen, CN, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}NR^{c1}C(O)OR^{a1}$, $S(O)R^{b1}$, $S(O)NR^{c1}R^{d1}$, $S(O)_2R^{b1}$ and $S(O)_2NR^{c1}R^{d1}$;

$A^1$ is $CR^1$;

$R^1$ is H, halogen, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$; and $R^2$ is H, halogen, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$;

or $A^1$ and $R^2$ in combination, together with the carbon atom to which $R^2$ is attached, form a 5, 6 or 7-membered unsaturated or partially saturated carbocyclic or heterocyclic ring containing 3 to 7 ring carbon atoms and 0, 1 or 2 ring heteroatoms, each independently selected from N, O and S, wherein the ring formed by the combination of $A^1$ and $R^2$ is unsubstituted or substituted by 1, 2 or 3 substituents independently selected from halogen, $C_{1-6}$ alkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c}C(O)R^{b2}$, $NR^{c2}C(O)NR^{c2}R^{d2}$, $NR^{c2}C(O)OR^{a2}$ and oxo;

$R^3$ is $NH_2$;
$R^4$ is H;
$A^5$ is N or $CR^5$;
$A^6$ is N or $CR^6$;
$A^7$ is N or $CR^7$;
$A^8$ is N or $CR^8$;
provided that 0, 1 or 2 of $A^5$, $A^6$, $A^7$ and $A^8$ are N;
$R^5$ is H or halogen;
$R^6$ is H or halogen;
$R^7$ is H, halogen, $C_{1-6}$ alkyl, $C_{2-6}$ alkenyl, $C_{2-6}$ alkynyl, $C_{1-6}$ haloalkyl, $Cy^7$, $-L^7-Cy^7$, CN, $OR^{a3}$, $SR^{a3}$, $C(O)$ $R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ or $S(O)_2NR^{c3}R^{d3}$, wherein said $C_{1-6}$ alkyl, $C_{2-6}$ alkenyl or $C_{2-6}$ alkynyl forming $R^7$ are each independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a3}SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$;

$Cy^7$ is unsubstituted or substituted $C_{6-10}$ aryl, unsubstituted or substituted 5-10 membered heteroaryl, unsubstituted or substituted $C_{3-6}$ cycloalkyl or unsubstituted or substituted 4-7 membered heterocycloalkyl, wherein the substituted $C_{6-10}$ aryl, 5-10 membered heteroaryl, $C_{3-6}$ cycloalkyl or 4-7 membered heterocycloalkyl forming $Cy^7$ is substituted with 1, 2, 3, 4 or 5 substituents each independently selected from halogen, $R^{Cy7}$, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$, wherein each $R^{Cy7}$ is $C_{1-6}$ alkyl, each of which is independently unsubstituted or substituted by 1, 2 or 3 substituents independently selected from halogen, CN, $OR^{a3}SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)$ $R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$;

$L^7$ is unsubstituted $C_{1-6}$ alkylene or $C_{1-6}$ alkylene substituted with 1, 2 or 3 substituents independently selected from F, Cl, CN, OH, $O(C_{1-6}$ alkyl), $NH_2$, $NH(C_{1-6}$ alkyl) and $N(C_{1-6}$ alkyl)$_2$;

$R^8$ is H, halogen, CN or $C_{1-6}$ alkyl;

$R^{a1}$, $R^{b1}$, $R^{c1}$ and $R^{d1}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a1}$, $R^{b1}$, $R^{c1}$ and $R^{d1}$ are each optionally substituted with 1, 2, 3, 4 or 5 substituents independently selected from $C_{1-6}$ alkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$ $S(O)$ $R^{b4}$, $S(O)NR^{c4}R^{d4}$, $S(O)_2R^{b4}$, $NR^{c4}S(O)_2R^{b4}$ and $S(O)_2NR^{c4}R^{d4}$;

or $R^{c1}$ and $R^{d1}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$ $S(O)R^{b4}$, $S(O)NR^{c4}R^{d4}$, $S(O)_2R^{b4}$, $NR^{c4}S(O)_2R^{b4}$ and $S(O)_2NR^{c4}R^{d4}$;

$R^{a2}$, $R^{b2}$, $R^{c2}$ and $R^{d2}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a2}$, $R^{b2}$, $R^{c2}$ and $R^{d2}$, are each optionally substituted with 1, 2, 3, 4 or 5 substituents independently selected from $C_{1-6}$ alkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$ and $S(O)_2NR^{c5}R^{d5}$;

or $R^{c2}$ and $R^{d2}$, attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a5}$, $SR^{a5}$, $C(O)R^{b5}$, $C(O)NR^{c5}SR^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$ and $S(O)_2NR^{c5}R^{d5}$;

$R^{a3}$, $R^{b3}$, $R^{c3}$ and $R^{d3}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a3}$, $R^{b3}$, $R^{c3}$ and $R^{d3}$ are each optionally substituted with 1, 2, 3, 4 or 5 substituents independently selected from $C_{1-6}$ alkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$ $S(O)R^{b6}$, $S(O)NR^{c6}R^{d6}$, $S(O)_2R^{b6}$, $NR^{c6}S(O)_2R^{b6}$ and $S(O)_2NR^{c6}R^{d6}$;

or $R^{c3}$ and $R^{d3}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$ $S(O)R^{b6}$, $S(O)NR^{c6}R^{d6}$, $S(O)_2R^{b6}$, $NR^{c6}S(O)_2R^{b6}$ and $S(O)_2NR^{c6}R^{d6}$;

$R^{a4}$, $R^{b4}$, $R^{c4}$ and $R^{d4}$ are each independently selected from H, $C_{1-6}$ alkyl, $C_{1-6}$ haloalkyl, $C_{2-6}$ alkenyl, $C_{2-6}$ alkynyl, aryl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a4}$, $R^{b4}$, $R^{c4}$ and $R^{d4}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c4}$ and $R^{d4}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

$R^{a5}$, $R^{b5}$, $R^{c5}$ and $R^{d5}$ are each independently selected from H, $C_{1-6}$ alkyl, $C_{1-6}$ haloalkyl, $C_{2-6}$ alkenyl, $C_{2-6}$ alkynyl, aryl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a5}$, $R^{b5}$, $R^{c5}$ and $R^{d5}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c5}$ and $R^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

$R^{a6}$, $R^{b6}$, $R^{c6}$ and $R^{d6}$ are each independently selected from H, $C_{1-6}$ alkyl, $C_{1-6}$ haloalkyl, $C_{2-6}$ alkenyl, $C_{2-6}$ alkynyl, aryl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a6}$, $R^{b6}$, $R^{c6}$ and $R^{d6}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c6}$ and $R^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy; and
$R^{e1}$, $R^{e2}$, $R^{e3}$, $R^{e4}$, $R^{e5}$ and $R^{e6}$ are each, independently, H, CN or NO$_2$.

2. The method of claim 1, wherein the cancer is a cancer wherein the expression or activity of at least one of Pim1, Pim2 and Pim3 is upregulated.

3. The method of claim 1, wherein $R^1$ is H, halogen or $C_{1-6}$ alkyl.

4. The method of claim 1, wherein $R^1$ is H.

5. The method of claim 1, wherein $R^2$ is H, halogen, CN, $C_{1-6}$ alkyl or $C_{1-6}$ alkoxy.

6. The method of claim 1, wherein $R^2$ is H.

7. The method of claim 1, wherein $A^1$ and $R^2$ in combination, together with the carbon atom to which $R^2$ is attached, form a 5, 6 or 7-membered unsaturated or partially saturated carbocyclic or heterocyclic ring containing 3 to 7 ring carbon atoms and 0, 1 or 2 ring heteroatoms, each independently selected from N, O and S; wherein the ring formed by the combination of $A^1$ and $R^2$ is unsubstituted or substituted by 1, 2 or 3 substituents independently selected from halogen, $C_{1-6}$ alkyl, CN, $OR^{a2}$, $OC(O)R^{a2}$ and oxo.

8. The method of claim 7, wherein $R^1$ and $R^2$ in combination form a $C_{3-5}$ alkylene that is unsubstituted or substituted by $OR^{a2}$.

9. The method of claim 8, wherein $R^1$ and $R^2$ in combination form a $C_{3-5}$ alkylene that is unsubstituted or substituted by OH.

10. The method of claim 1, wherein $A^5$ is $CR^5$.

11. The method of claim 10, wherein $R^5$ is H.

12. The method of claim 1, wherein $A^6$ is N.

13. The method of claim 1, wherein $A^6$ is $CR^6$.

14. The method of claim 13, wherein $R^6$ is H.

15. The method of claim 13, wherein $R^6$ is halogen.

16. The method of claim 1, wherein $A^7$ is N.

17. The method of claim 1, wherein $A^7$ is $CR^7$.

18. The method of claim 17, wherein $R^7$ is H, halogen, $C_{1-6}$ alkyl, $C_{2-6}$ alkenyl, $C_{2-6}$ alkynyl, $C_{1-6}$ haloalkyl, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$ $S(O)R^{b3}$, $S(O)NR^{c3}R^{d3}$, $S(O)_2R^{b3}$, $NR^{c3}S(O)_2R^{b3}$ or $S(O)_2NR^{c3}R^{d3}$, wherein said $C_{1-6}$ alkyl, $C_{2-6}$ alkenyl or $C_{2-6}$ alkynyl forming $R^7$ are each unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^3S(O)_2R^{b3}$ and $S(O)_2NR^{c3}R^{d3}$.

19. The method of claim 18, wherein $R^7$ is H, halogen, $C_{1-6}$ alkyl, $C_{2-6}$ alkenyl or $C_{2-6}$ alkynyl, wherein said $C_{1-6}$ alkyl, $C_{2-6}$ alkenyl or $C_{2-6}$ alkynyl forming $R^7$ are each unsubstituted or substituted with 1, 2 or 3 substituents independently selected from halogen, $C_{1-6}$ alkyl, $C_{2-6}$ alkenyl, $C_{2-6}$ alkynyl, CN, $OR^{a3}$, $OC(O)R^{b3}$, $NR^{c3}R^{d3}$ and $NR^{c3}C(O)R^{b3}$.

20. The method of claim 19, wherein $R^7$ is H, halogen or $C_{1-6}$ alkyl, wherein said $C_{1-6}$ alkyl forming $R^7$ is unsubstituted or substituted with a substituent selected from halogen, CN, $OR^{a3}$, $OC(O)R^{b3}$, $NR^{c3}R^{d3}$ and $NR^3C(O)R^{b3}$.

21. The method of claim 20, wherein $R^7$ is H, halogen, $C_{1-6}$ alkyl, ($C_1$-6 alkylene)-CN, ($C_{1-6}$ alkylene)-OH, ($C_{1-6}$ alkylene)-O($C_{1-6}$ alkyl) or ($C_{1-6}$ alkylene)-$NR^{c3}R^{d3}$.

22. The method of claim 21, wherein $R^7$ is H, halogen, methyl, ethyl, isopropyl, $CH_2CN$, $CH(OH)CH_3$, $C(OH)(CH_3)_2$, $CFCH_3$ or $CH_2N(CH_3)_2$.

23. The method of claim 17, wherein $R^7$ is $Cy^7$ or $-L^7-Cy^7$.

24. The method of claim 23, wherein $Cy^7$ is unsubstituted $C_{6-10}$ aryl or $C_{6-10}$ aryl substituted with 1, 2, 3, 4 or 5 substituents each independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$.

25. The method of claim 24, wherein $Cy^7$ is unsubstituted phenyl or phenyl substituted with 1, 2, 3, 4 or 5 substituents each independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$.

26. The method of claim 25, wherein $Cy^7$ is unsubstituted phenyl, 2,6-difluorophenyl, 2-carbamylphenyl, 2-carbamyl-6-fluorophenyl, 2-cyanophenyl, 2-cyano-6-fluorophenyl.

27. The method of claim 23, wherein $Cy^7$ is unsubstituted 5-10 membered heteroaryl or 5-10 membered heteroaryl substituted with 1, 2, 3, 4 or 5 substituents each independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$.

28. The method of claim 27, wherein $Cy^7$ is unsubstituted pyrazolyl or pyrazolyl substituted with 1, 2 or 3 $C_{1-6}$ alkyl substituents.

29. The method claim 23, wherein $Cy^7$ is unsubstituted $C_{3-7}$ cycloalkyl or $C_{3-7}$ cycloalkyl substituted with 1, 2, 3, 4 or 5 substituents each independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$.

30. The method of claim 29, wherein $Cy^7$ is unsubstituted $C_{3-7}$ cycloalkyl.

31. The method of claim 23, wherein $Cy^7$ is unsubstituted 4-7 membered heterocycloalkyl or 4-7 membered heterocycloalkyl substituted with 1, 2, 3, 4 or 5 substituents each independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$.

32. The method of claim 31, wherein $Cy^7$ is unsubstituted 4-7 membered heterocycloalkyl.

33. The method of claim 31, wherein $Cy^7$ is morpholinyl, piperidinyl, pyrrolidinyl or tetrahydropyranyl.

34. The method of claim 23, wherein $R^7$ is $-L^7-Cy^7$ and $L^7$ is unsubstituted $C_{1-6}$ alkylene.

35. The method of claim 34, wherein $L^7$ is $CH_2$.

36. The method of claim 23, wherein $R^7$ is -$L^7$-$Cy^7$ and $L^7$ is $C_{1-6}$ alkylene substituted with 1, 2 or 3 substituents independently selected from F, Cl, CN, OH, O($C_{1-6}$ alkyl), $NH_2$, NH($C_{1-6}$ alkyl) and N($C_{1-6}$ alkyl)$_2$.

37. The method of claim 36, wherein $L^7$ is $C_{1-6}$ alkylene substituted with 1 substituent selected from CN, OH, O($C_{1-6}$ alkyl), $NH_2$, NH($C_{1-6}$ alkyl) and N($C_{1-6}$ alkyl)$_2$ or 1, 2 or 3 substituents independently selected from F and Cl.

38. The method of claim 37, wherein $L^7$ is —CH(OH)—.

39. The method of claim 1, wherein $A^8$ is N.

40. The method of claim 1, wherein $A^8$ is $CR^8$.

41. The method of claim 40, wherein $R^8$ is H.

42. The method of claim 1, wherein $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$ and $R^{d6}$ are each independently selected from H and $C_{1-6}$ alkyl and $R^{e1}$, $R^{e2}$, $R^{e3}$, $R^{e4}$, $R^{e5}$ and $R^{e6}$ are each H.

43. The method of claim 1, wherein $A^5$ is $CR^5$ and $A^7$ is $CR^7$.

44. The method of claim 1, wherein $A^5$ is $CR^5$, $A^6$ is $CR^6$ and $A^7$ is $CR^7$.

45. A method of treating cancer, wherein the cancer is lymphoma, leukemia, multiple myeloma or myeloproliferative disorders, comprising administering to a patient in need of such treatment a therapeutically effective amount of a compound selected from the following compounds, or a pharmaceutically acceptable salt thereof:

3-amino-N-{4-[3-aminopiperidin-1-yl]pyridin-3-yl}-7-piperidin-4-ylquinoline-2-carboxamide;
3-amino-N-{4-[3-aminopiperidin-1-yl]pyridin-3-yl}-7-(tetrahydro-2H-pyran-4-yl)quinoline-2-carboxamide;
3-amino-N-{4-[3-aminopiperidin-1-yl]pyridin-3-yl}-7-(2,6-difluorophenyl)quinoline-2-carboxamide;
3-amino-N-{4-[3-aminopiperidin-1-yl]pyridin-3-yl}-7-(1-methyl-1H-pyrazol-5-yl)quinoline-2-carboxamide;
3-amino-N-{4-[3-aminopiperidin-1-yl]pyridin-3-yl}-7-(2-cyanophenyl)quinoline-2-carboxamide;
3-amino-7-[2-(aminocarbonyl)phenyl]-N-{4-[3-aminopiperidin-1-yl]pyridin-3-yl)}quinoline-2-carboxamide;
3-amino-N-{4-[3-aminopiperidin-1-yl]pyridin-3-yl}-7-(2-cyano-6-fluorophenyl)quinoline-2-carboxamide;
3-amino-7-[2-(aminocarbonyl)-6-fluorophenyl]-N-{4-[3-aminopiperidin-1-yl]pyridin-3-yl}quinoline-2-carboxamide;
3-amino-N-{4-[3-aminopiperidin-1-yl]pyridin-3-yl}-7-isopropylquinoline-2-carboxamide;
3-amino-N-{4-[3-aminopiperidin-1-yl]pyridin-3-yl}-7-ethylquinoline-2-carboxamide;
3-amino-N-{4-[3-aminopiperidin-1-yl]pyridin-3-yl}quinoline-2-carboxamide;
3-amino-N-{4-[3-aminopiperidin-1-yl]pyridin-3-yl}-7-bromoquinoline-2-carboxamide;
3-amino-N-{4-[3-aminopiperidin-1-yl]pyridin-3-yl}-7-(cyanomethyl)quinoline-2-carboxamide;
3-amino-N-{4-[3-aminopiperidin-1-yl]pyridin-3-yl}-7-ethyl-6-fluoroquinoline-2-carboxamide;
3-amino-N-{4-[3-aminopiperidin-1-yl]pyridin-3-yl}-7-(1-hydroxyethyl)quinoline-2-carboxamide;
3-amino-N-{4-[3-aminopiperidin-1-yl]pyridin-3-yl}-7-(1-hydroxy-1-methylethyl)quinoline-2-carboxamide;
3-amino-N-{4-[3-aminopiperidin-1-yl]pyridin-3-yl}-7-[hydroxy(phenyl)methyl]quinoline-2-carboxamide;
3-amino-N-{4-[3-aminopiperidin-1-yl]pyridin-3-yl}-7-(1-fluoroethyl)quinoline-2-carboxamide;
3-amino-N-{4-[3-aminopiperidin-1-yl]pyridin-3-yl}-7-(pyrrolidin-1-ylmethyl)quinoline-2-carboxamide;
3-amino-N-{4-[3-aminopiperidin-1-yl]pyridin-3-yl}-7-[(dimethylamino)methyl]quinoline-2-carboxamide;
3-amino-N-{4-[3-aminopiperidin-1-yl]pyridin-3-yl}-7-(morpholin-4-ylmethyl)quinoline-2-carboxamide; and
3-amino-N-{4-[3-aminopiperidin-1-yl]-7-hydroxy-6,7-dihydro-5H-cyclopenta[b]pyridin-3-yl}-7-ethylquinoline-2-carboxamide;
3-amino-N-[4-(3-aminocyclohexyl)pyridin-3-yl]-7-ethylquinoline-2-carboxamide;
3-amino-N-(4-(3-aminopiperidin-1-yl)-2,3-dihydrofuro[2,3-b]pyridin-5-yl)-7-ethylquinoline-2-carboxamide;
3-amino-N-{4-[3-aminopiperidin-1-yl]pyridin-3-yl}-7-ethoxy-1,8-naphthyridine-2-carboxamide;
3-amino-N-{4-[3-amino-4-hydroxy-5-methylpiperidin-1-yl]pyridin-3-yl}-7-ethoxy-1, 8-naphthyridine-2-carboxamide;
3-amino-N-{4-[3-aminopiperidin-1-yl]pyridin-3-yl}-7-ethyl-1,6-naphthyridine-2-carboxamide;
3-amino-N-{4-[3-amino-4-hydroxy-5-methylpiperidin-1-yl]-5-methylpyridin-3-yl}-7-ethylquinoline-2-carboxamide;
3-amino-N-{4-[3-amino-4-hydroxy-5-methylpiperidin-1-yl]pyridin-3-yl}-7-ethylquinoline-2-carboxamide;
3-amino-N-{4-[3-aminopiperidin-1-yl]-5-methylpyridin-3-yl}-7-ethylquinoline-2-carboxamide;
3-amino-N-{4-[3-aminopiperidin-1-yl]-6-methoxypyridin-3-yl}-7-ethylquinoline-2-carboxamide; and
3-amino-N-{4-[3-aminopiperidin-1-yl]-5-cyanopyridin-3-yl}-7-ethylquinoline-2-carboxamide;
3-amino-N-{4-[(3S)-3-aminopiperidin-1-yl]pyridin-3-yl}-7-piperidin-4-ylquinoline-2-carboxamide;
3-amino-N-{4-[(3S)-3-aminopiperidin-1-yl]pyridin-3-yl}-7-(tetrahydro-2H-pyran-4-yl)quinoline-2-carboxamide;
3-amino-N-{4-[(3S)-3-aminopiperidin-1-yl]pyridin-3-yl}-7-(2,6-difluorophenyl)quinoline-2-carboxamide;
3-amino-N-{4-[(3S)-3-aminopiperidin-1-yl]pyridin-3-yl}-7-(1-methyl-1H-pyrazol-5-yl)quinoline-2-carboxamide;
3-amino-N-{4-[(3S)-3-aminopiperidin-1-yl]pyridin-3-yl}-7-(2-cyanophenyl)quinoline-2-carboxamide;
3-amino-7-[2-(aminocarbonyl)phenyl]-N-{4-[(3S)-3-aminopiperidin-1-yl]pyridin-3-yl}quinoline-2-carboxamide;
3-amino-N-{4-[(3S)-3-aminopiperidin-1-yl]pyridin-3-yl}-7-(2-cyano-6-fluorophenyl)quinoline-2-carboxamide;
3-amino-7-[2-(aminocarbonyl)-6-fluorophenyl]-N-{4-[(3S)-3-aminopiperidin-1-yl]pyridin-3-yl)}quinoline-2-carboxamide;
3-amino-N-{4-[(3S)-3-aminopiperidin-1-yl]pyridin-3-yl}-7-isopropylquinoline-2-carboxamide;
3-amino-N-{4-[(3S)-3-aminopiperidin-1-yl]pyridin-3-yl}-7-ethylquinoline-2-carboxamide;
3-amino-N-{4-[(3S)-3-aminopiperidin-1-yl]pyridin-3-yl}quinoline-2-carboxamide;
3-amino-N-{4-[(3S)-3-aminopiperidin-1-yl]pyridin-3-yl}-7-bromoquinoline-2-carboxamide;
3-amino-N-{4-[(3S)-3-aminopiperidin-1-yl]pyridin-3-yl}-7-(cyanomethyl)quinoline-2-carboxamide;
3-amino-N-{4-[(3S)-3-aminopiperidin-1-yl]pyridin-3-yl}-7-ethyl-6-fluoroquinoline-2-carboxamide;
3-amino-N-{4-[(3S)-3-aminopiperidin-1-yl]pyridin-3-yl}-7-(1-hydroxyethyl)quinoline-2-carboxamide;
3-amino-N-{4-[(3S)-3-aminopiperidin-1-yl]pyridin-3-yl}-7-(1-hydroxy-1-methylethyl)quinoline-2-carboxamide;

3-amino-N-{4-[(3S)-3-aminopiperidin-1-yl]pyridin-3-yl}-7-[hydroxy(phenyl)methyl]quinoline-2-carboxamide;
3-amino-N-{4-[(3S)-3-aminopiperidin-1-yl]pyridin-3-yl}-7-(1-fluoroethyl)quinoline-2-carboxamide;
3-amino-N-{4-[(3S)-3-aminopiperidin-1-yl]pyridin-3-yl}-7-(pyrrolidin-1-ylmethyl)quinoline-2-carboxamide;
3-amino-N-{4-[(3S)-3-aminopiperidin-1-yl]pyridin-3-yl}-7-[(dimethylamino)methyl]quinoline-2-carboxamide;
3-amino-N-{4-[(3S)-3-aminopiperidin-1-yl]pyridin-3-yl}-7-(morpholin-4-ylmethyl)quinoline-2-carboxamide;
3-amino-N-{4-[(3S)-3-aminopiperidin-1-yl]-7-hydroxy-6,7-dihydro-5H-cyclopenta[b]pyridin-3-yl}-7-ethylquinoline-2-carboxamide;
3-amino-N-[4-(3-aminocyclohexyl)pyridin-3-yl]-7-ethylquinoline-2-carboxamide;
(S)-3-amino-N-(4-(3-aminopiperidin-1-yl)-2,3-dihydrofuro[2,3-b]pyridin-5-yl)-7-ethylquinoline-2-carboxamide;
3-amino-N-{4-[(3S)-3-aminopiperidin-1-yl]pyridin-3-yl}-7-ethoxy-1,8-naphthyridine-2-carboxamide;
3-amino-N-{4-[(3R,4R,5S)-3-amino-4-hydroxy-5-methylpiperidin-1-yl]pyridin-3-yl}-7-ethoxy-1,8-naphthyridine-2-carboxamide;
3-amino-N-{4-[(3S)-3-aminopiperidin-1-yl]pyridin-3-yl}-7-ethyl-1,6-naphthyridine-2-carboxamide;
3-amino-N-{4-[(3R,4R,5S)-3-amino-4-hydroxy-5-methylpiperidin-1-yl]-5-methylpyridin-3-yl}-7-ethylquinoline-2-carboxamide;
3-amino-N-{4-[(3R,4R,5S)-3-amino-4-hydroxy-5-methylpiperidin-1-yl]pyridin-3-yl}-7-ethylquinoline-2-carboxamide;
3-amino-N-{4-[(3S)-3-aminopiperidin-1-yl]-5-methylpyridin-3-yl}-7-ethylquinoline-2-carboxamide;
3-amino-N-{4-[(3 S)-3-aminopiperidin-1-yl]-6-methoxypyridin-3-yl}-7-ethylquinoline-2-carboxamide; and
3-amino-N-{4-[(3 S)-3-aminopiperidin-1-yl]-5-cyanopyridin-3-yl}-7-ethylquinoline-2-carboxamide.

46. The method of claim 1, wherein the compound is 3-Amino-N-{4-[(3 S)-3-aminopiperidin-1-yl]pyridin-3-yl}-7-ethyl-6-fluoroquinoline-2-carboxamide, or a pharmaceutically acceptable salt thereof.

47. The method of claim 1, wherein the cancer is lymphoma.

48. The method of claim 47, wherein the lymphoma is diffuse large B-cell lymphoma, mantle cell lymphoma, non-Hodgkin lymphoma, or Hodgkin lymphoma.

49. The method of claim 1, wherein the cancer is leukemia.

50. The method of claim 49, wherein leukemia is acute lymphoblastic leukemia, acute myelogenous leukemia, chronic lymphocytic leukemia, or chronic myelogenous leukemia.

51. The method of claim 1, wherein the cancer is multiple myeloma.

52. The method of claim 1, wherein the cancer is myeloproliferative disorders.

53. The method of claim 52, wherein the myeloproliferative disorder is polycythemia vera (PV), essential thrombocythemia (ET), chronic myelogenous leukemia (CML), primary myelofibrosis (PMF), myelofibrosis with myeloid metaplasia (MMM), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

* * * * *

UNITED STATES PATENT AND TRADEMARK OFFICE
CERTIFICATE OF CORRECTION

PATENT NO. : 9,676,750 B2
APPLICATION NO. : 15/001826
DATED : June 13, 2017
INVENTOR(S) : Yun-Long Li et al.

It is certified that error appears in the above-identified patent and that said Letters Patent is hereby corrected as shown below:

Column 171, Line 28, Claim 1, delete "$NR^{c1}C(O)NR^{c1}R^{d1}NR^{c1}C(O)OR^{a1}$," and insert -- $NR^{c1}C(O)NR^{c1}R^{d1}$, $NR^{c1}C(O)OR^{a1}$, --;

Column 172, Line 10, Claim 1, delete "$OR^{a3}SR^{a3}$," and insert -- $OR^{a3}$, $SR^{a3}$, --;

Column 172, Line 35, Claim 1, delete "$OR^{a3}SR^{a3}$," and insert -- $OR^{a3}$, $SR^{a3}$, --;

Column 172, Line 61, Claim 1, delete "$NR^{c4}C(=NR^{e4})NR^{c4}R^{d4}$" and insert -- $NR^{c4}C(=R^{e4})NR^{c4}R^{d4}$, --;

Column 173, Line 6, Claim 1, delete "$NR^{c4}C(=NR^{e4})NR^{c4}R^{d4}$" and insert -- $NR^{c4}C(=NR^{e4})NR^{c4}R^{d4}$, --;

Column 173, Line 28, Claim 1, delete "$R^{d2}$," and insert -- $R^{d2}$ --;

Column 173, Line 34, Claim 1, delete "$C(O)NR^{c5}SR^{d5}$," and insert -- $C(O)NR^{c5}R^{d5}$, --;

Column 173, Line 56, Claim 1, delete "$NR^{c6}C(=NR^{e6})NR^{c6}R^{d6}$" and insert -- $NR^{c6}C(=NR^{e6})NR^{c6}R^{d6}$, --;

Column 174, Line 1, Claim 1, delete "$NR^{c6}C(=NR^{e6})NR^{c6}R^{d6}$" and insert -- $NR^{c6}C(=NR^{e6})NR^{c6}R^{d6}$, --;

Column 174, Line 10, Claim 1, delete "alkynyl" and insert -- alkynyl, --;

Column 174, Line 32, Claim 1, delete "alkynyl" and insert -- alkynyl, --;

Column 174, Line 54, Claim 1, delete "alkynyl" and insert -- alkynyl, --.

Signed and Sealed this
Fourteenth Day of August, 2018

Andrei Iancu
*Director of the United States Patent and Trademark Office*

Column 175, Lines 43-44, Claim 18, delete "$NR^{c3}C(=NR^{e3})NR^{c3}R^{d3}$" and insert -- $NR^{c3}C(=NR^{e3})NR^{c3}R^{d3}$, --;

Column 175, Line 51, Claim 18, delete "$NR^3C(O)NR^{c3}R^{d3}$," and insert -- $NR^{c3}C(O)NR^{c3}R^{d3}$, --;

Column 175, Line 53, Claim 18, delete "$NR^3S(O)_2R^{b3}$" and insert -- $NR^{c3}S(O)_2R^{b3}$ --.

Column 175, Line 66, Claim 21, delete "($C_1$-6" and insert -- ($C_{1-6}$ --.

Column 176, Line 40, Claim 29, after "method" insert -- of --.

Column 180, Line 3, Claim 45, delete "(3 S)" and insert -- (3S) --;

Column 180, Line 5, Claim 45, delete "(3 S)" and insert -- (3S) --.

Column 180, Line 8, Claim 46, delete "(3 S)" and insert -- (3S) --.